(12) United States Patent
Behenna et al.

(10) Patent No.: US 10,800,783 B2
(45) Date of Patent: *Oct. 13, 2020

(54) CDK2/4/6 INHIBITORS

(71) Applicant: Pfizer Inc., New York, NY (US)

(72) Inventors: Douglas Carl Behenna, San Juan Capistrano, CA (US); Ping Chen, San Diego, CA (US); Kevin Daniel Freeman-Cook, Carlsbad, CA (US); Robert Louis Hoffman, San Diego, CA (US); Mehran Jalaie, San Diego, CA (US); Asako Nagata, San Diego, CA (US); Sajiv Krishnan Nair, Vista, CA (US); Sacha Ninkovic, La Jolla, CA (US); Martha Alicia Ornelas, San Diego, CA (US); Cynthia Louise Palmer, La Mesa, CA (US); Eugene Yuanjin Rui, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/251,032

(22) Filed: Jan. 17, 2019

(65) Prior Publication Data

US 2019/0135817 A1 May 9, 2019

Related U.S. Application Data

(63) Continuation of application No. 15/664,265, filed on Jul. 31, 2017, now Pat. No. 10,233,188.

(60) Provisional application No. 62/371,602, filed on Aug. 15, 2016, provisional application No. 62/533,347, filed on Jul. 17, 2017.

(51) Int. Cl.
| | | |
|---|---|---|
| *A61K 31/519* | (2006.01) | |
| *A61K 31/4375* | (2006.01) | |
| *A61K 31/4545* | (2006.01) | |
| *C07D 487/04* | (2006.01) | |
| *C07D 401/12* | (2006.01) | |
| *C07D 471/04* | (2006.01) | |
| *C07D 401/14* | (2006.01) | |

(52) U.S. Cl.
CPC ......... *C07D 487/04* (2013.01); *C07D 401/14* (2013.01); *C07D 471/04* (2013.01)

(58) Field of Classification Search
CPC .............. A61K 31/519; A61K 31/4375; A61K 31/4545; C07D 487/04; C07D 401/12
USPC ........... 514/264.11, 303, 322; 546/118, 122, 546/199; 544/279
See application file for complete search history.

(56) References Cited

U.S. PATENT DOCUMENTS

| | | |
|---|---|---|
| 6,498,163 B1 | 12/2002 | Boschelli et al. |
| 6,936,612 B2 | 9/2005 | Barvian et al. |
| 7,781,583 B2 | 8/2010 | Erdman et al. |
| 8,268,840 B2 * | 9/2012 | Brookfield .............. A61P 19/02 514/264.1 |
| 8,404,695 B2 | 3/2013 | Roche Palo Alto Llc |
| 9,321,786 B2 | 4/2016 | Celgene Avilomics Research Inc_; Sanofi |
| 10,233,188 B2 * | 3/2019 | Freeman-Cook .... C07D 471/04 |
| 2004/0224958 A1 | 11/2004 | Warner-Lambert Company |
| 2006/0014312 A1 | 1/2006 | Malone |
| 2009/0270389 A1 | 10/2009 | Brookfield et al. |

(Continued)

FOREIGN PATENT DOCUMENTS

| | | |
|---|---|---|
| WO | 9808846 | 3/1998 |
| WO | 9823613 | 6/1998 |
| WO | 9833798 | 8/1998 |

(Continued)

OTHER PUBLICATIONS

Alexander et al., Cyclin E overexpression as a biomarker for combination treatment strategies in inflammatory breast cancer, Oncotarget (2017) 8: 14897-14911.

(Continued)

*Primary Examiner* — Matthew P Coughlin
*Assistant Examiner* — Sagar Patel
(74) *Attorney, Agent, or Firm* — Leslie A. Robinson

(57) ABSTRACT

This invention relates to compounds of general Formula (I)

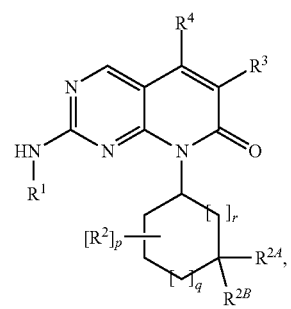

and pharmaceutically acceptable salts thereof, in which $R^1$, $R^2$, $R^{2A}$, $R^{2B}$, $R^3$, $R^4$, $R^{5A}$, $R^{5B}$, $R^6$, $R^7$, $R^8$, $R^9$, p, q and r are as defined herein, to pharmaceutical compositions comprising such compounds and salts, and to methods of using such compounds, salts and compositions for the treatment of abnormal cell growth, including cancer.

16 Claims, 6 Drawing Sheets
Specification includes a Sequence Listing.

(56) References Cited

U.S. PATENT DOCUMENTS

2016/0034466 A1   2/2016   Sinha et al.

FOREIGN PATENT DOCUMENTS

| WO | 0155148 | 8/2001 | |
|---|---|---|---|
| WO | 0170741 | 9/2001 | |
| WO | 02064594 | 8/2002 | |
| WO | 03062236 | 1/2003 | |
| WO | 2005005426 | 1/2005 | |
| WO | 2005082903 | 9/2005 | |
| WO | 2008032162 | 3/2008 | |
| WO | 2009132980 | 11/2009 | |
| WO | WO-2009132980 A1 * | 11/2009 | ........... C07D 471/04 |
| WO | 2014128588 | 8/2014 | |
| WO | 2016127963 | 8/2016 | |

OTHER PUBLICATIONS

Asghar et al. The history and future of targeting cyclin-dependent kinases in cancer therapy, Nat. Rev. Drug. Discov. 2015; 14(2): 130-146.
Au-Yeung et al., Selective Targeting of Cyclin E1-Amplified High-Grade Serous Ovarian Cancer by Cyclin-Dependent Kinase 2 and AKT Inhibition, Clin. Cancer Res. (2017) 23:1862-1874.
Ayhan et al., CCNE1 copy-number gain and overexpression identify ovarian clear cell carcinoma with a poor prognosis, Modern Pathology (2017) 30: 297-303.
Caballero et al., Structural requirements of pyrido[2,3-d]pyrimidin-7-one as CDK4/6 inhibitors: 2D autocorrelation, CoMFA and CoMSIA analyses, Bioorg. Med. Chem. (2008) 16:6103-6115.
Caldon et al., Cyclin E2 overexpression is associated with endocrine resistance but not insensitivity to CDK2 inhibition in human breast cancer cells. Mol Cancer Ther. (2012) 11:1488-99.
Cicenas et al. Highlights of the Latest Advances in Research on CDK Inhibitors. Cancers, (2014) 6:2224-2242.
Cordon Cardo C. Mutations of cell cycle regulators: biological and clinical implications for human neoplasia. Am. J. Pathol. (1995) 147:545 560.
Database PubChem [Online] U.S. National Library of Medicine; Oct. 26, 2006 (Oct. 26, 2006), Database accession No. SCHEMBL5900793; PubChem CID: CID11719977.
Database PubChem [Online] U.S. National Library of Medicine; Dec. 1, 2012 (Dec. 1, 2012), Database accession No. SCHEMBL5900476, PubChem CID: CID69600102.
Database PubChem [Online] U.S. National Library of Medicine; Dec. 1, 2012 (Dec. 1, 2012), Database accession No. SCHEMBL5900496, PubChem CID: CID69600116.
Database PubChem [Online] U.S. National Library of Medicine; Dec. 1, 2012 (Dec. 1, 2012), Database accession No. SCHEMBL5900546, PubChem CID: CID69600149.
Database PubChem [Online] U.S. National Library of Medicine; Dec. 1, 2012 (Dec. 1, 2012), Database accession No. SCHEMBL5900573, PubChem CID: CID69600163.
Database Registry [Online] Chemical Abstracts Service, Columbus, Ohio, US; Dec. 4, 2011 (Dec. 4, 2011), "Pyrido[2,3-d]pyrimidin-7(8H)-one, 8-cyclopentyl-2-[[1-(propylsulfonyl)-4-piperidinyl]amino]-6-(2-(pyridinylmethyl)-", Database accession No. 1347848-31-0, XP-002773746.
Elsawaf & Sinn, Triple Negative Breast Cancer: Clinical and Histological Correlations, Breast Care (2011) 6:273-278.
Etemadmoghadam et al., Resistance to CDK2 Inhibitors Is Associated with Selection of Polyploid Cells in CCNE1-Amplified Ovarian Cancer, Clin Cancer Res (2013) 19: 5960-71.
Hall M, Peters G. Genetic alterations of cyclins, cyclin dependent kinases, and Cdk inhibitors in human cancer. Adv. Cancer Res. (1996) 68:67 108.
Herrera-Abreu et al., Early Adaptation and Acquired Resistance to CDK4/6 Inhibition in Estrogen Receptor-Positive Breast Cancer, Cancer Res. (2016) 76: 2301-2313.
International Search Report for PCT/IB2017/054655, dated Oct. 9, 2017.
Johnson Dg, Walker Cl. Cyclins and Cell Cycle Checkpoints. Annu. Rev. Pharmacol. Toxicol. (1999) 39:295 312.
Karp Je, Broder S. Molecular foundations of cancer: new targets for intervention. Nat. Med. (1995) 1:309 320.
Keyomarsi et al., Cyclin E and survival in patients with breast cancer. N. Engl J Med. (2002) 347:1566-75.
Morgan Do. Cyclin dependent kinases: engines, clocks, and microprocessors. Annu. Rev. Cell. Dev. Biol. (1997) 13:261 291.
Nakayama et al., Gene amplification CCNE1 is related to poor survival and potential therapeutic target in ovarian cancer, Cancer (2010) 116: 2621-34.
Noske et al., Detection of CCNE1/URI (19q12) amplification by in situ hybridisation is common in high grade and type II endometrial cancer, Oncotarget (2017) 8: 14794-14805.
O'Leary et al. Treating cancer with selective CDK4/6 inhbitors. Nature Reviews (2016) 13:417-430.
Ooi et al., Gene amplification of CCNE1, CCND1, and CDK6 in gastric cancers detected by multiplex ligation-dependent probe amplification and fluorescence in situ hybridization, Hum Pathol. (2017) 61: 58-67.
Reddy et al., Discovery of 8-Cyclopentyl-2-[4-(4-mehtyl-piperazin-1-yl)-phneylamino]-7-oxo-7,8-dihydro-pyrido[23-d] pyrimidine-6-carbonitrile (7x) as a Potent Inhibitor of Cyclin-Dependent Kinase 4 (CDK4) and AMPK-Related Kinase 4 (ARK5), J. Med. Chem. (2014) 57:578-599.
Scaltriti et al. Cyclin E amplification/overexpression is a mechanism of trastuzumab resistance in HER2+breast cancer patients, Proc Natl Acad Sci. (2011) 108: 3761-6.
Smalley et al., Identification of a novel subgroup of melanomas with KIT/cyclin-dependent-4 overexpression, Cancer Res (2008) 68: 5743 52.
Written Opinion of the International Searching Authority for PCT/IB2017/054655, dated Sep. 14, 2017.
Zheng et al., "Pyridopyrimidinone Derivatives as Potent and Selective c-Jun N-Terminal Kinase (JNK) Inhibitors," Med. Chem. Lett. (2015) 6:413-418.

* cited by examiner

CDK2/4/6 INHIBITORS

CROSS REFERENCE TO RELATED APPLICATIONS

This application claims the benefit of priority to U.S. Provisional Application No. 62/371,602, filed on Aug. 15, 2016, and to U.S. Provisional Application No. 62/533,347, filed on Jul. 17, 2017, each of which is incorporated by reference herein in its entirety.

REFERENCE TO SEQUENCE LISTING

This application is being filed electronically via EFS-Web and includes an electronically submitted sequence listing in .txt format. The .txt file contains a sequence listing entitled "PC72302SEQLISTING_ST25.txt" created on Jul. 26, 2017 and having a size of 2 KB. The sequence listing contained in this .txt file is part of the specification and is herein incorporated by reference in its entirety.

FIELD OF THE INVENTION

The present invention relates to compounds of Formulae (I) to (VII), and their pharmaceutically acceptable salts, to pharmaceutical compositions comprising such compounds and salts, and to the uses thereof. The compounds, salts and compositions of the present invention are useful for treating or ameliorating abnormal cell proliferative disorders, such as cancer.

BACKGROUND

Cyclin-dependent kinases (CDKs) are important cellular enzymes that perform essential functions in regulating eukaryotic cell division and proliferation. The cyclin-dependent kinase catalytic units are activated by regulatory subunits known as cyclins. At least sixteen mammalian cyclins have been identified (Johnson D G, Walker C L. Cyclins and Cell Cycle Checkpoints. *Annu. Rev. Pharmacol. Toxicol.* (1999) 39:295-312). Cyclin B/CDK1, cyclin A/CDK2, cyclin E/CDK2, cyclin D/CDK4, cyclin D/CDK6, and likely other heterodynes are important regulators of cell cycle progression. Additional functions of cyclin/CDK heterodynes include regulation of transcription, DNA repair, differentiation and apoptosis (Morgan D O. Cyclin-dependent kinases: engines, clocks, and microprocessors. *Annu. Rev. Cell. Dev. Biol.* (1997) 13:261-291).

Cyclin-dependent kinase inhibitors have been demonstrated to be useful in treating cancer. Increased activity or temporally abnormal activation of cyclin-dependent kinases has been shown to result in the development of human tumors, and human tumor development is commonly associated with alterations in either the CDK proteins themselves or their regulators (Cordon-Cardo C. Mutations of cell cycle regulators: biological and clinical implications for human neoplasia. *Am. J. Pathol.* (1995) 147:545-560; Karp J E, Broder S. Molecular foundations of cancer: new targets for intervention. *Nat. Med.* (1995) 1:309-320; Hall M, Peters G. Genetic alterations of cyclins, cyclin-dependent kinases, and Cdk inhibitors in human cancer. *Adv. Cancer Res.* (1996) 68:67-108). Amplifications of the regulatory subunits of CDKs and cyclins, and mutation, gene deletion, or transcriptional silencing of endogenous CDK inhibitors have also been reported (Smalley et al. Identification of a novel subgroup of melanomas with KIT/cyclin-dependent kinase-4 overexpression. *Cancer Res* (2008) 68: 5743-52).

Clinical trials for the CDK4/6 inhibitors palbociclib, ribociclib and abemaciclib are ongoing for breast and other cancers, as single agents or in combination with other therapeutics. Palbociclib and ribociclib have been approved for treatment of hormone receptor (HR)-positive, human epidermal growth factor receptor 2 (HER2)-negative advanced or metastatic breast cancer in combination with aromatase inhibitors in post-menopausal women, and for palbociclib, in combination with fulvestrant after disease progression following endocrine therapy, (O'Leary et al. Treating cancer with selective CDK4/6 inhbitors. *Nature Reviews* (2016) 13:417-430). While CDK4/6 inhibitors have shown significant clinical efficacy in ER-positive metastatic breast cancer, as with other kinases their effects may be limited over time by the development of primary or acquired resistance.

Overexpression of CDK2 is associated with abnormal regulation of cell-cycle. The cyclin E/CDK2 complex plays and important role in regulation of the G1/S transition, histone biosynthesis and centrosome duplication. Progressive phosphorylation of Rb by cyclin D/Cdk4/6 and cyclin E/Cdk2 releases the G1 transcription factor, E2F, and promotes S-phase entry. Activation of cyclin A/CDK2 during early S-phase promotes phosphorylation of endogenous substrates that permit DNA replication and inactivation of E2F, for S-phase completion. (Asghar et al. *The history and future of targeting cyclin-dependent kinases in cancer therapy*, Nat. Rev. Drug. Discov. 2015; 14(2): 130-146).

Cyclin E, the regulatory cyclin for CDK2, is frequently overexpressed in cancer. Cyclin E amplification or overexpression has long been associated with poor outcomes in breast cancer. (Keyomarsi et al., Cyclin E and survival in patients with breast cancer. *N Engl J Med.* (2002) 347:1566-75). Cyclin E2 (CCNE2) overexpression is associated with endocrine resistance in breast cancer cells and CDK2 inhibition has been reported to restore sensitivity to tamoxifen or CDK4 inhibitors in tamoxifen-resistant and CCNE2 overexpressing cells. (Caldon et al., Cyclin E2 overexpression is associated with endocrine resistance but not insensitivity to CDK2 inhibition in human breast cancer cells. *Mol Cancer Ther*. (2012) 11:1488-99; Herrera-Abreu et al., Early Adaptation and Acquired Resistance to CDK4/6 Inhibition in Estrogen Receptor—Positive Breast Cancer, *Cancer Res.* (2016) 76: 2301-2313). Cyclin E amplification also reportedly contributes to trastuzumab resistance in HER2+ breast cancer. (Scaltriti et al. Cyclin E amplification/overexpression is a mechanism of trastuzumab resistance in HER2+ breast cancer patients, *Proc Natl Acad Sci*. (2011) 108: 3761-6). Cyclin E overexpression has also been reported to play a role in basal-like and triple negative breast cancer (TNBC), as well as inflammatory breast cancer. (Elsawaf & Sinn, Triple Negative Breast Cancer: Clinical and Histological Correlations, *Breast Care* (2011) 6:273-278; Alexander et al., Cyclin E overexpression as a biomarker for combination treatment strategies in inflammatory breast cancer, *Oncotarget* (2017) 8: 14897-14911.)

Amplification or overexpression of cyclin E1 (CCNE1) is also associated with poor outcomes in ovarian, gastric, endometrial and other cancers. (Nakayama et al., Gene amplification CCNE1 is related to poor survival and potential therapeutic target in ovarian cancer, Cancer (2010) 116: 2621-34; Etemadmoghadam et al., Resistance to CDK2 Inhibitors Is Associated with Selection of Polyploid Cells in CCNE1-Amplified Ovarian Cancer, *Clin Cancer Res* (2013) 19: 5960-71; Au-Yeung et al., Selective Targeting of Cyclin E1-Amplified High-Grade Serous Ovarian Cancer by Cyclin-Dependent Kinase 2 and AKT Inhibition, *Clin. Cancer Res.* (2017) 23:1862-1874; Ayhan et al., CCNE1 copy-number gain and overexpression identify ovarian clear cell carcinoma with a poor prognosis, *Modern Pathology* (2017) 30: 297-303; Ooi et al., Gene amplification of CCNE1, CCND1, and CDK6 in gastric cancers detected by multiplex ligation-dependent probe amplification and fluorescence in situ hybridization, *Hum Pathol.* (2017) 61: 58-67; Noske et al., Detection of CCNE1/URI (19q12) amplification by in situ hybridisation is common in high grade and type II endometrial cancer, *Oncotarget* (2017) 8: 14794-14805).

The small molecule inhibitor, dinaciclib (MK-7965) inhibits CDK1, CDK2, CDK5 and CDK9 and is currently in clinical development for breast and hematological cancers. Seliciclib (roscovitine or CYC202), which inhibits CDK2, CDK7 and CDK9, is being investigated for treatment of advanced solid tumors in conjunction with chemotherapy. Despite significant efforts, there are no approved agents targeting CDK2 to date. Cicenas et al. Highlights of the Latest Advances in Research on CDK Inhibitors. Cancers, (2014) 6:2224-2242. There remains a need to discover CDK inhibitors having novel activity profiles, in particular those targeting CDK2.

SUMMARY

The present invention provides, in part, compounds of Formulae (I) to (VII), and pharmaceutically acceptable salts thereof. Such compounds can inhibit the activity of CDKs, including CDK2, CDK4 and/or CDK6, thereby effecting biological functions. Also provided are pharmaceutical compositions and medicaments, comprising the compounds or salts of the invention, alone or in combination with additional anticancer therapeutic agents or palliative agents.

The present invention also provides, in part, methods for preparing the compounds, pharmaceutically acceptable salts and compositions of the invention, and methods of using the foregoing.

In one aspect, the invention provides a compound of Formula (I):

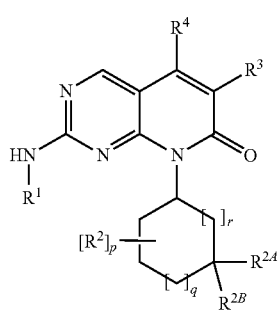

(I)

or a pharmaceutically acceptable salt thereof,
wherein:
$R^1$ is 3-10 membered heterocyclyl substituted by $R^{5A}$ or $C_3$-$C_8$ cycloalkyl substituted by $R^{5B}$, where said 3-10 membered heterocyclyl and $C_3$-$C_8$ cycloalkyl are optionally further substituted by one or more $R^6$;
each $R^2$ is independently F, OH, $C_1$-$C_4$ alkyl, $C_1$-$C_4$ fluoroalkyl, $C_1$-$C_4$ alkoxy or $C_1$-$C_4$ fluoroalkoxy;
$R^{2A}$ and $R^{2B}$ are independently H, F, OH, $C_1$-$C_4$ alkyl, $C_1$-$C_4$ fluoroalkyl, $C_1$-$C_4$ alkoxy or $C_1$-$C_4$ fluoroalkoxy;
where each said $C_1$-$C_4$ alkyl and $C_1$-$C_4$ fluoroalkyl in $R^2$, $R^{2A}$ and $R^{2B}$ is independently optionally substituted by OH, $C_1$-$C_4$ alkoxy or $C_1$-$C_4$ fluoroalkoxy;
$R^3$ is H, F, Cl, $NH_2$, $C_1$-$C_4$ alkyl or $C_1$-$C_4$ fluoroalkyl, where said $C_1$-$C_4$ alkyl and $C_1$-$C_4$ fluoroalkyl are optionally substituted by OH, CN, $C_1$-$C_4$ alkoxy, $C_1$-$C_4$ fluoroalkoxy, $CONH_2$ and COOH;
$R^4$ is H, $C_1$-$C_2$ alkyl or $C_1$-$C_2$ fluoroalkyl;
$R^{5A}$ is $SO_2R^7$, $SO_2NR^8R^9$, $NHSO_2R^7$ or $NHSO_2NR^8R^9$;
$R^{5B}$ is $NHSO_2R^7$ or $NHSO_2NR^8R^9$;
each $R^6$ is independently F, OH, $C_1$-$C_4$ alkyl, $C_1$-$C_4$ fluoroalkyl, $C_1$-$C_4$ alkoxy or $C_1$-$C_4$ fluoroalkoxy;
$R^7$ is $C_1$-$C_4$ alkyl, $C_1$-$C_4$ fluoroalkyl, -L-($C_3$-$C_8$ cycloalkyl), -L-(5-6 membered heterocyclyl) or -L-(5-6 membered heteroaryl);
$R^8$ and $R^9$ are independently H, $C_1$-$C_4$ alkyl, $C_1$-$C_4$ fluoroalkyl, -L-($C_3$-$C_8$ cycloalkyl), -L-(5-6 membered heterocyclyl) or -L-(5-6 membered heteroaryl); or
$R^8$ and $R^9$ may be taken together with the nitrogen atom to which they are attached to form a 5-6 membered heterocyclyl;
where each said $C_1$-$C_4$ alkyl and $C_1$-$C_4$ fluoroalkyl in $R^7$, $R^8$ and $R^9$ is optionally substituted by OH, $C_1$-$C_4$ alkoxy, $C_1$-$C_4$ fluoroalkoxy or $SO_2Me$, and each said $C_3$-$C_8$ cycloalkyl, 5-6 membered heterocyclyl and 5-6 membered heteroaryl in $R^7$, $R^8$ and $R^9$ is optionally substituted by $C_1$-$C_4$ alkyl, OH, $C_1$-$C_4$ alkoxy or $C_1$-$C_4$ fluoroalkoxy;
L is a bond or $C_1$-$C_4$ alkylene, where said $C_1$-$C_4$ alkylene is optionally substituted by OH, $C_1$-$C_4$ alkoxy or $C_1$-$C_4$ fluoroalkoxy;
p is 0, 1, 2, 3 or 4;
q is 0, 1, 2 or 3; and
r is 0, 1 or 2.

In another aspect, the invention provides a pharmaceutical composition comprising a compound of any one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof.

In another aspect, the invention provides a method for the treatment of abnormal cell growth, in particular cancer, in a subject in need thereof, comprising administering to the subject a therapeutically effective amount of a compound of the invention, or a pharmaceutically acceptable salt thereof. Compounds of the invention may be administered as single agents, or may be administered in combination with other anti-cancer therapeutic agents, in particular standard of care agents appropriate for the particular cancer.

In a further aspect, the invention provides a method for the treatment of abnormal cell growth, in particular cancer, in a subject in need thereof, comprising administering to the subject an amount of a compound of the invention, or a pharmaceutically acceptable salt thereof, in combination with an amount of an additional anti-cancer therapeutic agent, which amounts are together effective in treating said abnormal cell growth.

In another aspect, the invention relates to a compound of the invention, or a pharmaceutically acceptable salt thereof, for use as a medicament, in particular a medicament for treatment of cancer.

In another aspect, the invention relates to a compound of the invention, of a pharmaceutically acceptable salt thereof, for use in the treatment of abnormal cell growth, in particular cancer, in a subject.

In a further aspect, the invention provides the use of a compound of the invention, or a pharmaceutically acceptable salt thereof, for the treatment of abnormal cell growth, in particular cancer, in a subject.

In another aspect, the invention relates to a pharmaceutical composition for use in the treatment of abnormal cell growth in a subject in need thereof, which composition comprises a compound of the invention, or a pharmaceutically acceptable salt thereof, and a pharmaceutically acceptable carrier or excipient.

In yet another aspect, the invention provides the use of a compound of any one of the formulae described herein, or a pharmaceutically acceptable salt thereof, for the preparation of a medicament for the treatment of abnormal cell growth in a subject.

In frequent embodiments of the foregoing compounds, methods and uses, the abnormal cell growth is cancer.

In some embodiments, the methods and uses provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by CDK2 in a subject, comprising administering to the subject a compound of the invention, or a pharmaceutically acceptable salt thereof, in an amount that is effective for treating said disorder, in particular cancer. In some embodiments, the disorder is cancer that is characterized by amplification or overexpression of CCNE1 and/or CCNE2.

In another aspect, the invention provides a method for the treatment of a disorder mediated by CDK2, CDK4 and/or CDK6 in a subject, comprising administering to the subject a compound of the invention, or a pharmaceutically acceptable salt thereof, in an amount that is effective for treating said disorder, in particular cancer. In some embodiments, the disorder is cancer that is characterized by amplification or overexpression of CCNE1 and/or CCNE2.

In some embodiments, the methods and uses described herein further comprise administering to the subject an amount of an additional anticancer therapeutic agent or a palliative agent, which amounts are together effective in treating said abnormal cell growth. Each of the embodiments of the compounds of the present invention described below can be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein.

DETAILED DESCRIPTION

Figure 1:
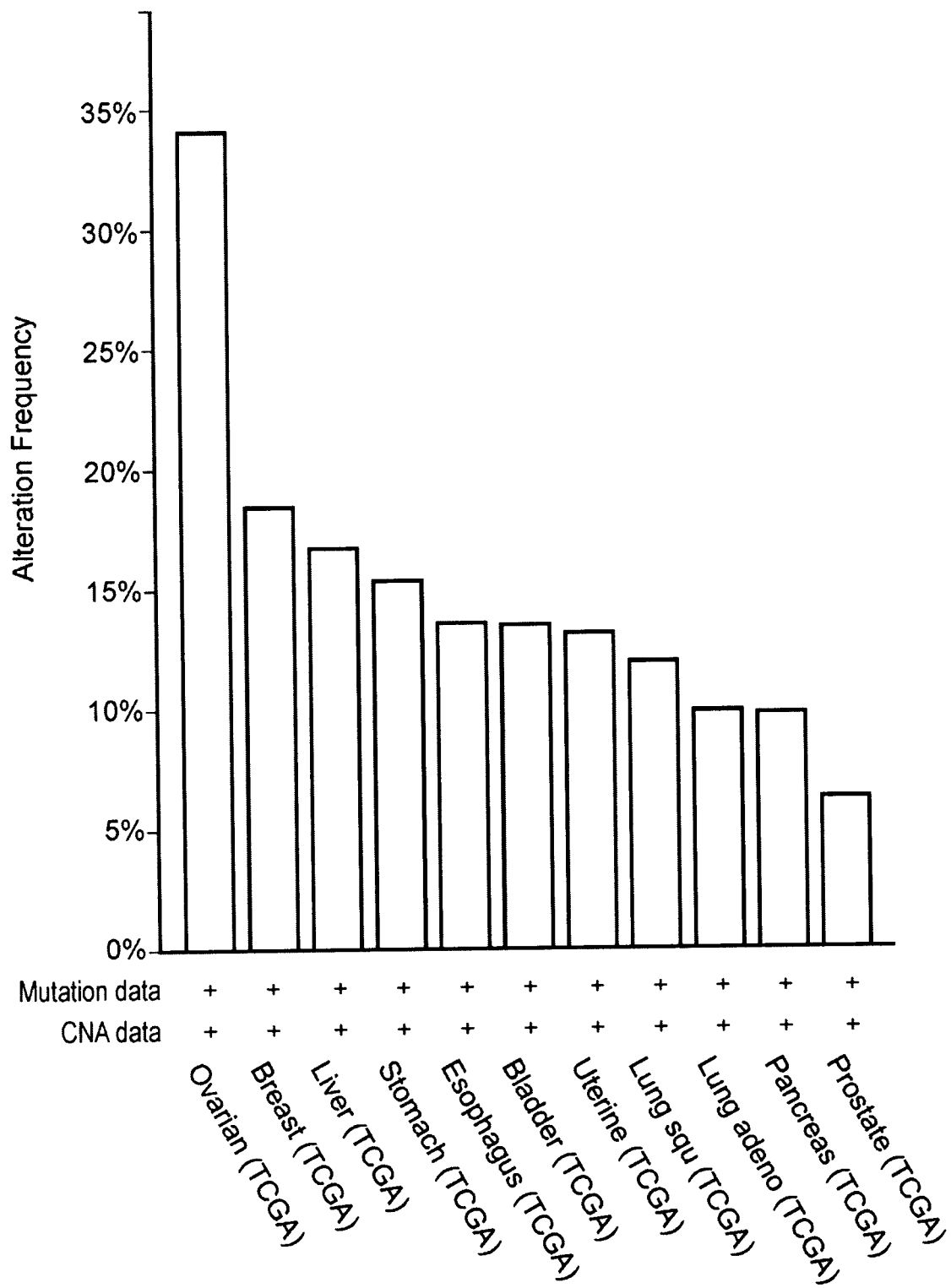
FIG. 1 shows cyclin E1/2 (CCNE1/2) amplification frequency by tumor type (http://oasis.pfizer.com/).

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

"Alkyl" refers to a saturated, monovalent aliphatic hydrocarbon radical including straight chain and branched chain groups having the specified number of carbon atoms. Alkyl substituents typically contain 1 to 20 carbon atoms ("$C_1$-$C_{20}$ alkyl"), preferably 1 to 12 carbon atoms ("$C_1$-$C_{12}$ alkyl"), more preferably 1 to 8 carbon atoms ("$C_1$-$C_8$ alkyl"), or 1 to 6 carbon atoms ("$C_1$-$C_6$ alkyl"), or 1 to 4 carbon atoms ("$C_1$-$C_4$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like. Alkyl groups may be substituted or unsubstituted. In particular, unless otherwise specified, alkyl groups may be substituted by one or more halo groups, up to the total number of hydrogen atoms present on the alkyl moiety. Thus, $C_1$-$C_4$ alkyl includes halogenated alkyl groups, and in particular fluorinated alkyl groups, having 1 to 4 carbon atoms, e.g., trifluoromethyl or difluoroethyl (i.e., $CF_3$ and —$CH_2CHF_2$).

Alkyl groups described herein as optionally substituted may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

Optional substituent groups suitable for alkyl include, but are not limited to $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—OR$^x$, =NR$^x$, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; wherein each R$^x$ and R$^y$ is independently H, C$_1$-C$_8$ alkyl, C$_1$-C$_8$ acyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S(O)$_q$ where q is 0-2; each R$^x$ and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, C$_1$-C$_8$ alkyl, C$_1$-C$_8$ acyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, or C$_5$-C$_{12}$ heteroaryl; and wherein each said C$_3$-C$_8$ cycloalkyl, 3-12 membered heterocyclyl, C$_6$-C$_{12}$ aryl and 5-12 membered heteroaryl is optionally substituted as further defined herein.

Typical substituent groups on alkyl include halo, —OH, C$_1$-C$_4$ alkoxy, —O—C$_6$-C$_{12}$ aryl, —CN, =O, —COOR$^x$, —O(O)R$^x$, —C(O)NR$^x$R$^y$, —NR$^x$C(O)R$^y$, —NR$^x$R$^y$, C$_3$-C$_8$ cycloalkyl, C$_6$-C$_{12}$ aryl, 5-12 membered heteroaryl and 3-12 membered heterocyclyl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S(O)$_q$ where q is 0-2; wherein each said C$_3$-C$_8$ cycloalkyl, C$_6$-C$_{12}$ aryl, 5-12 membered heteroaryl and 3-12 membered heterocyclyl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$.

In some embodiments, alkyl is optionally substituted by one or more substituents, and preferably by 1 to 3 substituents, which are independently selected from the group consisting of halo, —OH, C$_1$-C$_4$ alkoxy, —O—C$_6$-C$_{12}$ aryl, —CN, =O, —COOR$^x$, —OC(O)R$^x$, —C(O)NR$^x$R$^y$, —NR$^x$C(O)R$^y$, —NR$^x$R$^y$, C$_3$-C$_8$ cycloalkyl, C$_6$-C$_{12}$ aryl, 5-12 membered heteroaryl and 3-12 membered heterocyclyl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S(O)$_x$ where x is 0-2; and each said C$_3$-C$_8$ cycloalkyl, C$_6$-C$_{12}$ aryl, 5-12 membered heteroaryl and 3-12 membered heterocyclyl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$.

In other embodiments, alkyl is optionally substituted by one or more substituent, and preferably by 1 to 3 substituents, independently selected from the group consisting of halo, —OH, C$_1$-C$_4$ alkoxy, —CN, —NR$^x$R$^y$, C$_3$-C$_8$ cycloalkyl, 3-12 membered heterocyclyl, C$_6$-C$_{12}$ aryl and 5-12 membered heteroaryl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S(O)$_x$ where x is 0-2; and where each said cycloalkyl, heterocyclyl, aryl or heteroaryl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$.

In some instances, substituted alkyl groups are specifically named by reference to the substituent group. For example, "haloalkyl" refers to an alkyl group having the specified number of carbon atoms that is substituted by one or more halo substituents, and typically contain 1-6 carbon atoms, or preferably 1-4 carbon atoms or 1-2 carbon atoms and 1, 2 or 3 halo atoms (i.e., "C$_1$-C$_6$ haloalkyl", "C$_1$-C$_4$ haloalkyl" or "C$_1$-C$_2$ haloalkyl"). More specifically, fluorinated alkyl groups may be specifically referred to as fluoroalkyl groups, e.g., C$_1$-C$_6$, C$_1$-C$_4$ or C$_1$-C$_2$ fluoroalkyl groups, which are typically substituted by 1, 2 or 3 fluoro atoms. Thus, a C$_1$-C$_4$ fluoroalkyl includes trifluoromethyl (—CF$_3$), difluoromethyl (—CF$_2$H), fluoromethyl (—CFH$_2$), difluoroethyl (—CH$_2$CF$_2$H), and the like.

Similarly, "hydroxyalkyl" refers to an alkyl group having the specified number of carbon atoms that is substituted by one or more hydroxy substituents, and typically contain 1-6 carbon atoms, preferably 1-4 carbon atoms, and 1, 2 or 3 hydroxy (i.e., "C$_1$-C$_6$ hydroxyalkyl"). Thus, C$_1$-C$_6$ hydroxyalkyl includes hydroxymethyl (—CH$_2$OH) and 2-hydroxyethyl (—CH$_2$CH$_2$OH).

"Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 C$_1$-C$_4$ alkyoxy substituents. Such groups are sometimes described herein as C$_1$-C$_4$ alkyoxy-C$_1$-C$_6$ alkyl.

"Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a C$_1$-C$_6$ aminoalkyl includes, for example, aminomethyl (—CH$_2$NH$_2$), N,N-dimethylaminoethyl (—CH$_2$CH$_2$N(CH$_3$)$_2$), 3-(N-cyclopropylamino)propyl (—CH$_2$CH$_2$CH$_2$NH—$^c$Pr) and N-pyrrolidinylethyl (—CH$_2$CH$_2$_N-pyrrolidinyl).

"Alkenyl" refers to an alkyl group, as defined herein, consisting of at least two carbon atoms and at least one carbon-carbon double bond. Typically, alkenyl groups have 2 to 20 carbon atoms ("C$_2$-C$_{20}$ alkenyl"), preferably 2 to 12 carbon atoms ("C$_2$-C$_{12}$ alkenyl"), more preferably 2 to 8 carbon atoms ("C$_2$-C$_8$ alkenyl"), or 2 to 6 carbon atoms ("C$_2$-C$_6$ alkenyl"), or 2 to 4 carbon atoms ("C$_2$-C$_4$ alkenyl"). Representative examples include, but are not limited to, ethenyl, 1-propenyl, 2-propenyl, 1-, 2-, or 3-butenyl, and the like. Alkenyl groups are unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("C$_2$-C$_{20}$ alkynyl"), preferably 2 to 12 carbon atoms ("C$_2$-C$_{12}$ alkynyl"), more preferably 2 to 8 carbon atoms ("C$_2$-C$_8$ alkynyl"), or 2 to 6 carbon atoms ("C$_2$-C$_6$ alkynyl"), or 2 to 4 carbon atoms ("C$_2$-C$_4$ alkynyl"). Representative examples include, but are not limited to, ethynyl, 1-propynyl, 2-propynyl, 1-, 2-, or 3-butynyl, and the like. Alkynyl groups are unsubstituted or substituted by the same groups that are described herein as suitable for alkyl.

"Alkylene" as used herein refers to a divalent hydrocarbyl group having the specified number of carbon atoms which can link two other groups together. Sometimes it refers to a group —(CH$_2$)$_t$— where t is 1-8, and preferably t is 1-4. Where specified, an alkylene can also be substituted by other groups and may include one or more degrees of unsaturation (i.e., an alkenylene or alkynlene moiety) or rings. The open valences of an alkylene need not be at opposite ends of the chain. Thus branched alkylene groups such as —CH(Me)-, —CH$_2$CH(Me)- and —C(Me)$_2$- are also included within the scope of the term 'alkylenes', as are cyclic groups such as cyclopropan-1,1-diyl and unsaturated groups such as ethylene (—CH=CH—) or propylene (—CH$_2$—CH=CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N(R)—, —O— or —S(O)$_x$—, where R is H or a suitable substituent group (e.g., R$^6$) and x is 0-2. For example, the group —O—(CH$_2$)$_{1-4}$— is a 'C$_2$-C$_5$'-heteroalkylene group, where one of the carbon atoms of the corresponding alkylene is replaced by O.

"Alkoxy" refers to a monovalent —O-alkyl group, wherein the alkyl portion has the specified number of carbon atoms. Alkoxy groups typically contain 1 to 8 carbon atoms ("C$_1$-C$_8$ alkoxy"), or 1 to 6 carbon atoms ("C$_1$-C$_6$ alkoxy"), or 1 to 4 carbon atoms ("C$_1$-C$_4$ alkoxy"). For example, C$_1$-C$_4$ alkoxy includes methoxy, ethoxy, isopropoxy, tert-butyloxy (i.e., —OCH$_3$, —OCH$_2$CH$_3$, —OCH(CH$_3$)$_2$, —OC(CH$_3$)$_3$), and the like. Alkoxy groups are unsubstituted or substituted on the alkyl portion by the same groups that are described herein as suitable for alkyl. In particular, alkoxy groups may be optionally substituted by one or more halo atoms, and in particular one or more fluoro atoms, up to the total number of hydrogen atoms present on the alkyl portion. Such groups are referred to as "haloalkoxy" (or, where fluorinated, more specifically as "fluoroalkoxy") groups having the specified number of carbon atoms and substituted by one or more halo substituents, Typically such groups contain from 1-6 carbon atoms, preferably 1-4 carbon atoms, and sometimes 1-2 carbon atoms, and 1, 2 or 3 halo atoms (i.e., "C$_1$-C$_6$ haloalkoxy", "C$_1$-C$_4$ haloalkoxy" or "C$_1$-C$_2$ haloalkoxy"). More specifically, fluorinated alkyl groups may be specifically referred to as fluoroalkoxy groups, e.g., C$_1$-C$_6$, C$_1$-C$_4$ or C$_1$-C$_2$ fluoroalkoxy groups, which are typically substituted by 1, 2 or 3 fluoro atoms. Thus, a C$_1$-C$_4$ fluoroalkoxy includes trifluoromethyloxy (—OCF$_3$), difluoromethyloxy (—OCF$_2$H), fluoromethyloxy (—OCFH$_2$), difluoroethyloxy (—OCH$_2$CF$_2$H), and the like.

Similarly, "thioalkoxy" refers to a monovalent —S-alkyl group, wherein the alkyl portion has the specified number of carbon atoms, and is optionally substituted on the alkyl portion by the same groups that are described herein as suitable for alkyl. For example, a C$_1$-C$_4$ thioalkoxy includes —SCH$_3$ and —SCH$_2$CH$_3$.

"Cycloalkyl" refers to a non-aromatic, saturated or partially unsaturated carbocyclic ring system containing the specified number of carbon atoms, which may be a monocyclic, spirocyclic, bridged or fused bicyclic or polycyclic ring system that is connected to the base molecule through a carbon atom of the cycloalkyl ring. Typically, the cycloalkyl groups of the invention contain 3 to 12 carbon atoms ("C$_3$-C$_{12}$ cycloalkyl"), preferably 3 to 8 carbon atoms ("C$_3$-C$_8$ cycloalkyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups are unsubstituted or substituted by the same groups that are described herein as suitable for alkyl.

Illustrative examples of cycloalkyl rings include, but are not limited to, the following:

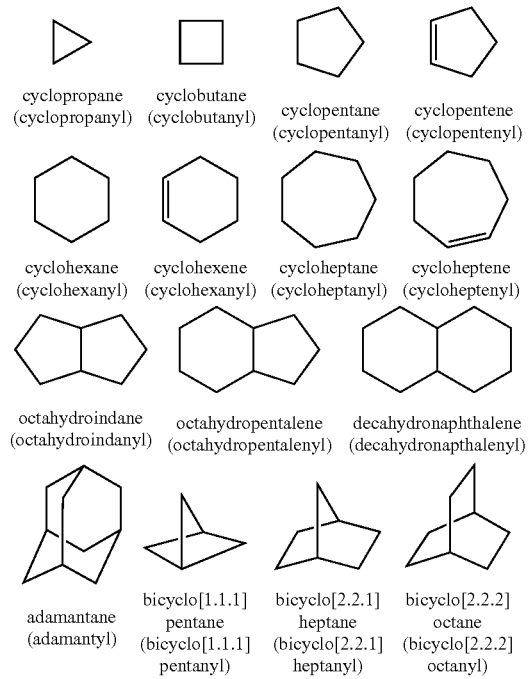

"Cycloalkylalkyl" is used to describe a cycloalkyl ring, typically a C$_3$-C$_8$ cycloalkyl, which is connected to the base molecule through an alkylene linker, typically a C$_1$-C$_4$ alkylene. Cycloalkylalkyl groups are sometimes described by the total number of carbon atoms in the carbocyclic ring and linker, and typically contain from 4-12 carbon atoms ("C$_4$-C$_{12}$ cycloalkylalkyl"). Thus a cyclopropylmethyl group is a C$_4$-cycloalkylalkyl group and a cyclohexylethyl is a C$_8$-cycloalkylalkyl. Cycloalkylalkyl groups are unsubstituted or substituted on the cycloalkyl and/or alkylene portions by the same groups that are described herein as suitable for alkyl groups. Sometimes cycloalkylalkyl groups are described herein, as -L- C$_3$-C$_8$-cycloalkyl, where the cycloalkyl group has the number of carbon atoms indicated and -L- refers to an alkylene linker. It will be understood that when -L- is a bond, the group is cycloalkyl.

The terms "heterocyclyl", "heterocyclic" or "heteroalicyclic" are used interchangeably herein to refer to a non-aromatic, saturated or partially unsaturated ring system containing the specified number of ring atoms, including at least one heteroatom selected from N, O and S as a ring member, where ring S atoms are optionally substituted by one or two oxo groups (i.e., S(O)$_x$, where x is 0, 1 or 2) and where the heterocyclic ring is connected to the base molecule via a ring atom, which may be C or N. Heterocyclic rings include rings which are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and S(O)$_q$ as ring members, and more preferably 1 to 2 ring heteroatoms, provided that such heterocyclic rings do not contain two contiguous oxygen atoms. Heterocyclyl groups are unsubstituted or substituted by suitable substituent groups, for example the same groups that are described herein as suitable for alkyl, aryl or heteroaryl. Such substituents may be present on the heterocycilic ring attached to the base molecule, or on a spirocyclic, bridged or fused ring attached thereto. In addition, ring N atoms are optionally substituted by groups suitable for an amine, e.g., alkyl, acyl, carbamoyl, sulfonyl substituents, and the like.

Heterocycles typically include 3-12 membered heterocyclyl groups, preferably 3-10 membered heterocyclyl groups, and more preferably 5-6 membered heterocyclyl groups, in accordance with the definition herein.

Illustrative examples of saturated heterocycles include, but are not limited to:

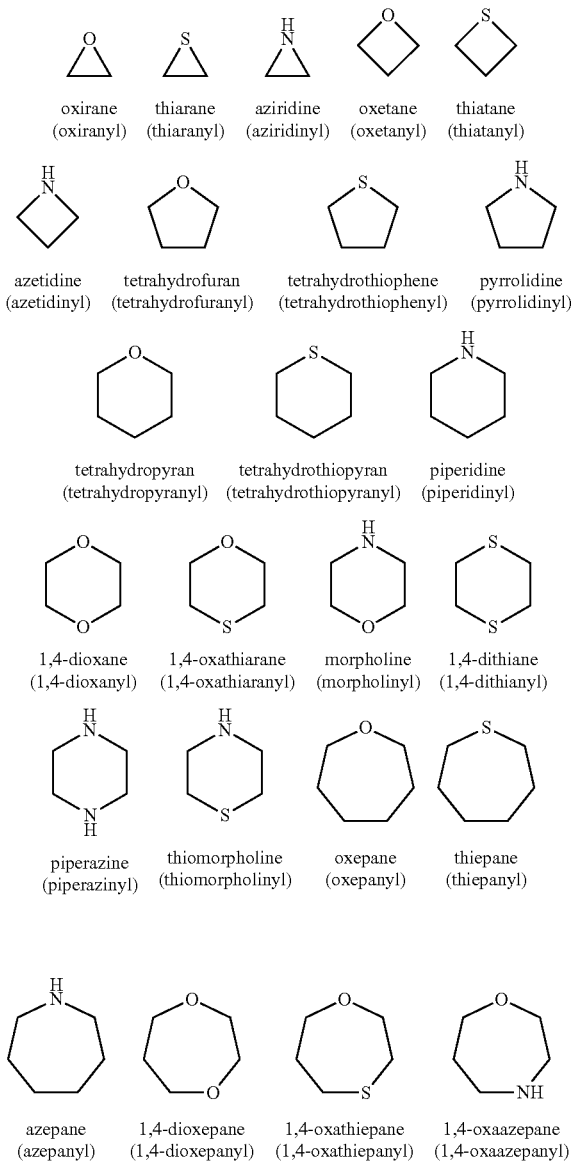

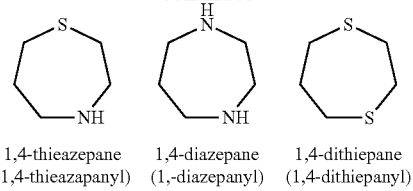

Illustrative examples of partially unsaturated heterocycles include, but are not limited to:

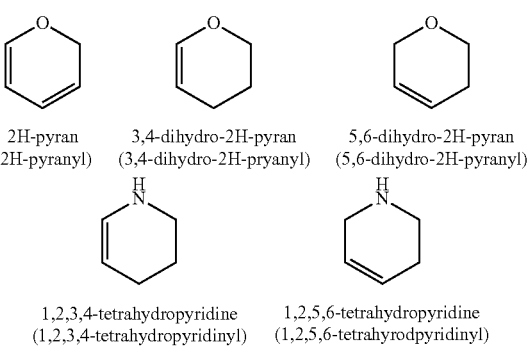

Illustrative examples of bridged, fused and spiro heterocycles include, but are not limited to:

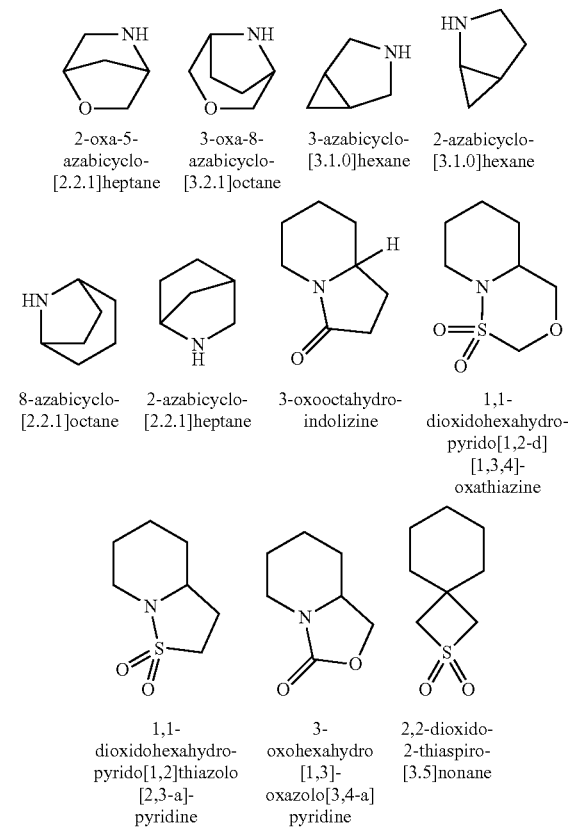

In frequent embodiments, heterocyclic groups contain 3-12 ring members, including both carbon and non-carbon heteroatoms, and preferably 4-7 ring members. In certain preferred embodiments, substituent groups comprising 3-12 membered heterocycles are selected from azetidinyl, pyrrolidinyl, piperidinyl, piperazinyl, azepanyl, diazepanyl, tetrahydrofuranyl, tetrahydropyranyl, tetrahydrothiophenyl, tetrahydrothiopyranyl, morpholinyl and thiomorpholinyl rings, each of which are optionally substituted as described for the particular substituent group, to the extent such substitution makes chemical sense.

It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

The term "heterocyclylalkyl" may be used to describe a heterocyclic group of the specified size that is connected to the base molecule through an alkylene linker of the specified length. Typically, such groups contain an optionally substituted 3-12 membered heterocycle attached to the base molecule through a $C_1$-$C_4$ alkylene linker. Where so indicated, such groups are optionally substituted on the alkylene portion by the same groups that are described herein as suitable for alkyl groups and on the heterocyclic portion by groups described as suitable for heterocyclic rings. Sometimes heterocyclylalkyl groups are described herein as -L-heterocyclylalkyl, where the heterocyclylalkyl group has the number of ring atoms indicated and -L- refers to an alkylene linker. It will be understood that when -L-is a bond, the group is heterocyclyl.

"Aryl" or "aromatic" refer to an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring, or fused to a saturated or partially unsaturated carbocyclic or heterocyclic ring, provided the point of attachment to the base molecule on such fused ring systems is an atom of the aromatic portion of the ring system. Examples, without limitation, of aryl groups include phenyl, biphenyl, naphthyl, anthracenyl, phenanthrenyl, indanyl, indenyl, and tetrahydronaphthyl. The aryl group is unsubstituted or substituted as further described herein.

Similarly, "heteroaryl" or "heteroaromatic" refer to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring, or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl and pyrimidinyl, pyrazinyl or pyridazinyl rings. The heteroaryl group is unsubstituted or substituted as further described herein.

Aryl, heteroaryl and heterocyclyl moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably from 1-2 optional substituents.

Optional substituent groups suitable for aryl, heteroaryl and heterocyclyl rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, =O, —CN, —C(O)$R^x$, —CO$_2R^x$, —C(O)N$R^xR^y$, —S$R^x$, —SO$R^x$, —SO$_2R^x$, —SO$_2$N$R^xR^y$, —NO$_2$, —N$R^xR^y$, —N$R^x$C(O)$R^y$, —N$R^x$C(O)N$R^xR^y$, —N$R^x$C(O)O$R^x$, —N$R^x$SO$_2R^y$, —N$R^x$SO$_2$N$R^xR^y$, —O$R^x$, —OC(O)$R^x$ and —OC(O)N$R^xR^y$; where each $R^x$ and $R^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or $R^x$ and $R^y$ may be taken together with the N atom to which they are attached to form a 3-12 membered heterocyclyl or 5-12 membered heteroaryl, each optionally containing 1, 2 or 3 additional heteroatoms selected from O, N and S(O)$_q$ where q is 0-2; each $R^x$ and $R^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl; and each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted as further defined herein.

In typical embodiments, optional substitution on aryl, heteroaryl and heterocyclyl rings includes one or more substituents, and preferably 1 to 3 substituents, independently selected from the group consisting of halo, $C_1$-$C_8$ alkyl, —OH, $C_1$-$C_8$ alkoxy, —CN, =O, —C(O)$R^x$, —CO-O$R^x$, —OC(O)$R^x$, —C(O)N$R^xR^y$, —N$R^x$C(O)$R^y$, —S$R^x$, —SO$R^x$, —SO$_2R^x$, —SO$_2$N$R^xR^y$, —NO$_2$, —N$R^xR^y$, —N$R^x$C(O)$R^y$, —N$R^x$C(O)N$R^xR^y$, —N$R^x$C(O)O$R^y$ —N$R^x$SO$_2R^y$, —N$R^x$SO$_2$N$R^xR^y$, —OC(O)$R^x$, —OC(O)N$R^xR^y$, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl); where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and $S(O)_q$ where q is 0-2; and wherein each said $C_1$-$C_8$ alkyl, $C_1$-$C_8$ alkoxy, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl) that is described as an optional substituent or is part of $R^x$ or $R^y$ is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl), —N($C_1$-$C_4$ alkyl)$_2$ and N-pyrrolidinyl.

Examples of monocyclic heteroaryl groups include, but are not limited to:

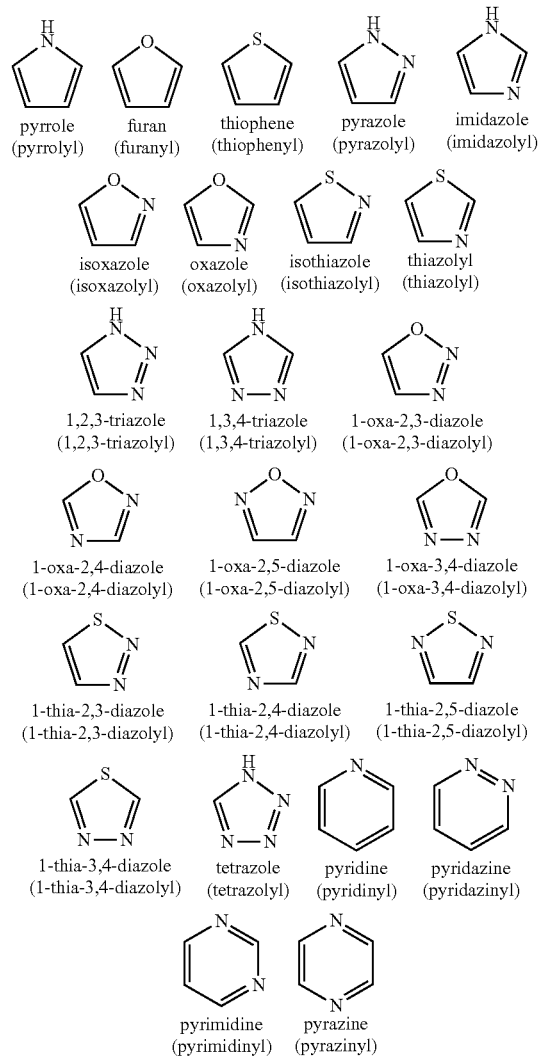

Illustrative examples of fused ring heteroaryl groups include, but are not limited to:

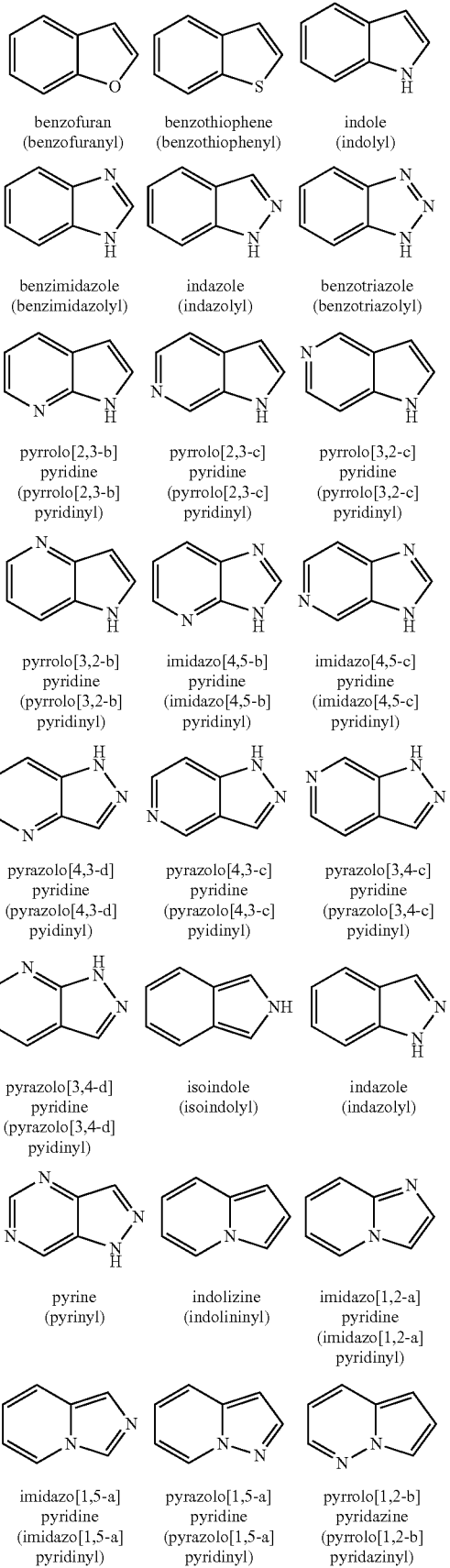

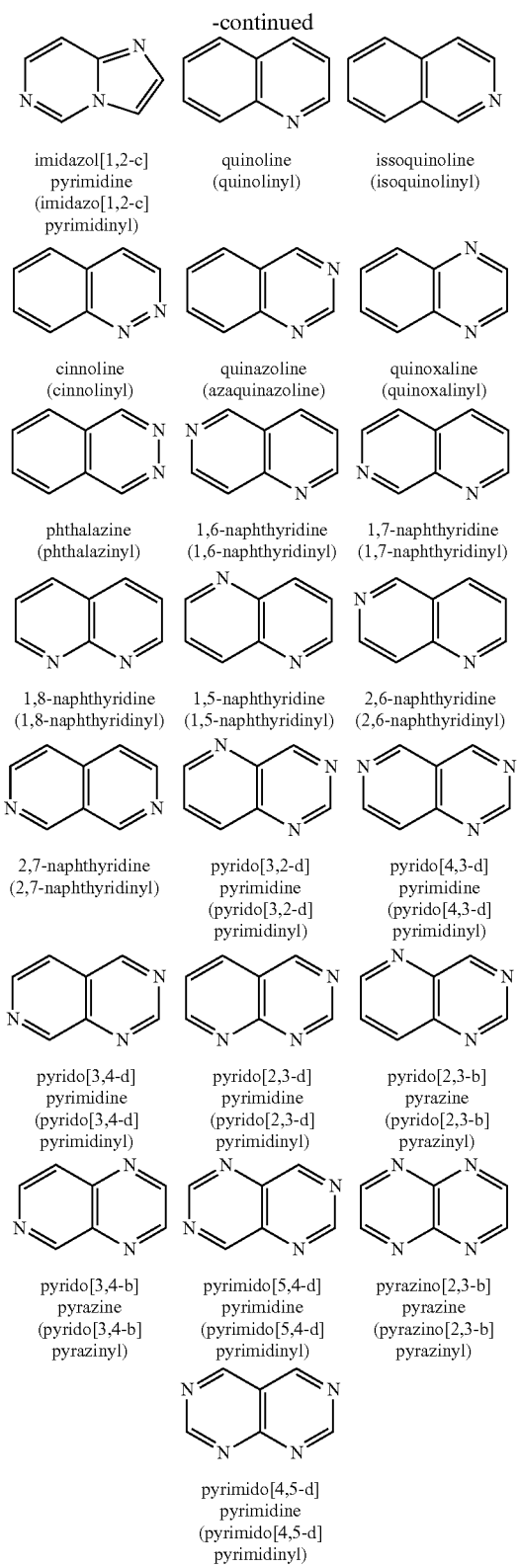

An "arylalkyl" group refers to an aryl group as described herein which is linked to the base molecule through an alkylene or similar linker. Arylalkyl groups are described by the total number of carbon atoms in the ring and linker. Thus a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1-4 carbon atoms. Such groups may also be represented as —$C_1$-$C_4$ alkylene-$C_6$-$C_{12}$ aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1-4 carbon atoms. Such groups may also be represented as —$C_1$-$C_4$ alkylene-5-12 membered heteroaryl. Sometimes heteroarylalkyl groups are described herein as -L- heteroarylalkyl, where the heteroarylalkyl group has the number of ring atoms indicated and -L- refers to an alkylene linker. It will be understood that when -L- is a bond, the group is heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as $C_8$-arylalkoxy and $C_8$-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an —OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) that are optionally substituted by groups suitable for alkyl. Thus, $C_1$-$C_4$ acyloxy includes an —OC(O)$C_1$-$C_4$ alkyl substituent, e.g., —OC(O)$CH_3$.

"Acyl" refers to a monovalent group —C(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl, e.g., by F, OH or alkoxy. Thus, optionally substituted —C(O)$C_1$-$C_4$ alkyl includes unsubstituted acyl groups, such as —C(O)$CH_3$ (i.e., acetyl) and —C(O)$CH_2CH_3$ (i.e., propionyl), as well as substituted acyl groups such as —C(O)$CF_3$ (trifluoroacetyl), —C(O)$CH_2$OH (hydroxyacetyl), —C(O)$CH_2OCH_3$ (methoxyacetyl), —C(O)$CF_2$H (difluoroacetyl), and the like.

"Acylamino" refers to a monovalent group, —NHC(O)alkyl or —NRC(O)alkyl, wherein the alkyl portion has the specified number of carbon atoms (typically $C_1$-$C_8$, preferably $C_1$-$C_6$ or $C_1$-$C_4$) and is optionally substituted by groups suitable for alkyl. Thus, $C_1$-$C_4$ acylamino includes an —NHC(O)$C_1$-$C_4$ alkyl substituent, e.g., —NHC(O)$CH_3$.

"Aryloxy" or "heteroaryloxy" refer to optionally substituted —O-aryl or —O-heteroaryl, in each case where aryl and heteroaryl are as further defined herein.

"Arylamino" or "heteroarylamino" refer to optionally substituted —NH-aryl, —NR-aryl, —NH-heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —NH$_2$. Where the amino is described as substituted or optionally substituted, the term includes groups of the form —NR$^x$R$^y$, where each or R$^x$ and R$^y$ is independently H, alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —NR$^x$R$^y$, wherein one of R$^x$ and R$^y$ is an alkyl moiety and the other is H, and "dialkylamino" refers to —NR$^x$R$^y$ wherein both of R$^x$ and R$^y$ are alkyl moieties, where the alkyl moieties having the specified number of carbon atoms (e.g., —NH—C$_1$-C$_4$ alkyl or —N(C$_1$-C$_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein R$^x$ and R$^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S(O)$_x$ where x is 0-2 as ring members, provided that such rings do not contain two contiguous oxygen atoms.

"Halogen" or "halo" refers to fluoro, chloro, bromo and iodo (F, Cl, Br, I). Preferably, halo refers to fluoro or chloro (F or Cl).

"Optional" or "optionally" means that the subsequently described event or circumstance may but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups are the same or different. Throughout the disclosure, it will be understood that the number and nature of optional substituent groups will be limited to the extent that such substitutions make chemical sense.

In one aspect, the invention provides a compound of Formula (I):

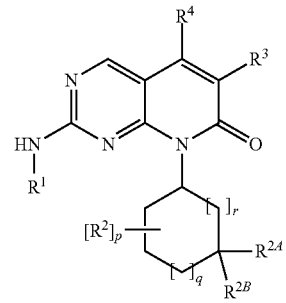

(I)

or a pharmaceutically acceptable salt thereof,
wherein:

R$^1$ is 3-10 membered heterocyclyl substituted by R$^{5A}$ or C$_3$-C$_8$ cycloalkyl substituted by R$^{5B}$, where said 3-10 membered heterocyclyl and C$_3$-C$_8$ cycloalkyl are optionally further substituted by one or more R$^6$;

each R$^2$ is independently F, OH, C$_1$-C$_4$ alkyl, C$_1$-C$_4$ fluoroalkyl, C$_1$-C$_4$ alkoxy or C$_1$-C$_4$ fluoroalkoxy;

R$^{2A}$ and R$^{2B}$ are independently H, F, OH, C$_1$-C$_4$ alkyl, C$_1$-C$_4$ fluoroalkyl, C$_1$-C$_4$ alkoxy or C$_1$-C$_4$ fluoroalkoxy;

where each said C$_1$-C$_4$ alkyl and C$_1$-C$_4$ fluoroalkyl in R$^2$, R$^{2A}$ and R$^{2B}$ is independently optionally substituted by OH, C$_1$-C$_4$ alkoxy or C$_1$-C$_4$ fluoroalkoxy;

R$^3$ is H, F, Cl, NH$_2$, C$_1$-C$_4$ alkyl or C$_1$-C$_4$ fluoroalkyl, where said C$_1$-C$_4$ alkyl and C$_1$-C$_4$ fluoroalkyl are optionally substituted by OH, CN, C$_1$-C$_4$ alkoxy, C$_1$-C$_4$ fluoroalkoxy, CONH$_2$ and COOH;

R$^4$ is H, C$_1$-C$_2$ alkyl or C$_1$-C$_2$ fluoroalkyl;

R$^{5A}$ is SO$_2$R$^7$, SO$_2$NR$^8$R$^9$, NHSO$_2$R$^7$ or NHSO$_2$NR$^8$R$^9$;

R$^{5B}$ is NHSO$_2$R$^7$ or NHSO$_2$NR$^8$R$^9$;

each R$^6$ is independently F, OH, C$_1$-C$_4$ alkyl, C$_1$-C$_4$ fluoroalkyl, C$_1$-C$_4$ alkoxy or C$_1$-C$_4$ fluoroalkoxy;

R$^7$ is C$_1$-C$_4$ alkyl, C$_1$-C$_4$ fluoroalkyl, -L-(C$_3$-C$_8$ cycloalkyl), -L-(5-6 membered heterocyclyl) or -L-(5-6 membered heteroaryl);

R$^8$ and R$^9$ are independently H, C$_1$-C$_4$ alkyl, C$_1$-C$_4$ fluoroalkyl, -L-(C$_3$-C$_8$ cycloalkyl), -L-(5-6 membered heterocyclyl) or -L-(5-6 membered heteroaryl); or R$^8$ and R$^9$ may be taken together with the nitrogen atom to which they are attached to form a 5-6 membered heterocyclyl;

where each said C$_1$-C$_4$ alkyl and C$_1$-C$_4$ fluoroalkyl in R$^7$, R$^8$ and R$^9$ is optionally substituted by OH, C$_1$-C$_4$ alkoxy, C$_1$-C$_4$ fluoroalkoxy or SO$_2$Me, and each said C$_3$-C$_8$ cycloalkyl, 5-6 membered heterocyclyl and 5-6 membered heteroaryl in R$^7$, R$^8$ and R$^9$ is optionally substituted by C$_1$-C$_4$ alkyl, OH, C$_1$-C$_4$ alkoxy or C$_1$-C$_4$ fluoroalkoxy;

L is a bond or C$_1$-C$_4$ alkylene, where said C$_1$-C$_4$ alkylene is optionally substituted by C$_1$-C$_4$ alkyl, OH, C$_1$-C$_4$ alkoxy or C$_1$-C$_4$ fluoroalkoxy;

p is 0, 1, 2, 3 or 4;

q is 0, 1 or 2; and r is 0, 1 or 2.

In some embodiments, the compound of Formula (I) has the absolute stereochemistry as shown in Formula (I-A), (I-B) or (I-C):

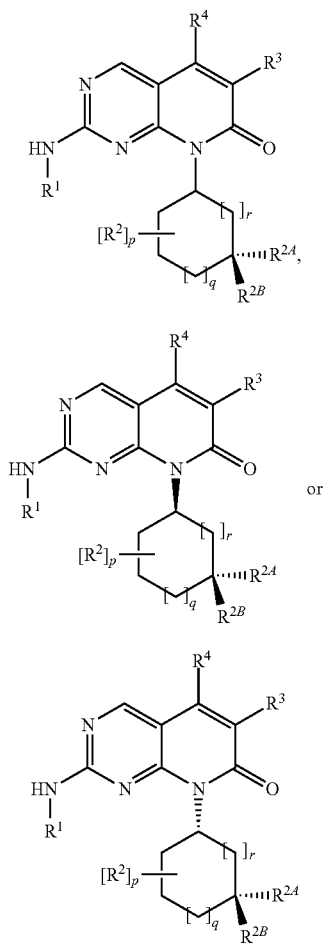

(I-A)

(I-B)

(I-C)

or a pharmaceutically acceptable salt thereof, where $R^1$, $R^2$, $R^{2A}$, $R^{2B}$, $R^3$, $R^4$, $R^{5A}$, $R^{5B}$, $R^6$, $R^7$, $R^8$, $R^9$, p, q and r are defined as for Formula (I).

Each of the aspects and embodiments described herein with respect to Formula (I) is also applicable to compounds of Formula (I-A), (I-B) or (I-C).

In compounds of Formula (I), $R^1$ is 3-10 membered heterocyclyl substituted by $R^{5A}$ or $C_3$-$C_8$ cycloalkyl substituted by $R^{5B}$, where said 3-10 membered heterocyclyl and $C_3$-$C_8$ cycloalkyl are optionally further substituted by one or more $R^6$.

In some embodiments of Formula (I), $R^1$ is 3-10 membered heterocyclyl substituted by $R^{5A}$ and optionally further substituted by one or more $R^6$. In some such embodiments, $R^1$ is 5-6 membered heterocyclyl substituted by $R^{5A}$ and optionally further substituted by one or more $R^6$. In some such embodiments, $R^1$ is 5-6 membered heterocyclyl substituted by $R^{5A}$. In particular embodiments, $R^1$ is a 5-6 membered nitrogen-containing heterocyclyl substituted by $R^{5A}$. In some such embodiments, $R^1$ is a piperidinyl or pyrrolidinyl ring. In specific embodiments, $R^1$ is a piperidin-4-yl, piperidin-3-yl or pyrrolidin-3-yl. In frequent embodiments, $R^1$ is a 5-6 membered nitrogen-containing heterocyclyl which is N-substituted by $R^{5A}$. In frequent embodiments, $R^1$ is a piperidin-4-yl for which $N^1$ of the piperidinyl ring is substituted by $R^{5A}$. In other embodiments, $R^1$ is a piperidin-3-yl for which $N^1$ of the piperidinyl ring is substituted by $R^{5A}$. In further embodiments, $R^1$ is a pyrrolidin-3-yl for which $N^1$ of the pyrrolidinyl ring is substituted by $R^{5A}$.

In each of the foregoing embodiments, $R^1$ is optionally further substituted by one or more $R^6$. In some embodiments, $R^1$ is optionally further substituted by one, two or three $R^6$. In further embodiments, $R^1$ is optionally further substituted by one or two $R^6$. In some embodiments, $R^1$ is a 3-10 membered nitrogen-containing heterocyclyl substituted by $R^{5A}$ and further substituted by one, two or three $R^6$, where each $R^6$ is independently F, OH, $C_1$-$C_4$ alkyl, $C_1$-$C_4$ fluoroalkyl, $C_1$-$C_4$ alkoxy or $C_1$-$C_4$ fluoroalkoxy, as further described herein. In some embodiments, $R^1$ is a 3-10 membered nitrogen-containing heterocyclyl substituted by $R^{5A}$ and further substituted by one or two $R^6$, where each $R^6$ is independently F or $CH_3$.

In particular embodiments, $R^1$ is a 5-6 membered nitrogen-containing heterocyclyl that is N-substituted by $R^{5A}$, which is selected from the group consisting of:

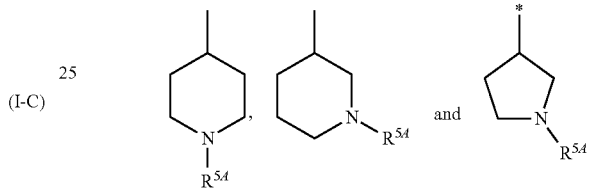

where the * represents the point of attachment to the 2-amino substituent.

In particular embodiments, $R^1$ is

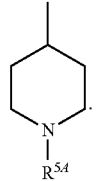

In some such embodiments, $R^{5A}$ is $SO_2R^7$ or $SO_2NR^8R^9$.

In compounds of Formula (I), $R^{5A}$ is $SO_2R^7$, $SO_2NR^8R^9$, $NHSO_2R^7$ or $NHSO_2NR^8R^9$, where $R^7$, $R^8$ and $R^9$ are as defined for Formula (I) and further described herein. In some embodiments of Formula (I), $R^1$ is 3-10 membered heterocyclyl and $R^{5A}$ is $SO_2R^7$ or $SO_2NR^8R^9$. In other embodiments, $R^1$ is 3-10 membered heterocyclyl and $R^{5A}$ is $NHSO_2R^7$ or $NHSO_2NR^8R^9$.

In some embodiments of Formula (I), $R^1$ is 3-10 membered heterocyclyl and $R^{5A}$ is $SO_2R^7$ or $SO_2NR^8R^9$. In some such embodiments, $R^1$ is piperidinyl or pyrrolidinyl and $R^{5A}$ is $SO_2R^7$ or $SO_2NR^8R^9$. In particular embodiments, $R^1$ is a piperidin-4-yl, piperidin-3-yl or pyrrolidin-3-yl and $R^{5A}$ is $SO_2R^7$ or $SO_2NR^8R^9$. In frequent embodiments, $R^1$ is a piperidin-4-yl for which $N^1$ of the piperidinyl ring is substituted by $R^{5A}$, where $R^{5A}$ is $SO_2R^7$ or $SO_2NR^8R^9$. In other embodiments, $R^1$ is a piperidin-3-yl for which $N^1$ of the piperidinyl ring is substituted by $R^{5A}$, where $R^{5A}$ is $SO_2R^7$ or $SO_2NR^8R^9$. In other embodiments, $R^1$ is a pyrrolidin-3-yl for which N of the pyrrolidinyl ring is substituted by $R^{5A}$, where $R^{5A}$ is $SO_2R^7$ or $SO_2NR^8R^9$. In each of the foregoing embodiments, $R^1$ is optionally further substituted by one or more $R^6$.

In some embodiments of Formula (I), $R^1$ is 5-6 membered heterocyclyl and $R^{5A}$ is $SO_2R^7$. In other embodiments of Formula (I), $R^1$ is 5-6 membered N-containing heterocyclyl and $R^{5A}$ is $SO_2R^7$. In frequent embodiments, $R^1$ is 5-6 membered N-containing heterocyclyl substituted at N by $R^{5A}$, where $R^{5A}$ is $SO_2R^7$. In some such embodiments, $R^7$ is $CH_3$. In specific embodiments, $R^1$ is a piperidin-4-yl substituted at $N^1$ by $R^{5A}$, where $R^{5A}$ is $SO_2R^7$ and $R^7$ is $CH_3$.

In still other embodiments of Formula (I), $R^1$ is 5-6 membered heterocyclyl and $R^{5A}$ is $SO_2NR^8R^9$. In some such embodiments, $R^8$ and $R^9$ are independently H or $CH_3$. In particular embodiments, $R^1$ is a piperidin-4-yl substituted at $N^1$ by $R^{5A}$, where $R^{5A}$ is $SO_2NR^8R^9$ and $R^8$ and $R^9$ are independently H or $CH_3$.

In other embodiments of Formula (I), $R^1$ is $C_3$-$C_8$ cycloalkyl, where said $C_3$-$C_8$ cycloalkyl is substituted by $R^{5B}$ and optionally further substituted by one or more $R^6$. In some such embodiments, $R^1$ is cyclopropyl, cyclobutyl, cyclopentyl or cyclohexyl. In each of the foregoing, $R^1$ is substituted by $R^{5B}$ and optionally further substituted by one or more $R^6$. In other embodiments of Formula (I), $R^{5B}$ is $NHSO_2R^7$ or $NHSO_2NR^8R^9$.

In compounds of Formula (I), $R^7$ is $C_1$-$C_4$ alkyl, $C_1$-$C_4$ fluoroalkyl, -L-($C_3$-$C_8$ cycloalkyl), -L-(5-6 membered heterocyclyl) or -L-(5-6 membered heteroaryl), where $R^7$ is optionally substituted as described for Formula (I) above.

In compounds of Formula (I), L is a bond or $C_1$-$C_4$ alkylene, where said $C_1$-$C_4$ alkylene is optionally substituted by OH, $C_1$-$C_4$ alkoxy or $C_1$-$C_4$ fluoroalkoxy. In some embodiments, $R^7$ is $C_1$-$C_4$ alkyl, optionally substituted by OH, $C_1$-$C_4$ alkoxy, $C_1$-$C_4$ fluoroalkoxy or $SO_2Me$. In particular embodiments, $R^7$ is $C_1$-$C_4$ alkyl. In some such embodiments, $R^7$ is $CH_3$. In other such embodiments, $R^7$ is $CH_2CH_3$. In further embodiments, $R^7$ is $C_1$-$C_4$ alkyl, optionally substituted by OH, $OCH_3$ or $SO_2Me$. In some embodiments, $R^7$ is $C_1$-$C_4$ fluoroalkyl. In some such embodiments, $R^7$ is $CH_2F$, $CHF_2$, $CH_2CF_2H$, $CF_3$ or $CH_2CF_3$.

In further embodiments, $R^7$ is -L-($C_3$-$C_8$ cycloalkyl), where said $C_3$-$C_8$ cycloalkyl is optionally substituted by $C_1$-$C_4$ alkyl, OH, $C_1$-$C_4$ alkoxy or $C_1$-$C_4$ fluoroalkoxy. In some such embodiments, L is a bond and $R^7$ is cyclopropyl, cyclobutyl, cyclopentyl. In other such embodiments, L is methylene (i.e. —$CH_2$—) and $R^7$ is cyclopropylmethyl, cyclobutylmethyl or cyclopentylmethyl.

In still other embodiments, $R^7$ is -L-(5-6 membered heterocyclyl) or -L-(5-6 membered heteroaryl), where said 5-6 membered heterocyclyl and 5-6 membered heteroaryl are optionally substituted by $C_1$-$C_4$ alkyl, OH, $C_1$-$C_4$ alkoxy or $C_1$-$C_4$ fluoroalkoxy. In some such embodiments, L is a bond, methylene or ethylene moiety (i.e., bond, —$CH_2$— or —$CH_2CH_2$—) and $R^7$ is an optionally substituted 5-6 membered heteroaryl selected from the group consisting of pyrazolyl, imidazolyl, thiazolyl or thiadiazolyl. In some such embodiments, L is a bond. In other such embodiments, L is a bond, methylene or ethylene and $R^7$ is an optionally substituted 5-6 membered heterocyclyl. In a specific embodiment, L is a bond and $R^7$ is dioxidotetrahydrothiophenyl.

In some embodiments $R^{5A}$ is $SO_2R^7$, where $R^7$ is selected from each of the foregoing embodiments described for $R^7$. In some embodiments, $R^{5A}$ is $SO_2R^7$ and $R^7$ is $C_1$-$C_4$ alkyl optionally substituted by OH, $C_1$-$C_4$ alkoxy, $C_1$-$C_4$ fluoroalkoxy or $SO_2Me$. In particular embodiments, $R^{5A}$ is $SO_2R^7$ and $R^7$ is $C_1$-$C_4$ alkyl. In specific embodiments of each of the foregoing embodiments of $R^7$, $R^1$ is piperidinyl or pyrrolidinyl, in particular piperidin-4-yl, piperidin-3-yl or pyrrolidin-3-yl, and $R^{5A}$ is $SO_2R^7$. In compounds of Formula (I), $R^8$ and $R^9$ are independently H, $C_1$-$C_4$ alkyl, $C_1$-$C_4$ fluoroalkyl, -L-($C_3$-$C_8$ cycloalkyl), -L-(5-6 membered heterocyclyl) or -L-(5-6 membered heteroaryl); or $R^8$ and $R^9$ may be taken together with the nitrogen atom to which they are attached to form a 5-6 membered heterocyclyl, where $R^8$ and $R^9$ are optionally substituted as described for Formula (I) above or further described herein.

In some embodiments of Formula (I), $R^8$ and $R^9$ are independently H or $C_1$-$C_4$ alkyl. In some such embodiments, $R^8$ and $R^9$ are independently H or $CH_3$. In some embodiments, both $R^8$ and $R^9$ are H. In other embodiments, $R^8$ is H and $R^9$ is $CH_3$. In still other embodiments, both $R^8$ and $R^9$ are $CH_3$. In further embodiments, one of $R^8$ and $R^9$ is H and the other is $C_1$-$C_4$ alkyl or $C_1$-$C_4$ fluoroalkyl, each optionally substituted as described herein. In some such embodiments, $R^8$ is H and $R^9$ is $C_1$-$C_4$ alkyl or $C_1$-$C_4$ fluoroalkyl, optionally substituted by OH or $C_1$-$C_4$ alkoxy. In still other embodiments, one of $R^8$ and $R^9$ is H and the other is -L-($C_3$-$C_8$ cycloalkyl), -L-(5-6 membered heterocyclyl) or -L-(5-6 membered heteroaryl), each optionally substituted as described herein. In some such embodiments, $R^8$ is H and $R^9$ is -L-(5-6 membered heterocyclyl), where L is a bond, methylene or ethylene. In specific embodiments, $R^8$ is H and $R^9$ is tetrahydrofuranyl or tetrahydropyranyl, wherein L is a bond, or tetrahydrofuranylmethyl or tetrahydropyranylmethyl, wherein L is methylene. In some such embodiments, L is a bond.

In some embodiments $R^{5A}$ is $SO_2NR^8R^9$ where $R^8$ and $R^9$ are selected from each of the foregoing embodiments described for $R^8$ and $R^9$. In particular embodiments of each of the foregoing embodiments of $R^8$ and $R^9$, $R^1$ is piperidinyl or pyrrolidinyl, in particular piperidin-4-yl, piperidin-3-yl or pyrrolidin-3-yl, and $R^{5A}$ is $SO_2NR^8R^9$.

In some embodiments of Formula (I), $R^8$ and $R^9$ are taken together with the nitrogen atom to which they are attached to form a 5-6 membered heterocyclyl, where said 5-6 membered heterocyclyl is optionally substituted by $C_1$-$C_4$ alkyl, OH, $C_1$-$C_4$ alkoxy or $C_1$-$C_4$ fluoroalkoxy. In some such embodiments, $R^8$ and $R^9$ are taken together with the nitrogen atom to which they are attached to form an optionally substituted piperidinyl ring. In addition to the N to which $R^8$ and $R^9$ are attached, said 5-6 membered heterocyclyl may optionally include an additional heteroatom selected from N, O and S as a ring member, where ring S atoms are optionally substituted by one or two oxo groups (i.e., $S(O)_x$, where x is 0, 1 or 2). In some such embodiments, $R^8$ and $R^9$ are taken together with the nitrogen atom to which they are attached to form an optionally substituted pyrrolidinyl ring. In further embodiments, $R^8$ and $R^9$ are taken together with the nitrogen atom to which they are attached to form an optionally substituted morpholinyl or a piperazinyl ring.

In compounds of Formula (I), each $R^6$ is independently F, OH, $C_1$-$C_4$ alkyl, $C_1$-$C_4$ fluoroalkyl, $C_1$-$C_4$ alkoxy or $C_1$-$C_4$ fluoroalkoxy. In frequent embodiments, $R^6$ is absent. In some such embodiments, each $R^6$ is independently F or $C_1$-$C_4$ alkyl. In some embodiments, $R^1$ is a 5-6 membered nitrogen-containing heterocyclyl substituted by $R^{5A}$ and further substituted by one, two or three $R^6$, where each $R^6$ is independently F or $C_1$-$C_4$ alkyl. In some such embodiments, $R^1$ is a 5-6 membered nitrogen-containing heterocyclyl substituted by $R^{5A}$ and further substituted by one $R^6$, where $R^6$ is F. In other embodiments, $R^1$ is a 5-6 membered nitrogen-containing heterocyclyl substituted by $R^{5A}$ and further substituted by one or two $R^6$, where each $R^6$ is $CH_3$.

In compounds of Formula (I), p is 0, 1, 2, 3 or 4, where p is an integer that represents the number of optional substituent groups, $R^2$.

In compounds of Formula (I), each $R^2$ is independently F, OH, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl and $C_1$-$C_4$ fluoroalkyl is optionally substituted by OH, $C_1$-$C_4$ alkoxy or $C_1$-$C_4$ fluoroalkoxy. In frequent embodiments, p is 0 and $R^2$ is absent. In other embodiments, p is 1 or 2. In some embodiments, p is 1 or 2, and each $R^2$ is independently F, OH or $C_1$-$C_4$ alkyl. In some embodiments, p is 1 or 2, and each $R^2$ is independently F, OH or $CH_3$. In some such embodiments p is 1 and $R^2$ is F or $CH_3$.

In compounds of Formula (I), $R^{2A}$ and $R^{2B}$ are independently H, F, OH, $C_1$-$C_4$ alkyl, $C_1$-$C_4$ fluoroalkyl, $C_1$-$C_4$ alkoxy or $C_1$-$C_4$ fluoroalkoxy, where each said $C_1$-$C_4$ alkyl and $C_1$-$C_4$ fluoroalkyl is optionally substituted by OH, $C_1$-$C_4$ alkoxy or $C_1$-$C_4$ fluoroalkoxy.

In some embodiments, $R^{2A}$ and $R^{2B}$ are independently H, OH or $C_1$-$C_4$ alkyl. In particular embodiments, $R^{2A}$ and $R^{2B}$ are independently H, OH or $CH_3$.

In preferred embodiments of Formula (I), at least one of $R^{2A}$ and $R^{2B}$ is not H. In particular embodiments, $R^{2A}$ and $R^{2B}$ are independently H, F, OH, $C_1$-$C_4$ alkyl, $C_1$-$C_4$ fluoroalkyl, $C_1$-$C_4$ alkoxy or $C_1$-$C_4$ fluoroalkoxy, provided at least one of $R^{2A}$ and $R^{2B}$ is not H. In specific embodiments, $R^{2A}$ and $R^{2B}$ are independently H, OH or $CH_3$, provided at least one of $R^{2A}$ and $R^{2B}$ is not H.

In some embodiments of Formula (I), one of $R^{2A}$ and $R^{2B}$ is OH and the other is $CH_3$. In other embodiments, one of $R^{2A}$ and $R^{2B}$ is OH and the other is H. In other embodiments, one of $R^{2A}$ and $R^{2B}$ is H and the other is $CH_3$.

In specific embodiments of Formula (I), (I-A), (I-B) or (I-C), $R^{2A}$ is OH and $R^{2B}$ is $CH_3$. In other such embodiments, $R^{2A}$ is OH and $R^{2B}$ is H. In further embodiments, $R^{2A}$ is H and $R^{2B}$ is $CH_3$.

In further embodiments of Formula (I), (I-A), (I-B) or (I-C), $R^{2B}$ is OH and $R^{2A}$ is $CH_3$. In other such embodiments, $R^{2B}$ is OH and $R^{2A}$ is H. In further embodiments, $R^{2B}$ is H and $R^{2A}$ is $CH_3$.

In compounds of Formula (I), $R^3$ is H, F, Cl, $NH_2$, $C_1$-$C_4$ alkyl or $C_1$-$C_4$ fluoroalkyl, where said $C_1$-$C_4$ alkyl and $C_1$-$C_4$ fluoroalkyl are optionally substituted by OH, CN, $C_1$-$C_4$ alkoxy, $C_1$-$C_4$ fluoroalkoxy, $CONH_2$ and COOH. In some embodiments of Formula (I), $R^3$ is H, F, Cl, $C_1$-$C_4$ alkyl or $C_1$-$C_4$ fluoroalkyl, where said $C_1$-$C_4$ alkyl or $C_1$-$C_4$ fluoroalkyl are optionally substituted by OH. In other embodiments, $R^3$ is H, F, Cl, $CH_3$, $CH_2CH_2OH$, $CF_2H$ or $CH_2CF_2H$. In other embodiments of Formula (I), $R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH, CN, $C_1$-$C_4$ alkoxy, $C_1$-$C_4$ fluoroalkoxy, $CONH_2$ and COOH. In some such embodiments, $R^3$ is F, Cl, $CH_3$, $CH_2CH_2OH$, $CF_2H$ or $CH_2CF_2H$. In some embodiments of Formula (I), $R^3$ is H.

In other embodiments of Formula (I), $R^3$ is F or Cl. In some such embodiments, $R^3$ is F. In other such embodiments, $R^3$ is Cl.

In other embodiments of Formula (I), $R^3$ is $NH_2$. In some embodiments of Formula (I), $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH, CN, $C_1$-$C_4$ alkoxy, $C_1$-$C_4$ fluoroalkoxy, $CONH_2$ and COOH. In some such embodiments, $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH.

In some embodiments of Formula (I), $R^3$ is $C_1$-$C_4$ alkyl, optionally substituted by OH, CN, $C_1$-$C_4$ alkoxy, $C_1$-$C_4$ fluoroalkoxy, $CONH_2$ and COOH. In some such embodiments, $R^3$ is $C_1$-$C_2$ alkyl, optionally substituted by OH, CN, $C_1$-$C_4$ alkoxy, $C_1$-$C_4$ fluoroalkoxy, $CONH_2$ and COOH. In some embodiments of Formula (I), $R^3$ is $C_1$-$C_2$ alkyl, optionally substituted by OH. In some embodiments, $R^3$ is $CH_3$ or $CH_2CH_3$. In some embodiments, $R^3$ is $CH_2OH$, $CH_2CH_2OH$, $CH_2OCH_3$ or $CH_2CH_2OCH_3$. In other embodiments, $R^3$ is $CH_2CN$, $CH_2CONH_2$ or $CH_2COOH$.

In other embodiments of Formula (I), $R^3$ is $C_1$-$C_4$ fluoroalkyl, optionally substituted by OH, CN, $C_1$-$C_4$ alkoxy, $C_1$-$C_4$ fluoroalkoxy, $CONH_2$ and COOH. In some such embodiments, $R^3$ is $C_1$-$C_2$ fluoroalkyl, optionally substituted by OH, CN, $C_1$-$C_4$ alkoxy, $C_1$-$C_4$ fluoroalkoxy, $CONH_2$ and COOH. In some embodiments of Formula (I), $R^3$ is $C_1$-$C_2$ alkyl, optionally substituted by OH.

In some embodiments, $R^3$ is $C_1$-$C_4$ fluoroalkyl. In other embodiments, $R^3$ is $C_1$-$C_2$ fluoroalkyl. In specific embodiments, $R^3$ is $CF_3$, $CHF_2$, $CH_2F$, $CH_2CF_3$, $CH_2CHF_2$ or $CH_2CH_2F$. In certain embodiments, $R^3$ is $CHF_2$ or $CH_2CHF_2$. In some such embodiments, $R^3$ is $CHF_2$. In other such embodiments, $R^3$ is $CH_2CHF_2$.

In compounds of Formula (I), $R^4$ is H, $C_1$-$C_2$ alkyl or $C_1$-$C_2$ fluoroalkyl. In frequent embodiments, $R^4$ is H. In some embodiments, $R^4$ is $C_1$-$C_2$ alkyl, such as $CH_3$.

In particular embodiments, $R^4$ is H and $R^3$ is $C_1$-$C_4$ fluoroalkyl. In some such embodiments, $R^4$ is H and $R^3$ is $C_1$-$C_2$ fluoroalkyl. In specific embodiments, $R^4$ is H and $R^3$ is $CF_3$, $CHF_2$, $CH_2F$, $CH_2CF_3$, $CH_2CHF_2$ or $CH_2CH_2F$. In certain preferred embodiments, $R^4$ is H and $R^3$ is $CHF_2$ or $CH_2CHF_2$.

In some embodiments of each of the foregoing embodiments described for $R^3$, $R^4$ is H. In other embodiments of each of the foregoing embodiments described for $R^3$, $R^4$ is $C_1$-$C_2$ alkyl or $C_1$-$C_2$ fluoroalkyl. In particular embodiments of each of the foregoing embodiments described for $R^3$, $R^4$ is $CH_3$, $CH_2CH_3$, $CF_3$, $CHF_2$, $CH_2F$, $CH_2CF_3$, $CH_2CHF_2$ or $CH_2CH_2F$.

In compounds of Formula (I), q is 0, 1 or 2; and r is 0, 1 or 2. In some embodiments, q is 1 and r is 0. In other embodiments, q is 0 and r is 1. In other embodiments, q is 1 and r is 1. In still other embodiments, q is 2 and r is 0. In further embodiments, q is 2 and r is 1. In some embodiments, the sum of q and r is 0, 1, 2 or 3. In some such embodiments, the ring comprising q and r is a cyclobutyl, cyclopentyl, cyclohexyl or cycloheptyl ring, substituted by $R^{2A}$ and $R^{2B}$ and optionally substituted by $R^2$. In preferred embodiments, the ring comprising q and r is a cyclopentyl or cyclohexyl ring. In some embodiments, the sum of q and r is less than or equal to 3. In other embodiments, the sum of q and r is less than or equal to 2. In still other embodiments, the sum of q and r is 1 or 2.

In certain preferred embodiments, the invention provides a compound of Formula (I), (I-A), (I-B) and (I-C), or a pharmaceutically acceptable salt thereof, having two or more of the following features:

$R^1$ is 3-10 membered heterocyclyl substituted by $R^{5A}$;
p is 0 and $R^2$ is absent;
q is 1 and r is 0; or
q is 1 and r is 1;
$R^{2A}$ and $R^{2B}$ are independently H, OH or $C_1$-$C_4$ alkyl;
$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
$R^4$ is H;
$R^{5A}$ is $SO_2R^7$ or $SO_2NR^8R^9$;

R$^6$ is absent;
R$^7$ is C$_1$-C$_4$ alkyl; and
R$^8$ and R$^9$ are independently H or C$_1$-C$_4$ alkyl.

In other preferred embodiments, the invention provides a compound of Formula (I), (I-A), (I-B) and (I-C), or a pharmaceutically acceptable salt thereof, having two or more of the following features:

R$^1$ is 3-10 membered heterocyclyl substituted by R$^{5A}$; or
R$^1$ is 3-10 membered heterocyclyl substituted by R$^{5A}$, where said 3-10 membered heterocyclyl is optionally further substituted by one or two R$^6$;
p is 0 and R$^2$ is absent; or
p is 1 or 2, and each R$^2$ is independently F, OH or CH$_3$;
q is 1 and r is 0; or
q is 0 and r is 1; or
q is 1 and r is 1;
R$^{2A}$ and R$^{2B}$ are independently H, OH or C$_1$-C$_4$ alkyl, provided at least one of R$^{2A}$ and R$^{2B}$ is not H;
R$^3$ is F, Cl, C$_1$-C$_4$ alkyl or C$_1$-C$_4$ fluoroalkyl, where said C$_1$-C$_4$ alkyl and C$_1$-C$_4$ fluoroalkyl are optionally substituted by OH; or
R$^3$ is C$_1$-C$_4$ alkyl or C$_1$-C$_4$ fluoroalkyl, where said C$_1$-C$_4$ alkyl and C$_1$-C$_4$ fluoroalkyl are optionally substituted by OH; or
R$^3$ is C$_1$-C$_4$ fluoroalkyl; or
R$^3$ is C$_1$-C$_2$ fluoroalkyl;
R$^4$ is H;
R$^{5A}$ is SO$_2$R$^7$ or SO$_2$NR$^8$R$^9$;
R$^6$ is absent; or
each R$^6$ is independently F or CH$_3$;
R$^7$ is C$_1$-C$_4$ alkyl; and
R$^8$ and R$^9$ are independently H or C$_1$-C$_4$ alkyl.

In further preferred embodiments, the invention provides a compound of Formula (I), (I-A), (I-B) and (I-C), or a pharmaceutically acceptable salt thereof, having three or more of the following features:

R$^1$ is 5-6 membered heterocyclyl substituted by R$^{5A}$; or
R$^1$ is 5-6 membered heterocyclyl substituted by R$^{5A}$, where said 5-6 membered heterocyclyl is optionally further substituted by one or two R$^6$;
p is 0 and R$^2$ is absent;
q is 1 and r is 0; or
q is 1 and r is 1;
R$^{2A}$ and R$^{2B}$ are independently H, OH or C$_1$-C$_4$ alkyl, provided at least one of R$^{2A}$ and R$^{2B}$ is not H;
R$^3$ is F, Cl, C$_1$-C$_4$ alkyl or C$_1$-C$_4$ fluoroalkyl, where said C$_1$-C$_4$ alkyl and C$_1$-C$_4$ fluoroalkyl are optionally substituted by OH; or
R$^3$ is C$_1$-C$_4$ alkyl or C$_1$-C$_4$ fluoroalkyl, where said C$_1$-C$_4$ alkyl and C$_1$-C$_4$ fluoroalkyl are optionally substituted by OH; or
R$^3$ is C$_1$-C$_4$ fluoroalkyl; or
R$^3$ is C$_1$-C$_2$ fluoroalkyl;
R$^4$ is H;
R$^{5A}$ is SO$_2$R$^7$ or SO$_2$NR$^8$R$^9$;
R$^6$ is absent; or
each R$^6$ is independently F or CH$_3$;
R$^7$ is C$_1$-C$_4$ alkyl; and
R$^8$ and R$^9$ are independently H or C$_1$-C$_4$ alkyl.

In other preferred embodiments, the invention provides a compound of Formula (I), (I-A), (I-B) and (I-C), or a pharmaceutically acceptable salt thereof, having two or more of the following features:

R$^1$ is piperidinyl, preferably piperidin-4-yl, substituted on N$^1$ by R$^{5A}$;
p is 0 and R$^2$ is absent;
q is 1 and r is 0;
R$^{2A}$ and R$^{2B}$ are independently H, OH or CH$_3$;
R$^3$ is H, F, Cl, CH$_3$, CH$_2$CH$_2$OH, CF$_2$H or CH$_2$CF$_2$H;
R$^4$ is H;
R$^{5A}$ is SO$_2$R$^7$ or SO$_2$NR$^8$R$^9$;
R$^6$ is absent;
R$^7$ is CH$_3$; and
R$^8$ and R$^9$ are independently H or CH$_3$.

In still other preferred embodiments, the invention provides a compound of Formula (I), (I-A), (I-B) and (I-C), or a pharmaceutically acceptable salt thereof, having three or more of the following features:

R$^1$ is piperidinyl, preferably piperidin-4-yl, substituted on N$^1$ by R$^{5A}$;
p is 0 and R$^2$ is absent;
q is 1 and r is 0; or
q is 1 and r is 1; R$^{2A}$ and R$^{2B}$ are independently H, OH or CH$_3$, provided at least one of R$^{2A}$ and R$^{2B}$ is not H;
R$^3$ is C$_1$-C$_4$ fluoroalkyl; or
R$^3$ is C$_1$-C$_2$ fluoroalkyl; or
R$^3$ is CF$_2$H or CH$_2$CF$_2$H;
R$^4$ is H;
R$^{5A}$ is SO$_2$R$^7$ or SO$_2$NR$^8$R$^9$;
R$^6$ is absent;
R$^7$ is CH$_3$; and
R$^8$ and R$^9$ are independently H or CH$_3$.

In further preferred embodiments, the invention provides a compound of Formula (I), (I-A), (I-B) and (I-C), or a pharmaceutically acceptable salt thereof, having two or more of the following features:

R$^1$ is piperidinyl, preferably piperidin-4-yl, substituted on N$^1$ by R$^{5A}$;
p is 0 and R$^2$ is absent;
q is 1 and r is 0;
one of R$^{2A}$ and R$^{2B}$ is OH and the other is CH$_3$; or
one of R$^{2A}$ and R$^{2B}$ is OH and the other is H; or
one of R$^{2A}$ and R$^{2B}$ is H and the other is CH$_3$;
R$^3$ is H, F, Cl, CH$_3$, CH$_2$CH$_2$OH, CF$_2$H or CH$_2$CF$_2$H;
R$^4$ is H;
R$^{5A}$ is SO$_2$R$^7$ or SO$_2$NR$^8$R$^9$;
R$^6$ is absent;
R$^7$ is CH$_3$; and
R$^8$ and R$^9$ are independently H or CH$_3$.

In other preferred embodiments, the invention provides a compound of Formula (I), (I-A), (I-B) and (I-C), or a pharmaceutically acceptable salt thereof, having two or more of the following features:

R$^1$ is piperidin-4-yl, substituted on N$^1$ by R$^{5A}$;
p is 0 and R$^2$ is absent;
q is 1 and r is 0;
R$^{2A}$ is OH and R$^{2B}$ is H; or
R$^{2A}$ is OH and R$^{2B}$ is CH$_3$; or
R$^{2A}$ is H and R$^{2B}$ is CH$_3$;
R$^3$ is C$_1$-C$_4$ fluoroalkyl; or
R$^3$ is C$_1$-C$_2$ fluoroalkyl; or
R$^3$ is CF$_2$H or CH$_2$CF$_2$H;
R$^4$ is H;
R$^{5A}$ is SO$_2$R$^7$;
R$^6$ is absent; and
R$^7$ is CH$_3$.

In specific embodiments, the invention provides compounds of Formula (I-B), or a pharmaceutically acceptable salt thereof, having two or more of the following features:

R$^1$ is piperidin-4-yl, substituted on N$^1$ by R$^{5A}$;
p is 0 and R$^2$ is absent;
q is 1 and r is 0;
R$^{2A}$ is H or OH and R$^{2B}$ is H or CH$_3$; or
R$^{2A}$ is OH and R$^{2B}$ is H; or $R^{2A}$ is OH and $R^{2B}$ is $CH_3$; or
$R^{2A}$ is H and $R^{2B}$ is $CH_3$; or
$R^{2A}$ is H and $R^{2B}$ is H;
$R^3$ is H, F, Cl, $CH_3$, $CH_2CH_2OH$, $CF_2H$ or $CH_2CF_2H$;
$R^4$ is H;
$R^{5A}$ is $SO_2R^7$ where $R^7$ is $CH_3$; or
$R^{5A}$ is $SO_2NR^8R^9$, where $R^8$ is H or $CH_3$ and $R^9$ is $CH_3$; and
$R^6$ is absent.

In another aspect, the invention provides a compound of Formula (II), (II-A), (II-B) or (II-C):

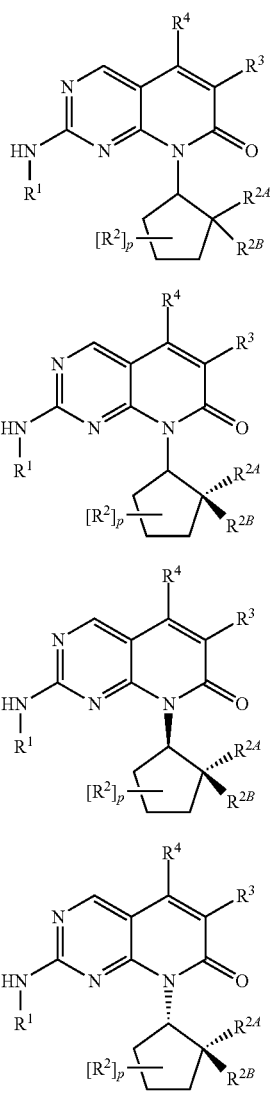

or a pharmaceutically acceptable salt thereof, where $R^1$, $R^2$, $R^{2A}$, $R^{2B}$, $R^3$, $R^4$, $R^{5A}$, $R^{5B}$, $R^6$, $R^7$, $R^8$, $R^9$ and p are defined as for Formula (I).

The embodiments described herein for Formula (I) with respect to $R^1$, $R^2$, $R^{2A}$, $R^{2B}$, $R^3$, $R^4$, $R^{5A}$, $R^{5B}$, $R^6$, $R^7$, $R^8$, $R^9$ and p are also applicable to compounds of Formulae (II), (II-A), (II-B) and (II-C) to the extent they are not inconsistent.

In certain preferred embodiments, the invention provides a compound of Formula (II), (II-A), (II-B) and (II-C), or a pharmaceutically acceptable salt thereof, having two or more of the following features:
$R^1$ is 3-10 membered heterocyclyl substituted by $R^{5A}$;
p is 0 and $R^2$ is absent;
$R^{2A}$ and $R^{2B}$ are independently H, OH or $C_1$-$C_4$ alkyl;
$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
$R^4$ is H;
$R^{5A}$ is $SO_2R^7$ or $SO_2NR^8R^9$;
$R^6$ is absent;
$R^7$ is $C_1$-$C_4$ alkyl; and
$R^8$ and $R^9$ are independently H or $C_1$-$C_4$ alkyl.

In other preferred embodiments, the invention provides a compound of Formula (II), (II-A), (II-B) and (II-C), or a pharmaceutically acceptable salt thereof, having two or more of the following features:
$R^1$ is 3-10 membered heterocyclyl substituted by $R^{5A}$; or
$R^1$ is 3-10 membered heterocyclyl substituted by $R^{5A}$, where said 3-10 membered heterocyclyl is optionally further substituted by one or two $R^6$;
p is 0 and $R^2$ is absent; or
p is 1 or 2, and each $R^2$ is independently F, OH or $CH_3$;
$R^{2A}$ and $R^{2B}$ are independently H, OH or $C_1$-$C_4$ alkyl, provided at least one of $R^{2A}$ and $R^{2B}$ is not H;
$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl; $R^4$ is H;
$R^{5A}$ is $SO_2R^7$ or $SO_2NR^8R^9$;
$R^6$ is absent; or
each $R^6$ is independently F or $CH_3$;
$R^7$ is $C_1$-$C_4$ alkyl; and
$R^8$ and $R^9$ are independently H or $C_1$-$C_4$ alkyl.

In other preferred embodiments, the invention provides a compound of Formula (II), (II-A), (II-B) and (II-C), or a pharmaceutically acceptable salt thereof, having two or more of the following features:
$R^1$ is 5-6 membered heterocyclyl substituted by $R^{5A}$; or
$R^1$ is 5-6 membered heterocyclyl substituted by $R^{5A}$, where said 5-6 membered heterocyclyl is optionally further substituted by one or more $R^6$;
p is 0 and $R^2$ is absent; $R^{2A}$ and $R^{2B}$ are independently H, OH or $C_1$-$C_4$ alkyl, provided at least one of $R^{2A}$ and $R^{2B}$ is not H;
$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl;
$R^4$ is H;
$R^{5A}$ is $SO_2R^7$ or $SO_2NR^8R^9$;
$R^6$ is absent; or
each $R^6$ is independently F or $CH_3$;
$R^7$ is $C_1$-$C_4$ alkyl; and
$R^8$ and $R^9$ are independently H or $C_1$-$C_4$ alkyl.

In still other preferred embodiments, the invention provides a compound of Formula (II), (II-A), (II-B) and (II-C), or a pharmaceutically acceptable salt thereof, having two or more of the following features:

$R^1$ is piperidinyl, preferably piperidin-4-yl, substituted on $N^1$ by $R^{5A}$;
p is 0 and $R^2$ is absent;
$R^{2A}$ and $R^{2B}$ are independently H, OH or $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In other preferred embodiments, the invention provides a compound of Formula (II), (II-A), (II-B) and (II-C), or a pharmaceutically acceptable salt thereof, having two or more of the following features:
$R^1$ is piperidinyl, preferably piperidin-4-yl, substituted on $N^1$ by $R^{5A}$;
p is 0 and $R^2$ is absent;
$R^{2A}$ and $R^{2B}$ are independently H, OH or $CH_3$, provided at least one of $R^{2A}$ and $R^{2B}$ is not H;
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In further preferred embodiments, the invention provides a compound of Formula (II), (II-A), (II-B) and (II-C), or a pharmaceutically acceptable salt thereof, having two or more of the following features:
$R^1$ is piperidinyl, preferably piperidin-4-yl, substituted on $N^1$ by $R^{5A}$;
p is 0 and $R^2$ is absent;
one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In further preferred embodiments, the invention provides compounds of Formula (II-B), or a pharmaceutically acceptable salt thereof, having two or more of the following features:
$R^1$ is piperidin-4-yl, substituted on $N^1$ by $R^{5A}$;
p is 0 and $R^2$ is absent;
$R^{2A}$ is OH and $R^{2B}$ is H; or
$R^{2A}$ is OH and $R^{2B}$ is $CH_3$; or
$R^{2A}$ is H and $R^{2B}$ is $CH_3$; or
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$;
$R^6$ is absent; and
$R^7$ is $CH_3$.

In further preferred embodiments, the invention provides compounds of Formula (II-B), or a pharmaceutically acceptable salt thereof, having two or more of the following features:
$R^1$ is piperidin-4-yl, substituted on $N^1$ by $R^{5A}$;
p is 0 and $R^2$ is absent;
$R^{2A}$ is H or OH and $R^{2B}$ is H or $CH_3$; or
$R^{2A}$ is OH and $R^{2B}$ is H; or $R^{2A}$ is OH and $R^{2B}$ is $CH_3$; or
$R^{2A}$ is H and $R^{2B}$ is $CH_3$; or
$R^{2A}$ is H and $R^{2B}$ is H;
$R^3$ is H, F, Cl, $CH_3$, $CH_2CH_2OH$, $CF_2H$ or $CH_2CF_2H$;
$R^4$ is H;
$R^{5A}$ is $SO_2R^7$, where $R^7$ is $CH_3$; or
$R^{5A}$ is $SO_2NR^8R^9$, where $R^8$ is H or $CH_3$ and $R^9$ is $CH_3$; and
$R^6$ is absent.

In another aspect, the invention provides a compound of Formula (III), (III-A), (III-B) or (III-C):

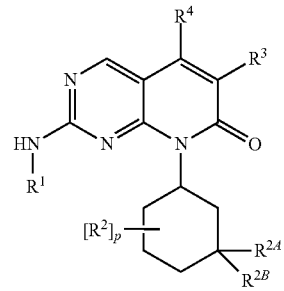
(III)

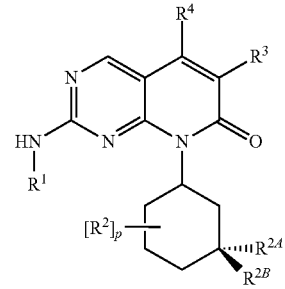
(III-A)

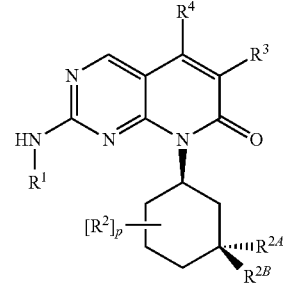
(III-B)

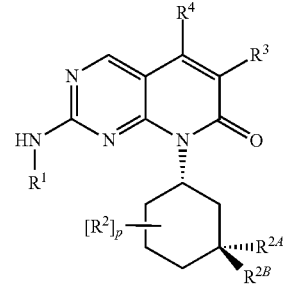
(III-C)

or a pharmaceutically acceptable salt thereof, where $R^1$, $R^2$, $R^{2A}$, $R^{2B}$, $R^3$, $R^4$, $R^{5A}$, $R^{5B}$, $R^6$, $R^7$, $R^8$, $R^9$ and p are defined as for Formula (I).

The embodiments described herein for Formula (I) with respect to $R^1$, $R^2$, $R^{2A}$, $R^{2B}$, $R^3$, $R^4$, $R^{5A}$, $R^{5B}$, $R^6$, $R^7$, $R^8$, $R^9$ and p are also applicable to compounds of Formulae (III), (III-A), (III-B) and (III-C) to the extent they are not inconsistent.

In certain preferred embodiments, the invention provides a compound of Formula (III), (III-A), (III-B) and (III-C), or a pharmaceutically acceptable salt thereof, having two or more of the following features:
- $R^1$ is 3-10 membered heterocyclyl substituted by $R^{5A}$;
- p is 0 and $R^2$ is absent;
- $R^{2A}$ and $R^{2B}$ are independently H, OH or $C_1$-$C_4$ alkyl;
- $R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
- $R^4$ is H;
- $R^{5A}$ is $SO_2R^7$ or $SO_2NR^8R^9$;
- $R^6$ is absent;
- $R^7$ is $C_1$-$C_4$ alkyl; and
- $R^8$ and $R^9$ are independently H or $C_1$-$C_4$ alkyl.

In other embodiments, the invention provides a compound of Formula (III), (III-A), (III-B) and (III-C), or a pharmaceutically acceptable salt thereof, having two or more of the following features:
- $R^1$ is 3-10 membered heterocyclyl substituted by $R^{5A}$; or
- $R^1$ is 3-10 membered heterocyclyl substituted by $R^{5A}$, where said 3-10 membered heterocyclyl is optionally further substituted by one or two $R^6$;
- p is 0 and $R^2$ is absent; or
- p is 1 or 2, and each $R^2$ is independently F, OH or $CH_3$;
- $R^{2A}$ and $R^{2B}$ are independently H, OH or $C_1$-$C_4$ alkyl, provided at least one of $R^{2A}$ and $R^{2B}$ is not H;
- $R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
- $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
- $R^3$ is $C_1$-$C_4$ fluoroalkyl; or
- $R^3$ is $C_1$-$C_2$ fluoroalkyl;
- $R^4$ is H;
- $R^{5A}$ is $SO_2R^7$ or $SO_2NR^8R^9$;
- $R^6$ is absent; or
- each $R^6$ is independently F or $CH_3$;
- $R^7$ is $C_1$-$C_4$ alkyl; and
- $R^8$ and $R^9$ are independently H or $C_1$-$C_4$ alkyl.

In other preferred embodiments, the invention provides a compound of Formula (III), (III-A), (III-B) and (III-C), or a pharmaceutically acceptable salt thereof, having two or more of the following features:
- $R^1$ is 5-6 membered heterocyclyl substituted by $R^{5A}$; or
- $R^1$ is 5-6 membered heterocyclyl substituted by $R^{5A}$, where said 5-6 membered heterocyclyl is optionally further substituted by one or more $R^6$;
- p is 0 and $R^2$ is absent;
- $R^{2A}$ and $R^{2B}$ are independently H, OH or $C_1$-$C_4$ alkyl, provided at least one of $R^{2A}$ and $R^{2B}$ is not H;
- $R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
- $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
- $R^3$ is $C_1$-$C_4$ fluoroalkyl; or
- $R^3$ is $C_1$-$C_2$ fluoroalkyl;
- $R^4$ is H;
- $R^{5A}$ is $SO_2R^7$ or $SO_2NR^8R^9$;
- $R^6$ is absent; or
- each $R^6$ is independently F or $CH_3$;
- $R^7$ is $C_1$-$C_4$ alkyl; and
- $R^8$ and $R^9$ are independently H or $C_1$-$C_4$ alkyl.

In other preferred embodiments, the invention provides a compound of Formula (III), (II-A), (III-B) and (III-C), or a pharmaceutically acceptable salt thereof, having two or more of the following features:
- $R^1$ is piperidinyl, preferably piperidin-4-yl, substituted on $N^1$ by $R^{5A}$;
- p is 0 and $R^2$ is absent;
- $R^{2A}$ and $R^{2B}$ are independently H, OH or $CH_3$;
- $R^3$ is H, F, Cl, $CH_3$, $CH_2CH_2OH$, $CF_2H$ or $CH_2CF_2H$;
- $R^4$ is H;
- $R^{5A}$ is $SO_2R^7$ or $SO_2NR^8R^9$;
- $R^6$ is absent;
- $R^7$ is $CH_3$; and
- $R^8$ and $R^9$ are independently H or $CH_3$.

In other preferred embodiments, the invention provides a compound of Formula (III), (III-A), (III-B) and (III-C), or a pharmaceutically acceptable salt thereof, having two or more of the following features:
- $R^1$ is piperidinyl, preferably piperidin-4-yl, substituted on $N^1$ by $R^{5A}$;
- p is 0 and $R^2$ is absent;
- $R^{2A}$ and $R^{2B}$ are independently H, OH or $CH_3$, provided at least one of $R^{2A}$ and $R^{2B}$ is not H;
- $R^3$ is $C_1$-$C_4$ fluoroalkyl; or
- $R^3$ is $C_1$-$C_2$ fluoroalkyl; or
- $R^3$ is $CF_2H$ or $CH_2CF_2H$;
- $R^4$ is H;
- $R^{5A}$ is $SO_2R^7$ or $SO_2NR^8R^9$;
- $R^6$ is absent;
- $R^7$ is $CH_3$; and
- $R^8$ and $R^9$ are independently H or $CH_3$.

In further preferred embodiments, the invention provides a compound of Formula (III), (III-A), (III-B) and (III-C), or a pharmaceutically acceptable salt thereof, having two or more of the following features:
- $R^1$ is piperidinyl, preferably piperidin-4-yl, substituted on $N^1$ by $R^{5A}$;
- p is 0 and $R^2$ is absent;
- one of $R^{2A}$ and $R^{2B}$ is OH and the other is $CH_3$; or
- one of $R^{2A}$ and $R^{2B}$ is OH and the other is H; or
- one of $R^{2A}$ and $R^{2B}$ is H and the other is $CH_3$;
- $R^3$ is H, F, Cl, $CH_3$, $CH_2CH_2OH$, $CF_2H$ or $CH_2CF_2H$;
- $R^4$ is H;
- $R^{5A}$ is $SO_2R^7$ or $SO_2NR^8R^9$;
- $R^6$ is absent;
- $R^7$ is $CH_3$; and
- $R^8$ and $R^9$ are independently H or $CH_3$.

In another aspect, the invention provides a compound of Formula (IV), (IV-A), (IV-B) or (IV-C):

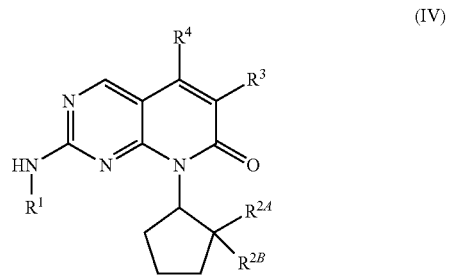

(IV-A)

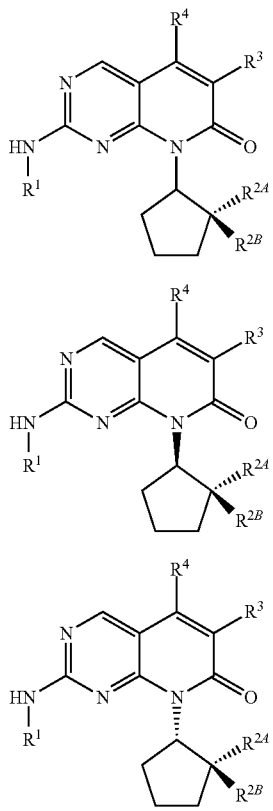

(IV-B)

(IV-C)

or a pharmaceutically acceptable salt thereof, where $R^1$, $R^{2A}$, $R^{2B}$, $R^3$, $R^4$, $R^{5A}$, $R^{5B}$, $R^6$, $R^7$, $R^8$ and $R^9$ are defined as for Formula (I).

The embodiments described herein for Formula (I) with respect to $R^1$, $R^{2A}$, $R^{2B}$, $R^3$, $R^4$, $R^{5A}$, $R^{5B}$, $R^6$, $R^7$, $R^8$ and $R^9$ are also applicable to compounds of Formulae (IV), (IV-A), (IV-B) and (IV-C) to the extent they are not inconsistent.

In specific embodiments, the compounds of Formula (IV), (IV-A), (IV-B) and (IV-C) have the structure:

(iv)

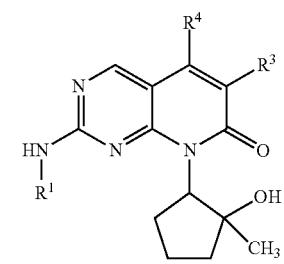

(iv-a)

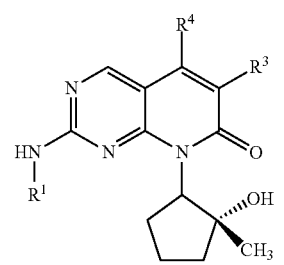

(iv-b)

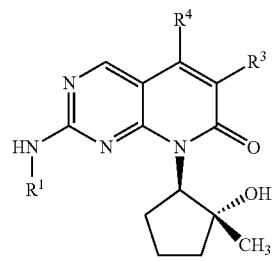

(iv-c)

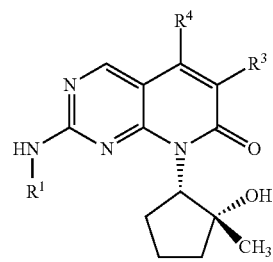

(iv-d)

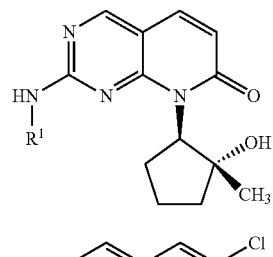

(iv-e)

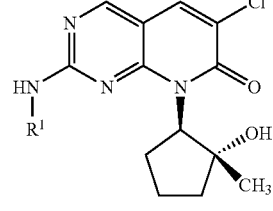

(iv-f)

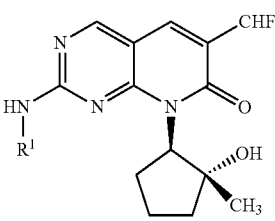

(iv-g)

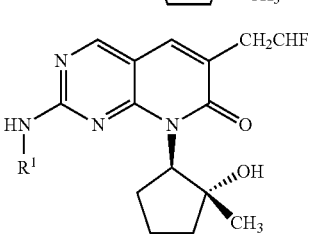

or a pharmaceutically acceptable salt thereof, where $R^1$, $R^3$, $R^4$, $R^{5A}$, $R^{5B}$, $R^6$, $R^7$, $R^8$ and $R^9$ are defined as for Formula (I).

In certain preferred embodiments, the invention provides a compound of Formula (IV), (IV-A), (IV-B) and (IV-C), or a pharmaceutically acceptable salt thereof, having two or more of the following features:

$R^1$ is 3-10 membered heterocyclyl substituted by $R^{5A}$;

$R^{2A}$ and $R^{2B}$ are independently H, OH or $C_1$-$C_4$ alkyl;

$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
$R^4$ is H;
$R^{5A}$ is $SO_2R^7$ or $SO_2NR^8R^9$;
$R^6$ is absent;
$R^7$ is $C_1$-$C_4$ alkyl; and
$R^8$ and $R^9$ are independently H or $C_1$-$C_4$ alkyl.

In another preferred embodiments, the invention provides a compound of Formula (IV), (IV-A), (IV-B) and (IV-C), or a pharmaceutically acceptable salt thereof, having two or more of the following features:
$R^1$ is 3-10 membered heterocyclyl substituted by $R^{5A}$;
$R^{2A}$ and $R^{2B}$ are independently H, OH or $C_1$-$C_4$ alkyl, provided at least one of $R^{2A}$ and $R^{2B}$ is not H;
$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl; $R^4$ is H;
$R^{5A}$ is $SO_2R^7$ or $SO_2NR^8R^9$;
$R^6$ is absent;
$R^7$ is $C_1$-$C_4$ alkyl; and
$R^8$ and $R^9$ are independently H or $C_1$-$C_4$ alkyl.

In another preferred embodiments, the invention provides a compound of Formula (IV), (IV-A), (IV-B) and (IV-C), or a pharmaceutically acceptable salt thereof, having two or more of the following features:
$R^1$ is 5-6 membered heterocyclyl substituted by $R^{5A}$;
$R^{2A}$ and $R^{2B}$ are independently H, OH or $C_1$-$C_4$ alkyl, provided at least one of $R^{2A}$ and $R^{2B}$ is not H;
$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl; $R^4$ is H;
$R^{5A}$ is $SO_2R^7$ or $SO_2NR^8R^9$;
$R^6$ is absent;
$R^7$ is $C_1$-$C_4$ alkyl; and
$R^8$ and $R^9$ are independently H or $C_1$-$C_4$ alkyl.

In other preferred embodiments, the invention provides a compound of Formula (IV), (IV-A), (IV-B) and (IV-C), or a pharmaceutically acceptable salt thereof, having two or more of the following features:
$R^1$ is piperidinyl, preferably piperidin-4-yl, substituted on $N^1$ by $R^{5A}$;
$R^{2A}$ and $R^{2B}$ are independently H, OH or $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In another preferred embodiments, the invention provides a compound of Formula (IV), (IV-A), (IV-B) and (IV-C), or a pharmaceutically acceptable salt thereof, having two or more of the following features:
$R^1$ is piperidinyl, preferably piperidin-4-yl, substituted on $N^1$ by $R^{5A}$;
$R^{2A}$ and $R^{2B}$ are independently H, OH or $CH_3$, provided at least one of $R^{2A}$ and $R^{2B}$ is not H;
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In further preferred embodiments, the invention provides a compound of Formula (IV), (IV-A), (IV-B) and (IV-C), or a pharmaceutically acceptable salt thereof, having two or more of the following features:
$R^1$ is piperidinyl, preferably piperidin-4-yl, substituted on $N^1$ by $R^{5A}$;
one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In further preferred embodiments, the invention provides compounds of Formula (IV-B), or a pharmaceutically acceptable salt thereof, having two or more of the following features:
$R^1$ is piperidin-4-yl, substituted on $N^1$ by $R^{5A}$;
$R^{2A}$ is OH and $R^{2B}$ is H; or
$R^{2A}$ is OH and $R^{2B}$ is $CH_3$; or
$R^{2A}$ is H and $R^{2B}$ is $CH_3$; or
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$;
$R^6$ is absent; and
$R^7$ is $CH_3$.

In further preferred embodiments, the invention provides compounds of Formula (IV-B), or a pharmaceutically acceptable salt thereof, having two or more of the following features:
$R^1$ is piperidin-4-yl, substituted on $N^1$ by $R^{5A}$;
$R^{2A}$ is H or OH and $R^{2B}$ is H or $CH_3$; or
$R^{2A}$ is OH and $R^{2B}$ is H; or
$R^{2A}$ is OH and $R^{2B}$ is $CH_3$; or
$R^{2A}$ is H and $R^{2B}$ is $CH_3$; or
$R^{2A}$ is H and $R^{2B}$ is H;
$R^3$ is H, F, Cl, $CH_3$, $CH_2CH_2OH$, $CF_2H$ or $CH_2CF_2H$;
$R^4$ is H;
$R^{5A}$ is $SO_2R^7$, where $R^7$ is $CH_3$; or
$R^{5A}$ is $SO_2NR^8R^9$, where $R^8$ is H or $CH_3$ and $R^9$ is $CH_3$; and
$R^6$ is absent.

In other preferred embodiments, the invention provides compounds of Formula (iv), (iv-a), (iv-b) or (iv-c), or a pharmaceutically acceptable salt thereof, having two or more of the following features:
$R^1$ is piperidin-4-yl, substituted on $N^1$ by $R^{5A}$;
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$, where $R^7$ is $CH_3$; or
$R^{5A}$ is $SO_2NR^8R^9$, where $R^8$ is H or $CH_3$ and $R^9$ is $CH_3$; and
$R^6$ is absent.

In other preferred embodiments, the invention provides compounds of Formula (iv-f) or (iv-g), or a pharmaceutically acceptable salt thereof, wherein:
R$^1$ is piperidin-4-yl, substituted on N$^1$ by R$^{5A}$;
R$^{5A}$ is SO$_2$R$^7$, where R$^7$ is CH$_3$; or
R$^{5A}$ is SO$_2$NR$^8$R$^{9'}$ where R$^8$ is H or CH$_3$ and R$^9$ is CH$_3$; and
R$^6$ is absent.

In another aspect, the invention provides a compound of Formula (V), (V-A), (V-B) or (V-C):

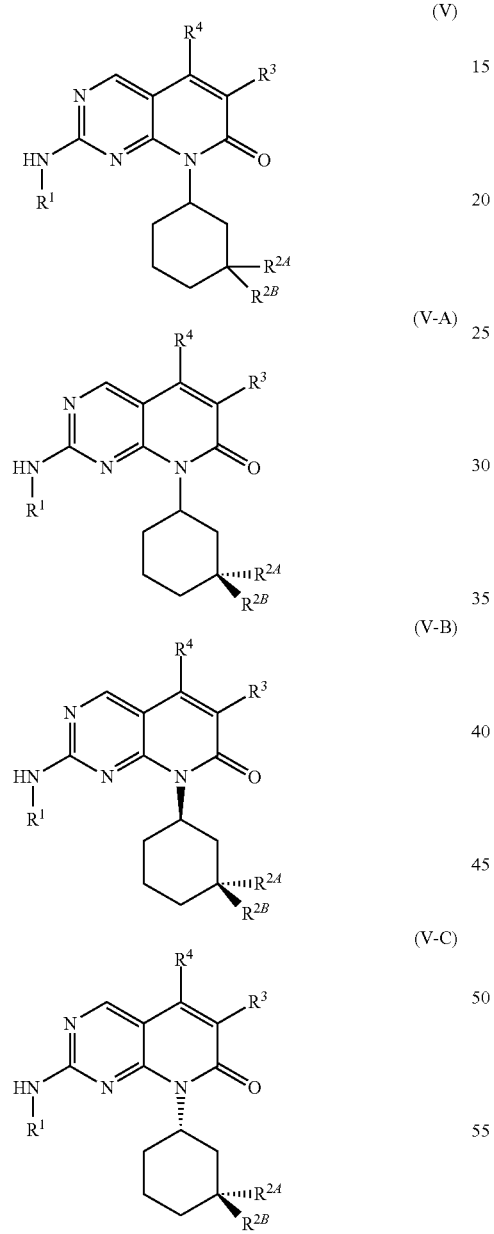

(V)

(V-A)

(V-B)

(V-C)

or a pharmaceutically acceptable salt thereof, where R$^1$, R$^{2A}$, R$^{2B}$, R$^3$, R$^4$, R$^{5A}$, R$^{5B}$, R$^6$, R$^7$, R$^8$ and R$^9$ are defined as for Formula (I).

The embodiments described herein for Formula (I) with respect to R$^1$, R$^{2A}$, R$^{2B}$, R$^3$, R$^4$, R$^{5A}$, R$^{5B}$, R$^6$, R$^7$, R$^8$ and R$^9$ are also applicable to compounds of Formulae (V), (V-A), (V-B) and (V-C) to the extent they are not inconsistent.

In specific embodiments, the compounds of Formula (V), (V-A), (V-B) and (V-C) have the structure:

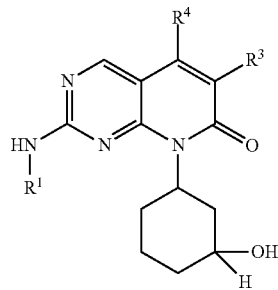

(v)

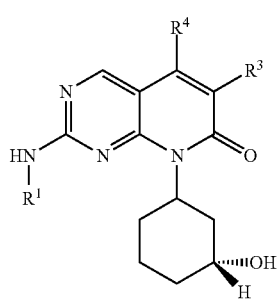

(v-a)

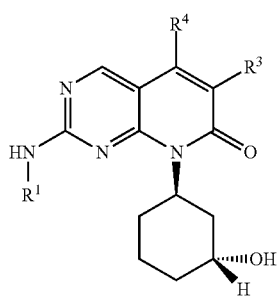

(v-b)

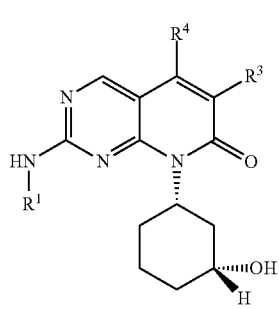

(v-c)

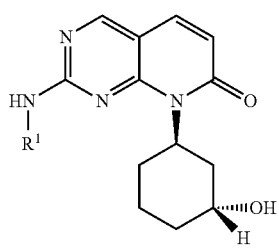

(v-d)

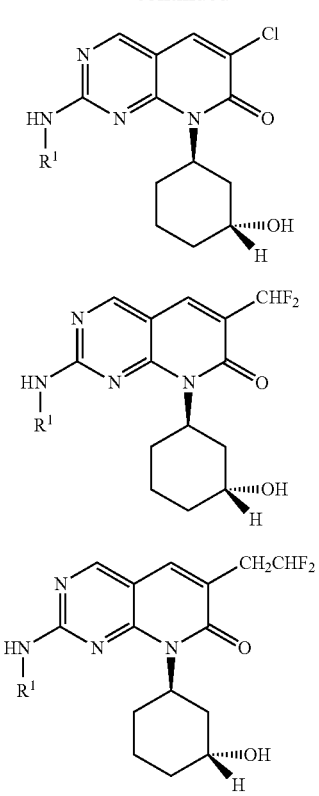

or a pharmaceutically acceptable salt thereof, where $R^1$, $R^3$, $R^4$, $R^{5A}$, $R^{5B}$, $R^6$, $R^7$, $R^8$ and $R^9$ are defined as for Formula (I).

In certain preferred embodiments, the invention provides a compound of Formula (V), (V-A), (V-B) and (V-C), or a pharmaceutically acceptable salt thereof, having two or more of the following features:

$R^1$ is 3-10 membered heterocyclyl substituted by $R^{5A}$;

$R^{2A}$ and $R^{2B}$ are independently H, OH or $C_1$-$C_4$ alkyl;

$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;

$R^4$ is H;

$R^{5A}$ is $SO_2R^7$ or $SO_2NR^8R^9$;

$R^6$ is absent;

$R^7$ is $C_1$-$C_4$ alkyl; and $R^8$ and $R^9$ are independently H or $C_1$-$C_4$ alkyl.

In another preferred embodiments, the invention provides a compound of Formula (V), (V-A), (V-B) and (V-C), or a pharmaceutically acceptable salt thereof, having two or more of the following features:

$R^1$ is 3-10 membered heterocyclyl substituted by $R^{5A}$; or $R^1$ is 3-10 membered heterocyclyl substituted by $R^{5A}$, where said 3-10 membered heterocyclyl is optionally further substituted by one or two $R^6$;

$R^{2A}$ and $R^{2B}$ are independently H, OH or $C_1$-$C_4$ alkyl, provided at least one of $R^{2A}$ and $R^{2B}$ is not H;

$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or $R^3$ is $C_1$-$C_4$ fluoroalkyl; or $R^3$ is $C_1$-$C_2$ fluoroalkyl;

$R^4$ is H;

$R^{5A}$ is $SO_2R^7$ or $SO_2NR^8R^9$;

$R^6$ is absent; or each $R^6$ is independently F or $CH_3$;

$R^7$ is $C_1$-$C_4$ alkyl; and $R^8$ and $R^9$ are independently H or $C_1$-$C_4$ alkyl.

In another preferred embodiments, the invention provides a compound of Formula (V), (V-A), (V-B) and (V-C), or a pharmaceutically acceptable salt thereof, having two or more of the following features:

$R^1$ is 5-6 membered heterocyclyl substituted by $R^{5A}$; or $R^1$ is 5-6 membered heterocyclyl substituted by $R^{5A}$, where said 5-6 membered heterocyclyl is optionally further substituted by one or two $R^6$;

$R^{2A}$ and $R^{2B}$ are independently H, OH or $C_1$-$C_4$ alkyl, provided at least one of $R^{2A}$ and $R^{2B}$ is not H;

$R^3$ is F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH; or $R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or $R^3$ is $C_1$-$C_4$ fluoroalkyl; or $R^3$ is $C_1$-$C_2$ fluoroalkyl;

$R^4$ is H;

$R^{5A}$ is $SO_2R^7$ or $SO_2NR^8R^9$;

$R^6$ is absent; or each $R^6$ is independently F or $CH_3$;

$R^7$ is $C_1$-$C_4$ alkyl; and $R^8$ and $R^9$ are independently H or $C_1$-$C_4$ alkyl.

In other preferred embodiments, the invention provides a compound of Formula (V), (V-A), (V-B) and (V-C), or a pharmaceutically acceptable salt thereof, having two or more of the following features:

$R^1$ is piperidinyl, preferably piperidin-4-yl, substituted on $N^1$ by $R^{5A}$;

$R^{2A}$ and $R^{2B}$ are independently H, OH or $CH_3$;

$R^3$ is H, F, Cl, $CH_3$, $CH_2CH_2OH$, $CF_2H$ or $CH_2CF_2H$;

$R^4$ is H;

$R^{5A}$ is $SO_2R^7$ or $SO_2NR^8R^9$;

$R^6$ is absent;

$R^7$ is $CH_3$; and $R^8$ and $R^9$ are independently H or $CH_3$.

In another preferred embodiments, the invention provides a compound of Formula (V), (V-A), (V-B) and (V-C), or a pharmaceutically acceptable salt thereof, having two or more of the following features:

$R^1$ is piperidinyl, preferably piperidin-4-yl, substituted on $N^1$ by $R^{5A}$;

$R^{2A}$ and $R^{2B}$ are independently H, OH or $CH_3$, provided at least one of $R^{2A}$ and $R^{2B}$ is not H;

$R^3$ is $C_1$-$C_4$ fluoroalkyl; or $R^3$ is $C_1$-$C_2$ fluoroalkyl; or $R^3$ is $CF_2H$ or $CH_2CF_2H$;

$R^4$ is H;

$R^{5A}$ is $SO_2R^7$ or $SO_2NR^8R^9$;

$R^6$ is absent;

$R^7$ is $CH_3$; and $R^8$ and $R^9$ are independently H or $CH_3$.

In further preferred embodiments, the invention provides a compound of Formula (V), (V-A), (V-B) and (V-C), or a pharmaceutically acceptable salt thereof, having two or more of the following features:

R¹ is piperidinyl, preferably piperidin-4-yl, substituted on N¹ by $R^{5A}$;

one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^6$ is absent;
$R^7$ is $CH_3$; and
$R^8$ and $R^9$ are independently H or $CH_3$.

In another aspect, the invention provides a compound of Formula (VI), (VI-A), (VI-B) or (VI-C):

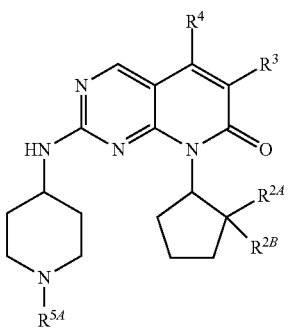

(VI)

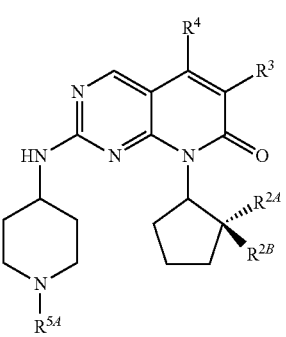

(VI-A)

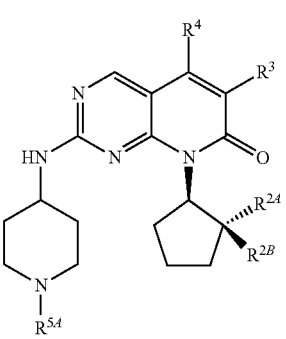

(VI-B)

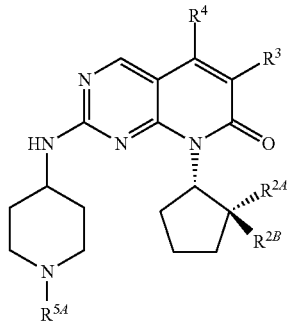

(VI-C)

or a pharmaceutically acceptable salt thereof, where $R^{2A}$, $R^{2B}$, $R^3$, $R^4$, $R^{5A}$, $R^7$, $R^8$ and $R^9$ are defined as for Formula (I).

The embodiments described herein for Formula (I) with respect to $R^{2A}$, $R^{2B}$, $R^3$, $R^4$, $R^{5A}$, $R^{5B}$, $R^6$, $R^7$, $R^8$ and $R^9$ are also applicable to compounds of Formulae (VI), (VI-A), (VI-B) and (VI-C) to the extent they are not inconsistent.

In certain preferred embodiments, the invention provides a compound of Formula (VI), (VI-A), (VI-B) and (VI-C), or a pharmaceutically acceptable salt thereof, having two or more of the following features:
$R^{2A}$ and $R^{2B}$ are independently H, OH or $C_1$-$C_4$ alkyl;
$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
$R^4$ is H;
$R^{5A}$ is $SO_2R^7$ or $SO_2NR^8R^9$;
$R^7$ is $C_1$-$C_4$ alkyl; and
$R^8$ and $R^9$ are independently H or $C_1$-$C_4$ alkyl.

In other preferred embodiments, the invention provides a compound of Formula (VI), (VI-A), (VI-B) and (VI-C), or a pharmaceutically acceptable salt thereof, having two or more of the following features:
$R^{2A}$ and $R^{2B}$ are independently H, OH or $C_1$-$C_4$ alkyl, provided at least one of $R^{2A}$ and $R^{2B}$ is not H;
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$ or $SO_2NR^8R^9$;
$R^7$ is $C_1$-$C_4$ alkyl; or
$R^7$ is $CH_3$; and
$R^8$ and $R^9$ are independently H or $C_1$-$C_4$ alkyl; or
$R^8$ and $R^9$ are independently H or $CH_3$.

In other preferred embodiments, the invention provides a compound of Formula (VI), (VI-A), (VI-B) and (VI-C), or a pharmaceutically acceptable salt thereof, having two or more of the following features:
$R^{2A}$ and $R^{2B}$ are independently H, OH or $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^7$ is $CH_3$; and
$R^8$ and $R^9$ are independently H or $CH_3$.

In further preferred embodiments, the invention provides a compound of Formula (VI), (VI-A), (VI-B) and (VI-C), or a pharmaceutically acceptable salt thereof, having two or more of the following features:

one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^7$ is $CH_3$; and
$R^8$ and $R^9$ are independently H or $CH_3$.

In further preferred embodiments, the invention provides compounds of Formula (VI-B), or a pharmaceutically acceptable salt thereof, having two or more of the following features:
$R^{2A}$ is H or OH and $R^{2B}$ is H or $CH_3$; or
$R^{2A}$ is OH and $R^{2B}$ is H; or
$R^{2A}$ is OH and $R^{2B}$ is $CH_3$; or
$R^{2A}$ is H and $R^{2B}$ is $CH_3$; or
$R^{2A}$ is H and $R^{2B}$ is H;
$R^3$ is H, F, Cl, $CH_3$, $CH_2CH_2OH$, $CF_2H$ or $CH_2CF_2H$;
$R^4$ is H; and
$R^{5A}$ is $SO_2R^7$, where $R^7$ is $CH_3$; or
$R^{5A}$ is $SO_2NR^8R^9$, where $R^8$ is H or $CH_3$ and $R^9$ is $CH_3$.

In further preferred embodiments, the invention provides compounds of Formula (VI-B), or a pharmaceutically acceptable salt thereof, having two or more of the following features:
one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$; or
$R^{2A}$ is OH and $R^{2B}$ is H; or
$R^{2A}$ is OH and $R^{2B}$ is $CH_3$; or
$R^{2A}$ is H and $R^{2B}$ is $CH_3$;
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H; and
$R^{5A}$ is $SO_2R^7$; and
$R^7$ is $CH_3$.

In another aspect, the invention provides a compound of Formula (VII), (VII-A), (VII-B) or (VII-C):

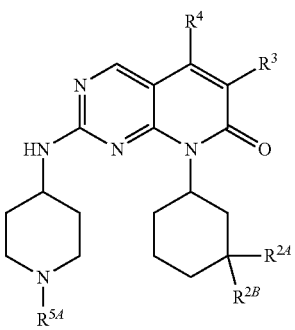

(VII)

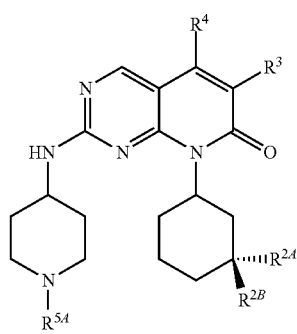

(VII-A)

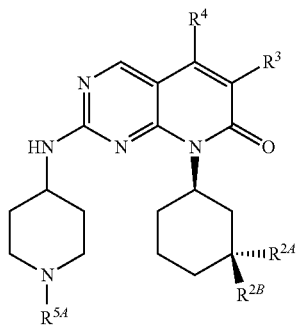

(VII-B)

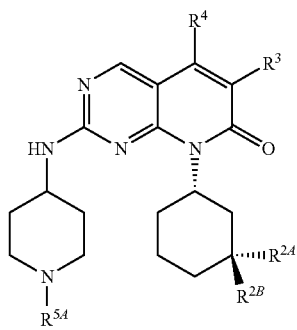

(VII-C)

or a pharmaceutically acceptable salt thereof, where $R^{2A}$, $R^{2B}$, $R^3$, $R^4$, $R^{5A}$, $R^7$, $R^8$ and $R^9$ are defined as for Formula (I).

The embodiments described herein for Formula (I) with respect to $R^{2A}$, $R^{2B}$, $R^3$, $R^4$, $R^{5A}$, $R^7$, $R^8$ and $R^9$ are also applicable to compounds of Formulae (VII), (VII-A), (VII-B) and (VII-C) to the extent they are not inconsistent.

In certain preferred embodiments, the invention provides a compound of Formula (VII), (VII-A), (VII-B) and (VII-C), or a pharmaceutically acceptable salt thereof, having two or more of the following features:
$R^{2A}$ and $R^{2B}$ are independently H, OH or $C_1$-$C_4$ alkyl;
$R^3$ is H, F, Cl, $C_1$-$C_4$ alkyl or $C_1$-$C_4$ fluoroalkyl, where said $C_1$-$C_4$ alkyl and $C_1$-$C_4$ fluoroalkyl are optionally substituted by OH;
$R^4$ is H;
$R^{5A}$ is $SO_2R^7$ or $SO_2NR^8R^9$;
$R^7$ is $C_1$-$C_4$ alkyl; and
$R^8$ and $R^9$ are independently H or $C_1$-$C_4$ alkyl.

In other preferred embodiments, the invention provides a compound of Formula (VII), (VII-A), (VII-B) and (VII-C), or a pharmaceutically acceptable salt thereof, having two or more of the following features:
$R^{2A}$ and $R^{2B}$ are independently H, OH or $C_1$-$C_4$ alkyl, provided at least one of $R^{2A}$ and $R^{2B}$ is not H;
$R^3$ is $C_1$-$C_4$ alkyl or $C_1$-$C_4$ fluoroalkyl, where said $C_1$-$C_4$ alkyl and $C_1$-$C_4$ fluoroalkyl are optionally substituted by OH; or
$R^3$ is $C_1$-$C_4$ fluoroalkyl; or
$R^3$ is $C_1$-$C_2$ fluoroalkyl; or
$R^3$ is $CF_2H$ or $CH_2CF_2H$;
$R^4$ is H;
$R^{5A}$ is $SO_2R^7$ or $SO_2NR^8R^9$;
$R^7$ is $C_1$-$C_4$ alkyl; or
$R^7$ is $CH_3$; and
$R^8$ and $R^9$ are independently H or $C_1$-$C_4$ alkyl; or
$R^8$ and $R^9$ are independently H or $CH_3$.

In other preferred embodiments, the invention provides a compound of Formula (VII), (VII-A), (VII-B) and (VII-C), or a pharmaceutically acceptable salt thereof, having two or more of the following features:

$R^{2A}$ and $R^{2B}$ are independently H, OH or $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^7$ is $CH_3$; and
$R^8$ and $R^9$ are independently H or $CH_3$.

In further preferred embodiments, the invention provides a compound of Formula (VII), (VII-A), (VII-B) and (VII-C), or a pharmaceutically acceptable salt thereof, having two or more of the following features:

one of $R^{2A}$ and $R^{2B}$ is OH and the other is $CH_3$; or
one of $R^{2A}$ and $R^{2B}$ is OH and the other is H; or
one of $R^{2A}$ and $R^{2B}$ is H and the other is $CH_3$;
$R^3$ is H, F, Cl, $CH_3$, $CH_2CH_2OH$, $CF_2H$ or $CH_2CF_2H$;
$R^4$ is H;
$R^{5A}$ is $SO_2R^7$ or $SO_2NR^8R^9$;
$R^7$ is $CH_3$; and
$R^8$ and $R^9$ are independently H or $CH_3$.

In another aspect, the invention provides a compound selected from the group consisting of:

8-cyclopentyl-2-{[1-(methylsulfonyl)piperidin-4-yl]amino}pyrido[2,3-d]pyrimidin-7(8H)-one;

8-[(1R,2R)-2-hydroxy-2-methylcyclopentyl]-2-{[1-(methylsulfonyl)piperidin-4-yl]amino}pyrido[2,3-d]pyrimidin-7(8H)-one;

8-[(1R,3R)-3-hydroxycyclohexyl]-2-{[1-(methylsulfonyl)piperidin-4-yl]amino}pyrido[2,3-d]pyrimidin-7(8H)-one;

4-({6-(2-hydroxyethyl)-8-[(1R,2S)-2-methylcyclopentyl]-7-oxo-7,8-dihydropyrido[2,3-d]pyrimidin-2-yl}amino)-N-methylpiperidine-1-sulfonamide;

(+)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one;

(−)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one;

(+)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one;

(−)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one;

6-chloro-8-[(1R,2R)-2-hydroxy-2-methylcyclopentyl]-2-{[1-(methylsulfonyl)piperidin-4-yl]amino}pyrido[2,3-d]pyrimidin-7(8H)-one; and 6-(difluoromethyl)-8-[(1R,2R)-2-hydroxy-2-methylcyclopentyl]-2-{[1-(methylsulfonyl)piperidin-4-yl]amino}pyrido[2,3-d]pyrimidin-7(8H)-one;

or a pharmaceutically acceptable salt thereof.

In another aspect, the invention provides a compound selected from the group consisting of:

(−)-6-(difluoromethyl)-8-[(1R*,3R*)-3-hydroxycyclopentyl]-2-{[1-(methylsulfonyl)-piperidin-4-yl]amino}pyrido[2,3-d]pyrimidin-7(8H)-one;

(+)-6-(difluoromethyl)-8-[(1R*,3R*)-3-hydroxycyclopentyl]-2-{[1-(methylsulfonyl)-piperidin-4-yl]amino}pyrido[2,3-d]pyrimidin-7(8H)-one;

(8-cyclopentyl-2-{[1-(methylsulfonyl)piperidin-4-yl]amino}-7-oxo-7,8-dihydropyrido[2,3-d]pyrimidin-6-yl)acetonitrile;

8-cyclopentyl-6-(2-hydroxyethyl)-2-{[1-(propan-2-ylsulfonyl)piperidin-4-yl]amino}pyrido[2,3-d]pyrimidin-7(8H)-one;

6-amino-2-{[1-(but-3-yn-1-ylsulfonyl)piperidin-4-yl]amino}-8-cyclopentylpyrido[2,3-d]pyrimidin-7(8H)-one;

8-cyclopentyl-6-ethenyl-2-{[1-(methylsulfonyl)piperidin-4-yl]amino}pyrido[2,3-d]pyrimidin-7(8H)-one;

8-cyclopentyl-2-{[1-(methylsulfonyl)piperidin-4-yl]amino}-6-(prop-2-en-1-yl)pyrido[2,3-d]pyrimidin-7(8H)-one; and 6-(2,2-difluoroethyl)-8-[(1R,3R)-3-hydroxycyclohexyl]-2-{[1-(methylsulfonyl)-piperidin-4-yl]amino}pyrido[2,3-d]pyrimidin-7(8H)-one;

or a pharmaceutically acceptable salt thereof.

In another aspect, the invention provides a compound selected from the group consisting of the compounds exemplified in Table 1, comprising Examples 11-132 and 141-226, inclusive, or a pharmaceutically acceptable salt thereof.

In another aspect, the invention provides a compound selected from the group consisting of the compounds exemplified in Examples 1 to 226 herein, or a pharmaceutically acceptable salt thereof.

The compounds of the invention were optimized for selectivity against CDK2 versus CDK1. Preferably, compounds showed at least 20-fold selectivity for CDK2 versus CDK1, and more preferably, compounds showed at least 30-fold selectivity for CDK2 versus CDK1. Compounds of the invention were also optimized to enhance physicochemical properties, such as increased aqueous solubility and decreased clearance in human liver microsome (HLM) models.

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients. In other embodiments, the pharmaceutical composition further comprises at least one additional anticancer therapeutic agent.

In another aspect the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent or a palliative agent. In some such embodiments, the at least one additional agent is an anti-cancer therapeutic agent as described below. In some such embodiments, the combination provides an additive, greater than additive, or synergistic anti-cancer effect.

In one aspect, the invention provides a method for the treatment of abnormal cell growth in a subject in need thereof, comprising administering to the subject a therapeutically effective amount of a compound of the invention, or a pharmaceutically acceptable salt thereof.

In another aspect, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In frequent embodiments of the methods provided herein, the abnormal cell growth is cancer. Compounds of the invention may be administered as single agents, or may be administered in combination with other anti-cancer therapeutic agents, in particular standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by CDK2, CDK4 and/or CDK6, in a subject, such as certain cancers, comprising administering to the subject a compound of the invention, or a pharmaceutically acceptable salt thereof, in an amount that is effective for treating said disorder.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts.

The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella)' and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms. The carbon-carbon bonds of the compounds of the invention may be depicted herein using a solid line (———), a solid wedge (———), or a dotted wedge (·······). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, N.Y., 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de).

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a subject comprising administering to the subject a therapeutically effective amount of a compound of the invention, or a pharmaceutically acceptable salt thereof. In frequent embodiments, the abnormal cell growth is cancer.

In another aspect, the invention provides a method for the treatment of cancer in a subject comprising administering to the subject an amount of a compound of the invention, or a pharmaceutically acceptable salt thereof, in combination with an amount of an additional anticancer therapeutic agent, which amounts are together effective in treating said cancer.

Compounds of the invention include compounds of any of the formulae described herein, or a pharmaceutically acceptable salt thereof.

In still another aspect, the invention provides a method of inhibiting cancer cell proliferation in a subject, comprising administering to the subject a compound of the invention, or a pharmaceutically acceptable salt thereof, in an amount effective to inhibit cell proliferation.

In another aspect, the invention provides a method of inhibiting cancer cell invasiveness in a subject, comprising administering to the subject a compound of the invention, or a pharmaceutically acceptable salt thereof, in an amount effective to inhibit cell invasiveness.

In another aspect, the invention provides a method of inducing apoptosis in cancer cells in a subject, comprising administering to the subject a compound of the invention, or a pharmaceutically acceptable salt thereof, in an amount effective to induce apoptosis.

In frequent embodiments of the methods provided herein, the abnormal cell growth is cancer characterized by amplification or overexpression of CCNE1 and/or CCNE2. In some embodiments of the methods provided herein, the subject is identified as having a cancer characterized by amplification or overexpression of CCNE1 and/or CCNE2.

In frequent embodiments of the methods provided herein, the abnormal cell growth is cancer, wherein the cancer is selected from the group consisting of breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (i.e., gastric) cancer and thyroid cancer. In further embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer. In some such embodiments, the cancer is characterized by amplification or overexpression of CCNE1 and/or CCNE2.

In some embodiments, the cancer is selected from the group consisting of breast cancer and ovarian cancer. In some such embodiments, the cancer is breast cancer or ovarian cancer characterized by amplification or overexpression of CCNE1 and/or CCNE2. In some such embodiments, the cancer is (a) breast cancer or ovarian cancer; (b) characterized by amplification or overexpression of cyclin E1 (CCNE1) or cyclin E2 (CCNE2); or (c) both (a) and (b).

In some embodiments, the cancer is ovarian cancer. In some such embodiments, the ovarian cancer is characterized by amplification or overexpression of CCNE1 and/or CCNE2.

In other embodiments, the cancer is breast cancer, including, e.g., ER-positive/HR-positive breast cancer, HER2-negative breast cancer; ER-positive/HR-positive breast cancer, HER2-positive breast cancer; triple negative breast cancer (TNBC); or inflammatory breast cancer. In some embodiments, the breast cancer is endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification or overexpression of CCNE1 and/or CCNE2.

In some embodiments, the compound of the invention is administered as first line therapy. In other embodiments, the compound of the invention is administered as second (or later) line therapy. In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent. In some embodiments, the compound of the invention is administered as second (or later) line therapy following treatment with a CDK4/CDK6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with HER2 targeted agents, e.g., trastuzumab. The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "subject" refers to a human or animal subject. In certain preferred embodiments, the subject is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of: (1) tumor cells (tumors) that show increased expression of CDK2; (2) tumors that proliferate by aberrant CDK2 activation; (3) tumors characterized by amplification or overexpression of CCNE1 and/or CCNE2; and (4) tumors that are resistant to endocrine therapy, HER2 antagonists or CDK4/6 inhibition.

The term "additional anticancer therapeutic agent" as used herein means any one or more therapeutic agent, other than a compound of the invention, that is or can be used in the treatment of cancer, such as agents derived from the following classes: mitotic inhibitors, alkylating agents, antimetabolites, antitumor antibiotics, topoisomerase I and II inhibitors, plant alkaloids, hormonal agents and antagonists, growth factor inhibitors, radiation, inhibitors of protein tyrosine kinases and/or serine/threonine kinases, cell cycle inhibitors, biological response modifiers, enzyme inhibitors, antisense oligonucleotides or oligonucleotide derivatives, cytotoxics, and immuno-oncology agents.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer. In some such embodiments, the cancer is characterized by amplification or overexpression of CCNE1 and/or CCNE2.

Dosage Forms and Regimens

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) anti-cancer therapeutic agents.

In particular embodiments, a compound of the invention may be administered in combination with one or more: targeted agents, such as inhibitors of PI3 kinase, mTOR, PARP, IDO, TDO, ALK, ROS, MEK, VEGF, FLT3, AXL, ROR2, EGFR, FGFR, Src/Abl, RTK/Ras, Myc, Raf, PDGF, AKT, c-Kit, erbB, CDK4/CDK6, CDK5, CDK7, CDK9, SMO, CXCR4, HER2, GLS1, EZH2 or Hsp90, or immunomodulatory agents, such as PD-1 or PD-L1 antagonists, OX40 agonists or 4-1BB agonists.

In other embodiments, a compound of the invention may be administered in combination with a standard of care agent, such as tamoxifen, docetaxel, paclitaxel, cisplatin, capecitabine, gemcitabine, vinorelbine, exemestane, letrozole, fulvestrant, anastrozole or trastuzumab.

Synthetic Methods

Compounds of the invention are prepared according to the exemplary procedures provided herein and modifications thereof known to those of skill in the art.

The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "DBU" means 1,8-diazabicyclo[5.4.0]undec-7-ene, "Cbz" means benzyloxycarbonyl, "DCM" ($CH_2Cl_2$) means methylene chloride, "de" means diastereomeric excess, "DEA" means diethylamine, "DIPEA" means diisopropyl ethyl amine, "DMA" means N,N-dimethylacetamide, "DME" means 1,2-dimethoxyethane, "DMF" means N,N-dimethyl formamide, "DMSO" means dimethylsulfoxide, "EDTA" means ethylenediaminetetraacetic acid, "ee" means enantiomeric excess, "Et" means ethyl, "EtOAc" means ethyl acetate, "EtOH" means ethanol, "HOAc" or "AcOH" means acetic acid, "i-Pr" or "ⁱPr" means isopropyl, "IPA" means isopropyl alcohol, "LAH" means lithium aluminum hydride, "LHMDS" means lithium hexamethyldisilazide (lithium bis (trimethylsilyl)amide), "mCPBA" means meta-chloroperoxy-benzoic acid, "Me" means methyl, "MeOH" means methanol, "MS" means mass spectrometry, "MTBE" means methyl tert-butyl ether, "NCS" means N-chlorosuccinimide, "Ph" means phenyl, "TBHP" means tert-butyl hydroperoxide, "TFA" means trifluoroacetic acid, "THF" means tetrahydrofuran, "SFC" means supercritical fluid chromatography, "TLC" means thin layer chromatography, "Rf" means retention fraction, "~" means approximately, "rt" means retention time, "h" means hours, "min" means minutes, "equiv" means equivalents, "sat." means saturated.

Preparation of Synthetic Intermediates

Intermediate 1: (±)-4-{[(1R*,2R*)-2-hydroxy-2-methylcyclopentyl]amino}-2-(methylsulfanyl)pyrimidine-5-carbaldehyde

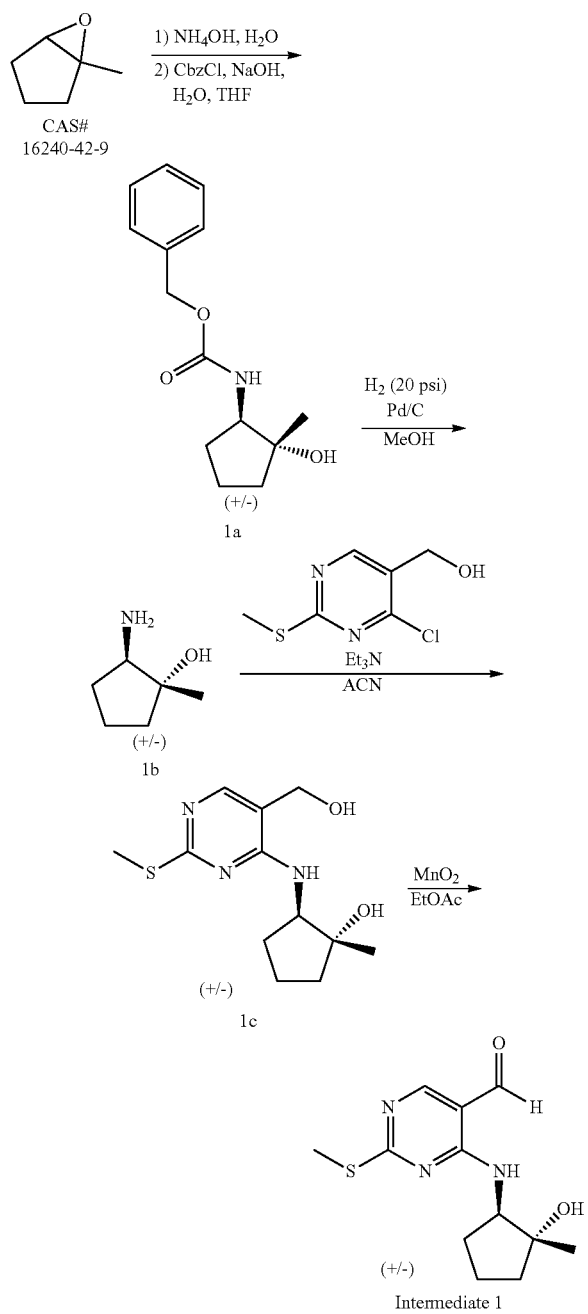

A solution of 1-methyl-6-oxabicyclo[3.1.0]hexane (CAS #16240-42-9, 330 g, 3.36 mol) in ammonium hydroxide (28 wt % in water, 1.5 L) was stirred at 85° C. for 24 h. The solution was concentrated to a brown gum, the gum dissolved in water (2.0 L) and THF (200 mL), and the solution cooled to 0° C. Sodium hydroxide (287 g, 7.16 mol) and benzyl chloroformate (587 g, 3.44 mol) were added dropwise. The resulting mixture was stirred at room temperature for 18 h, then extracted with DCM (1000 mL×3). The combined organic layers were washed with sat. aq NaCl (500 mL), dried over sodium sulfate, and concentrated. The residue was purified by silica gel chromatography (eluting with 10-33% EtOAc in petroleum ether), to give a yellow solid (550 g, 77% pure by NMR). This solid was washed by petroleum ether/EtOAc (3000 mL/100 mL) and petroleum ether/MTBE (2000 mL/500 mL) to give (±)-benzyl [(1R*,2R*)-2-hydroxy-2-methylcyclopentyl]carbamate (1a, 239 g, 28%, 90% pure by NMR) as a pale yellow solid. $^1$H NMR (400 MHz, DMSO-$d_6$) δ=7.37 (t, J=3.9 Hz, 5H), 5.16-4.95 (m, 3H), 4.44 (s, 1H), 3.81-3.68 (m, 1H), 2.15-1.99 (m, 1H), 1.59 (br s, 4H), 1.45-1.31 (m, 1H), 1.19-1.11 (m, 3H).

A solution of (±)-benzyl [(1R*,2R*)-2-hydroxy-2-methylcyclopentyl]carbamate (1a, (109 g, 437 mmol) in MeOH (1000 mL) was treated with wet Pd/C (11 g). The black suspension was stirred at 20° C. under hydrogen (20 psi) for 18 h. After removal of the solids by filtration, the filtrate was concentrated to give (±)-(1R*,2R*)-2-amino-1-methylcyclopentanol (1b, 48.0 g, 95%) as a pale yellow gum. $^1$H NMR (400 MHz, DMSO-$d_6$) δ=2.86 (t, J=6.9 Hz, 1H), 1.99-1.86 (m, 1H), 1.60-1.49 (m, 4H), 1.28-1.17 (m, 1H), 1.08 (s, 3H).

A solution of [4-chloro-2-(methylsulfanyl)pyrimidin-5-yl]methanol (CAS #1044145-59-6, 6.6 g, 35 mmol), (±)-(1R*,2R*)-2-amino-1-methylcyclopentanol (1b, 4.4 g, 46 mmol) and triethylamine (14.5 mL, 104 mmol) in ACN (86 mL) was stirred in a 50° C. oil bath for 16 h. The reaction solution was evaporated to dryness. Water (25 mL), sat. aq NaCl (25 mL) and sat. aq NaHCO$_3$ (25 mL) were added to the residue, and the mixture extracted with EtOAc (200 mL×3). The combined organics were dried over sodium sulfate, and concentrated to dryness. The residue (9.3 g light yellow gum) was suspended in EtOAc (50 mL) with sonication to produce a thick white slurry. This slurry was heated at 60° C. with stirring. Heptane (~150 mL) was added slowly to the heated suspension, then the mixture allowed to cool to room temperature overnight. The resulting solid was collected by filtration, rinsed with heptane (30 mL), and dried to give (±)-(1R*,2R*)-2-{[5-(hydroxymethyl)-2-(methylsulfanyl)pyrimidin-4-yl]amino}-1-methylcyclopentanol (1c, 6.91 g, 74%) as a white solid. $^1$H NMR (400 MHz, DMSO-$d_6$) δ=7.82 (s, 1H), 6.32 (d, J=7.9 Hz, 1H), 5.27 (t, J=5.4 Hz, 1H), 4.66 (s, 1H), 4.36 (d, J=5.3 Hz, 2H), 4.30 (q, J=7.7 Hz, 1H), 2.42 (s, 3H), 2.22-2.10 (m, 1H), 1.75-1.56 (m, 4H), 1.52-1.39 (m, 1H), 1.09 (s, 3H). MS: 270 [M+H]$^+$.

Manganese dioxide (33.4 g, 384 mmol) was added to a suspension of (±)-(1R*,2R*)-2-{[5-(hydroxymethyl)-2-(methylsulfanyl)pyrimidin-4-yl]amino}-1-methylcyclopentanol (1c, 6.9 g, 25.6 mmol) in EtOAc (384 mL), and the mixture stirred in a 50° C. oil bath for 7 h, and then at room temperature overnight. Solids were removed by filtration. The flask and filter cake were washed with EtOAc (~300 mL). The combined filtrates were filtered again to remove a small amount of residual black solid, then concentrated to give (±)-4-{[(1R*,2R*)-2-hydroxy-2-methylcyclopentyl]amino}-2-(methylsulfanyl)-pyrimidine-5-carbaldehyde (Intermediate 1, 5.84 g, 85%) as an off-white solid. $^1$H NMR (400 MHz, CDCl$_3$) δ=9.72 (s, 1H), 8.66 (br s, 1H), 8.35 (s, 1H), 4.39 (ddd, J=6.5, 8.2, 9.5 Hz, 1H), 4.15 (br s, 1H), 2.57

(s, 3H), 2.33-2.23 (m, 1H), 2.03-1.92 (m, 1H), 1.91-1.70 (m, 3H), 1.68-1.56 (m, 1H), 1.17 (s, 3H). MS: 268 [M+H]⁺.

Intermediate 2: 4-{[(1R,2R)-2-hydroxy-2-methylcyclopentyl]amino}-2-(methylsulfanyl)-pyrimidine-5-carbaldehyde

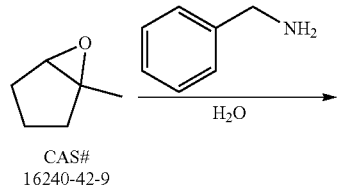

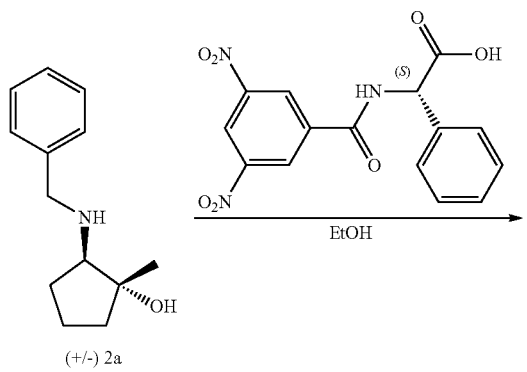

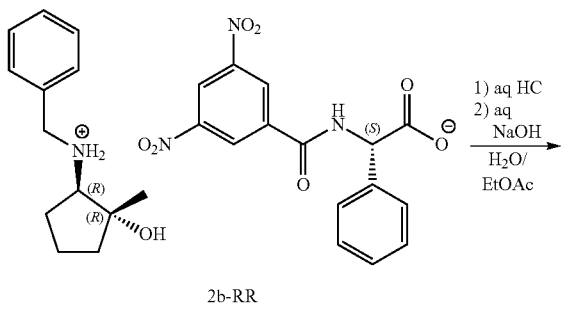

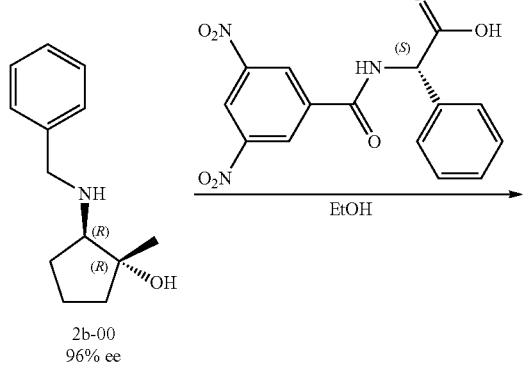

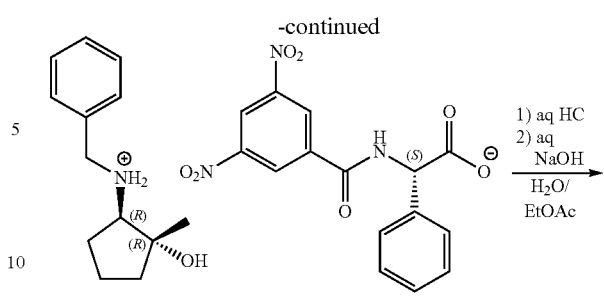

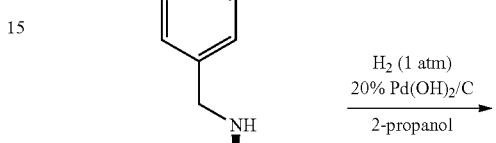

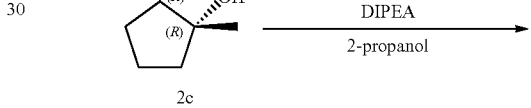

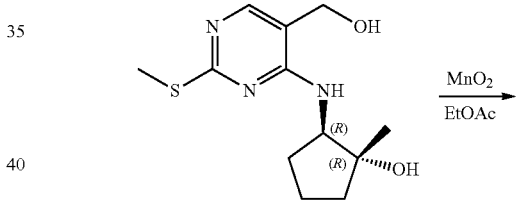

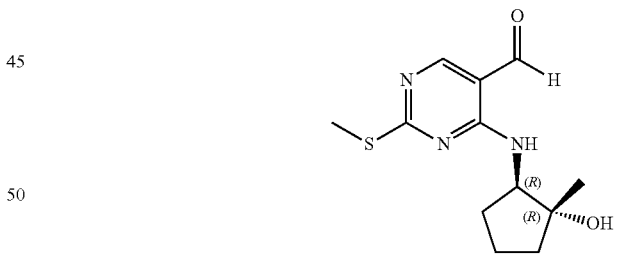

Intermediate 2

A 150 mL sealable flask was charged with water (50.9 mL) and benzylamine (10.9 g, 11.1 mL, 102 mmol), then purged with nitrogen for 5 min, before 1-methyl-6-oxabicyclo[3.1.0]hexane (CAS #16240-42-9, 10 g, 102 mmol) was added. The flask was sealed and heated at 100° C. for 18 h, at which time a biphasic mixture was observed. After cooling to room temperature the flask was further cooled in an ice-water bath. Concentrated aqueous HCl (~12 M, 13 mL) was added to bring the pH to 1. The organic impurities were extracted with EtOAc (150 mL) and set aside. The acidic aqueous layer was cooled in an ice-water bath and adjusted to pH 10 using 5N aq NaOH. The resulting biphasic mixture was extracted with EtOAc (250 mL×3). The combined organic extracts were dried over sodium sulfate and concentrated to a brown oil. The remaining benzylamine was evaporated under higher vacuum (~5 mmHg) at 80° C. for several h, until $^1$HNMR of a sample showed only ~20 mole % benzylamine remaining. The residual oil was triturated with heptane (100 mL), causing white crystals to form. The crystals were collected by filtration and dried to give (±)-(1R*,2R*)-2-(benzylamino)-1-methylcyclopentanol (2a, 13 g, 62%) as a white crystalline solid. $^1$H NMR (400 MHz, CDCl$_3$) δ=7.36-7.31 (m, 4H), 7.28-7.23 (m, 1H), 3.91-3.85 (m, 1H), 3.79-3.74 (m, 1H), 2.86 (dd, J=7.8, 8.5 Hz, 1H), 2.12-2.03 (m, 1H), 1.75-1.53 (m, 5H), 1.37-1.27 (m, 1H), 1.22 (s, 3H).

A magnetically-stirred solution of (±)-(1R*,2R*)-2-(benzylamino)-1-methylcyclopentanol (2a, 100 g, 487 mmol) and EtOH (700 mL) in a 1 L flask was heated in an 80° C. oil bath for 30 min. A separate 5 L, three-neck flask equipped with an overhead stirrer, internal thermometer, and water-cooled condenser was charged with (2S)-[(3,5-dinitrobenzoyl)amino](phenyl)ethanoic acid (CAS #74927-72-3, 84.1 g, 244 mmol, 0.5 equiv) and EtOH (1.4 L). This flask was also heated in an 80° C. oil bath with stirring until the solid dissolved, ~15 min, and stirring continued for another 30 min. The hot solution of amine 2a from the first flask was poured via funnel, in a steady flow over 1 min, into the hot, mechanically stirred solution of chiral acid in the second flask. The transfer was quantitated with EtOH (10 mL). The reaction mixture remained clear for about 1 min, then precipitation began. After 5 min, a thick white suspension had formed, but did not hinder mechanical stirring. Stirring was continued at 80° C. for 4 h, then heating was discontinued and the mixture was stirred while gradually cooling to room temperature overnight. The resulting solid was collected by filtration, washed with EtOH (350 mL), and dried in a vacuum oven (10 mmHg, 40° C.) for 1.5 days, affording (1R,2R)-N-benzyl-2-hydroxy-2-methylcyclopentanaminium (2S)-[(3,5-dinitrobenzoyl)amino](phenyl)acetate (2b-RR, 110.22 g, 82%) as a white solid. $^1$H NMR (400 MHz, DMSO-d$_6$) δ=9.64 (d, J=7.0 Hz, 1H), 9.09 (d, J=2.1 Hz, 2H), 8.96 (t, J=2.1 Hz, 1H), 7.55-7.48 (m, 2H), 7.43-7.23 (m, 8H), 5.47 (d, J=7.1 Hz, 1H), 4.02-3.75 (m, 2H), 2.86 (t, J=8.0 Hz, 1H), 2.03-1.87 (m, 1H), 1.66-1.48 (m, 4H), 1.48-1.32 (m, 1H), 1.17 (s, 3H). MS: 206 [M+H]$^+$ for amine cation. A small-molecule X-ray crystal structure of this salt confirmed absolute (1R,2R) stereochemistry on the cyclopentane ring.

The chiral salt (1R,2R)-N-benzyl-2-hydroxy-2-methylcyclopentanaminium (2S)-[(3,5-dinitrobenzoyl)amino](phenyl)acetate (2b-RR, 110.22 g, 200.2 mmol) was suspended in water (500 mL) and EtOAc (700 mL) in a 2 L separatory funnel. Aqueous HCl (4 M, 200 mL, 800 mmol) was added and the mixture agitated for ~30 seconds. A clear biphasic mixture was obtained. The layers were separated, and the organic layer was further washed with aqueous HCl (0.2 M, 125 mL×2). The acidic aqueous layers were combined, split into two portions, and each portion cooled in an ice-water bath. Aqueous NaOH (4 N, 150 mL, 600 mmol) was added to each portion to bring the pH to 10. A white suspension formed at this pH. The two portions were combined, diluted with sat. aq NaCl (150 mL), and extracted with EtOAc (250 mL×4). The combined organic extracts were dried over sodium sulfate and evaporated to give (1R,2R)-2-(benzylamino)-1-methylcyclopentanol (2b-00, 41.4 g, 100%, 96% ee). $^1$H NMR (400 MHz, DMSO-d$_6$) δ=7.36-7.25 (m, 4H), 7.24-7.16 (m, 1H), 4.23 (s, 1H), 3.78-3.65 (m, 2H), 2.70 (t, J=7.5 Hz, 1H), 1.86 (dt, J=3.9, 7.8 Hz, 1H), 1.73 (br s, 1H), 1.62-1.44 (m, 4H), 1.35-1.23 (m, 1H), 1.12 (s, 3H). Chiral purity: 96% ee. Chiral SFC/MS analysis was performed on a Chiralpak AS-3, 4.6×100 mm, 3 μm column heated to 25° C. and eluted with a mobile phase of CO$_2$ and 5% diethylamine in ethanol (20 mM v/v) in 1 min flowing at 3.5 mL/min and maintained at 160 bar outlet pressure. A gradient to 50% modifier in 3 min was added to elute any remaining counter ions. The detection was APCl(+)MS monitored from 100-800 Da with single ion monitoring (SIM) at 206 Da. The product peak had a retention time of 1.81 min. Optical rotation of a sample made by this method gave $[α]_D^{22}$ –42.6 (c 1.0, MeOH).

Since higher chiral purity was desired, the classical resolution was repeated on the enantio-enriched amine: A solution of (1R,2R)-2-(benzylamino)-1-methylcyclopentanol (2b-00, (41.0 g, 200 mmol, 96% ee) in EtOH (200 mL) was heated at 80° C. with stirring for 30 minutes. A separate 2 L, three-necked flask equipped with an overhead stirrer, internal thermometer and water-cooled condenser was charged with (2S)-[(3,5-dinitrobenzoyl)amino](phenyl)ethanoic acid (CAS #74927-72-3, 67 g, 194 mmol, 0.97 equiv; since amine was ~96% ee) and EtOH (1.3 L). This flask was stirred and heated at 80° C. (internal) until the solid dissolved (~15 min) then for 30 min more. The hot amine solution was added to the hot acid solution through a funnel in a steady flow (less than 1 min), and the transfer quantitated with EtOH (10 mL). Precipitation began in about 1 min, and by 5 min a thick white suspension had formed, though stirring was not hindered. Stirring was continued at 80° C. for 4 h, then heating was discontinued and the reaction stirred and allowed to gradually cool to room temperature overnight. The resulting solid was collected by filtration, washed with EtOH (350 mL) and dried (10 mmHg, 40° C.) for 1.5 days to give (1R,2R)-N-benzyl-2-hydroxy-2-methylcyclopentanaminium (2S)-[(3,5-dinitrobenzoyl)amino](phenyl)acetate (2b-RR, 106 g, 99%). $^1$H NMR (400 MHz, DMSO-d$_6$) δ=9.66 (d, J=7.0 Hz, 1H), 9.09 (d, J=2.1 Hz, 2H), 8.96 (t, J=2.1 Hz, 1H), 7.55-7.46 (m, 2H), 7.44-7.22 (m, 8H), 5.48 (d, J=7.1 Hz, 1H), 4.63 (br s, 1H), 3.96-3.79 (m, 2H), 3.66-2.97 (m, 2H), 2.84 (t, J=7.9 Hz, 1H), 2.00-1.85 (m, 1H), 1.64-1.48 (m, 4H), 1.45-1.32 (m, 1H), 1.16 (s, 3H). MS: 206 [M+H]$^+$ for amine cation.

A stirred suspension of (1R,2R)-N-benzyl-2-hydroxy-2-methylcyclopentanaminium (2S)-[(3,5-dinitrobenzoyl)amino](phenyl)acetate (2b-RR, 106 g, 193 mmol) in water (500 mL) and EtOAc (700 mL) was treated with aq HCl (4 M, 193 mL, 770 mmol) and agitated for ~30 seconds. A clear biphasic mixture was obtained. The layers were separated, and the aqueous layer was extracted with more EtOAc (125 mL×2). The organic layers were set aside. The acidic aqueous layer was cooled in an ice-water bath, and basified to pH 10 with aq NaOH (4 N, 289 mL, 6 equiv, 1160 mmol). The resulting white suspension was diluted with sat. aq NaCl (300 mL) and extracted with EtOAc (700 mL×4). The combined organic extracts were dried over sodium sulfate, and evaporated to give (1R,2R)-2-(benzylamino)-1-methylcyclopentanol (2b-00, 38.5 g, 97%, 98% ee). $^1$H NMR (400 MHz, CDCl$_3$) δ=7.38-7.30 (m, 4H), 7.27-7.23 (m, 1H), 3.94-3.75 (m, 2H), 2.88 (dd, J=7.8, 8.4 Hz, 1H), 2.16-2.03 (m, 1H), 1.79-1.57 (m, 4H), 1.53-1.39 (m, 2H), 1.38-1.28 (m, 1H), 1.25 (s, 3H). MS: 206 [M+H]$^+$. Chiral purity: 98% ee. Chiral SFC/MS analysis was performed on a Chiralpak AS-3, 4.6×100 mm, 3 μm column heated to 25° C. and eluted with a mobile phase of CO$_2$ and 5% diethylamine in ethanol (20 mM v/v) in 1 min flowing at 3.5 mL/min and maintained at 160 bar outlet pressure. A gradient to 50% modifier in 3 min was added to elute any remaining counter ions. The detection was APCl(+)MS monitored from 100-800 Da with single ion monitoring (SIM) at 206 Da. The product peak had a retention time of 1.82 min. Optical rotation of this batch was not determined.

To a nitrogen-filled 3-L three-necked flask was added 20%-Pd(OH)$_2$/C (Aldrich 212911-10G, Lot # SHBC7570V, 3.85 g) and 2-propanol (260 mL). A solution of (1R,2R)-2-(benzylamino)-1-methylcyclopentanol (2b-00, 38.5 g, 188 mmol, 98% ee) in 2-propanol (1300 mL) was added. The transfer was quantitated with 2-propanol (30 mL). The solution was purged with hydrogen gas for ~2 min, and then stirred at room temperature under a hydrogen atmosphere (three balloons) for 16 h. The balloons were replenished with hydrogen and stirring continued at room temperature for 6 h, at which time $^1$H NMR of an aliquot indicated the reaction was complete. The reaction mixture was purged with nitrogen, and the catalyst removed by filtration through a Celite® cake. The flask and filter cake were washed with 2-propanol (500 mL). A small aliquot of the combined filtrate was evaporated for analysis. The remainder of the filtrate was concentrated under reduced pressure (~10 mmHg, 20° C.) to about 350 mL, and the crude (1R,2R)-2-amino-1-methylcyclopentanol (2c) used directly in the next step without further purification. $^1$H NMR (400 MHz, CDCl$_3$) δ=3.03 (t, J=7.4 Hz, 1H), 2.19-2.01 (m, 1H), 1.83-1.58 (m, 4H), 1.42 (s, 3H), 1.35-1.25 (m, 1H), 1.22 (s, 3H). MS: 116 [M+H]$^+$. Chiral SFC analysis: 96% ee. Chiral SFC/MS analysis was performed on a ChiroSil RCA (+), 4.6×150 mm 5µ column heated to 40° C. and eluted with a mobile phase of 20% ACN, 60% formic Acid in MeOH(1% v/v), 20% ammonium formate in MeOH (20 mM w/v) flowing at 1.5 mL/min. The detection was ESI (+) MS monitored from 100-650 Da with single ion monitoring (SIM) at 116 Da. The product peak had a retention time of 2.09 min. Optical rotation of a previous batch made by this method gave [α]$_D^{22}$–37.7 (c 0.3, MeOH).

To the crude solution of (1R,2R)-2-amino-1-methylcyclopentanol (2c, 188 mmol theoretical) in 2-propanol (~350 mL) was added solid [4-chloro-2-(methylsulfanyl)pyrimidin-5-yl]methanol (CAS #1044145-59-6, 34.8 g, 182 mmol) and DIPEA (95.3 mL, 547 mmol). The mixture was degassed with nitrogen and stirred under a nitrogen atmosphere at room temperature for 15 min, then at 80° C. for 40 h. The volatiles were removed, and the residual oil (95 g) was partitioned between EtOAc (800 mL) and sat. aq NaCl (250 mL). The aq layer was further extracted with EtOAc (500 mL×3). The combined organic extracts were dried over sodium sulfate and evaporated to give an oil (75 g). This oil was dissolved in EtOAc (200 mL), and the clear solution heated at 60° C. Some white solid was observed 5 min after initiation of heating. When at 60° C., heptane (400 mL) was slowly added to the suspension, and stirring continued at 60° C. for 15 min. The suspension was cooled to room temperature, and then cooled in an ice-water bath for 15 min. The resulting precipitate was collected by filtration and dried to give (1R,2R)-2-{[5-(hydroxymethyl)-2-(methylsulfanyl)pyrimidin-4-yl]amino}-1-methylcyclopentanol (2d, 47.8 g, 97%, 98% ee). $^1$H NMR (400 MHz, CDCl$_3$) δ=7.76 (s, 1H), 6.01 (d, J=4.6 Hz, 1H), 5.31 (br s, 1H), 4.55 (s, 2H), 4.26 (ddd, J=5.7, 8.2, 10.5 Hz, 1H), 2.50 (s, 3H), 2.21 (ddd, J=3.5, 8.2, 12.1 Hz, 1H), 1.97 (dt, J=3.5, 7.7 Hz, 1H), 1.89-1.76 (m, 2H), 1.75-1.63 (m, 1H), 1.60-1.50 (m, 2H), 1.11 (s, 3H). MS: 270 [M+H]$^+$. Optical rotation: [α]$_D^{22}$+37.7 (c 1.0, MeOH). Chiral purity: 98% ee. Chiral SFC/MS analysis was performed on a Chiralpak IC-3, 4.6×150 mm, 3 µm column heated to 25° C. and eluted with a mobile phase of CO$_2$ and 30% ammonia in methanol (20 mM v/v) flowing at 4.0 mL/min and maintained at 160 bar outlet pressure. The product peak had a retention time of 1.85 min.

To a 2 L, 3-necked flask equipped with a mechanical stirrer and a reflux condenser was added solid manganese dioxide (10 µm mesh, reagent grade, 278 g, 2660 mmol), EtOAc (1.2 L, 0.14 M) and solid (1R,2R)-2-{[5-(hydroxymethyl)-2-(methylsulfanyl)pyrimidin-4-yl]amino}-1-methylcyclopentanol (2d, 47.7 g, 177 mmol). The mixture was stirred under nitrogen and heated in a 50° C. oil bath for 4 h. More manganese dioxide (80 g) was added; stirring and heating were continued for another 16 h, until the reaction was complete by LCMS. The solid was removed by filtration, and the flask and filter cake were washed with EtOAc (1 L). The combined filtrates were refiltered to completely remove trace insolubles, and then evaporated to give 4-{[(1R,2R)-2-hydroxy-2-methylcyclopentyl]amino}-2-(methylsulfanyl)pyrimidine-5-carbaldehyde (Intermediate 2, 43.8 g, 93%, >98% ee) as a white solid. $^1$H NMR (400 MHz, CDCl$_3$) δ=9.73 (s, 1H), 8.66 (br s, 1H), 8.35 (s, 1H), 4.39 (ddd, J=6.5, 8.2, 9.6 Hz, 1H), 4.16 (s, 1H), 2.57 (s, 3H), 2.33-2.22 (m, 1H), 2.03-1.92 (m, 1H), 1.89-1.68 (m, 3H), 1.68-1.56 (m, 1H), 1.17 (s, 3H). MS: 268 [M+H]$^+$. Optical rotation [α]$_D^{22}$+12.7 (c 1.0, CHCl$_3$). Chiral purity: >98% ee. Chiral SFC/MS analysis was performed on a Chiralpak IC-3, 4.6×150 mm, 3 µm column heated to 25° C. and eluted with a mobile phase of CO$_2$ and 30% ammonia in methanol (20 mM v/v) flowing at 4.0 mL/min and maintained at 160 bar outlet pressure. The product peak had a retention time of 2.83 min.

Intermediate 3: 4-{[(1R,3R)-3-hydroxycyclohexyl]amino}-2-(methylsulfanyl)pyrimidine-5-carbaldehyde

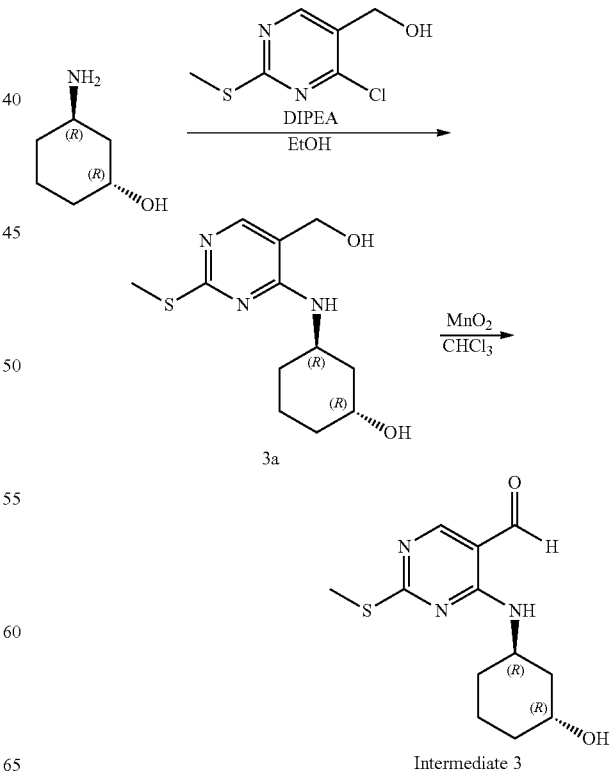

Intermediate 3

A solution of [4-chloro-2-(methylsulfanyl)pyrimidin-5-yl]methanol (CAS #1044145-59-6, 3.5 g, 18.4 mmol), (1R,3R)-3-aminocyclohexanol (3.34 g, 22.0 mmol) [Brocklehurst, C. E.; Laumen, K.; La Vecchia, L.; Shaw, D.; Vögtle, M. Org. Process Res. Dev. 2011, 15, 294. $[\alpha]_D^{22}$ −4.9 (c 1.2, MeOH)], and DIPEA (11.9 g, 16.3 mL) in EtOH (40 mL) was stirred at 85° C. for 20 h. After cooling to room temperature, the mixture was partitioned between water and DCM. The organics were concentrated to dryness and purified by silica gel chromatography (eluting with 0-30% MeOH in DCM) to give (1R,3R)-3-{[5-(hydroxymethyl)-2-(methylsulfanyl)pyrimidin-4-yl]amino}cyclohexanol (3a, 4.80 g, 97%) as a yellow foam. $^1$H NMR (400 MHz, CDCl$_3$) δ=7.62-7.47 (m, 1H), 6.05 (d, J=7.5 Hz, 1H), 4.58-4.31 (m, 3H), 4.02 (br d, J=3.0 Hz, 1H), 2.54-2.34 (m, 3H), 1.88-1.71 (m, 4H), 1.70-1.52 (m, 3H), 1.43 (br s, 1H). MS: 270 [M+H]$^+$. Optical rotation: $[\alpha]_D^{22}$+0.14 (c 2.8, MeOH). Chiral purity: >95% ee. Chiral SFC/MS analysis was performed on a Chiralpak AD-3, 4.6×150 mm, 3 μm column heated to 40° C. and eluted with a mobile phase of CO$_2$ and a gradient of 5 to 40% EtOH (0.05% DEA) over 5.5 min, flowing at 2.5 mL/min. Flow at 40% EtOH (0.05% DEA) was continued for 3 min to elute any remaining counter ions. The product peak had a retention time of 3.79 min.

A suspension of (1R,3R)-3-{[5-(hydroxymethyl)-2-(methylsulfanyl)pyrimidin-4-yl]amino}cyclohexanol (3a, 4.80 g, 17.8 mmol) and manganese dioxide (15.5 g, 178 mmol) in chloroform (70 mL) was stirred at room temperature for 18 h. The mixture was filtered, the flask and filter cake rinsed with EtOAc (100 mL) and THF (100 mL), and the combined filtrates concentrated to dryness. The residue was purified by silica gel chromatography (eluting with 0-40% EtOAc in petroleum ether) to give 4-{[(1R,3R)-3-hydroxycyclohexyl]amino}-2-(methylsulfanyl)pyrimidine-5-carbaldehyde (Intermediate 3, 3.70 g, 80%) as a yellow gum. $^1$H NMR (400 MHz, CDCl$_3$) δ=9.69 (s, 1H), 8.61 (br s, 1H), 8.30 (s, 1H), 4.75-4.49 (m, 1H), 4.27-4.01 (m, 1H), 2.56 (s, 3H), 2.00-1.87 (m, 2H), 1.87-1.56 (m, 6H). MS: 268 [M+H]$^+$. Optical rotation: $[\alpha]_D^{22}$+2.8 (c 1.4, MeOH). Chiral purity: 96%. Chiral SFC/MS analysis was performed on a Chiralpak AD-3, 4.6×150 mm, 3 μm column heated to 40° C. and eluted with a mobile phase of CO$_2$ and a gradient of 5 to 40% EtOH (0.05% DEA) over 5.5 min, flowing at 2.5 mL/min. Flow at 40% EtOH (0.05% DEA) was continued for 3 min to elute any remaining counter ions. The product peak had a retention time of 4.42 min.

Intermediate 4: 4-{[(1R,2R)-2-hydroxycyclopentyl]amino}-2-(methylsulfanyl)pyrimidine-5-carbaldehyde

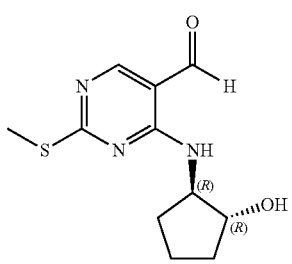

Intermediate 4

By the same method as Intermediate 3, (1R,2R)-2-aminocyclopentanol hydrochloride (CAS #68327-11-7) was used to produce 4-{[(1R,2R)-2-hydroxycyclopentyl]amino}-2-(methylsulfanyl)pyrimidine-5-carbaldehyde (Intermediate 4). $^1$H NMR (400 MHz, CDCl$_3$) δ=9.70 (s, 1H); 8.72-8.62 (m, 1H), 8.34 (s, 1H), 4.24-4.14 (m, 1H), 4.12-4.02 (m, 1H), 3.97 (s, 1H), 2.57 (s, 3H), 2.34-2.21 (m, 1H), 2.13-2.01 (m, 1H), 1.93-1.60 (m, 4H). MS: 254 [M+H]$^+$.

Intermediate 5: 4-(cycloheptylamino)-2-(methylsulfanyl)pyrimidine-5-carbaldehyde

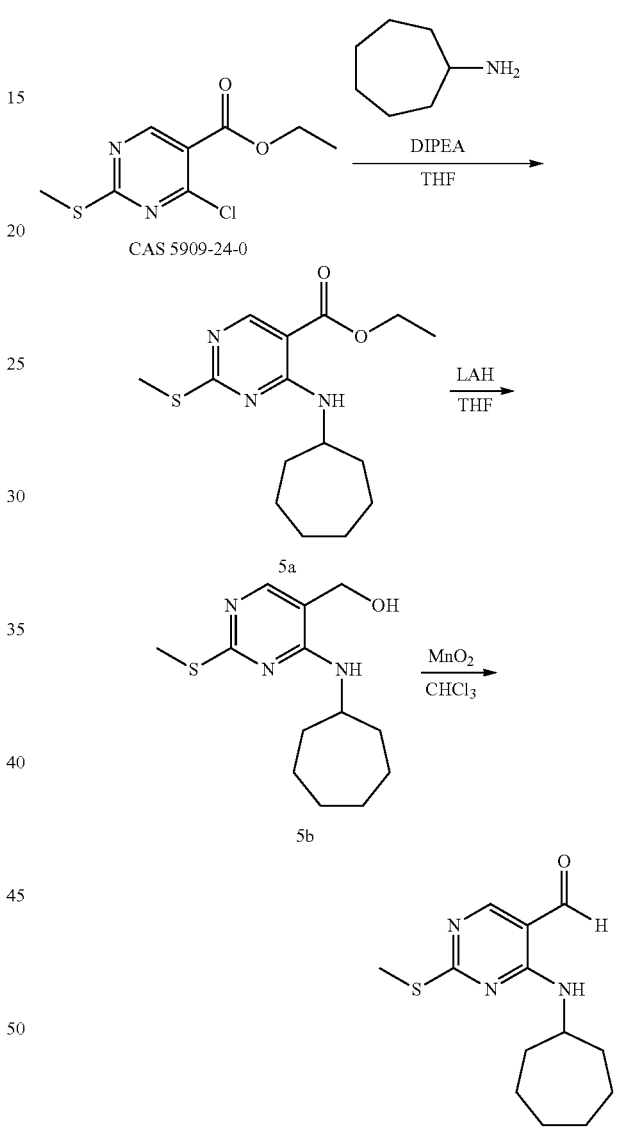

A suspension of ethyl 4-chloro-2-(methylsulfanyl)pyrimidine-5-carboxylate (CAS #5909-24-0, 16 g, 68.7 mmol), cycloheptylamine (9.34 g, 82.5 mmol) and DIPEA (17.8 g, 138 mmol) in THF (150 mL) was stirred at room temperature for 18 h. Solvents were evaporated, the residue dissolved in water (150 mL), and the solution extracted with EtOAc (150 mL×2). The combined organics were washed with sat. aq NaCl (150 mL×2), dried over sodium sulfate, and concentrated to give ethyl 4-(cycloheptylamino)-2-(methylsulfanyl)pyrimidine-5-carboxylate (5a, 21 g, 99%) as yellow oil. MS: 310 [M+H]$^+$.

A cooled (5° C.) solution of ethyl 4-(cycloheptylamino)-2-(methylsulfanyl)pyrimidine-5-carboxylate (5a, 21 g, 67.9 mmol) in THF (200 mL) was treated LAH (2.5 M solution in THF, 81.4 mL, 204 mmol) in portions over 1.5 h. The resulting suspension stirred at 5 to 10° C. for an additional hour, then at room temperature for 18 h. The mixture was cooled slightly (15° C.), then water (10 mL) and 2 N NaOH (10 mL) were added dropwise to quench any residual LAH. After stirring for 1 hour at room temperature, the suspension was filtered, and the flask and filter cake were rinsed with THF (300 mL×4). The combined filtrates were concentrated to remove most of the solvent. The residue was partitioned between water (100 mL) and EtOAc (250 mL×2). The combined organic layers were washed with sat. aq NaCl (100 mL), dried over sodium sulfate, and concentrated to dryness. The crude product was recrystallized from petroleum ether/EtOAc (200 m L/50 mL) to give [4-(cycloheptylamino)-2-(methylsulfanyl)pyrimidin-5-yl]methanol (5b, 13.6 g, 75%) as a white solid. MS: 268 [M+H]$^+$.

Manganese dioxide (43.3 g, 860 mmol) was added to a solution of [4-(cycloheptylamino)-2-(methylsulfanyl)pyrimidin-5-yl]methanol (5b, 13.6 g, 50 mmol) in chloroform (200 mL), and the resulting suspension stirred at room temperature for 15 h. The solids were removed by filtration. The flask and filter cake were rinsed with DCM (150 mL×4). The combined filtrates were filtered again to remove trace solids, and concentrated to give 4-(cycloheptylamino)-2-(methylsulfanyl)pyrimidine-5-carbaldehyde (Intermediate 5, 12.9 g, 98%) as a yellow oil. $^1$H NMR (400 MHz, CDCl$_3$) δ=9.68 (s, 1H), 8.63 (br s, 1H), 8.28 (s, 1H), 4.36-4.32 (m, 1H), 2.55 (s, 3H), 2.03-1.99 (m, 2H), 1.67-1.58 (m, 10H). MS: 266 [M+H]$^+$.

Intermediate 6: 4-{[(1R,2S)-2-methylcyclopentyl]amino}-2-(methylsulfanyl)pyrimidine-5-carbaldehyde Intermediate 6

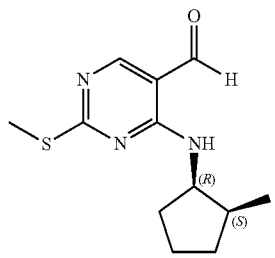

By the same method as Intermediate 5, (1R,2S)-2-methylcyclopentanamine [Wiehl, W.; Frahm, A. W. *Chem. Ber.* 1986, 119, 2668] was used to produce 4-{[(1R,2S)-2-methylcyclopentyl]amino}-2-(methylsulfanyl)pyrimidine-5-carbaldehyde (Intermediate 6). $^1$H NMR (400 MHz, CDCl$_3$) δ=9.70 (s, 1H), 8.67 (br s, 1H), 8.29 (s, 1H), 4.65-4.58 (m, 1H), 2.55 (s, 3H), 2.32-2.23 (m, 1H), 2.11-2.02 (m, 1H), 1.95-1.77 (m, 2H), 1.70-1.62 (m, 2H), 1.46-1.37 (m, 1H), 0.93 (d, J=6.8, 3H). MS: 252 [M+H]$^+$.

Intermediate 7: 4-{[(1S,2R)-2-methylcyclopentyl]amino}-2-(methylsulfanyl)pyrimidine-5-carbaldehyde Intermediate 7

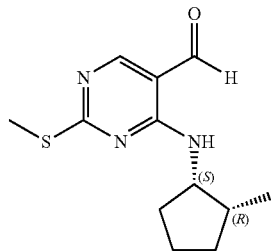

By the same method as Intermediate 5, (1S,2R)-2-methylcyclopentanamine [Wiehl, W.; Frahm, A. W. *Chem. Ber.* 1986, 119, 2668] was used to produce 4-{[(1S,2R)-2-methylcyclopentyl]amino}-2-(methylsulfanyl)pyrimidine-5-carbaldehyde (Intermediate 7). $^1$H NMR (400 MHz, CDCl$_3$) δ=9.68 (s, 1H), 8.73-8.59 (m., 1H), 8.27 (s, 1H), 4.67-4.52 (m, 1H), 2.53 (s, 3H), 2.29-2.20 (m, 1H), 2.12-1.99 (m, 1H), 1.92-1.75 (m, 2H), 1.63 (s, 2H), 1.45-1.34 (m, 1H), 0.91 (d, J=7.0, 3H). MS: 252 [M+H]$^+$.

Intermediate 8: (±)-4-{[(1R*,3R*)-3-hydroxycyclopentyl]amino}-2-(methylsulfanyl)-pyrimidine-5-carbaldehyde

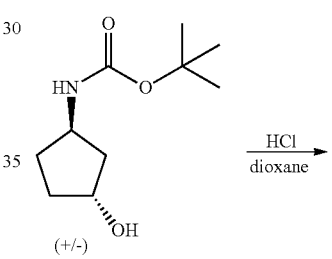

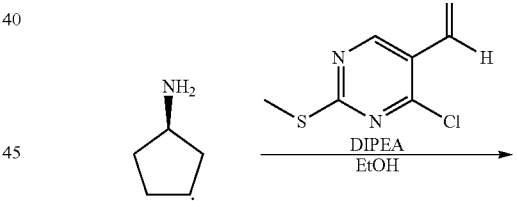

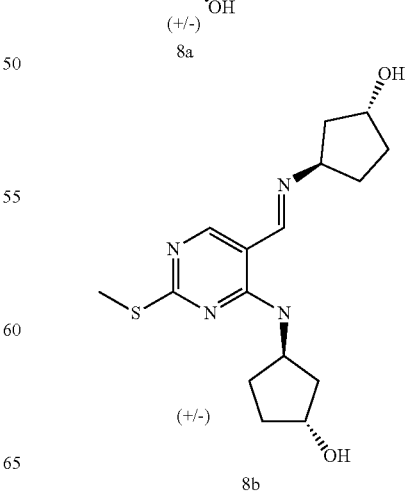

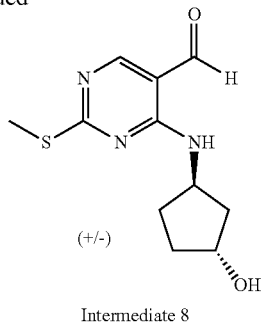

Intermediate 8

To a cooled (0° C.) solution of (±)-trans-(3-hydroxy-cyclopentyl)-carbamic acid tert-butyl ester (2.03 g, 10.1 mmol) [Kulagowski, J. J. et al. *J. Med. Chem.* 2012 55, 5901] in 1,4-dioxane (20 mL) was added HCl (4.0 mL solution in 1,4-dioxane, 20 mL, 80 mmol), and the mixture stirred at 0° C. for 1 h and at room temperature for 3 h. The solvents were evaporated, the residue dissolved DCM (50 mL), and a solution of NaOH (502.2 mg, 12.6 mmol) in water (1.5 mL) was added. After stirring at room temperature for 1 h, the reaction mixture was dried over a mixture of anhydrous sodium carbonate and anhydrous sodium sulfate, filtered, and concentrated to give (±)-trans-(3-hydroxy-cyclopentyl amine (8a, 0.68 g, 67%) as an amber liquid, which was used without further purification in the following reaction. $^1$H NMR (400 MHz, DMSO-d6) δ=4.29 (br s, 1H), 4.19-4.10 (m, 1H), 3.35 (quin, J=6.4 Hz, 1H), 1.93-1.80 (m, 2H), 1.64 (ddd, J=3.4, 6.9, 13.0 Hz, 1H), 1.54 (br s, 2H), 1.41-1.32 (m, 2H), 1.19-1.07 (m, 1H).

A solution of 4-chloro-2-(methylsulfanyl)pyrimidine-5-carbaldehyde (613.7 mg, 3.25 mmol) [Zheng, K.; Min Park, C.; Iqbal, S. Hernandez, P.; Park, H.; LoGrasso, P. V.; Feng, Y. *ACS Med. Chem. Lett.* 2015, 6, 413], (±)-trans-(3-hydroxy-cyclopentyl amine (8a, 0.68 g, 6.7 mmol), and DIPEA (3.0 mL, 17 mmol) in EtOH (32.5 mL) was heated in a 70° C. oil bath for 18 h. Solvents were evaporated and the residue partitioned between sat. aq NaHCO$_3$ (50 mL) and EtOAc (50 mL×3). The combined organic layers were dried over magnesium sulfate, filtered, and concentrated. The brown gummy residue was dissolved in ACN (20 mL), causing a precipitate to form. The slurry was concentrated to dryness, leaving crude imine diadduct (8b, 0.90 g, 82%) as a dark yellow solid, with minor impurities. $^1$H NMR (400 MHz, DMSO-d$_6$) δ=9.96 (d, J=6.8 Hz, 1H), 8.29 (s, 1H), 8.14 (s, 1H), 4.60 (d, J=3.9 Hz, 1H), 4.58 (d, J=3.9 Hz, 1H), 4.51 (sxt, J=6.8 Hz, 1H), 4.34-4.27 (m, 1H), 4.26-4.19 (m, 1H), 3.88 (quin, J=6.0 Hz, 1H), 2.47 (s, 3H), 2.25-2.14 (m, 1H), 2.10-1.78 (m, 5H), 1.77-1.68 (m, 1H), 1.63-1.45 (m, 4H), 1.38 (tdd, J=6.2, 8.7, 12.7 Hz, 1H).

The crude imine diadduct (8b, 0.90 g) was dissolved in THF (20 mL) and treated with HCl (4.0 M solution in 1,4-dioxane, 4.1 mL, 16.4 mmol). A light-colored precipitate formed immediately on contact with the acid, hindering stirring. More THF (10 mL) was added and the mixture manually shaken and sonicated until stirring could be re-established, then continued stirring at room temperature for 2 h. The reaction mixture was diluted with EtOAc (50 mL). While stirring, sat. aq NaHCO$_3$ (30 mL) was added drop-wise, causing mild gas evolution. The layers of the resulting clear, biphasic solution were separated and the aqueous layer further extracted with EtOAc (50 mL). The combined organic layers were dried over magnesium sulfate, filtered, and concentrated to give (±)-4-{[(1R*,3R*)-3-hydroxycyclopentyl]amino}-2-(methylsulfanyl)pyrimidine-5-carbaldehyde (Intermediate 8, 659.9 mg, 74% from 4-chloro-2-(methylsulfanyl)pyrimidine-5-carbaldehyde) as a brown oil. $^1$H NMR (400 MHz, DMSO-d$_6$) δ=9.74 (s, 1H), 8.52 (s, 1H), 8.54 (br s, 1H), 4.72-4.61 (m, 1H), 4.59 (d, J=3.8 Hz, 1H), 4.28-4.19 (m, 1H), 2.52 (s, 3H), 2.26-2.14 (m, 1H), 2.04-1.88 (m, 2H), 1.66 (ddd, J=5.9, 7.8, 13.4 Hz, 1H), 1.58-1.41 (m, 2H). MS: 254 [M+H]$^+$.

Intermediate 9:
4-amino-N-methylpiperidine-1-sulfonamide

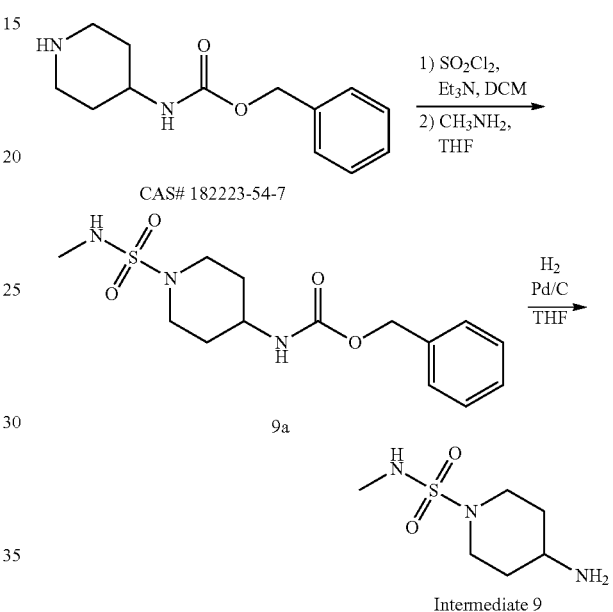

Intermediate 9

A solution of benzyl 4-piperidinylcarbamate (CAS #182223-54-7, 7.0 g, 27 mmol) and triethylamine (3.27 g, 32.3 mmol) in DCM (80 mL) was added to a chilled (0° C.) solution of sulfuryl chloride (3.99 g, 29.6 mmol) in DCM (70 mL), slowly enough to keep the internal temperature below 10° C. The cooling bath was removed and the mixture stirred at room temperature for 2 h. The reaction mixture was cooled again to 0° C., then a solution of methylamine (2.0 M in THF, 26.9 mL, 53.8 mmol) and more triethylamine (15 mL, 108 mmol) in DCM (50 mL) was added dropwise, keeping the internal temperature below 10° C. The resulting suspension was stirred at room temperature for 15 h. Because LCMS indicated the presence of residual chlorosulfonyl intermediate, the solution was cooled to 0° C. and more methylamine (2.0 M in THF, 40 mL, 80 mmol) added. Stirring was continued at room temperature for 3 h, at which time no chlorosulfonyl intermediate could be detected by LCMS. The reaction was partitioned between water (100 mL) and DCM (150 mL×2). The combined organic extracts were dried, concentrated, and purified by silica gel chromatography (eluting with 50-80% EtOAc in petroleum ether) to give benzyl [1-(methylsulfamoyl)piperidin-4-yl]carbamate (9a, 4.0 g, 90% purity, 45% yield) as a white solid. $^1$H NMR (400 MHz, CDCl$_3$) δ=7.42-7.31 (m, 5H), 5.17-5.06 (m, 2H), 4.73 (d, J=6.5 Hz, 1H), 4.12 (q, J=4.9 Hz, 1H), 3.67 (d, J=12.3 Hz, 3H), 2.97-2.88 (m, 2H), 2.72 (d, J=5.3 Hz, 3H), 2.03 (d, J=11.3 Hz, 2H), 1.57-1.46 (m, 2H). MS: 350 [M+Na]$^+$.

A suspension of benzyl [1-(methylsulfamoyl)piperidin-4-yl]carbamate (9a, 4.0 g, 12 mmol) and Pd/C(50% H₂O, 2 g) in THF (100 mL) was deoxygenated and purged with hydrogen (3 cycles), then stirred under a hydrogen balloon at room temperature for 4 h. The suspension was filtered, and the filtrate concentrated to give crude product (2.3 g, 85% purity, 100% yield) as a white solid.

Multiple batches made by this method were combined to give 45 g of crude product, which was then recrystallized from hot DCM to give pure 4-amino-N-methylpiperidine-1-sulfonamide (Intermediate 9, 40 g, 89%). ¹H NMR (400 MHz, DMSO-d6) δ=3.45-3.37 (m, 2H), 2.75-2.59 (m, 3H), 2.50 (s, 3H), 1.78-1.67 (m, 2H), 1.30-1.15 (m, 2H). MS: 194 [M+H]⁺.

Intermediate 10: 4-amino-N-(2-methoxy-2-methyl-propyl)piperidine-1-sulfonamide Intermediate 10

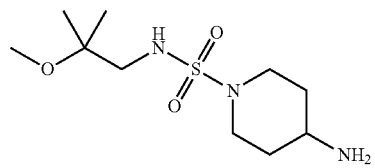

By the method of Intermediate 9, 2-methoxy-2-methyl-propan-1-amine was used to synthesize 4-amino-N-(2-methoxy-2-methylpropyl)piperidine-1-sulfonamide (Intermediate 10). ¹H NMR (400 MHz, CDCl₃) δ=4.54-4.42 (m, 1H), 3.67 (d, J=12.3 Hz, 2H), 3.19 (s, 3H), 3.01 (d, J=5.8 Hz, 2H), 2.88-2.76 (m, 3H), 1.89 (d, J=10.5 Hz, 2H), 1.39 (d, J=9.3 Hz, 2H), 1.21 (s, 6H)

Intermediate 11: 4-amino-N-(tetrahydro-2H-pyran-4-yl)piperidine-1-sulfonamide Intermediate 11

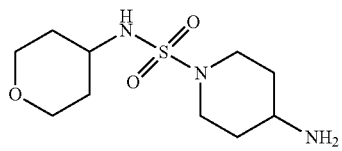

By the method of Intermediate 9, 4-aminotetrahydropyran was used to synthesize the compound 4-amino-N-(tetrahydro-2H-pyran-4-yl)piperidine-1-sulfonamide (Intermediate 11). ¹H NMR (400 MHz, CDCl₃) δ=4.24-4.13 (m, 1H), 3.95 (td, J=3.6, 11.7 Hz, 2H), 3.77-3.74 (m, 1H), 3.67 (d, J=12.5 Hz, 2H), 3.43 (dt, J=2.3, 11.7 Hz, 3H), 2.89-2.77 (m, 3H), 2.02-1.86 (m, 5H), 1.59-1.48 (m, 2H), 1.46-1.38 (m, 3H)

Other 4-amino-N-alkyl-piperidine-1-sulfonamides were synthesized by the method of Intermediate 9 and used crude, without purification or characterization, in the preparation of the example compounds of Table 1.

Intermediate 12: 1-[(2,2,2-trifluoroethyl)sulfonyl]piperidin-4-amine trifluoroacetate

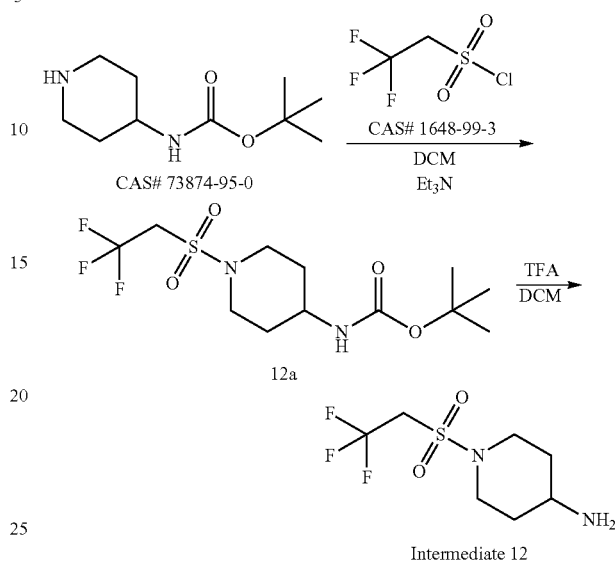

To an ice-bath-cooled solution of 4-(N-Boc-amino)piperidine (300 mg, 1.5 mmol) and triethylamine (303 mg, 3 mmol1) in DCM (10 mL) was added 2,2,2-trifluoroethanesulfonyl chloride (301 mg, 1.65 mmol), and the mixture stirred at room temperature for 2 h. The resulting precipitate was collected by filtration and dried under vacuum to give tert-butyl {1-[(2,2,2-trifluoroethyl)sulfonyl]piperidin-4-yl}carbamate (12a, 300 mg, 58%) as a white solid. ¹H NMR (400 MHz, DMSO-d6) δ=4.47 (q, J=10.2 Hz, 2H), 3.63-3.51 (m, 2H), 3.44-3.36 (m, 1H), 3.01-2.83 (m, 2H), 1.80 (d, J=10.5 Hz, 2H), 1.47-1.27 (m, 2H), 1.39 (s, 9H).

Trifluoroacetic acid (1 mL) was added to a solution of tert-butyl {1-[(2,2,2-trifluoroethyl)sulfonyl]piperidin-4-yl}carbamate (12a, 300 mg, 0.87 mmol) in DCM (10 mL), and the mixture stirred at room temperature for 14 h. Volatiles were evaporated and the residue dried under vacuum to give 1-[(2,2,2-trifluoroethyl)sulfonyl]piperidin-4-amine TFA salt (Intermediate 12, 300 mg, 74%) as a white gum. ¹H NMR (400 MHz, DMSO-d6) δ=8.05 (br s, 3H), 4.65-4.35 (m, 2H), 3.70 (d, J=12.8 Hz, 2H), 3.20 (d, J=4.8 Hz, 1H), 2.95 (t, J=11.7 Hz, 2H), 1.98 (d, J=10.5 Hz, 2H), 1.66-1.38 (m, 2H).

Intermediate 13: 1-(but-3-yn-1-ylsulfonyl)piperidin-4-amine Methanesulfonate

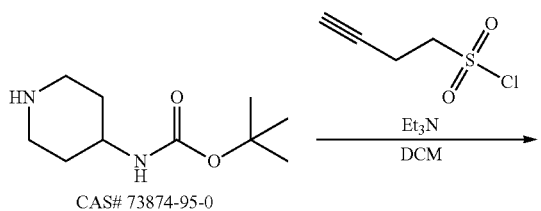

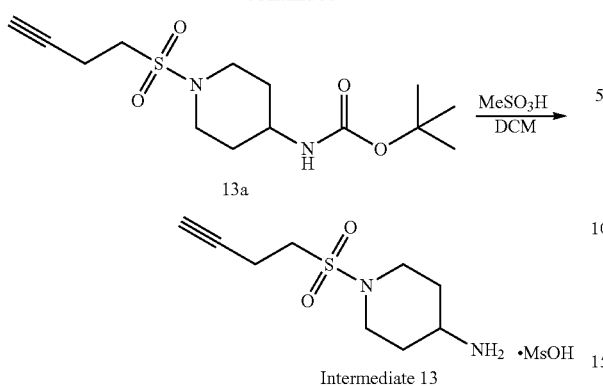

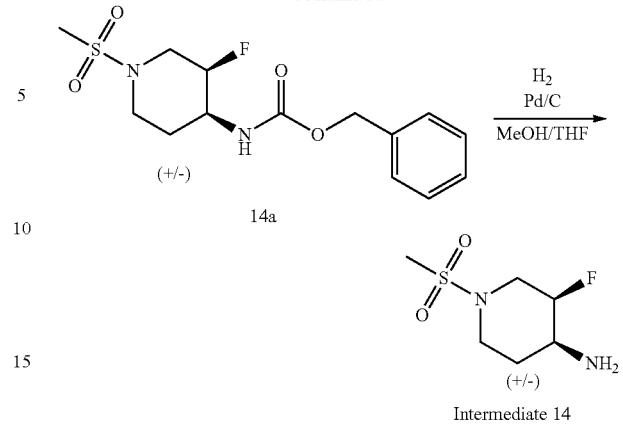

A solution of but-3-yne-1-sulfonyl chloride (653 mg, 4.3 mmol) in DCM (36 mL) under nitrogen was cooled in an acetone/dry ice bath. Solid 4-(N-Boc-amino)piperidine (714 mg, 3.6 mmol) was partially dissolved in DCM (8 mL) and was added via syringe. Triethylamine (646 μL, 4.6 mmol) was added dropwise over 1 minute. The mixture was stirred in the cooling bath under nitrogen for 30 minutes. While still cooled, the reaction was diluted with saturated aqueous NaHCO$_3$ (10 mL) and deionized water (10 mL). The mixture was extracted with DCM (50 mL). The organic layer was dried over sodium sulfate and evaporated to give tert-butyl (1-(but-3-yn-1-ylsulfonyl)piperidin-4-yl)carbamate (13a, 1.08 g, 96%) as a white solid. $^1$H NMR (400 MHz, CDCl$_3$) δ=4.45 (br s, 1H), 3.76 (d, J=12.7 Hz, 2H), 3.66-3.48 (m, 1H), 3.17-3.08 (m, 2H), 3.03-2.88 (m, 2H), 2.70 (dt, J=2.7, 7.6 Hz, 2H), 2.17-2.07 (m, 1H), 2.03 (dd, J=2.9, 13.1 Hz, 2H), 1.54-1.35 (m, 11H).

To a solution of tert-butyl (1-(but-3-yn-1-ylsulfonyl)piperidin-4-yl)carbamate (13a, 253 mg, 0.8 mmol) in DCM (8 mL) was added methanesulfonic acid (318 μL, 4.8 mmol), and the resulting solution stirred at room temperature for 30 minutes. The volatiles were evaporated and the residue suspended in ethyl ether (15 mL). The ether was decanted and the solid dried under high vacuum at room temperature to give 1-(but-3-yn-1-ylsulfonyl)piperidin-4-amine methanesulfonate (Intermediate 13, 248 mg, 99%) as a white solid. $^1$H NMR (400 MHz, DMSO-d6) δ=7.90 (br s, 3H), 3.65 (d, J=12.7 Hz, 2H), 3.27 (t, J=7.5 Hz, 2H), 2.93 (t, J=11.4 Hz, 2H), 2.57 (dt, J=2.6, 7.5 Hz, 2H), 2.36 (s, 5H), 1.96 (d, J=10.5 Hz, 2H), 1.51 (dq, J=3.9, 12.0 Hz, 2H). MS: 217 [M+H]$^+$.

Intermediate 14: (+/−)-cis-3-fluoro-1-(methylsulfonyl)piperidin-4-amine

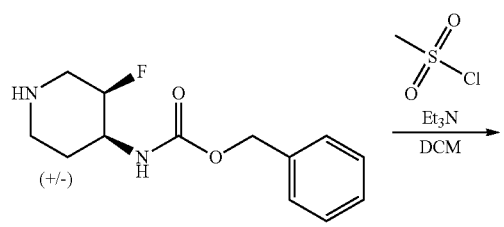

Racemic cis-(3-fluoro-piperidin-4-yl)-carbamic acid benzyl ester [Array Biopharma Inc. Patent: Triazolopyridine Compounds as PIM Kinase Inhibitors, WO2010/22081 A1, 2010] was sulfonylated by the method of Intermediate 12 and deprotected by the method of Intermediate 9 to give (+/−)-cis-3-fluoro-1-(methylsulfonyl)piperidin-4-amine (Intermediate 14) as a light yellow solid. $^1$H NMR (400 MHz, CD$_3$OD) δ=ppm 4.66 (d, J=48.4 Hz, 1H), 4.01-3.94 (m, 1H), 3.78-3.74 (m, 1H), 3.00 (dd, J=36.9, 14.0 Hz, 1H), 2.98-2.91 (m, 1H), 2.88 (s, 3H), 2.82 (t, J=8 Hz, 1H), 1.79-1.73 (m, 2H). MS: 197 [M+H]$^+$.

Other alkyl- and aryl-substituted sulfonylpiperidin-4-amines were synthesized by the methods of Intermediate 9, Intermediate 12, or Intermediate 13 and used crude, without purification or characterization, in the preparation of the example compounds on Table 1.

Intermediate 15: (±)-(1R*,2R*)-2-amino-1-ethylcyclopentan-1-ol

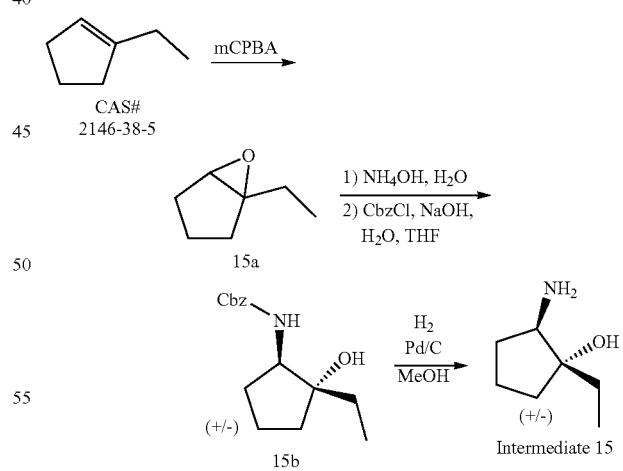

Epoxidation of 1-ethylcyclopentene (CAS #2146-38-5) followed by ring opening and Cbz-deprotection by the method of Intermediate 1 afforded (±)-(1R*,2R*)-2-amino-1-ethylcyclopentan-1-ol (Intermediate 15) as a yellow gum. $^1$H NMR (400 MHz, DMSO-d6) δ=2.86 (dd, J=3.5, 6.3 Hz, 1H), 2.03-1.92 (m, 1H), 1.63-1.51 (m, 4H), 1.41-1.35 (m, 2H), 1.20 (ddd, J=3.9, 7.2, 13.1 Hz, 1H), 0.87 (t, J=7.5 Hz, 3H).

Intermediate 15 was further elaborated by the method of Intermediate 2 and Method A to make Examples 194 and 195, as shown in Table 1.

Intermediate 16: (±)-(1R*,2S*,4R*)-4-((tert-butyldiphenylsilyl)oxy)-2-methylcyclopentan-1-amine

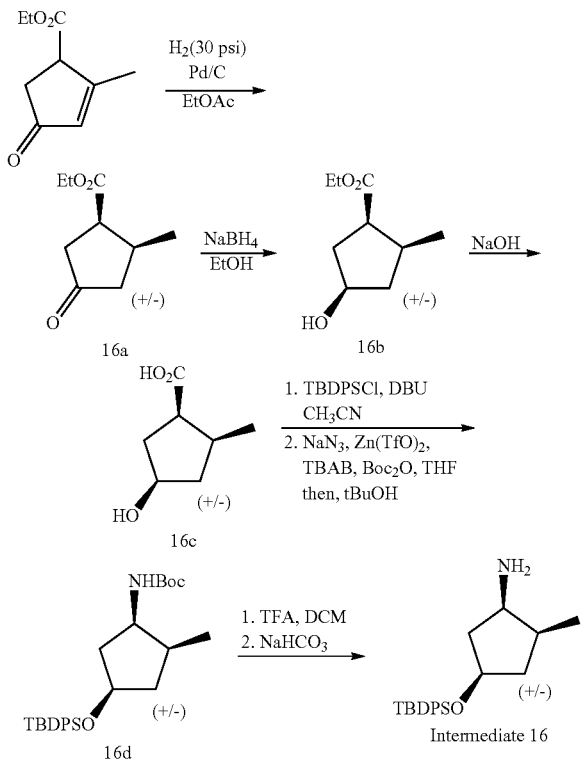

To a solution of ethyl 2-methyl-4-oxocyclopent-2-ene-1-carboxylate [Dolby, L. J. et al. *J. Org. Chem.* 1968, 33(12), 4508] (24.0 g, 119 mmol) in EtOAc (500 mL) was added 10 wt % Pd/C (6.0 g). Hydrogen gas was bubbled through the mixture for about 5 minutes, then the mixture was stirred under 30 psi hydrogen for 48 h. The hydrogen source was removed and the mixture was purged with nitrogen for 5 minutes. The Pd/C was filtered off using a pad of Celite®, which was washed with ethyl acetate. The filtrate was concentrated to afford 24 g yellow oil. The crude oil was purified via silica gel chromatography (eluting with petroleum ether/EtOAc 10/1 to 3/1) to give (±)-ethyl (1R*,2S*)-2-methyl-4-oxocyclopentane-1-carboxylate (16a, 19.3 g, 80%) as an oil. $^1$H NMR (400 MHz, CDCl$_3$) δ=4.16-4.09 (m, 2H), 3.15-3.08 (m, 1H), 2.63 (td, J=7.4, 14.6 Hz, 1H), 2.58-2.49 (m, 1H), 2.36-2.24 (m, 2H), 2.13-2.04 (m, 1H), 1.22 (t, J=7.2 Hz, 3H), 1.00 (d, J=7.0 Hz, 3H).

A solution of (±)-ethyl (1R*,2S*)-2-methyl-4-oxocyclopentane-1-carboxylate (16a, 10 g, 59 mmol) in ethanol (300 mL) was chilled to 0° C. under nitrogen. Sodium borohydride (1.11 g, 29.4 mmol) was added in small portions. The reaction was allowed to stir at 0° C. for 1 hour. The reaction was quenched by the slow addition of sat. aq. ammonium chloride solution (50 mL), followed by water (50 mL) to dissolve any solids. Ethanol was removed under reduced pressure and the aqueous residue extracted with MTBE (2×300 mL). The combined organics were washed with sat. aq. NaCl (500 mL), dried over anhydrous sodium sulfate, filtered, and concentrated under reduced pressure to give (±)-ethyl (1R*,2S*,4R*)-4-hydroxy-2-methylcyclopentane-1-carboxylate (16b, 9.9 g, 97%) as a yellow oil. $^1$H NMR (400 MHz, CDCl$_3$) δ=4.24-4.16 (m, 1H), 4.14-4.03 (m, 2H), 3.57 (br s, 1H), 2.74 (dt, J=3.8, 7.4 Hz, 1H), 2.29-2.11 (m, 2H), 2.04-1.95 (m, 1H), 1.89 (td, J=3.6, 14.2 Hz, 1H), 1.35-1.26 (m, 1H), 1.23-1.18 (m, 3H), 0.95 (d, J=6.8 Hz, 3H).

A mixture of (±)-ethyl (1R*,2S*,4R*)-4-hydroxy-2-methylcyclopentane-1-carboxylate (16b, 9.9 g, 57 mmol) in aqueous NaOH (115 mL of 1 M, 115 mmol) was stirred at room temperature for 18 h. MTBE (100 mL) was added and the layers separated. The aqueous layer was cooled to 0° C. and acidified to pH 1 by slow addition of aqueous HCl (5N). The aqueous suspension was extracted with EtOAc (4×200 mL). The combined organic layers were washed with sat. aq. NaCl (100 mL), dried over anhydrous magnesium sulfate, filtered and concentrated to give (±)-(1R*,2S*,4R*)-4-hydroxy-2-methylcyclopentane-1-carboxylic acid (16c, 7.9 g, 95%) as a yellow oil. $^1$H NMR (400 MHz, DMSO-d6) δ=12.01 (br s, 1H), 4.67 (br s, 1H), 4.02 (t, J=6.9 Hz, 1H), 2.67 (q, J=7.9 Hz, 1H), 2.19 (td, J=7.1, 14.1 Hz, 1H), 2.03-1.93 (m, 2H), 1.81-1.67 (m, 1H), 1.28-1.15 (m, 1H), 0.93 (d, J=6.3 Hz, 3H).

A solution of (±)-(1R*,2S*,4R*)-4-hydroxy-2-methylcyclopentane-1-carboxylic acid (16c, 7.9 g, 55 mmol), tert-butyl(chloro)diphenylsilane (TBDPSCl, 15.8 g, 57.5 mmol), and DBU (10 g, 66 mmol) in acetonitrile (200 mL) was stirred at room temperature for 15 h. The reaction mixture was concentrated and partitioned between DCM and sat. aq. ammonium chloride. The organic layer was washed with sat. aq. NaCl over sodium sulfate, concentrated, and purified by silica gel chromatography (eluting with 100% DCM to DCM/MeOH 20/1) to give (±)-(1R*,2S*,4R*)-4-((tert-butyldiphenylsilyl)oxy)-2-methylcyclopentane-1-carboxylic acid (18 g, 85%) as an impure yellow oil which was used in the next step without further purification.

To a solution of (±)-(1R*,2S*,4R*)-4-((tert-butyldiphenylsilyl)oxy)-2-methylcyclopentane-1-carboxylic acid (700 mg, 1.83 mmol), sodium azide (297 mg, 4.57 mmol), tetrabutylammonium bromide (TBAB, 118 mg, 0.366 mmol), and zinc triflate (200 mg, 0.549 mmol) in THF (20 mL) was added di-tert-butyl dicarbonate (599 mg, 2.74 mmol). The mixture was stirred in a sealed tube under argon at 60° C. for 24 h, then tert-butanol (67.8 mg, 0.915 mmol) was added via syringe. Stirring was continues at 60° C. for another 24 h. The mixture was cooled to room temperature and quenched with 10% aqueous NaNO$_2$ (10 mL). Ethyl acetate was added and the biphasic mixture stirred for 30 min at room temperature. The two layers were separated, and the organic layer was washed successively with sat. aq. NH$_4$Cl (15 mL), and brine (15 mL). The organic solution was dried over sodium sulfate, filtered, and concentrated to give crude 16d as yellow oil. A total of seven individual batches were run separately on 700 mg scale as described above, then the batches were combined and purified via silica gel chromatography (petroleum ether/EtOAc 10/1) to give (±)-tert-butyl ((1R*,2S*,4R*)-4-((tert-butyldiphenylsilyl)oxy)-2-methylcyclopentyl)carbamate (16d, 3.3 g, 56% from a total of seven batches of 700 mg each). MS: 476.1 [M+H]$^+$, $^1$H NMR (400 MHz, DMSO-d6) δ=7.62-7.57 (m, 4H), 7.48-7.40 (m, 6H), 6.59 (d, J=8.8 Hz, 1H), 4.13 (t, J=6.1 Hz, 1H), 3.77-3.61 (m, 1H), 1.99-1.82 (m, 3H), 1.66 (td, J=6.6, 12.9 Hz, 1H), 1.37 (s, 10H), 1.00 (s, 9H), 0.88 (d, J=6.5 Hz, 3H). 2D NMR analysis confirmed the relative stereochemical assignment of all cis.

Trifluoroacetic acid (10 mL) was added to a solution of (±)-tert-butyl ((1R*,2S*,4R*)-4-((tert-butyldiphenylsilyl)oxy)-2-methylcyclopentyl)carbamate (16d, 1.9 g, 4.2 mmol) in DCM (30 mL), and the solution was stirred at room temperature for 2 h. The reaction solution was concentrated, the residue diluted with DCM (100 mL), and sat. aq. NaHCO₃ (50 mL) was added to neutralize residual acid. The layers were separated and aqueous layer extracted with DCM (100 mL). The combined organic layers were dried, filtered and concentrated to give the crude (±)-(1R*,2S*,4R*)-4-((tert-butyldiphenylsilyl)oxy)-2-methylcyclopentan-1-amine (Intermediate 16, 1.5 g) as an oil. ¹H NMR (400 MHz, CDCl₃) δ=7.72 (dd, J=1.8, 7.8 Hz, 1H), 7.66 (ddd, J=1.5, 3.5, 7.8 Hz, 3H), 7.48-7.32 (m, 6H), 4.30-4.19 (m, 1H), 3.08 (d, J=4.3 Hz, 1H), 2.03-1.90 (m, 2H), 1.79 (br s, 1H), 1.68 (td, J=3.2, 13.9 Hz, 1H), 1.51-1.39 (m, 1H), 1.13-0.95 (m, 12H).

Intermediate 16 was further elaborated using the method of Intermediate 5, via $S_NAr$ addition to ethyl 4-chloro-2-(methylsulfanyl)pyrimidine-5-carboxylate, reduction of the ester by LAH, and oxidation of the resulting alcohol by MnO₂. The tert-butyldiphenylsilyl protecting group was incidentally cleaved during LAH reduction. Subsequent synthesis following Method A produced Examples 199 and 200, as shown in Table 1.

Intermediate 17 (±)-(1R*,3S*,4S*)-3-amino-4-fluorocyclohexan-1-ol hydrochloride

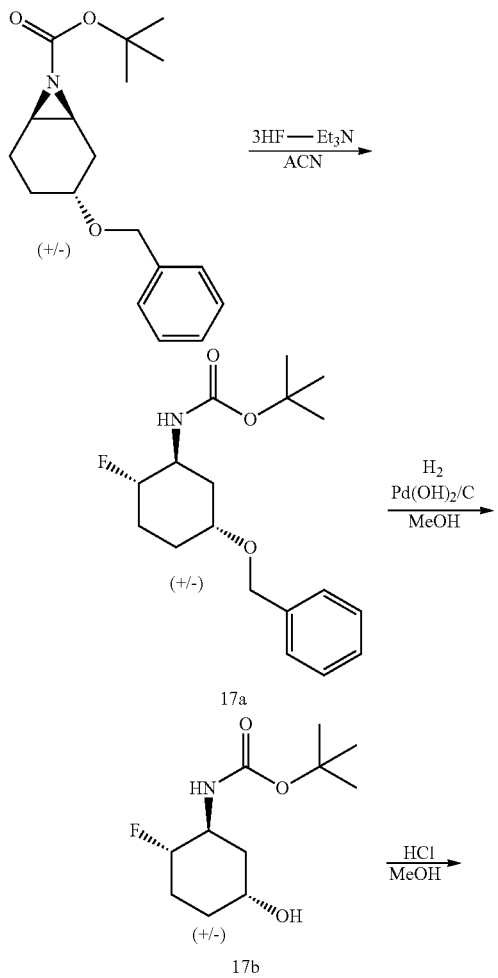

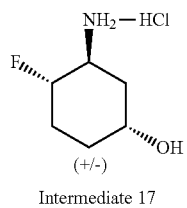

Intermediate 17

In a sealed polypropylene vessel a solution of (±)-(tert-butyl (1S*,3R*,6R*)-3-(benzyloxy)-7-azabicyclo[4.1.0]heptane-7-carboxylate [Crotti, P. et al. *J. Org. Chem.* 1995, 60, 2514](4.0 g, 13 mmol) and triethylamine trihydrofluoride (12.8 g, 79.2 mmol) in acetonitrile (10 mL) was stirred at 90° C. for 18 h. After cooling to room temperature, the mixture was partitioned between water and ethyl acetate. The organic layer was washed with sat. aq. NaCl, dried over sodium sulfate, concentrated, and purified by silica gel chromatography (eluting with petroleum ether/EtOAc 10/1 to 1/1) to afford 2.4 g of the desired product but with 85% purity by HPLC. This material was further purified by preparative HPLC to afford (±)-tert-butyl ((1S*,2S*,5R*)-5-(benzyloxy)-2-fluorocyclohexyl)carbamate (17a, 1.88 g, 44%) as white solid. ¹H NMR (400 MHz, CD₃OD) δ=7.47-7.18 (m, 5H), 4.62-4.48 (m, 2H), 4.40-4.18 (m, 1H), 3.92 (br dd, J=3.9, 10.7 Hz, 1H), 3.78-3.68 (m, 1H), 2.16 (br dd, J=1.8, 11.0 Hz, 1H), 2.04-1.84 (m, 3H), 1.57-1.39 (m, 11H).

A solution of (±)-tert-butyl ((1S*,2S*, 5R*)-5-(benzyloxy)-2-fluorocyclohexyl)carbamate (17a, 1.88 g, 5.81 mmol) and Pd(OH)₂/C (1.0 g) in methanol (100 mL) was stirred under 45 psi hydrogen at room temperature for 18 h. The catalyst was filtered off and the filtrate concentrated to afford (±)-tert-butyl ((1S*,2S*,5R*)-2-fluoro-5-hydroxycyclohexyl)carbamate (17b, 1.36 g, 100%) as white solid which was used without further purification. ¹H NMR (400 MHz, CD₃OD) δ=4.42-4.15 (m, 1H), 4.04-3.86 (m, 2H), 3.33 (td, J=1.6, 3.3 Hz, 1H), 2.00-1.82 (m, 3H), 1.81-1.71 (m, 1H), 1.62-1.50 (m, 2H), 1.46 (s, 9H).

To a solution of (±)-tert-butyl ((1S*,2S*,5R*)-2-fluoro-5-hydroxycyclohexyl)carbamate (17b, 1.36 g, 5.83 mmol) in MeOH (20 mL) was added 4 M HCl in MeOH (20 mL, 80 mmol). The mixture was stirred at room temperature for 1 hour, then concentrated and lyophilized to give (±)-(1R*,3S*,4S*)-3-amino-4-fluorocyclohexan-1-ol hydrochloride (Intermediate 17, 0.985 g, 100%) as a white hygroscopic solid. MS: 134.1 [M+H]⁺, ¹H NMR (400 MHz, D₂O) δ=4.75-4.52 (m, 1H), 4.23-4.09 (m, 1H), 3.69-3.53 (m, 1H), 2.22-2.03 (m, 2H), 1.95-1.80 (m, 2H), 1.75-1.61 (m, 2H), ¹⁹F NMR (376 MHz, D₂O) δ=−179.8 (s, 1F).

Intermediate 17 was used without further purification as described for Intermediate 3 and Method A to afford Examples 217-220 shown in Table 1.

Intermediate 18: (1S,2S,5R)-5-((tert-butyldiphenylsilyl)oxy)-2-methylcyclohexan-1-amine

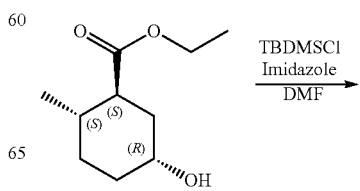

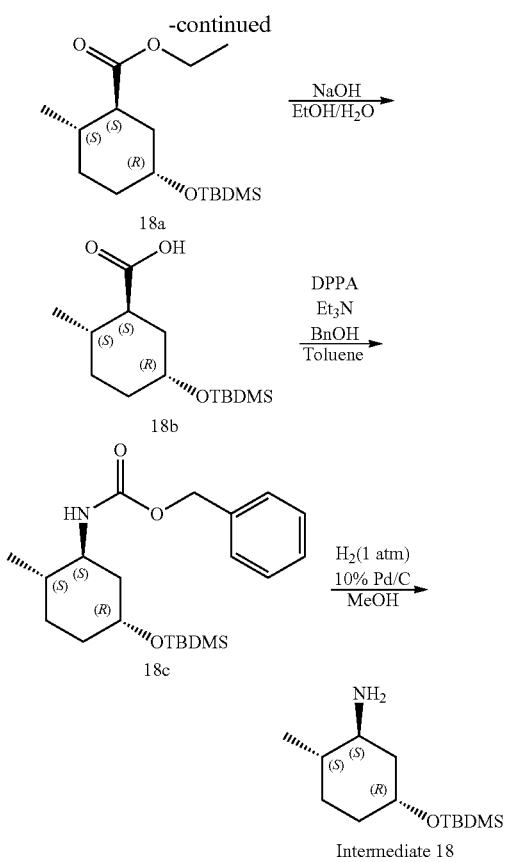

A solution of ethyl (1S,2S,5R)-5-hydroxy-2-methylcyclohexane-1-carboxylate [Raw, A. S. and Jang, E. B. *Tetrahedron* 2000, 56, 3285-3290] (6.25 g, 33.6 mmol), imidazole (6.85 g, 101 mmol), and tert-butyl(chloro)diphenylsilane (18.4 g, 67.1 mmol) in DMF (80 mL) was stirred at 20° C. for 40 h. The reaction was quenched with deionized water (200 mL) and extracted with ethyl acetate (3×80 mL). The combined organics were washed with sat. aq. NaCl, dried over sodium sulfate, concentrated, and purified by silica gel chromatography (eluting with ethyl acetate in pet. ether) to give ethyl (1S,2S,5R)-5-((tert-butyldimethylsilyl)oxy)-2-methylcyclohexane-1-carboxylate (18a, 10.5 g, 74%) as a light yellow oil. $^1$H NMR (400 MHz, CDCl$_3$) δ=7.72-7.62 (m, 4H), 7.47-7.35 (m, 6H), 4.21-4.02 (m, 3H), 2.67-2.50 (m, 1H), 1.87-1.77 (m, 1H), 1.69-1.58 (m, 3H), 1.52-1.32 (m, 3H), 1.26 (t, J=7.2 Hz, 3H), 1.10-1.07 (m, 9H), 0.95 (d, J=6.0 Hz, 3H).

A mixture of sodium hydroxide (4.71 g, 118 mmol) and (1S,2S,5R)-5-((tert-butyldimethylsilyl)oxy)-2-methylcyclohexane-1-carboxylate (18a, 5.0 g, 11.8 mmol) in ethanol (80 mL) and deionized water (80 mL) was stirred at 80° C. for 15 h. The volatiles were evaporated and the aqueous residue neutralized to pH 6 with 1N HCl. The product was extracted with ethyl acetate (3×100 mL). The combined organics were washed with sat. aq. NaCl, dried over sodium sulfate, concentrated, and purified by silica gel chromatography (eluting with ethyl acetate in pet. ether) to give (1S,2S,5R)-5-((tert-butyldimethylsilyl)oxy)-2-methylcyclohexane-1-carboxylic acid (18b, 2.55 g, 55%) as a light grey solid. Chiral SFC showed no epimerization. [Major peak at rt 2.72 min, Chiral SFC method: Column: ChiralCel OJ-H 150×4.6 mm I.D., 5 µm. Mobile phase: A: CO$_2$ B: ethanol (0.05% DEA). Gradient: from 5% to 40% of B in 5.5 min and hold 40% for 3 min, then 5% of B for 1.5 min. Flow rate: 2.5 mL/m in Column temperature at 40° C.].

A solution of (1S,2S,5R)-5-((tert-butyldimethylsilyl)oxy)-2-methylcyclohexane-1-carboxylic acid (18b, 4.0 g, 10.1 mmol), triethylamine (3.1 g, 30.3 mmol), and diphenyl phosphoryl azide (DPPA, 4.2 g, 15.1 mmol) in toluene (100 mL) was stirred at 110° C. for 3 h. Benzyl alcohol (5.5 g, 50.4 mmol) was added and stirring continued at 110° C. for 32 h more. After cooling to room temperature, the reaction was concentrated and the residue was purified by silica gel chromatography (eluting with ethyl acetate in pet. ether) to give benzyl ((1S,2S,5R)-5-((tert-butyldiphenylsilyl)oxy)-2-methylcyclohexyl)carbamate (18c, 2.8 g, 55%) as an oil. $^1$H NMR (400 MHz, CDCl$_3$) δ=7.79-7.62 (m, 4H), 7.48-7.31 (m, 11H), 5.26-5.07 (m, 2H), 4.49-4.37 (m, 1H), 4.18-4.05 (m, 1H), 3.92-3.71 (m, 1H), 2.11-1.92 (m, 1H), 1.78-1.60 (m, 3H), 1.35-1.19 (m, 3H), 1.14-1.01 (m, 12H). MS: 524 [M+Na]$^+$.

Benzyl ((1S,2S,5R)-5-((tert-butyldiphenylsilyl)oxy)-2-methylcyclohexyl)carbamate (18c, 3.50 g, 6.98 mmol) in methanol (75 mL) was treated with 10% palladium on carbon (350 mg) and stirred at 30° C. under a hydrogen balloon for 16 h. The catalyst was removed by filtration and the filtrate was evaporated to give (1S,2S,5R)-5-((tert-butyldiphenylsilyl)oxy)-2-methylcyclohexan-1-amine (Intermediate 18, 2.5 g, 98%) as an oil. $^1$HNMR (400 MHz, CDCl$_3$) δ=7.77-7.61 (m, 4H), 7.47-7.35 (m, 6H), 4.26-4.09 (m, 1H), 2.95-2.77 (m, 1H), 1.91-1.83 (m, 1H), 1.67-1.58 (m, 3H), 1.53-1.43 (m, 1H), 1.35-1.23 (m, 1H), 1.20-1.12 (m, 2H), 1.09 (s, 12H). MS: 368 [M+H]$^+$.

Intermediate 18 was employed in synthesis using the methods of Intermediate 3 and Method A, with silyl deprotection by TBAF as an additional step before thioether oxidation with OXONE®, to produce Example 216, as shown in Table 1.

Intermediate 19: (±)-(3S*,4R*)-44(5-(hydroxymethyl)-2-(methylthio)pyrimidin-4-yl)amino)-3-methyltetrahydrofuran-3-ol

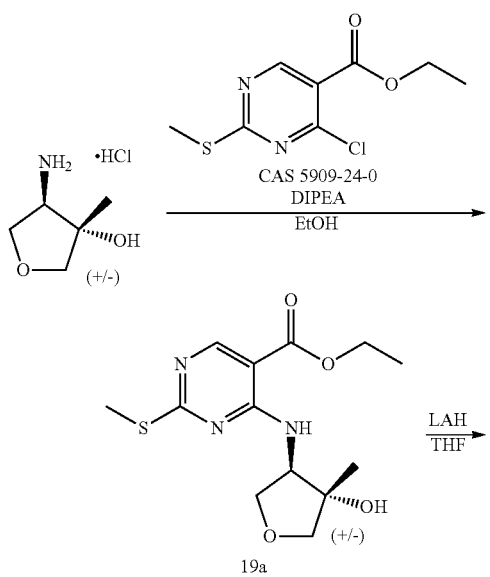

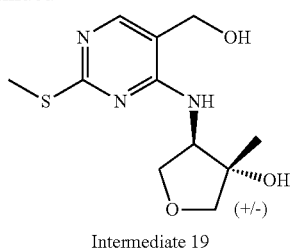

Intermediate 19

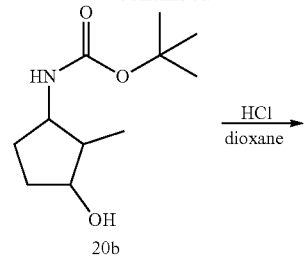

By the method of Intermediate 5, S$_N$Ar addition of ethyl 4-chloro-2-(methylsulfanyl)pyrimidine-5-carboxylate (CAS #5909-24-0) (6.0 g, 26 mmol), and (±)-(3S*,4R*)-4-amino-3-methyltetrahydrofuran-3-ol hydrochloride [Eli Lilly and Co. Patent: Selective Androgen Receptor Modulators. WO 2013/055577 A1, 2013] (6.1 g, 28 mmol) with diisopropylethyl amine (20 g, 155 mmol) in ethanol (120 mL) afforded (±)-ethyl 4-(((3R*,4S*)-4-hydroxy-4-methyltetrahydrofuran-3-yl)amino)-2-(methylthio)pyrimidine-5-carboxylate (19a, 6.2 g, 77%), which was then reduced by LAH (1.91 g, 50.5 mmol) in THF (150 mL). After aqueous workup, the major isomer was isolated by preparative HPLC, to give (±)-(3S*,4R*)-44(5-(hydroxymethyl)-2-(methylthio)pyrimidin-4-yl)amino)-3-methyltetrahydrofuran-3-ol (Intermediate 19, 1.51 g, 33%) as a white solid. $^1$H NMR (400 MHz, CDCl$_3$) δ=7.80 (s, 1H), 6.08 (d, J=6.0 Hz, 1H), 4.65-4.56 (m, 3H), 4.36 (dd, J=9.16, 7.65 Hz, 1H), 3.90 (d, J=9.0 Hz, 1H), 3.76 (d, J=9.3 Hz, 1H), 3.65 (dd, J=9.16, 6.90 Hz, 1H), 2.54-2.49 (m, 3H), 1.26 (s, 3H).

Intermediate 19 was oxidized to the corresponding aldehyde using MnO$_2$ by the method of Intermediate 5, and further elaborated by Method A to synthesize Examples 197 and 198 and Example 198, as shown in Table 1.

Intermediate 20: (±)-(1R*,2S*,3R*)-34(5-(hydroxymethyl)-2-(methylthio)pyrimidin-4-yl)amino)-2-methylcyclopentan-1-ol Intermediate 21: (±)-(1R*,2R*,3S*)-34(5-(hydroxymethyl)-2-(methylthio)pyrimidin-4-yl)amino)-2-methylcyclopentan-1-ol Intermediate 22: (±)-(1R*,2R*,3R*)-34(5-(hydroxymethyl)-2-(methylthio)pyrimidin-4-yl)amino)-2-methylcyclopentan-1-ol

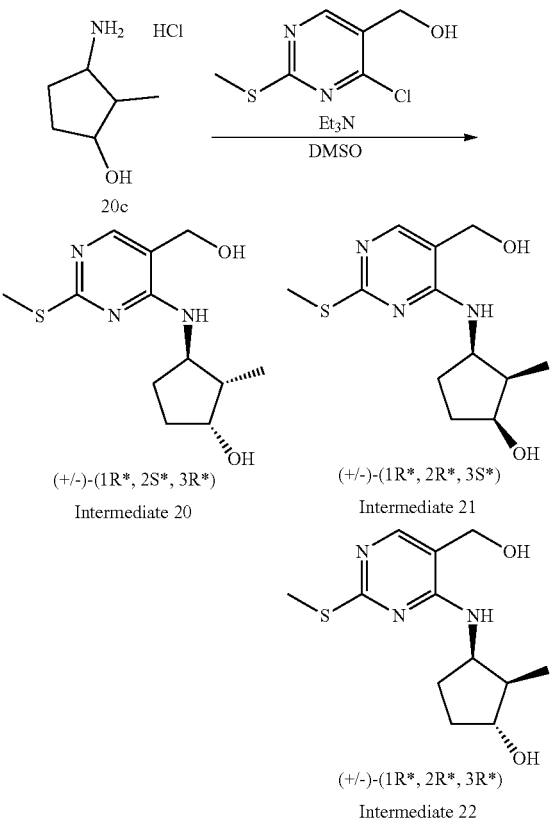

A suspension of N-(2-methyl-3-oxocyclopent-1-en-1-yl)acetamide [Huang, K.; Guan, Z.-H.; Zhang, X., Tet. Lett., 2014, 55, 1686-1688] (17.6 g, 115 mmol), 20% Pd(OH)$_2$ (wet) (4.4 g, 28.8 mmol), and DIPEA (37.2 g, 288 mmol) in ethyl acetate (80 mL) was hydrogenated in a stainless steel reactor at 20 Bar and 80° C. for 18 h. The catalyst was removed by filtration through a bed of Celite®, and the filter cake washed with ethyl acetate (100 mL) and water (100 mL). The biphasic filtrate layers were separated, and the aqueous layer extracted with ethyl acetate (3×30 mL). The combined organics were dried over sodium sulfate and concentrated to give a mixture of diastereomers of N-(3-hydroxy-2-methylcyclopentyl)acetamide (20a, 2.32 g), as a yellow oil. A different mixture of 20a diastereomers remained in the aqueous layer, which were not isolated but carried on in solution. Both fractions were taken to the next step without further purification.

Solid potassium hydroxide (8.21 g, 146 mmol) was added portion wise to a solution of N-(3-hydroxy-2-methylcyclopentyl)acetamide (20a, 2.30 g, from the organic extracts above) in water (100 mL). The mixture was heated to 90° C. for 72 h. After cooling the solution to room temperature, di-tert-butyl-dicarbonate (6.39 g, 29.3 mmol) and tetrahydrofuran (150.0 mL) were added. The reaction was stirred at room temperature for 48 h. After aqueous work-up the products were purified by silica gel chromatography (eluting with 0-80% ethyl acetate/heptane) to give tert-butyl (3-hydroxy-2-methylcyclopentyl)carbamate (20b, 3.15 g) as a mixture of diastereomers. The aqueous layer from the first step, containing a different mixture of 20a diastereomers, was hydrolyzed and Boc-protected by the same procedure to give a second batch of 20b (10.1 g, mixture of diastereomers).

A solution of tert-butyl (3-hydroxy-2-methylcyclopentyl) carbamate (20b, 9.3 g, 43.2 mmol) in 1,4-dioxane (50 mL) was treated with hydrochloric acid (216 mL of a 4M solution in 1,4-dioxane, 864 mmol), and stirred at room temperature for 2 h. The volatiles were evaporated, leaving crude 3-amino-2-methylcyclopentan-1-ol hydrochloride (20c, 7.0 g) as a mixture of diastereomers, which was used in the subsequent reaction without further purification. The other batches of 20b were treated similarly to obtain batches of 20c with different mixtures of diastereomers.

A solution of crude 3-amino-2-methylcyclopentan-1-ol hydrochloride (20c, 7.0 g, 60.78 mmol, mixture of diastereomers), diisopropylethyl amine (39.3 g, 304 mmol), [4-chloro-2-(methylsulfanyl)pyrimidin-5-yl]methanol (CAS #1044145-59-6) (11.6 g, 60.8 mmol) in DMSO (20 mL) was heated to 50° C. for 48 h. Triethylamine (18.5 g, 182 mmol) was added, and heating continued for 20 h more. The reaction mixture was poured into ice/water and extracted with ethyl acetate (3×100 mL). The combined organics were washed with saturated aqueous NaCl (3×100 mL), washed with deionized water (100 mL), dried over sodium sulfate and concentrated to give 3-((5-(hydroxymethyl)-2-(methylthio)pyrimidin-4-yl)amino)-2-methylcyclopentan-1-ol as a mixture of diastereomers. The other batches of 20c were treated similarly to obtain different mixtures of diastereomers.

The various mixtures of 34(5-(hydroxymethyl)-2-(methylthio)pyrimidin-4-yl)amino)-2-methylcyclopentan-1-ol diastereomers were resolved into four separate racemic pairs over several steps by crystallization, flash chromatography, and non-chiral preparative HPLC. Stereochemistry of the resulting enantiomeric pairs was determined by 2-D NMR.

(±)-(1R*,2S*,3R*)-3-((5-(hydroxymethyl)-2-(methylthio)pyrimidin-4-yl)amino)-2-methylcyclopentan-1-ol (Intermediate 20): ¹H NMR (400 MHz, DMSO-d6) δ=7.81 (s, 1H), 6.46 (d, J=7.8 Hz, 1H), 5.10 (t, J=5.5 Hz, 1H), 4.43 (d, J=4.2 Hz, 1H), 4.33 (d, J=5.5 Hz, 2H), 4.24 (quin, J=8.5 Hz, 1H), 3.99 (d, J=3.0 Hz, 1H), 2.42 (s, 3H), 2.12-2.23 (m, 1H), 1.87-2.00 (m, 1H), 1.75-1.87 (m, 1H), 1.46-1.59 (m, 1H), 1.27-1.41 (m, 1H), 0.94 (d, J=6.8 Hz, 3H). MS: 270 [M+H]⁺.

(±)-(1R*,2R*,3S*)-3-((5-(hydroxymethyl)-2-(methylthio)pyrimidin-4-yl)amino)-2-methylcyclopentan-1-ol (Intermediate 21): ¹H NMR (400 MHz, DMSO-d6) δ=7.81 (s, 1H), 6.57 (d, J=7.8 Hz, 1H), 5.11 (t, J=5.5 Hz, 1H), 4.73 (d, J=4.6 Hz, 1H), 4.32 (d, J=5.5 Hz, 2H), 3.86-4.13 (m, 1H), 3.48-3.69 (m, 1H), 2.40 (s, 3H), 1.93-2.08 (m, 1H), 1.79-1.93 (m, 1H), 1.65-1.79 (m, 1H), 1.44-1.62 (m, 2H), 0.98 (d, J=6.8 Hz, 3H). MS: 270 [M+H]⁺.

(±)-(1R*,2R*,3R*)-34(5-(hydroxymethyl)-2-(methylthio)pyrimidin-4-yl)amino)-2-methylcyclopentan-1-ol (Intermediate 22): ¹H NMR (400 MHz, DMSO-d6) δ=7.81 (s, 1H), 6.34 (d, J=7.9 Hz, 1H), 5.21 (t, J=5.4 Hz, 1H), 4.57-4.70 (m, 2H), 4.25-4.41 (m, 2H), 3.74 (quin, J=5.1 Hz, 1H), 2.34-2.46 (m, 3H), 2.00-2.12 (m, 2H), 1.89-2.00 (m, 1H), 1.49-1.63 (m, 1H), 1.31-1.47 (m, 1H), 0.74 (d, J=7.2 Hz, 3H). MS: 270 [M+H]⁺.

The fourth of the four possible pairs of enantiomers was also isolated, but not used in further synthesis. (±)-(1R*,2S*,3S*)-34(5-(hydroxymethyl)-2-(methylthio)-pyrimidin-4-yl)amino)-2-methylcyclopentan-1-ol: ¹H NMR (400 MHz, DMSO-d6) δ=7.78 (s, 1H), 6.64 (d, J=8.7 Hz, 1H), 5.13 (t, J=5.2 Hz, 1H), 4.75 (d, J=3.4 Hz, 1H), 4.44-4.62 (m, 1H), 4.30 (s, 2H), 3.89-4.05 (m, 1H), 2.41 (s, 3H), 1.91-2.04 (m, 2H), 1.73-1.81 (m, 1H), 1.54-1.73 (m, 2H), 0.89 (d, J=7.1 Hz, 3H). MS: 270 [M+H]⁺.

Intermediate 20, Intermediate 21, and Intermediate 22 were separately oxidized to the corresponding aldehydes by MnO2 using the method of Intermediate 1, and further elaborated by Method A and other general synthetic methods described herein to synthesize Examples 201-210 shown in Table 1.

Intermediate 23: (±)-(1S*,2R*,3S*)-34(5-(hydroxymethyl)-2-(methylthio)pyrimidin-4-yl)amino)-2-methylcyclohexan-1-ol

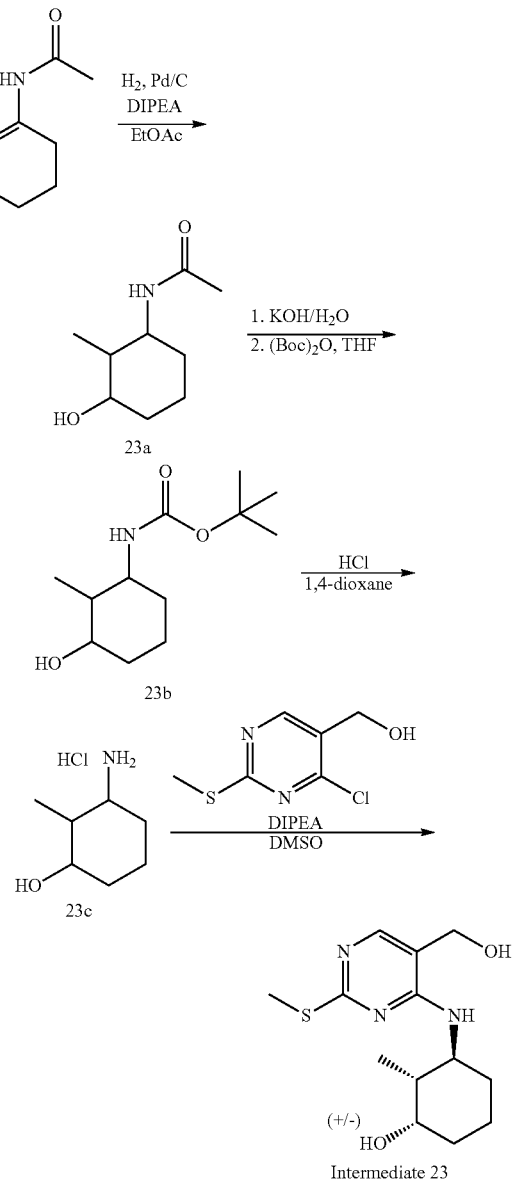

Intermediate 23

A solution of N-(2-methyl-3-oxocyclohex-1-en-1-yl)acetamide [CAS #36887-93-1] (20 g, 120 mmol), DIPEA (38.8 g, 300 mmol) and 20% Pd/C (2 g, 12 mmol) in ethyl acetate (80 mL) was hydrogenated in a stainless steel vessel under 20 bar hydrogen at 80° C. for 20 h. The reaction mixture was filtered while still hot, and the filter cake washed with hot ethyl acetate. The combined filtrate was concentrated and the solid residue crystallized in DCM/heptane to give a mixture of diastereomers of N-(3-hydroxy-2-methylcyclohexyl)acetamide (23a, 10.0 g, 51%) as a white solid.

Solid potassium hydroxide (22.9 g, 409 mmol) was added portion wise to a solution of N-(3-hydroxy-2-methylcyclohexyl)acetamide (23a, 7.0 g, 40 mmol) in water (200.0 mL). The reaction was heated to 100° C. for 24 h and then to 90° C. for 72 h more. The solution was cooled to room temperature and di-tert-butyl dicarbonate (9.8 g, 45.0 mmol) and tetrahydrofuran (150 mL) were added. Stirring was continued at room temperature for 48 h. The solution was extracted with ethyl acetate (3×100 mL) and the organics were combined, dried over sodium sulfate and concentrated. The residue was purified by silica gel chromatography (eluting with 0-100% ethyl acetate in heptane) to give tert-butyl (3-hydroxy-2-methylcyclohexyl)carbamate (23b, 2.50 g, 30%) as a diastereomeric mixture. $^1$H NMR (400 MHz, CDCl$_3$) δ=4.20-4.60 (m, 1H), 3.84-4.04 (m, 1H), 3.44-3.66 (m, 1H), 1.89-2.02 (m, 1H), 1.67-1.88 (m, 2H), 1.49-1.58 (m, 1H), 1.45 (s, 9H), 1.14-1.42 (m, 2H), 0.95-1.12 (m, 3H).

A solution of tert-butyl (3-hydroxy-2-methylcyclohexyl)carbamate (23b, 2.50 g, 10.9 mmol) in 1,4-dioxane (100 mL) was treated with hydrochloric acid (40.9 mL of a 4M solution in 1,4-dioxane, 164 mmol), and stirred at room temperature for 20 h. The volatiles were removed and the residue dried in a vacuum oven for 72 h to give a mixture of diastereomers of 3-amino-2-methylcyclohexan-1-ol hydrochloride (23c, 1.68 g, 93%) as a yellow solid. $^1$H NMR (400 MHz, DMSO-d6) δ=7.57-8.28 (m, 3H), 3.58-3.78 (m, 1H), 2.55-3.19 (m, 1H), 1.71-2.01 (m, 1H), 1.60-1.71 (m, 1H), 1.51-1.60 (m, 2H), 1.06-1.51 (m, 3H), 0.70-1.06 (m, 3H).

A solution of [4-chloro-2-(methylsulfanyl)pyrimidin-5-yl]methanol (CAS #1044145-59-6) (2 g, 10.5 mmol), 3-amino-2-methylcyclohexan-1-ol hydrochloride (23c 1.5 g, 11.7 mmol, mixture of diastereomers) and DIPEA (4.5 g, 35.1 mmol) in DMSO (20.0 mL) was heated to 50° C. for 20 h, then poured over ice/water and extracted with ethyl acetate (3×100 mL). The organics were washed with sat. aq. NaCl (3×50 mL), dried over sodium sulfate, concentrated, and purified by silica gel chromatography, eluting with 0-100% ethyl acetate in heptane. This method was adequate to separate the desired diastereomer, (±)-(1S*,2R*,3S*)-34 (5-(hydroxymethyl)-2-(methylthio)pyrimidin-4-yl)amino)-2-methylcyclohexan-1-ol (Intermediate 23, 169 mg, 5.7%, the least polar of the product peaks) as a white solid. The relative stereochemistry was determined by 2-D NMR. $^1$H NMR (400 MHz, DMSO-d6) δ=7.79 (s, 1H), 6.30 (d, J=8.6 Hz, 1H), 5.12 (t, J=5.5 Hz, 1H), 4.36 (d, J=3.9 Hz, 1H), 4.32 (d, J=5.5 Hz, 2H), 4.05-4.17 (m, 1H), 3.77 (br s, 1H), 2.41 (s, 3H), 1.78-1.94 (m, 1H), 1.68-1.75 (m, 1H), 1.54-1.65 (m, 1H), 1.33-1.50 (m, 2H), 1.11-1.29 (m, 2H), 0.89 (d, J=6.8 Hz, 3H). MS: 284 [M+H]$^+$.

Intermediate 23 was oxidized to the corresponding aldehyde with MnO$_2$, then further elaborated by Method A to make Examples 221 and 222 shown in Table 1.

EXAMPLES

General Methods and Representative Examples

Method A (Aldol cyclization)

Example 1

8-cyclopentyl-2-{[1-(methylsulfonyl)piperidin-4-yl]amino}pyrido[2,3-d]pyrimidin-7(8H)-one

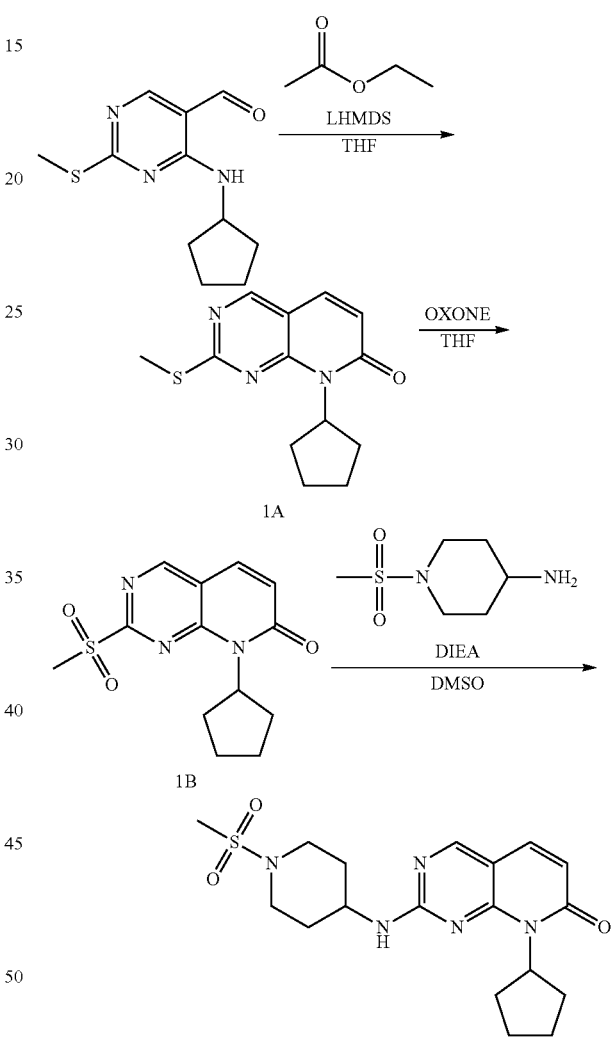

Example 1

To a solution of 4-(cyclopentylamino)-2-(methylsulfanyl)pyrimidine-5-carbaldehyde [VanderWel, et al. *J. Med. Chem.* 2005, 48, 2371] (2.0 g, 8.4 mmol) in anhydrous THF (50 mL) was added EtOAc (2.23 g, 25.3 mmol) at −70° C. The mixture was stirred at this temperature for 15 min, then LHMDS (1.0 M in THF, 29.5 mmol, 29.5 mL) was added dropwise. The reaction was stirred at −70° C. for 30 min and then at 20° C. for 16 h. The solution was cooled in an ice bath, quenched with water, and then extracted with EtOAc (50 mL×3). The combined organic layers were washed with aq NH$_4$Cl (30 mL), and sat. aq NaCl (30 mL), dried over sodium sulfate, and concentrated. The residue was purified by silica gel chromatography (eluting with petroleum ether/ EtOAc 10/1 to 3/1) to give 8-cyclopentyl-2-(methylsulfanyl) pyrido[2,3-d]pyrimidin-7(8H)-one (1A, 2.01 g, 91%) as a white solid. MS: 262 [M+H]+.

OXONE®, (23.5 g, 38.3 mmol) was added to a cooled (0° C.) solution of 8-cyclopentyl-2-(methylsulfanyl)pyrido[2,3-d]pyrimidin-7(8H)-one (1A, 5.0 g, 19.13 mmol) in THF (100 mL) and water (20 mL), and the mixture stirred at room temperature for 2 h. The mixture was diluted with EtOAc (300 mL), washed with water (100 mL), dried over sodium sulfate, and concentrated to give crude 8-cyclopentyl-2-(methylsulfonyl)pyrido[2,3-d]pyrimidin-7(8H)-one (1B, 5.40 g, 96%) as a gray solid. MS: 315 [M+Na]+.

A solution of crude 8-cyclopentyl-2-(methylsulfonyl) pyrido[2,3-d]pyrimidin-7(8H)-one (1B, 5.40 g, 17.0 mmol), 4-amino-1-methanesulfonylpiperidine (CAS #402927-97-3, 5.34 g, 24.9 mmol) and DIPEA (14.7 mL, 82.8 mmol) in DMSO (70 mL) was stirred at 65° C. for 18 h. The reaction mixture was diluted with DCM (150 mL), washed with aq NH₄Cl (80 mL×2), dried over sodium sulfate, and concentrated to dryness. The crude product was recrystallized with 1/2 EtOAc:petroleum ether (50 mL) to give 8-cyclopentyl-2-{[1-(methylsulfonyl)piperidin-4-yl]amino}pyrido[2,3-d]pyrimidin-7(8H)-one (Example 1, 4.65 g, 72%) as a gray solid. ¹H NMR (400 MHz, DMSO-d6) δ=8.68-8.54 (m, 1H), 7.88 (d, J=6.3 Hz, 1H), 7.68 (d, J=9.3 Hz, 1H), 6.28-6.16 (m, 1H), 5.92-5.74 (m, 1H), 4.02-3.82 (m, 1H), 3.58 (d, J=10.8 Hz, 2H), 2.96-2.82 (m, 5H), 2.33 (d, J=1.8 Hz, 1H), 2.19 (br s, 1H), 2.03-1.91 (m, 4H), 1.78-1.55 (m, 6H). MS: 392 [M+H]+.

Example 2

8-[(1R,2R)-2-hydroxy-2-methylcyclopentyl]-2-{[1-(methylsulfonyl)piperidin-4-yl]amino}pyrido[2,3-d]pyrimidin-7(8H)-one

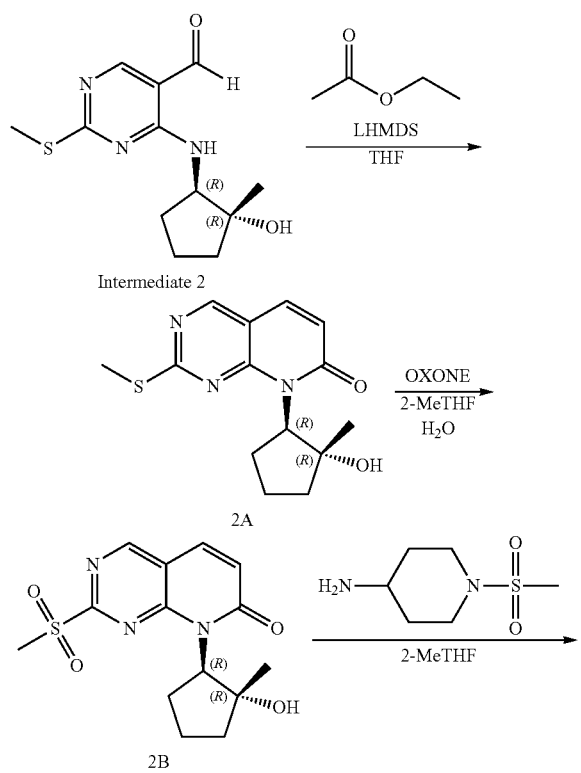

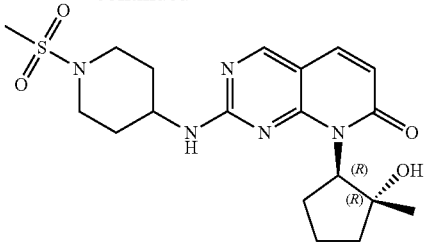

Example 2

To a 2 L three-necked flask equipped with a mechanical stirrer and an internal thermometer was added solid 4-{[(1R, 2R)-2-hydroxy-2-methylcyclopentyl]amino}-2-(methylsulfanyl)pyrimidine-5-carbaldehyde (Intermediate 2, 34.2 g, 128 mmol), THF (400 mL), and EtOAc (33.4 mL, 333 mmol). The solution was purged with nitrogen and cooled in a MeOH-ice bath to −5° C. internal. Via cannula, LHMDS (1.0 M solution in THF, 4×100 mL freshly opened bottles, 400 mmol) was added, slowly enough to keep the internal temperature at −5° C. A light yellow precipitate began to form after ~300 mL LHMDS solution had been added. Stirring was continued as the mixture was allowed to gradually warm to room temperature overnight. The resulting red solution was cooled in an ice-water bath to ~3° C. internal, then EtOH (224 mL, 3840 mmol) was added via cannula, slowly enough to keep the internal temp at ~3° C. internal. The mixture was stirred in the ice bath for 1 hour, then the cooling bath was removed, the solution allowed to warm to 20° C. internal, and stirring continued for 1 h. The solvents were evaporated, the residue diluted with water (180 mL) and sat. aq NaCl (180 mL), and the aqueous layer extracted with EtOAc (700 mL, then 600 mL×2). The combined organic extracts were dried over sodium sulfate and concentrated to a light yellow-brown foam (43.8 g). This foam was dissolved in EtOAc (70 mL) and sonicated to induce precipitation. The resulting solid was collected by filtration, rinsed with EtOAc (10 mL), and dried to give 8-[(1R,2R)-2-hydroxy-2-methylcyclopentyl]-2-(methylsulfanyl)pyrido[2,3-d]pyrimidin-7(8H)-one (2A, 21.4 g, 58%, >99% ee) as a white solid. ¹H NMR (400 MHz, CDCl₃) δ=8.61 (s, 1H), 7.56 (d, J=9.4 Hz, 1H), 6.60 (d, J=9.4 Hz, 1H), 5.84 (t, J=8.6 Hz, 1H), 2.92-2.76 (m, 1H), 2.64 (s, 3H), 2.34-2.19 (m, 2H), 2.13-2.01 (m, 2H), 2.00-1.81 (m, 2H), 1.16 (s, 3H). MS: 292 [M+H]+. Optical rotation: [α]_D^{22}=−12.9 (c 1.0, MeOH). Chiral purity: >99% ee. Chiral SFC/MS analysis was performed on a Chiralpak AD-3, 4.6×100 mm, 3 μm column heated to 25° C. and eluted with a mobile phase of CO₂ and 40% methanol flowing at 4.0 mL/min and maintained at 120 bar outlet pressure. The product peak had a retention time of 0.85 min.

The mother liquor from the above precipitation was evaporated to dryness. The residue (24.5 g) was dissolved in EtOAc (30 mL) and the solution sonicated to induce precipitation. After filtration and drying, a second crop of 8-[(1R,2R)-2-hydroxy-2-methylcyclopentyl]-2-(methylsulfanyl)pyrido[2,3-d]pyrimidin-7(8H)-one (2A, 4.70 g, 13%, >99% ee) was obtained as a white solid. The total yield for both crops was 26.1 g (71% at >99% ee) after crystallization.

A solution of 8-[(1R,2R)-2-hydroxy-2-methylcyclopentyl]-2-(methylsulfanyl)-pyrido[2,3-d]pyrimidin-7(8H)-one (2A, >99% ee, 2.33 g, 8 mmol), 2-MeTHF (40 mL), water (8 mL) and OXONE® (12.3 g, 20 mmol) was stirred at room temperature for 4 h. The solution was cooled in a water bath, diluted with water (10 mL) and sat. aq NaCl (10 mL), and extracted with EtOAc (80 mL×3). The combined organic extracts were dried over sodium sulfate, evaporated to a dark oil (3.76 g), and purified by silica gel chromatography (eluting with a gradient of 20-100% EtOAc in heptane) to give 8-[(1R,2R)-2-hydroxy-2-methylcyclopentyl]-2-(methylsulfonyl)pyrido[2,3-d]pyrimidin-7(8H)-one (2B, 2.2 g, 84%) as a foamy solid. $^1$H NMR (400 MHz, CDCl$_3$) δ=8.96 (s, 1H), 7.74 (d, J=9.5 Hz, 1H), 6.90 (d, J=9.4 Hz, 1H), 5.77 (t, J=8.5 Hz, 1H), 3.40 (s, 3H), 2.92-2.73 (m, 1H), 2.36-2.25 (m, 1H), 2.19-2.08 (m, 2H), 2.03-1.85 (m, 2H), 1.14 (s, 3H). MS: 306 [M–18]$^+$.

A solution of 8-[(1R,2R)-2-hydroxy-2-methylcyclopentyl]-2-(methylsulfonyl)-pyrido[2,3-d]pyrimidin-7(8H)-one (2B, 800 mg, 2.47 mmol), and 4-amino-1-methanesulfonylpiperidine (CAS #402927-97-3, 970 mg, 5.44 mmol) in 2-MeTHF (12.4 mL) was heated in a 60° C. oil bath for 24 h. After cooling to room temperature, the mixture was partitioned between EtOAc (80 mL), water (10 mL) and sat. aq NaHCO$_3$ (10 mL). The aqueous layer was further extracted with EtOAc (60 mL×2). The combined organic extracts were dried over sodium sulfate and evaporated to dryness. The residue (1.23 g) was dissolved in EtOAc (11 mL), seed crystals were added, and the solution allowed to stand at room temperature overnight. The resulting solid was collected by filtration, rinsed with EtOAc (3 mL) and dried to give 8-[(1R,2R)-2-hydroxy-2-methylcyclopentyl]-2-{[1-(methylsulfonyl)piperidin-4-yl]amino}pyrido[2,3-d]pyrimidin-7(8H)-one (Example 2, 680 mg, 63%, >99% ee) as a white solid. $^1$H NMR (400 MHz, CDCl$_3$) δ=8.43 (s, 1H), 7.45 (d, J=9.3 Hz, 1H), 6.36 (d, J=9.4 Hz, 1H), 5.73 (t, J=8.4 Hz, 1H), 5.34 (br s, 1H), 4.01 (br s, 1H), 3.88-3.74 (m, 2H), 3.01-2.89 (m, 2H), 2.83 (s, 4H), 2.36 (br s, 1H), 2.29-2.14 (m, 3H), 2.03 (dt, J=2.9, 6.3 Hz, 2H), 1.98-1.89 (m, 1H), 1.88-1.81 (m, 1H), 1.78-1.60 (m, 2H), 1.18 (s, 3H). MS: 422 [M+H]$^+$. Optical rotation: $[α]_D^{22}$ –17.0 (c 1.0, CHCl$_3$). Chiral purity: >99% ee. Chiral SFC/MS analysis was performed on a Lux Cellulose-1, 4.6×100 mm, 3 μm column heated to 25° C. and eluted with a mobile phase of CO$_2$ and 5-60% methanol gradient in 3.0 min flowing at 4.0 mL/min and maintained at 120 bar outlet pressure. The product peak had a retention time of 2.37 min.

The filtrate from the above crystallization was concentrated to dryness, the residue dissolved in EtOAc (50 mL), and the solution washed with aq HCl (0.1 M, 12.4 mL). The organic layer was washed with sat. aq NaHCO$_3$ (20 mL), dried over sodium sulfate, and concentrated, affording a second batch of 8-[(1R,2R)-2-hydroxy-2-methylcyclopentyl]-2-{[1-(methylsulfonyl)piperidin-4-yl]amino}pyrido[2,3-d]pyrimidin-7(8H)-one (Example 2, 361 mg, 31%, 94% total yield), with NMR and LCMS spectra consistent with the first crop.

Example 3

8-[(1R,3R)-3-hydroxycyclohexyl]-2-{[1-(methylsulfonyl)piperidin-4-yl]-amino}pyrido[2,3-d]pyrimidin-7(8H)-one

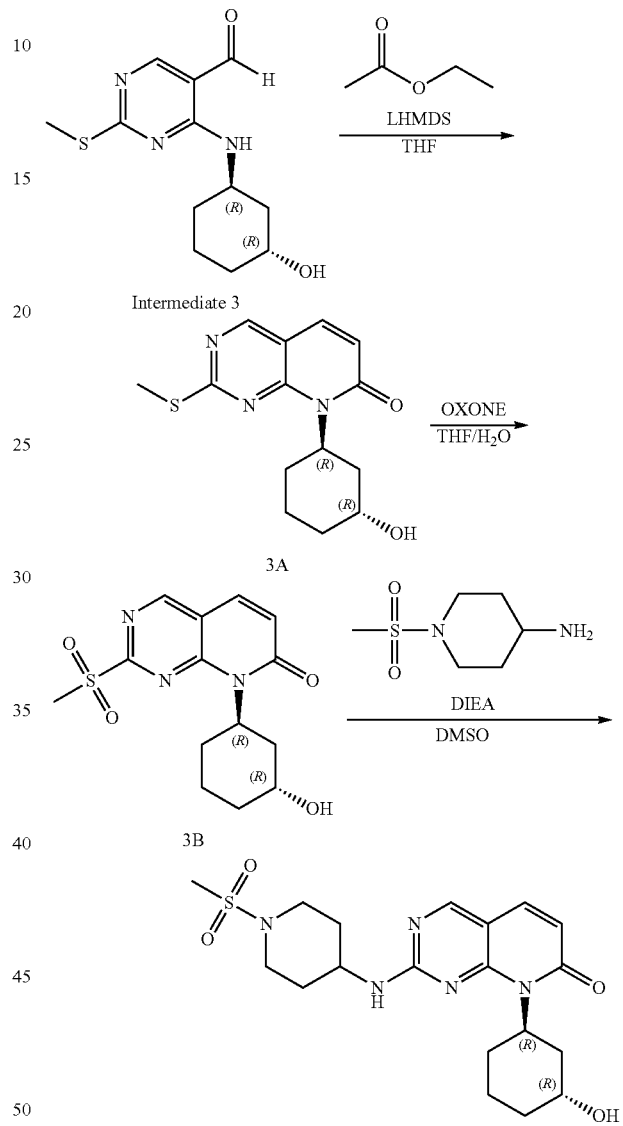

Example 3

A solution of LHMDS (1.0 M in THF, 60.7 mL, 60.7 mmol) was added dropwise to a chilled (–70° C.) solution of EtOAc (3.56 g, 40.4 mmol) in THF (40 mL). The mixture was stirred at 0° C. for 30 min, then a solution of 4-{[(1R,3R)-3-hydroxycyclohexyl]amino}-2-(methylsulfanyl)pyrimidine-5-carbaldehyde (Intermediate 3, 2.70 g, 10.1 mmol) in THF (10 mL) was added dropwise. When addition was complete, stirring was continued at room temperature for 18 h. The solution was quenched with water (40 mL) and extracted with EtOAc (40 mL×3). The combined organic extracts were dried over sodium sulfate, concentrated, and the residue purified by silica gel chromatography (eluting with 0-4% MeOH in DCM) to give 8-[(1R,3R)-3-hydroxycyclohexyl]-2-(methylsulfanyl)pyrido[2,3-d]pyrimidin-7

(8H)-one (3A, 1.46 g, 50%) as a light yellow solid. $^1$H NMR (400 MHz, CDCl$_3$) δ=8.57 (s, 1H), 7.53 (d, J=9.3 Hz, 1H), 6.58 (br d, J=9.3 Hz, 1H), 6.02 (br s, 1H), 4.37 (t, J=2.6 Hz, 1H), 2.97 (br s, 1H), 2.66-2.61 (m, 3H), 1.96-1.69 (m, 6H), 1.61 (br t, J=13.4 Hz, 2H). MS: 292 [M+H]$^+$. Optical rotation: [α]$_D^{22}$+15.2 (c 1.8, MeOH).

Solid OXONE® (13.8 g, 22.4 mmol) was added in portions to a chilled (0° C.) solution of 8-[(1R,3R)-3-hydroxycyclohexyl]-2-(methylsulfanyl)pyrido[2,3-d]pyrimidin-7(8H)-one (3A, 2.18 g, 7.48 mmol) in THF (30 mL) and water (20 mL). The mixture was stirred for 2 h, as it was allowed to gradually warm to ~15° C. The solution was diluted with EtOAc (50 mL) and washed with water (50 mL). The organic layer was dried over sodium sulfate and concentrated to give an ~3:1 mixture of sulfone 8-[(1R,3R)-3-hydroxycyclohexyl]-2-(methylsulfonyl)pyrido[2,3-d]pyrimidin-7(8H)-one and sulfoxide 8-[(1R,3R)-3-hydroxycyclohexyl]-2-(methylsulfinyl)pyrido[2,3-d]pyrimidin-7(8H)-one (3B, 1.80 g, 79%) as a light yellow solid. MS: 330 [M+Na]$^+$ for sulfoxide; 346 [M+Na]$^+$ for sulfone.

A solution of the sulfone/sulfoxide mixture prepared above (1.80 g, 5.6 mmol), 4-amino-1-methanesulfonylpiperidine (CAS #402927-97-3, 2.08 g, 11.7 mmol), and DIPEA (3.60 g, 34.9 mL) in DMSO (30 mL) was stirred in a 60° C. oil bath for 2 h, then at room temperature overnight. The mixture was partitioned between DCM (30 mL) and water (30 mL×2). The organic layer was washed with sat. aq NaCl (30 mL), dried over sodium sulfate, and concentrated. The residue was purified by silica gel chromatography (eluting with 0-3% MeOH in DCM) to give 8-[(1R,3R)-3-hydroxycyclohexyl]-2-{[1-(methylsulfonyl)piperidin-4-yl]amino}pyrido[2,3-d]pyrimidin-7(8H)-one (Example 3, 2.12 g, 90%) as a yellow solid. $^1$H NMR (400 MHz, CDCl$_3$) δ=8.38 (s, 1H), 7.41 (d, J=9.3 Hz, 1H), 6.32 (br d, J=8.3 Hz, 1H), 5.94 (br d, J=9.0 Hz, 1H), 5.68 (br s, 1H), 4.34 (br s, 1H), 3.97 (br s, 1H), 3.86-3.76 (m, 2H), 3.02-2.86 (m, 3H), 2.86-2.78 (m, 3H), 2.67 (br d, J=8.5 Hz, 1H), 2.21 (br d, J=11.5 Hz, 2H), 1.87-1.52 (m, 8H). MS: 444 [M+Na]$^+$. Optical rotation: [α]$_D^{22}$+7.9 (c 0.11, CHCl$_3$). Chiral purity: 99% ee. Chiral SFC/MS analysis was performed on a Lux Cellulose-2 4.6×150 mm, 3 μm column heated to 40° C. and eluted with a mobile phase of CO$_2$ and 40% EtOH (0.05% DEA) flowing at 2.5 mL/min. The product peak had a retention time of 5.69 min.

Example 4

4-({6-(2-hydroxyethyl)-8-[(1R,2S)-2-methylcyclopentyl]-7-oxo-7,8-dihydropyrido[2,3-d]pyrimidin-2-yl}amino)-N-methylpiperidine-1-sulfonamide

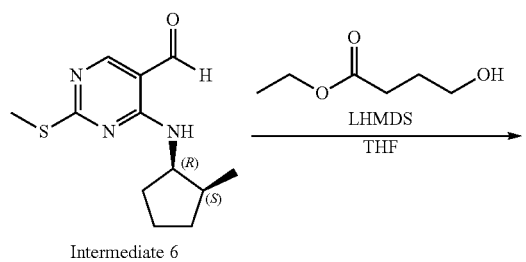

Intermediate 6

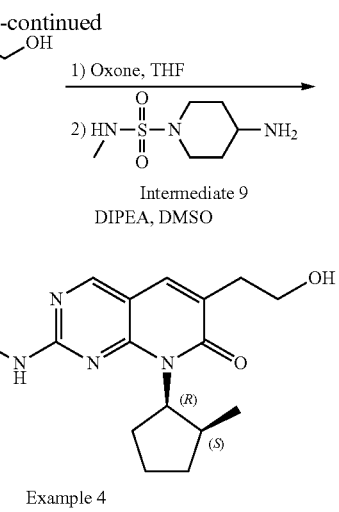

Example 4

A solution of LHMDS (1.0 M in THF, 3.58 mL, 3.58 mmol) was added dropwise to a chilled (−78° C.) solution of ethyl γ-hydroxybutyrate (237 mg, 1.79 mmol) in anhydrous THF (3 mL). The reaction was stirred for 20 min, then a solution of 4-{[(1R,2S)-2-methylcyclopentyl]amino}-2-(methylsulfanyl)pyrimidine-5-carbaldehyde (Intermediate 6, 150 mg, 0.597 mmol) in THF (2 mL) was added dropwise. The mixture was gradually warmed to room temperature with stirring for 18 h. The reaction was quenched with acetic acid (573 mg, 9.55 mmol) and partitioned between water and EtOAc. The aqueous layer was further extracted with EtOAc (20 mL×3). The combined organic layers were washed with sat. aq NaCl, dried over sodium sulfate, filtered, concentrated, and purified by silica gel chromatography (eluting with 0-2% MeOH in DCM) to give 6-(2-hydroxyethyl)-8-[(1R,2S)-2-methylcyclopentyl]-2-(methylsulfanyl)pyrido[2,3-d]pyrimidin-7(8H)-one (4A, 181 mg, 95%) as a yellow oil. MS: 320 [M+H]$^+$.

Solid OXONE® (523 mg, 0.85 mmol) was added to a chilled (0° C.) solution of 6-(2-hydroxyethyl)-8-[(1R,2S)-2-methylcyclopentyl]-2-(methylsulfanyl)pyrido[2,3-d]pyrimidin-7(8H)-one (4A, 181 mg, 0.567 mmol) in THF (6 mL) and water (3 mL). The resulting mixture was stirred at room temperature for 1 h. Water (10 mL) was added, and the mixture extracted with EtOAc (20 mL×3). The combined organics were washed with sat. aq NaCl, dried over sodium sulfate, filtered, and concentrated to a yellow solid (178.2 mg). LCMS showed this to be a ~4:3 mixture of sulfone and sulfoxide products. This mixture was dissolved in DMSO (5 mL), 4-amino-N-methylpiperidine-1-sulfonamide (Intermediate 9, 147 mg, 0.76 mmol) and DIPEA (196 mg, 1.52 mmol) were added, and the resulting solution stirred at 85° C. for 16 h. After cooling to rt, the mixture was partitioned between water (15 mL) and EtOAc (20 mL×3). The combined organics were washed with sat. aq NaCl (20 mL×3), dried over sodium sulfate, filtered, concentrated, and purified by silica gel chromatography (eluting with 0-3% MeOH in DCM). The material thus obtained (182 mg, 81% purity by LCMS) was further purified by preparative HPLC [DuraShell 150×25 mm×5 μm column; water (0.05% NH$_4$OH)-ACN] to give 4-({6-(2-hydroxyethyl)-8-[(1R,2S)-2-methylcyclopentyl]-7-oxo-7,8-dihydropyrido[2,3-d]pyrimidin-2-yl}amino)-N-methylpiperidine-1-sulfonamide (Example 4, 90 mg, 38%) as an off-white solid. $^1$H NMR (400 MHz, CDCl$_3$) δ=8.37 (s, 1H), 7.36 (s, 1H), 5.97 (q, J=8.9 Hz, 1H), 4.59-4.45 (m, 1H), 4.08-3.93 (m, 1H), 3.83 (br s, 2H), 3.77-3.64 (m, 2H) 3.15-2.92 (m, 1H) 2.80 (t, J=5.8 Hz, 2H), 2.74 (d, J=5.5 Hz, 3H), 2.72-2.60 (m, 1H), 2.41-2.27 (m, 1H), 2.19-2.10 (m, 2H), 2.09-1.99 (m, 1H), 1.86 (d, J=11.8 Hz, 1H), 1.73-1.47 (m, 3H), 0.75 (d, J=7.0 Hz, 3H). MS: 465 [M+H]$^+$. Optical rotation: $[\alpha]_D^{22}$ −10.3 (c 0.5 MeOH). Chiral purity: >99% ee. Chiral SFC/MS analysis was performed on a Chiracel OD-3 4.6×100 mm, 3 μm column heated to 40° C. and eluted with a mobile phase of $CO_2$ and a gradient of 5 to 40% EtOH (0.05% DEA) over 5.5 min, flowing at 2.8 mL/min. Flow at 40% EtOH (0.05% DEA) was continued for 2.5 min to elute any remaining counter ions. The product peak had a retention time of 4.049 min.

Method B (Wittig cyclization)

Example 5

(+)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one

Example 6

(−)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one

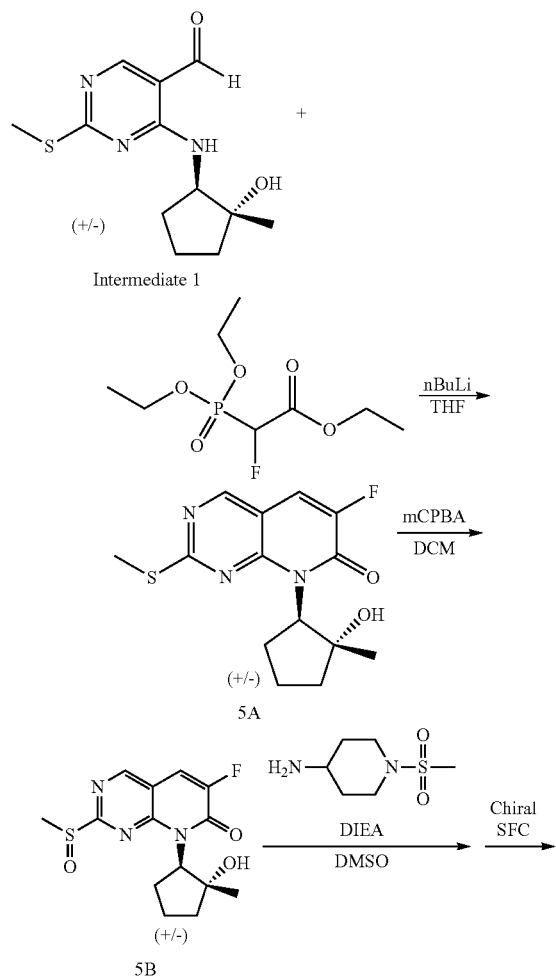

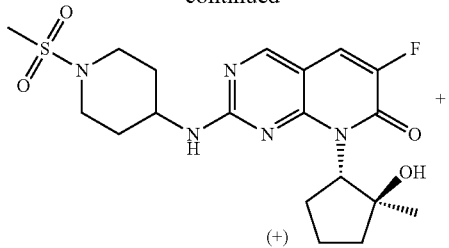

Example 5

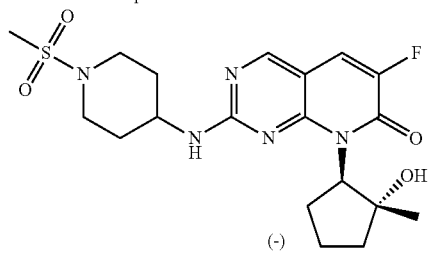

Example 6

To a cooled (−70° C.) solution of ethyl (diethoxyphosphoryl)(fluoro)acetate (407 μL, 2 mmol) in THF (15 mL) under a nitrogen atmosphere was added dropwise n-BuLi (1.6 M in hexanes, 1.9 mL, 3 mmol), then the mixture was stirred at −70° C. for 40 min. To this solution was added a solution of (±)-4-{[(1R*,2R*)-2-hydroxy-2-methylcyclopentyl]amino}-2-(methylsulfanyl)pyrimidine-5-carbaldehyde (Intermediate 1, 267 mg, 1 mmol) in THF (5 mL). The mixture was stirred and allowed to warm gradually to room temperature overnight. The solution was then cooled in an ice-water bath, EtOH (2 mL) was added, followed by sat. aq $NaHCO_3$ (10 mL) and EtOAc (80 mL). The layers were separated, the organic layer was dried over sodium sulfate, concentrated to dryness, and the residue purified by silica gel chromatography (eluting with 40% heptane/60% EtOAc) to give (±)-6-fluoro-8-[(1R*,2R*)-2-hydroxy-2-methylcyclopentyl]-2-(methylsulfanyl)pyrido[2,3-d]pyrimidin-7(8H)-one (5A, 218 mg, 71%). $^1$H NMR (400 MHz, $CDCl_3$) δ=8.64 (s, 1H), 7.30 (d, J=7.5 Hz, 1H), 5.94 (t, J=8.4 Hz, 1H), 2.87-2.72 (m, 1H), 2.65 (s, 3H), 2.36-2.25 (m, 1H), 2.18-2.07 (m, 2H), 2.02-1.92 (m, 1H), 1.91-1.83 (m, 1H), 1.37 (td, J=6.9, 13.9 Hz, 1H), 1.17 (s, 3H). $^{19}$F NMR (377 MHz, $CDCl_3$) δ=−125.5 (s, 1F). MS: 310 [M+H]$^+$.

To a solution of (±)-6-fluoro-8-[(1R*,2R*)-2-hydroxy-2-methylcyclopentyl]-2-(methylsulfanyl)pyrido[2,3-d]pyrimidin-7(8H)-one (5A, 374 mg, 1.2 mmol) in DCM (30 mL) was added mCPBA (70%, 313 mg, 1.27 mmol) in one portion. The resulting mixture was stirred at room temperature for 30 min. The volatiles were removed under reduced pressure to give crude (±)-6-fluoro-8-[(1R*,2R*)-2-hydroxy-2-methylcyclopentyl]-2-(methylsulfinyl)-pyrido-[2,3-d]pyrimidin-7(8H)-one (5B), which was used immediately without further purification in the following step. MS: 308 [M+H]$^+$.

To the above crude (±)-6-fluoro-8-[(1R*,2R*)-2-hydroxy-2-methylcyclopentyl]-2-(methylsulfinyl)pyrido[2,3-d]pyrimidin-7(8H)-one (5B, ~1.2 mmol) was added DMSO (5 mL), 4-amino-1-methanesulfonylpiperidine (CAS #402927-97-3, 237 mg, 1.33 mmol), and DIPEA (0.42 mL, 2.42 mmol). The mixture was stirred at 60° C. (oil bath temperature) under nitrogen for 2 h. Acetic acid (69 μL) was added, and the entire reaction mixture was purified by chiral preparative SFC on a Chiralpak AD-H 30 mm×250 mm column at 40° C. and eluted with a mobile phase of 42% MeOH w/0.05% diethylamine (v:v) in CO$_2$ held at 100 bar, flowing at 90 mL/min, using UV detection at 340 nm. After lyophilization of the product fractions, Example 5 (peak 1, 178 mg, 34%, >99% ee) and Example 6 (peak 2, 193 mg, 36%, ~98% ee) were obtained as off-white solids. The absolute stereochemistry of each isomer was not determined, but optical rotation measurements were obtained.

Example 5: (+)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one. $^1$H NMR (700 MHz, DMSO-d6) δ=8.59 (br s, 1H), 7.85 (br s, 1H), 7.69 (d, J=7.0 Hz, 1H), 4.41 (br s, 1H), 4.09-3.78 (m, 1H), 3.68-3.44 (m, 2H), 3.01-2.69 (m, 6H), 2.17 (br s, 2H), 1.96 (br s, 2H), 1.90-1.77 (m, 2H), 1.73-1.41 (m, 3H), 0.98 (br s, 3H). $^{19}$F NMR (377 MHz, DMSO-d6) δ=−134.1 to −138.0 (m, 1F). MS 440 [M+H]$^+$. Optical rotation: [α]$_D^{22}$=+18.5 (c 0.1, CHCl$_3$). Chiral purity: >99% ee. Chiral SFC/MS analysis was performed on a Chiralpak AD-3 4.6 mm×100 mm column at rt, eluted with a mobile phase of 70% CO$_2$/30% MeOH held at 120 bar and flowing at 4.0 mL/min. This peak had a retention time of 1.33 min.

Example 6: (−)-6-fluoro-8-[(1R*,2R*)-2-hydroxy-2-methylcyclopentyl]-2-{[1-(methylsulfonyl)piperidin-4-yl]amino}pyrido[2,3-d]pyrimidin-7(8H)-one. $^1$H NMR (700 MHz, DMSO-d6) δ=8.59 (br s, 1H), 7.84 (br s, 1H), 7.72-7.58 (m, 1H), 5.89 (br s, 1H), 4.42 (br s, 1H), 4.06-3.84 (m, 1H), 3.63-3.48 (m, 2H), 2.96-2.73 (m, 6H), 2.40-2.12 (m, 2H), 1.96 (br s, 2H), 1.87 (br s, 2H), 1.73-1.41 (m, 3H), 0.97 (br s, 3H). $^{19}$F NMR (377 MHz, DMSO-d6) δ=−136.0 (d, J=144.2 Hz, 1F). MS: 440 [M+H]$^+$. Optical rotation: [α]$_D^{22}$=−15.9 (c 0.2, CHCl$_3$). Chiral purity: ~98% ee. Chiral SFC/MS analysis was performed on a Chiralpak AD-3 4.6 mm×100 mm column at rt, eluted with a mobile phase of 70% CO$_2$/30% MeOH held at 120 bar and flowing at 4.0 mL/min. This peak had a retention time of 2.47 min.

Method C (Heck Coupling/Cyclization)

Example 7

(+)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one Example 8

(−)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one

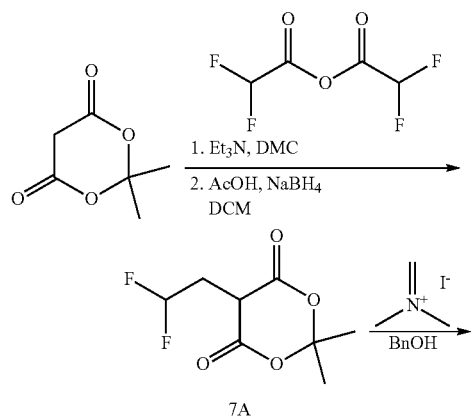

To a solution of 2,2-dimethyl-1,3-dioxane-4,6-dione (Meldrum's acid, 3.76 g, 26.1 mmol) in DCM (100 mL) at 0° C. was added difluoroacetic anhydride (3.25 mL, 26 mmol) followed by triethylamine (9.09 mL, 65.2 mmol). The cooling bath was removed and stirring continued at room temperature for 3 h. The reaction was poured into a separatory funnel, washed with 6N HCl and sat. aq. NaCl, dried over MgSO$_4$, and filtered. The filtrate was cooled to 0° C. and acidified with acetic acid (16.4 mL, 287 mmol). To this mixture was then added sodium borohydride (2.17 g, 57.4 mmol) in three portions over 0.5 h. The reaction was allowed to stand at 4° C. overnight, then quenched with sat. aq NaCl and stirred vigorously for 0.5 h. Additional water was added to dissolve solids, and the layers were separated. The organic layer washed with sat. aq NaCl and concentrated to give 5-(2,2-difluoroethyl)-2,2-dimethyl-1,3-dioxane-4,6-dione (7A, 2.78 g, 51%) as a light yellow solid. $^1$H NMR (400 MHz, CDCl$_3$) δ=6.50-6.17 (m, 1H), 3.70 (t, J=6.2 Hz, 1H), 2.64 (ddt, J=5.1, 6.1, 15.6 Hz, 2H), 1.86 (s, 3H), 1.81 (s, 3H).

A suspension of 5-(2,2-difluoroethyl)-2,2-dimethyl-1,3-dioxane-4,6-dione (7A, 2.78 g, 12.51 mmol) in benzyl alcohol (10 mL, 97 mmol) was treated with N,N-dimethylmethyleneiminium iodide (Eschenmoser's salt, 5.86 g, 31.7 mmol) and heated at 65° C. for 6 h. The mixture was poured into MTBE and washed with water (2x) and sat. aq NaCl. The organic layer was concentrated and purified by silica gel chromatography (eluting with 0-20% EtOAc in heptane) to give benzyl 4,4-difluoro-2-methylidenebutanoate (7B, 2.52 g, 89%) as a clear oil. $^1$H NMR (400 MHz, CDCl$_3$) δ=7.40-7.35 (m, 5H), 6.44 (s, 1H), 5.84 (s, 1H), 6.01 (tt, J=4.8, 56.9 Hz, 1H), 5.23 (s, 2H), 2.95-2.83 (m, 2H).

To a solution of 2,4-dichloro-5-bromo pyrimidine (0.735 g, 3.23 mmol) in ACN (20 mL) was added (±)-(1R*,2R*)-2-amino-1-methylcyclopentanol (Intermediate 1b, 0.400 g, 3.47 mmol) and triethylamine (0.50 mL, 3.6 mmol). The reaction was stirred at room temperature for 4 h, and then concentrated under vacuum. The resulting solid was purified by silica gel chromatography (eluting with 20-70% EtOAc in heptane) to give (±)-(1R*,2R*)-2-[(5-bromo-2-chloropyrimidin-4-yl)amino]-1-methylcyclopentanol (7C, 0.774 g, 78%) as a white solid. $^1$H NMR (400 MHz, CDCl$_3$) δ=8.18 (s, 1H), 5.48 (br s, 1H), 4.28 (s, 1H), 4.23 (ddd, J=5.7, 8.1, 10.1 Hz, 1H), 2.36-2.26 (m, 1H), 2.05-1.98 (m, 1H), 1.93-1.69 (m, 3H), 1.63-1.52 (m, 1H), 1.16 (s, 3H). MS: 306, 308 [M+H]$^+$ (Br+Cl isotope splitting).

To a solution of (±)-(1R*,2R*)-2-[(5-bromo-2-chloropyrimidin-4-yl)amino]-1-methylcyclopentanol (7C, 300 mg, 0.978 mmol) in DMSO (0.80 mL) was added 4-amino-1-methanesulfonylpiperidine (CAS #402927-97-3, 250 mg, 1.40 mmol) and DIPEA (0.20 mL, 1.15 mmol). The mixture was heated at 100° C. for 6 h and to 110° C. for 6 h more. The reaction was diluted with DCM and washed with water. The water layer was extracted with DCM, and the combined organic layers were concentrated and purified by silica gel chromatography (eluting with 50-90% EtOAc in heptane) to give (±)-(1R*,2R*)-2-[(5-bromo-2-{[1-(methylsulfonyl)piperidin-4-yl]amino}pyrimidin-4-yl)amino]-1-methylcyclopentanol (7D, 0.264 g, 60%) as a white solid. MS; 448, 450 [M+H]$^+$ (Br isotope splitting).

A solution of benzyl 4,4-difluoro-2-methylidenebutanoate (7B, 2.20 g, 9.72 mmol), (±)-(1R*,2R*)-2-[(5-bromo-2-{[1-(methylsulfonyl)piperidin-4-yl]amino}pyrimidin-4-yl) amino]-1-methylcyclopentanol (7D, 235 mg, 0.524 mmol), and triethylamine (0.290 mL, 2.10 mmol) in DMA (5.00 mL) was degassed by sparging with nitrogen for 15 min. Palladium(II) acetate (23.5 mg, 0.105 mmol) and tri(o-tolyl) phosphine (63.8 mg, 0.210 mmol) were added and the reaction heated at 100° C. for 3 h. After cooling the solution to rt, MeOH (1.00 mL), DBU (1.0 mL, 6.4 mmol), and sodium thiomethoxide (65 mg, 0.93 mmol) were added, and the reaction heated at 60° C. for 2 h. The resulting mixture was concentrated under vacuum and purified by silica gel chromatography (eluting with 0-10% MeOH in DCM). The resulting dark oil was further purified by preparative SFC on a Nacalai Cosmosil 3-Hydroxyphenyl bonded column (20x 150 mm I.D., 5 μm particle size) at a flow rate of 60 mL/min and a gradient of 15-25% methanol in CO$_2$ at 3%/min, with pressure set at 100 bar. The racemic mixture was separated by preparative SFC on a Chiralpak AD-H column (250×21 mm I.D., 5 μm particle size) with 26% methanol in CO$_2$ at a of flow rate 60 mL/min and pressure set at 100 bar, affording Example 7 (peak 1, 18.54 mg, 7.2%, >99% ee) and Example 8 (peak 2, 19.56 mg, 7.7%, >99% ee) as white powders. The absolute stereochemistry of each isomer was not determined, but optical rotation measurements were obtained.

Example 7: (+)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one. $^1$H NMR (400 MHz, DMSO-d6, 80° C.) δ=8.58 (s, 1H), 7.70 (s, 1H), 7.48 (br s, 1H), 6.19 (td, J=5.1, 57.2 Hz, 1H), 5.89 (t, J=8.6 Hz, 1H), 4.04 (s, 1H), 3.99 (br s, 1H), 3.68-3.55 (m, 2H), 3.10-2.99 (m, 2H), 2.87 (s, 3H), 2.97-2.84 (m, 2H), 2.29-2.17 (m, 1H), 2.14-1.83 (m, 5H), 1.76-1.53 (m, 3H), 1.00 (s, 3H). $^{19}$F NMR (377 MHz, DMSO-d6) δ=−114.9 to −114.2 (m, 2F). MS; 486 [M+H]$^+$. Optical rotation: [α]$_D^{22}$+31.9° (c 0.1, MeOH). Chiral purity: >99% ee. Chiral SFC/MS analysis was performed on a Chiralpak AD-3 (100×4.6 mm I.D., 3 μm) column eluted with 30% methanol in CO$_2$ and pressure set at 120 bar, flowing at 4 mL/min. This peak had a retention time of 0.91 min Example 8 (−)-6-(2,2-difluoroethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one. $^1$H NMR (400 MHz, DMSO-d6, 80° C.) δ=8.58 (s, 1H), 7.70 (s, 1H), 7.47 (br s, 1H), 6.19 (td, J=4.8, 57.1 Hz, 1H), 5.89 (t, J=8.3 Hz, 1H), 4.04 (s, 1H), 4.02-3.93 (m, 1H), 3.68-3.55 (m, 2H), 3.10-2.99 (m, 2H), 2.87 (s, 3H), 2.98-2.81 (m, 2H), 2.29-2.17 (m, 1H), 2.14-1.82 (m, 5H), 1.76-1.50 (m, 3H), 1.00 (s, 3H). $^{19}$F NMR (377 MHz, DMSO-d6) δ=−114.6 to −114.4 (m, 2F). MS; 486 [M+H]$^+$. Optical rotation: [α]$_D^{22}$−19.3 (c 0.1, MeOH). Chiral purity: >99% ee. Chiral SFC/MS analysis was performed on a Chiralpak AD-3 (100×4.6 mm I.D., 3 μm) column eluted with 30% methanol in CO$_2$ and pressure set at 120 bar, flowing at 4 mL/min. This peak had a retention time of 1.615 min.

Method D (Chlorination at C-6 After Cyclization)

Example 9

6-chloro-8-[(1R,2R)-2-hydroxy-2-methylcyclopentyl]-2-{[1-(methylsulfonyl)-piperidin-4-yl]amino}pyrido[2,3-d]pyrimidin-7(8H)-one

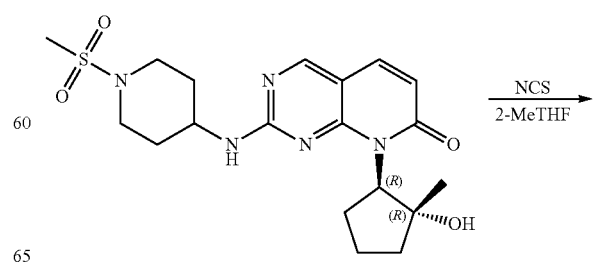

Example 2

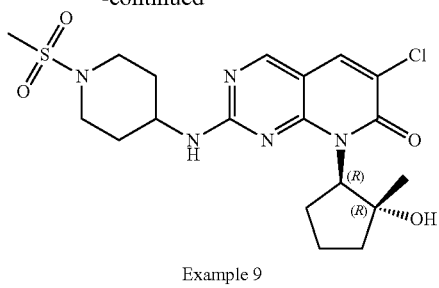

Example 9

A solution of 8-[(1R,2R)-2-hydroxy-2-methylcyclopentyl]-2-{[1-(methylsulfonyl)-piperidin-4-yl]amino}pyrido[2,3-d]pyrimidin-7(8H)-one (Example 2, 4.22 g, 10 mmol) and NCS (1.53 g, 11 mmol) in 2-MeTHF (100 mL) was stirred in a 50° C. oil bath for 44 h. After cooling to room temperature, EtOH (1.75 mL, 30 mmol) was added and the mixture stirred at room temperature for 1 h. The solution was diluted with EtOAc (120 mL) and washed with a mixture of water (15 mL) and sat. aq NaHCO₃ (15 mL). The aqueous layer was further extracted with EtOAc (80 mL). The combined organic layers were washed with sat. aq NaCl (15 mL), dried over sodium sulfate, filtered, and concentrated to dryness. Ethanol (45 mL) was added to the residue, and the resulting suspension stirred in a 55° C. oil bath for 1 h, then allowed to gradually cool with stirring to room temperature overnight. The resulting white solid was collected by filtration, rinsed with EtOH (3 mL), and dried under vacuum (~10 mmHg, 50° C.) to give 6-chloro-8-[(1R,2R)-2-hydroxy-2-methylcyclopentyl]-2-{[1-(methylsulfonyl)piperidin-4-yl]amino}pyrido[2,3-d]pyrimidin-7(8H)-one (Example 9, 3.86 g, 84%) as a white solid. ¹H NMR (400 MHz, DMSO-d6, 20° C.) δ=8.71-8.54 (m, 1H), 8.09 (s, 1H), 8.05-7.65 (m, 1H), 5.91 (t, J=8.2 Hz, 1H), 4.46-4.28 (m, 1H), 4.03-3.81 (m, 1H), 3.65-3.48 (m, 2H), 2.98-2.77 (m, 5H), 2.46-2.27 (m, 1H), 2.18 (d, J=10.3 Hz, 2H), 1.99-1.77 (m, 4H), 1.75-1.37 (m, 3H), 0.96 (br s, 3H). ¹H NMR (400 MHz, DMSO-d6, 80° C.) δ=8.60 (s, 1H), 8.02 (s, 1H), 7.61 (br s, 1H), 5.91 (dd, J=7.4, 9.2 Hz, 1H), 4.09 (s, 1H), 4.04-3.94 (m, 1H), 3.70-3.49 (m, 2H), 2.97-2.88 (m, 2H), 2.87 (s, 3H), 2.48-2.42 (m, 1H), 2.20 (dt, J=8.1, 11.4 Hz, 2H), 2.09 (d, J=12.3 Hz, 1H), 2.05-1.96 (m, 2H), 1.96-1.84 (m, 2H), 1.79-1.66 (m, 2H), 1.65-1.51 (m, 1H), 1.01 (s, 3H). MS: 456/458 (Cl isotope pattern) [M+H]⁺. Optical rotation: [α]_D²²−31.4 (c 0.4, MeOH). Chiral analysis: >99% ee. Chiral SFC/MS analysis was performed on a Phenomenex Lux Cellulose-1 4.6×100 mm 3μ column at room temperature and eluted with a mobile phase of 30% MeOH in CO₂ maintained at 120 bar outlet pressure, flowing at 4 mL/min. The product peak had a retention time of 1.52 min.

Method E (Di- and Tri-Fluoromethylation at C-6 After Cyclization)

Example 10

6-(difluoromethyl)-8-[(1R,2R)-2-hydroxy-2-methylcyclopentyl]-2-{[1-(methylsulfonyl)piperidin-4-yl]amino}pyrido[2,3-d]pyrimidin-7(8H)-one

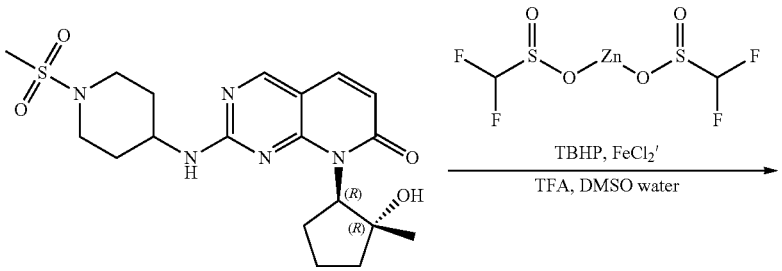

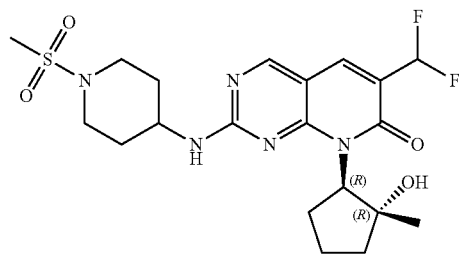

Example 10

A solution of zinc difluoromethanesulfinate (3.34 g, 11.4 mmol) and iron (II) chloride (377 mg, 1.90 mmol) in water (10 mL) was added portionwise to a solution of 8-[(1R,2R)-2-hydroxy-2-methylcyclopentyl]-2-{[1-(methylsulfonyl)piperidin-4-yl]amino}pyrido[2,3-d]pyrimidin-7(8H)-one (Example 2, 1.60 g, 3.80 mmol) and TFA (0.290 mL, 3.80 mmol) in DMSO (60 mL) at room temperature. The resulting mixture was treated with TBHP (70 wt % solution in water, 0.400 mL, 342 mg, 3.80 mmol), causing a slight increase in internal temperature to 32° C. Stirring was continued at room temperature for 19 h, at which time LCMS showed ~30% conversion. A second portion of TBHP solution (0.400 mL, 342 mg, 3.80 mmol was added and stirring continued for 3 h. A third portion of TBHP solution (0.400 mL, 342 mg, 3.80 mmol) was added and stirring continued at room temperature for 45 min, at which time LCMS showed ~50% conversion. More zinc difluoromethanesulfinate (1.1 g, 3.7 mmol) and TBHP solution (0.400 mL, 342 mg, 3.80 mmol) were added, and the mixture stirred at room temperature for 20 h. At this time, LCMS showed ~90% conversion. The reaction solution was poured into a mixture of 10% aq sodium EDTA/ice, and extracted with EtOAc (50 mL). The aqueous layer was saturated with NaCl, and extracted further with EtOAc (50 mL×3). The combined organics were washed with dilute aq sodium EDTA (50 mL) and sat. aq NaCl (50 mL). The deep blue organic layer was treated with activated charcoal and sodium sulfate, filtered, and evaporated to dryness. The residue (1.49 g foam) was purified by preparative SFC (Diol/Mono) column with MeOH/$CO_2$) to give 6-(difluoromethyl)-8-[(1R,2R)-2-hydroxy-2-methylcyclopentyl]-2-{[1-(methyl-sulfonyl)piperidin-4-yl]amino}pyrido[2,3-d]pyrimidin-7(8H)-one (Example 10, 568 mg, 32%) as a white solid. $^1$H NMR (400 MHz, DMSO-d6) δ=8.72 (s, 1H), 8.03 (s, 1H), 7.76 (br s, 1H), 7.00-6.50 (m, 1H), 5.87 (t, J=8.3 Hz, 1H), 4.08 (s, 1H), 4.06-3.89 (m, 1H), 3.62 (t, J=11.7 Hz, 2H), 2.98-2.89 (m, 2H), 2.87 (s, 3H), 2.57-2.51 (m, 1H), 2.27-2.14 (m, 1H), 2.10 (d, J=9.4 Hz, 1H), 2.04-1.93 (m, 2H), 1.93-1.80 (m, 2H), 1.76-1.69 (m, 2H), 1.69-1.55 (m, 1H), 1.03 (s, 3H). $^{19}$F NMR (377 MHz, DMSO-d6) δ=−125.7 to −113.3 (m, 2F). $^{13}$C NMR (101 MHz, DMSO-d6) Shift 159.5, 159.2, 154.9, 133.4, 110.3, 102.6, 102.0, 78.9, 61.5, 45.8, 43.0, 42.8, 40.2, 32.9, 28.5, 25.1, 22.2, 21.8. MS: 472 [M+H]$^+$. Optical rotation: $[\alpha]_D^{22}$−35.8 (c 0.7, MeOH); $[\alpha]_D^{22}$−25.3 (c 0.6, CHCl$_3$). Chiral SFC analysis: >99% ee. Retention time 2.78 min on Phenomenex Lux Cellulose-1 4.6×100 mm 3μ column (ambient temp); mobile phase: 15% MeOH in $CO_2$, 120 bar, 4 mL/min.

Example 133

(−)-6-(difluoromethyl)-8-[(1R*,3R*)-3-hydroxycyclopentyl]-2-{[1-(methylsulfonyl)piperidin-4-yl]amino}pyrido[2,3-d]pyrimidin-7(8H)-one Example 134

(+)-6-(difluoromethyl)-8-[(1R*,3R*)-3-hydroxycyclopentyl]-2-{[1-(methylsulfonyl)piperidin-4-yl]amino}pyrido[2,3-d]pyrimidin-7(8H)-one

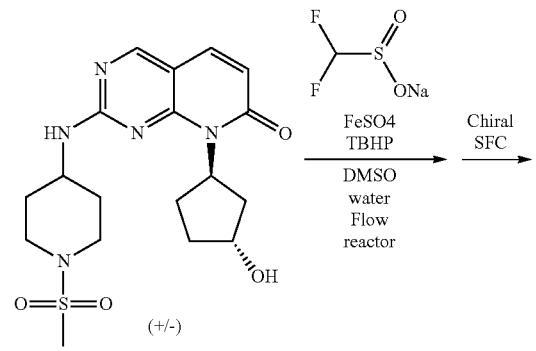

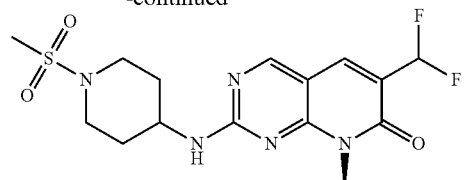

(-)
Example 133

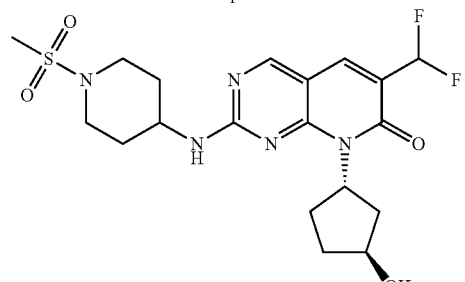

(+)
Example 134

Figure 5:
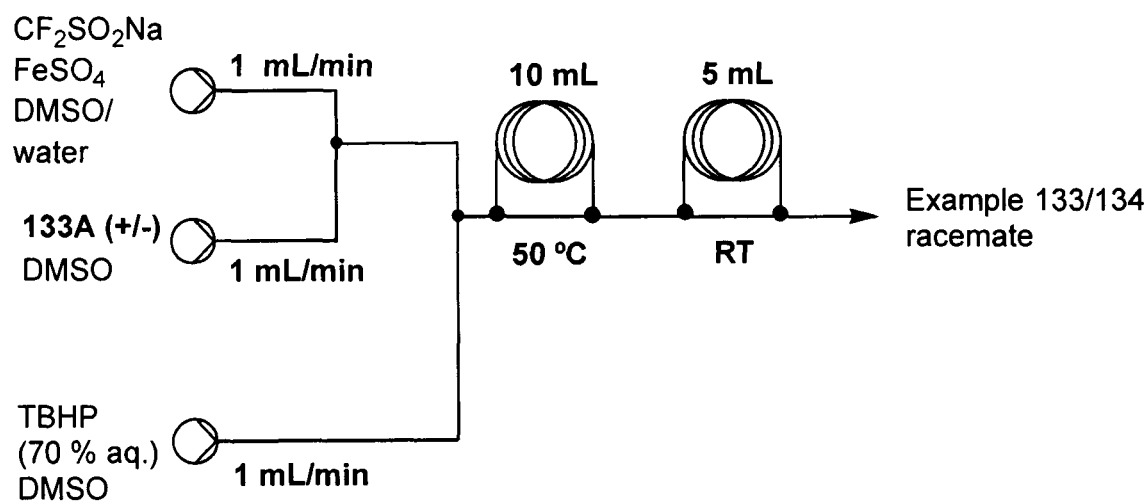
FIG. 5 shows the flow reactor set up for the preparation of Example 133 and Example 134.

In a flow reactor set up according to the scheme provided in FIG. 5, the following solutions were prepared and passed through the corresponding mixing valves at 1 mL/min: tert-butyl hydroperoxide (TBHP, 0.632 g, 4.91 mmol, 0.675 mL) in 29 mL of DMSO; sodium difluoromethanesulfinate (882 mg, 6.39 mmol) and iron sulfate (11.2 mg, 0.0737 mmol) in 3 ml of water+27 mL of DMSO; and (±)-8-[3-hydroxycyclopentyl]-2{[1-(methylsulfonyl)piperidin-4-yl]amino}pyrido[2,3-d]pyrimidin-7(8H)-one (synthesized from Intermediate 8 by the method of Example 1, 500 mg, 1.23 mmol) in 30 mL of DMSO.

The DMSO solution containing the product mixture was collected in a single bottle. After the substrate solution was consumed, the product mixture was poured over a solution of ethylenediaminetetraacetic acid (1.080 g, 3.68 mmol) and sodium bicarbonate (2.4 g, 28.57 mmol) in 150 mL of water and ice, and the resulting solution extracted with ethyl acetate (3×100 mL). The organics were combined, washed with brine (3×100 mL), dried over sodium sulfate and evaporated. The crude concentrate was loaded into a silica column and eluted with ethyl acetate/heptane 0-80%. The fractions containing the product were combined and evaporated to give a yellow solid. The enantiomers were resolved by SFC using a ChiralPak AD-H 21×250 mm column at 40° C. eluted with 20% IPA in CO2 and held at 120 bar at a flow of 85 mL/min.

Example 133: (−)-6-(difluoromethyl)-8-[(1R*,3R*)-3-hydroxycyclopentyl]-2-{[1-(methylsulfonyl)piperidin-4-yl]amino}pyrido[2,3-d]pyrimidin-7(8H)-one (82 mg, 15%) white solid. $^1$H NMR (400 MHz, DMSO-d6) δ=8.76 (d, J=18.8 Hz, 1H), 8.06 (s, 1H), 8.21-7.98 (m, 1H), 6.87 (t, J=55.5 Hz, 1H), 6.23-6.02 (m, 1H), 4.64-4.50 (m, 1H), 4.43 (br. s., 1H), 4.12-3.83 (m, 1H), 3.65-3.52 (m, J=6.6 Hz, 2H), 2.94-2.81 (m, 5H), 2.42-2.10 (m, 2H), 2.09-1.87 (m, 3H), 1.75-1.52 (m, 4H). $^{19}$F NMR (376 MHz, DMSO-d6) δ=−120.0 to −115.8 (m, 2F). MS: 485 [M+H]$^+$, Optical rotation $[\alpha]_D^{22}$−15.6 (c 0.1, MeOH); >99% ee. Retention time 1.828 min in a ChiralPak AD-3 4.6×100 mm 3μ column, mobile phase 20% IPA; 120 bar at 4 mL/min.

Example 134: (+)-6-(difluoromethyl)-8-[(1R*,3R*)-3-hydroxycyclopentyl]-2-{[1-(methylsulfonyl)piperidin-4-yl]amino}pyrido[2,3-d]pyrimidin-7(8H)-one (76 mg, 14%) white solid. $^1$H NMR (400 MHz, DMSO-d6) δ=8.76 (d, J=18.7 Hz, 1H), 8.06 (s, 1H), 8.22-7.97 (m, 1H), 6.87 (t, J=55.3 Hz, 1H), 6.21-6.01 (m, 1H), 4.64-4.51 (m, 1H), 4.43 (br. s., 1H), 4.13-3.83 (m, 1H), 3.63-3.52 (m, J=5.9 Hz, 2H), 2.92-2.81 (m, 5H), 2.41-2.13 (m, 2H), 2.11-1.89 (m, 3H), 1.75-1.53 (m, 4H). $^{19}$F NMR (376 MHz, DMSO-d6) δ=−121.8 to −115.6 (m, 2F). MS: 485 [M+H]$^+$, Optical rotation [α]$_D^{22}$+14.8 (c 0.1, MeOH); >99% ee. Retention time 3.08 min in a ChiralPak AD-3 4.6×100 mm 3μ column, mobile phase 20% IPA; 120 bar at 4 mL/min Method F (Post-Cyclization Amidation and Dehydration to Nitrile)

Example 135

(8-cyclopentyl-2-{[(methylsulfonyl)piperidin-4-yl]amino}-7-oxo-7,8-dihydropyrido[2,3-d]pyrimidin-6-yl)acetonitrile

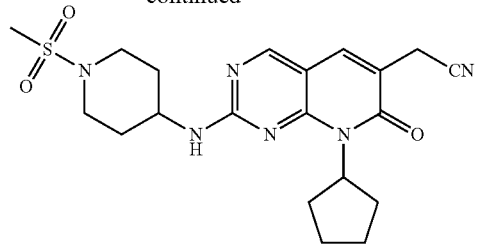

Example 135

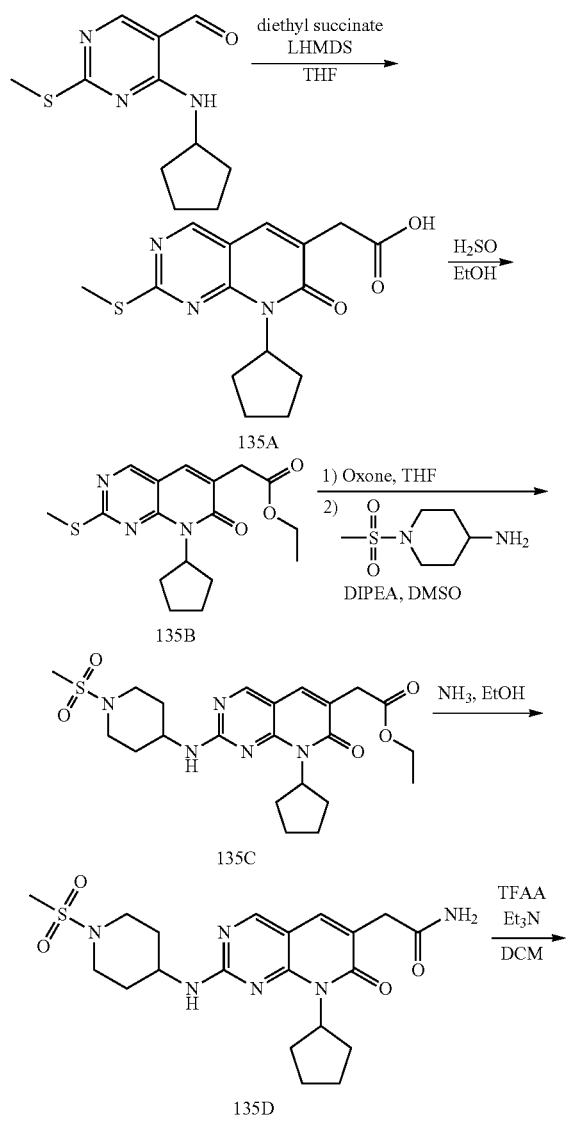

Diethyl succinate (6.61 g, 37.9 mmol) was added dropwise to a cooled (−70° C.) solution of LiHMDS (1.0 M in THF, 75.8 mL, 75.8 mmol) in THF (100 mL). After stirring for 10 minutes, a solution of 4-(cyclopentylamino)-2-(methylsulfanyl)pyrimidine-5-carbaldehyde [VanderWel, et al. *J. Med. Chem.* 2005, 48, 2371] (6.00 g, 25.3 mmol) in THF (40 mL) was added and the mixture stirred at −70° C. for 30 minutes. The solution was allowed to warm to room temperature and stirred overnight. The mixture was partitioned between water (100 mL) and EtOAc (200 mL), and the aqueous layer further extracted with EtOAc (2×50 mL). No product was observed in the combined organic layers by TLC. The aqueous layer was acidified to pH 2 with conc. HCl. The resulting precipitate was collected by suction filtration, washed with water and petroleum ether, dried under vacuum, and then purified by silica gel chromatography (eluting with 2-5% MeOH in DCM) to give 2-(8-cyclopentyl-2-(methylthio)-7-oxo-7,8-dihydropyrido[2,3-d]pyrimidin-6-yl)acetic acid (135A, 5.00 g, 62%) as a yellow solid.

A suspension of 2-(8-cyclopentyl-2-(methylthio)-7-oxo-7,8-dihydropyrido[2,3-d]pyrimidin-6-yl)acetic acid (135A, 5.00 g, 15.7 mmol) in EtOH (80 mL) was treated with conc. sulfuric acid (5 mL) and heated to 80° C. for 18 h, affording a clear yellow solution. After cooling to room temperature, the solution was concentrated to dryness, the residue dissolved in DCM (100 mL), and basified to pH ~8 with sat. aq. Na$_2$CO$_3$. The layers were separated and the aqueous layer further extracted with DCM (2×50 mL). The combined organics were dried over sodium sulfate, filtered, concentrated, and purified by silica gel chromatography (eluting with 0-20% EtOAc in DCM) to give ethyl 2-(8-cyclopentyl-2-(methylthio)-7-oxo-7,8-dihydropyrido[2,3-d]pyrimidin-6-yl)acetate (135B, 4.90 g, 90%) as a yellow solid.

By the method of Example 1, 135B was used to produce ethyl 2-(8-cyclopentyl-2-((1-(methylsulfonyl)piperidin-4-yl)amino)-7-oxo-7,8-dihydropyrido[2,3-d]pyrimidin-6-yl)acetate (135C, ~87% purity) as a crude yellow gum. A sample of this crude gum (150 mg, 0.31 mmol) was dissolved in methanol (6 mL), and anhydrous gaseous ammonia bubbled in for 10 minutes. The mixture was stirred at 80° C. overnight. After cooling to room temperature, the solvent was evaporated, and the residue purified by preparative HPLC [column: DuraShell 150*25 mm*5 um; mobile phase: from 25% ACN in water (0.05% ammonium hydroxide v/v) to 45% ACN in H$_2$O(0.05% ammonium hydroxide v/v)] to give 2-(8-cyclopentyl-2((1-(methylsulfonyl)-piperidin-4-yl)amino)-7-oxo-7,8-dihydropyrido[2,3-d]pyrimidin-6-Aacetamide (135D, 40 mg, 28%) as white solid. $^1$H NMR (400 MHz, DMSO-d6) δ=8.59 (s., 1H), 7.85-7.49 (m, 2H), 7.35 (s., 1H), 6.86 (s., 1H), 5.93-5.75 (m, 1H), 4.07-3.80 (m, 1H), 3.57 (d, J=11.0 Hz, 2H), 3.25 (s, 2H), 2.93-2.82 (m, 5H), 2.17 (m, 2H), 1.98 (m, 4H), 1.79-1.55 (m, 6H). MS: 448.9 [M+H]$^+$.

A second run (135C, 260 mg, 0.54 mmol), in ethanol (120° C. for 12 h) yielded crude 135D (200 mg of ~60% purity) as a brown solid, which was used without purification in the subsequent dehydration reaction.

A cooled (0° C.) solution of crude 2-(8-cyclopentyl-2-((1-(methylsulfonyl)-piperidin-4-yl)amino)-7-oxo-7,8-dihydropyrido[2,3-d]pyrimidin-6-yl)acetamide (135D, 100 mg, 0.13 mmol) and triethylamine (67.7 mg, 0.67 mmol) in DCM (5 mL) was treated with trifluoroacetic acid anhydride (56.2 mg, 0.27 mmol). The cooling bath was removed and the mixture stirred at room temperature for 2 h. The resulting yellow suspension was washed with deionized water (20 mL), then with sat. aq. NaCl. The organic layer was dried over magnesium sulfate, filtered, and concentrated. This crude product was combined with that from another run (starting with 80 mg, 0.11 mmol, of 135D) for purification by preparative HPLC [column: DuraShell 150*25 mm*5 um; mobile phase: from 36% ACN in water (0.05% ammonium hydroxide v/v) to 56% ACN in H$_2$O(0.05% ammonium hydroxide v/v)] to give (8-cyclopentyl-2-{[1-(methylsulfonyl)piperidin-4-yl]amino}-7-oxo-7,8-dihydropyrido[2,3-d]pyrimidin-6-yl)acetonitrile (Example 135, 27.1 mg, 26% yield for the combined batches) as a white solid. $^1$H NMR (400 MHz, CDCl$_3$) δ=8.49 (s, 1H), 7.70 (s, 1H), 5.87 (quin, J=8.9 Hz, 1H), 5.42 (br s, 1H), 4.05 (br s, 1H), 3.92-3.73 (m, 2H), 3.66 (d, J=1.0 Hz, 2H), 2.95 (br s, 2H), 2.85 (s, 3H), 2.32 (br s, 2H), 2.21 (br d, J=9.8 Hz, 2H), 2.04 (br s, 2H), 1.86 (br d, J=9.5 Hz, 2H), 1.70 (br s, 4H). MS: 431 [M+H]$^+$.

Method G (Post-Cyclization Functionalization of Piperidine)

Example 136

8-cyclopentyl-6-(2-hydroxyethyl)-2-{[1-(propan-2-ylsulfonyl)piperidin-4-yl]amino}pyrido[2,3-d]pyrimidin-7(8H)-one

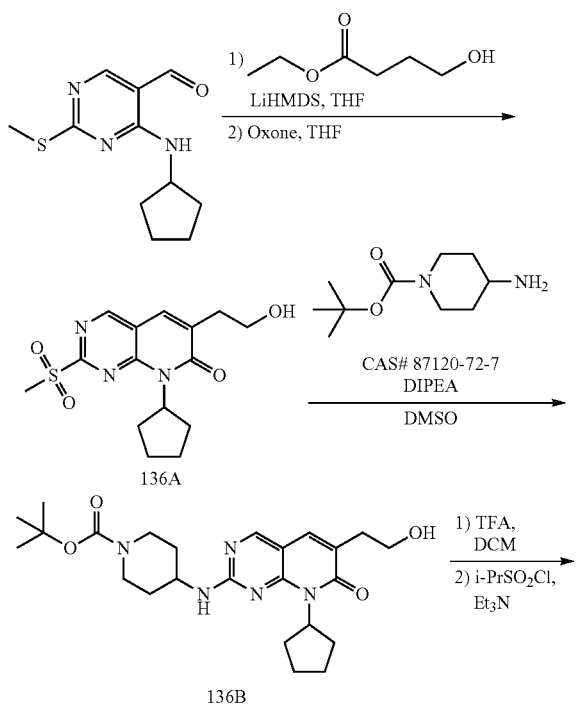

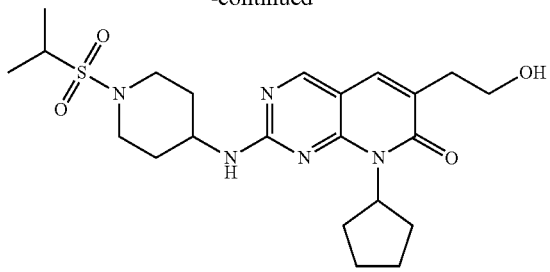

Example 136

8-Cyclopentyl-6-(2-hydroxyethyl)-2-(methylsulfonyl) pyrido[2,3-d]pyrimidin-7(8H)-one (136A), was synthesized from 4-(cyclopentylamino)-2-(methylsulfanyl)pyrimidine-5-carbaldehyde [VanderWel, et al. *J. Med. Chem.* 2005, 48, 2371] and ethyl-γ-hydroxybutyrate by the method of Example 4. A solution of 136A (95 mg, 0.284 mmol), tert-butyl 4-aminopiperidine-1-carboxylate [CAS #87120-72-7] (78.9 mg, 0.394), and DIPEA (0.187 mL, 1.13 mmol) in DMSO (2.5 mL) was heated at 65° C. for 15 h. The mixture was cooled to room temperature and diluted with water (8 mL), EtOAc (5 mL) and 4 M NaOH (1 mL) and separated. The organic layer was concentrated to give crude tert-butyl 4((8-cyclopentyl-6-(2-hydroxyethyl)-7-oxo-7,8-dihydropyrido[2,3-d]pyrimidin-2-yl)amino)piperidine-1-carboxylate (136B, 130 mg, 100%) which was used without further purification. MS: 458 [M+H]$^+$.

Trifluoroacetic acid (2.0 mL, 26 mmol) was added to a solution of crude tert-butyl 4((8-cyclopentyl-6-(2-hydroxyethyl)-7-oxo-7, 8-dihydropyrido[2,3-d]pyrimidin-2-yl)-amino)piperidine-1-carboxylate (136B, 130 mg, 0.284 mmol) in dichloromethane (6 mL). The mixture was stirred at room temperature for 30 minutes, then concentrated to dryness. The residue was dissolved in dichloromethane (6 mL). Triethylamine (0.238 mL, 1.70 mmol) and isopropylsulfonyl chloride (0.035 mL, 0.313 mmol) were added, and the mixture stirred at room temperature. After 20 minutes, more isopropylsulfonyl chloride (0.015 mL, 0.134 mmol) was added, and after another 20 min an additional amount of isopropylsulfonyl chloride (0.030 mL, 0.269 mmol) was added. The mixture was stirred for 15 more minutes, then was quenched with 4 N NaOH (0.6 mL) and stirred vigorously. Extraction with dichloromethane and purification by preparative SFC afforded 8-cyclopentyl-6-(2-hydroxyethyl)-2-{[1-(propan-2-ylsulfonyl)piperidin-4-yl]-amino}pyrido[2,3-d]pyrimidin-7(8H)-one (Example 136, 28.3 mg, 22%) as a solid. $^1$H NMR (400 MHz, DMSO-d6, 80° C.) δ=8.51 (s, 1H), 7.51 (s, 1H), 7.30 (d, J=4.4 Hz, 1H), 5.85 (quin, J=8.9 Hz, 1H), 3.99 (br s, 1H), 3.70 (d, J=13.0 Hz, 2H), 3.63 (t, J=6.5 Hz, 2H), 3.31 (td, J=6.8, 13.6 Hz, 1H), 2.62 (t, J=6.5 Hz, 2H), 2.32 (br s, 2H), 2.06-1.91 (m, 4H), 1.83-1.71 (m, 2H), 1.70-1.56 (m, 4H), 1.27 (d, J=6.7 Hz, 6H). 1H obscured by H$_2$O. MS: 464 [M+H]$^+$.

Method H (Curtius Rearrangement at C-6)

Example 137

6-amino-2-{[1-(but-3-yn-1-ylsulfonyl)piperidin-4-yl]amino}-8-cyclopentylpyrido[2,3-d]pyrimidin-7(8H)-one

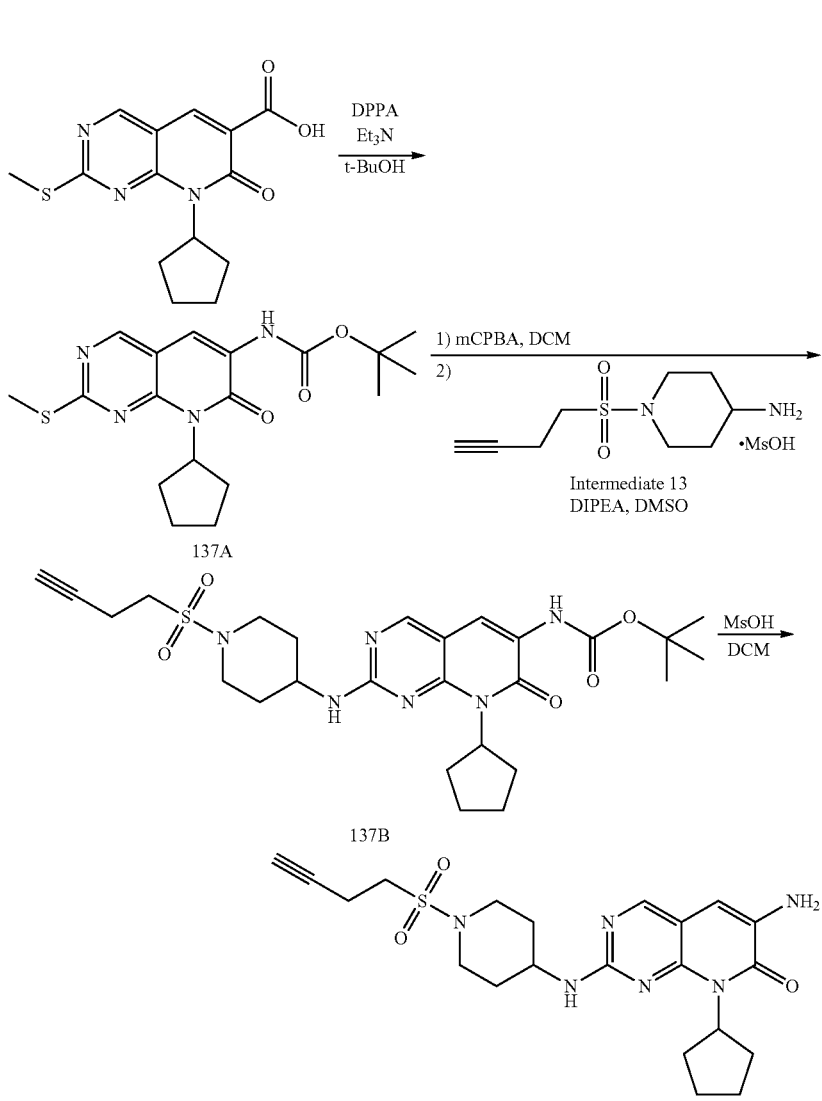

Example 137

Diphenyl phosphoryl azide (5.41 g, 19.6 mmol) was added to a room temperature solution of 8-cyclopentyl-2-(methylthio)-7-oxo-7,8-dihydropyrido[2,3-d]pyrimidine-6-carboxylic acid [Toogood, et al. *J. Med. Chem.*, 2005, 48, 2388-2406] (5.0 g, 16.37 mmol) and triethylamine (1.99 g, 19.6 mmol) in tert-butanol (60 mL). The resulting suspension was stirred at 79° C. for 18 h. The solids were removed by filtration. The filter cake was rinsed with ethyl acetate (50 mL) and the combined filtrates concentrated and purified by silica gel chromatography (eluting with pet. ether/ethyl acetate) to give tert-butyl (8-cyclopentyl-2-(methylthio)-7-oxo-7,8-dihydropyrido[2,3-d]pyrimidin-6-yl)-carbamate (137A, 4.1 g, 67%) as a light yellow solid. $^1$H NMR (400 MHz, CDCl$_3$): δ=8.60 (s, 1H), 8.15 (s, 1H), 7.80 (s, 1H), 6.04-6.00 (m, 1H), 2.59 (s, 3H), 2.30-2.27 (m, 2H), 2.07-2.05 (m, 2H), 1.91-1.89 (m, 2H), 1.71-1.69 (m, 2H), 1.50 (s, 9H). MS: 377 [M+H]$^+$.

To a solution of tert-butyl (8-cyclopentyl-2-(methylthio)-7-oxo-7,8-dihydropyrido[2,3-d]pyrimidin-6-yl)carbamate (137A, 495 mg, 1.3 mmol) in DCM (13 mL) was added mCPBA (~70%, 389 mg, 1.58 mmol). The mixture was stirred at room temperature for 1 hour. The reaction was diluted with DCM (30 mL), and washed with saturated Na$_2$SO$_3$ (10 mL) and then with saturated aqueous NaHCO$_3$ (10 mL). The organic layer was dried over sodium sulfate and evaporated to give a white solid which was a 9:1 mixture of sulfoxide and sulfone intermediates. MS: 393 ([M+H]$^+$ sulfoxide) and 409 ([M+H]$^+$ sulfone). A portion of this mixture (235 mg, 0.6 mmol) was dissolved in DMSO (3 mL). Diisopropylethyl amine (0.52 mL, 3 mmol) and 1-(but-3-yn-1-ylsulfonyl)piperidin-4-amine methanesulfonate (Intermediate 13, 225 mg, 0.72 mmol) were added. The mixture was heated at 55° C. for 16 h, then at 65° C. for 3 h. After cooling to room temperature, the reaction mixture was partitioned between saturated aqueous NaHCO$_3$ (10 mL) and DCM (30 mL). The organic layer was dried over sodium sulfate, concentrated, and purified by silica gel chromatography (eluting with ethyl acetate/heptane) to give tert-butyl (2-((1-(but-3-yn-1-ylsulfonyl)piperidin-4-yl)amino)-8-cyclopentyl-7-oxo-7,8-dihydropyrido[2,3-d]pyrimidin-6-yl)carbamate (137B, 166 mg, 51%) as a white solid. $^1$H NMR (400 MHz, DMSO-d6) δ=8.65 (br s, 1H), 8.03 (s, 1H), 7.89 (s, 1H), 7.75-7.36 (m, 1H), 5.92 (br s, 1H), 4.02-3.80 (m, 1H), 3.62 (d, J=12.5 Hz, 2H), 3.28-3.23 (m, 2H), 3.08-2.92 (m, 3H), 2.59 (dt, J=2.7, 7.5 Hz, 2H), 2.37-2.09 (m, 2H), 2.02-1.91 (m, 4H), 1.79 (d, J=4.6 Hz, 2H), 1.71-1.53 (m, 4H), 1.47 (s, 9H). MS: 545 [M+H]$^+$.

A solution of tert-butyl (2-((1-(but-3-yn-1-ylsulfonyl)piperidin-4-yl)amino)-8-cyclopentyl-7-oxo-7,8-dihydropyrido[2,3-d]pyrimidin-6-yl)carbamate (137B, 166 mg, 0.29 mmol) and methanesulfonic acid (195 µL, 2.9 mmol) in DCM (10 mL) was stirred at room temperature for 1 hour. The solution was concentrated to dryness, and the residue treated with ice (10 g) and saturated aqueous NaHCO$_3$ (10 mL), causing some gas evolution. The resulting suspension was stirred at room temperature for 1 hour, then the solids collected by filtration. The precipitate was washed with water and dried in a vacuum oven (45° C., 10 mmHg) to give 6-amino-2-{[1-(but-3-yn-1-ylsulfonyl)piperidin-4-yl]amino}-8-cyclopentylpyrido[2,3-d]pyrimidin-7(8H)-one (Example 137, 119 mg, 91%) as a light yellow solid. $^1$H NMR (400 MHz, DMSO-d6) δ=8.41 (s, 1H), 7.16 (br s, 1H), 6.62 (s, 1H), 5.93 (t, J=8.7 Hz, 1H), 5.70-4.31 (m, 2H), 3.89 (br s, 1H), 3.61 (d, J=12.5 Hz, 2H), 3.28-3.24 (m, 2H), 3.07-2.94 (m, 3H), 2.59 (dt, J=2.4, 7.4 Hz, 2H), 2.30-2.21 (m, 2H), 2.08-1.89 (m, 4H), 1.85-1.70 (m, 2H), 1.68-1.44 (m, 4H). MS: 445 [M+H]$^+$.

Method I (Pd-Catalyzed Cross-Coupling at C-6)

Example 138

8-cyclopentyl-6-ethenyl-2-{[1-(methylsulfonyl)piperidin-4-yl]amino}pyrido[2,3-d]pyrimidin-7(8H)-one

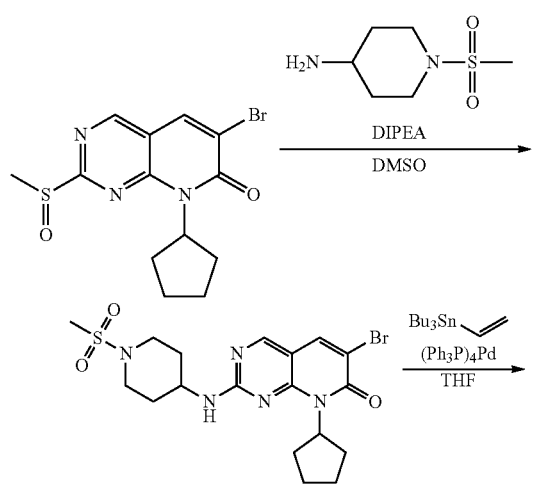

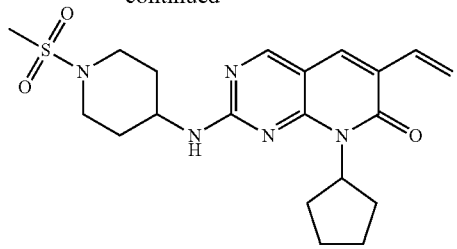

Example 138

6-Bromo-8-cyclopentyl-2-((1-(methylsulfonyl)piperidin-4-yl)amino)pyrido[2,3-d]pyrimidin-7(8H)-one (138A) was synthesized from 6-bromo-8-cyclopentyl-2-(methylsulfinyl)pyrido[2,3-d]pyrimidin-7(8H)-one [Toogood, et al. *J. Med. Chem.*, 2005, 48, 2388-2406] by the method of Example 1. $^1$H NMR (400 MHz, DMSO-d6) δ=8.55-8.68 (m, 1H), 8.25 (s, 1H), 7.79-8.09 (m, 1H), 5.74-6.10 (m, 1H), 3.80-4.16 (m, 1H), 3.57 (d, J=11.2 Hz, 2H), 2.76-3.00 (m, 5H), 2.20-2.35 (m, 1H), 2.15 (br s, 1H), 1.97 (br s, 4H), 1.77 (br s, 2H), 1.61 (d, J=11.4 Hz, 4H). MS: 470/472 (Br isotope splitting, [M+H]$^+$.

A solution of 6-Bromo-8-cyclopentyl-2-((1-(methylsulfonyl)piperidin-4-yl)amino)pyrido[2,3-d]pyrimidin-7(8H)-one (138A, 5.00 g, 12.0 mmol) and tri-n-butyl(ethenyl)stannane (3.80 g, 12.0 mmol) in THF (100 mL, 0.1 M) was degassed with nitrogen, then palladium tetrakis(triphenylphosphine) (692 mg, 0.599 mmol) was added. The mixture was heated at 65° C. for 48 h. The volatiles were removed under reduced pressure and the residue purified on silica (eluting 0-20% ethyl acetate/dichloromethane). The product was then recrystallized from DCM/diethyl ether (1/10, 50 mL) to give 8-cyclopentyl-6-ethenyl-2-{[1-(methylsulfonyl)piperidin-4-yl]amino}pyrido[2,3-d]pyrimidin-7(8H)-one (Example 138, 2.5 g, 50%), still containing 10% triphenylphosphine oxide.

For biological testing, a sample of this batch (102 mg, 0.244 mmol) was further purified by preparative SFC to give analytically pure 8-cyclopentyl-6-ethenyl-2-{[1-(methylsulfonyl)piperidin-4-yl]amino}pyrido[2,3-d]pyrimidin-7(8H)-one (Example 138, 76.48 mg, 75% recovery) as a white solid. $^1$H NMR (400 MHz, CDCl$_3$) δ=8.44 (s, 1H), 7.55 (s, 1H), 6.89 (dd, J=11.25, 17.73 Hz, 1H), 5.79-5.99 (m, 2H), 5.12-5.44 (m, 2H), 3.95-4.17 (m, 1H), 3.81 (d, J=12.2 Hz, 2H), 2.90-3.06 (m, 2H), 2.84 (s, 3H), 2.27-2.47 (m, 2H), 2.21 (dd, J=3.06, 13.08 Hz, 2H), 2.00-2.13 (m, 2H), 1.80-1.91 (m, 2H), 1.64-1.79 (m, 4H). MS: 418 [M+H]$^+$.

Example 139

8-cyclopentyl-2-{[1-(methylsulfonyl)piperidin-4-yl]amino}-6-(prop-2-en-1-yl)pyrido[2,3-d]pyrimidin-7(8H)-one

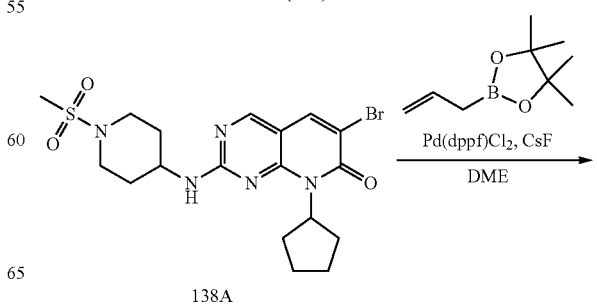

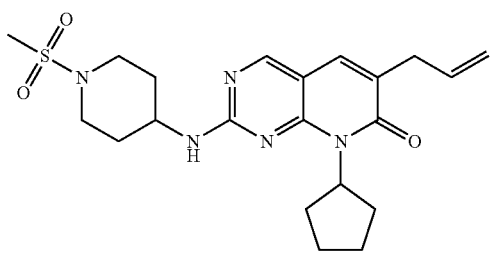

Example 139

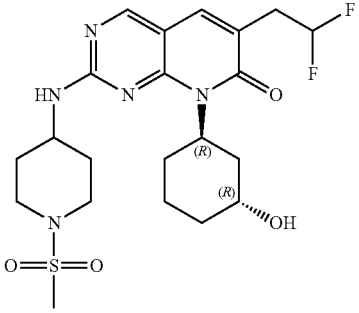

Example 140

To a vial with a stir bar was added 6-Bromo-8-cyclopentyl-2-((1-(methylsulfonyl)piperidin-4-yl)amino)pyrido[2,3-d]pyrimidin-7(8H)-one (138A, 470 mg, 1 mmol), DME (10 mL, 0.1 M), 4,4,5,5-tetramethyl-2-(prop-2-en-1-yl)-1,3,2-dioxaborolane (281 µL, 1.5 mmol), CsF (304 mg, 2 mmol), and PdCl$_2$(dppf) (37 mg, 0.05 mmol). The mixture was degassed with nitrogen for 1 minute, then the vial was capped and placed in an 80° C. heating block for 16 h. The reaction was diluted with ethyl acetate (100 mL) and saturated aqueous NaHCO$_3$ (20 mL). The organic layer was separated and the product was extracted with ethyl acetate (20 mL). The combined organic layers were dried over sodium sulfate, concentrated, and purified on silica (eluted with heptane/ethyl acetate) to give 8-cyclopentyl-2-{[1-(methylsulfonyl)piperidin-4-yl]amino}-6-(prop-2-en-1-yl)pyrido[2,3-d]pyrimidin-7(8H)-one (Example 139, 154 mg, 40%) as a light-colored solid. $^1$H NMR (400 MHz, DMSO-d6) δ=8.58 (br s, 1H), 7.48 (s, 1 H), 5.95 (tdd, J=6.69, 10.16, 17.04 Hz, 1H), 5.05-5.19 (m, 2H), 3.57 (d, J=12.2 Hz, 3H), 3.18 (d, J=6.6 Hz, 2H), 2.79-2.96 (m, 7H), 1.99 (s, 6H), 1.53-1.69 (m, 4H). MS: 432 [M+H]$^+$.

Method J (Radical Addition at C-6)

Example 140

6-(2,2-difluoroethyl)-8-[(1R,3R)-3-hydroxycyclohexyl]-2-{[1-(methylsulfonyl)piperidin-4-yl]amino}pyrido[2,3-d]pyrimidin-7(8H)-one

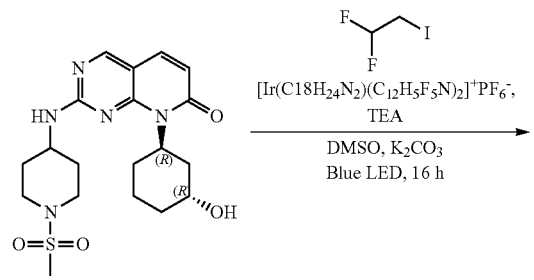

Example 3

To a solution 8-[(1R,3R)-3-hydroxycyclohexyl]-2-{[1-(methylsulfonyl)piperidin-4-yl]amino}pyrido[2,3-d]pyrimidin-7(8H)-one (Example 3, 0.161 g, 0.382 mmol) in DMSO (1.5 mL) was added (4,4'-di-t-butyl-2,2'-bipyridine)bis[3,5-difluoro-2-(5-trifluoromethyl-2-pyridinyl-kN)phenyl-kC]iridium(III) hexafluorophosphate (0.012 g, 0.0107 mmol), 1,1-difluoro-2-iodoethane (0.27 mL, 3.1 mmol), potassium carbonate (0.150 g, 0.960 mmol) and triethylamine (30 µL, 0.22 mmol). Nitrogen was bubbled through the mixture for ten minutes, and then the vial was sealed. The reaction was irradiated with blue light (Kessil, H150-Blue, 34 W) for 16 h. The reaction was filtered and concentrated, and the residue purified by preparative HPLC (Waters SFC 200 Glacier/2-Cosmosil 3HOP 150×21.1 mm I.D., 5 um columns. co-solvent methanol. 14% B for 2.5 min, to 22% in 7.5 min, to 50% in 1 min, hold 1 min @ 100 bar, 35 C, 80 g/min.) to give 6-(2,2-difluoroethyl)-8-[(1R,3R)-3-hydroxycyclohexyl]-2-{[1-(methylsulfonyl)piperidin-4-yl]amino}pyrido[2,3-d]pyrimidin-7(8H)-one (Example 140, 29.35 mg, 16% yield). $^1$H NMR (400 MHz, DMSO-d6) δ=8.58 (s, 1H), 7.85 (d, J=7.0 Hz, 1H), 7.70 (s, 1H), 6.22 (tt, J=4.8, 57.2 Hz, 1H), 4.46 (br s, 1H), 4.12 (br s, 1H), 3.99 (br s, 1H), 3.66-3.55 (m, 2H), 3.02 (dt, J=4.0, 17.1 Hz, 2H), 2.89 (s, 3H), 2.87-2.77 (m, 2H), 2.18-1.38 (m, 11H). MS: 486 [M+H]$^+$. $[\alpha]_D^{22}$+18.0 (c 0.1, MeOH).

Additional compounds of the invention were prepared by modifications of the methods exemplified herein. Except where otherwise indicated, all compounds having chiral centers were prepared and/or isolated as a single enantiomer having a known relative configuration. Compounds marked "absolute stereochemistry unknown" were typically prepared from racemic intermediates and resolved into single enantiomers by an appropriate chiral preparative SFC method before characterization and testing. Where the absolute stereochemistry is unknown for a pair of enantiomers, the stereochemistry represented in Table 1 is assigned based on the sign of the optical rotation ($[\alpha]_D^{20}$) and the relative biological activity, by analogy to compounds having known absolute configurations. Compounds marked "absolute stereochemistry known" were typically prepared from chiral intermediates having known stereochemistry.

Selected compounds and their corresponding characterization data are presented in Table 1 below.

TABLE 1

| Ex. No. (Method) | Structure/IUPAC name | LCMS [M + H]+ | 1H NMR (ppm); 19F NMR (ppm); optical rotation; stereochem. notes |
|---|---|---|---|
| 1-10 | in methods text | | |
| 11 (A) | 4-[(8-cyclopentyl-7-oxo-7,8-dihydropyrido[2,3-d]pyrimidin-2-yl)amino]-N-methylpiperidine-1-sulfonamide | 407 | 1H NMR (400 MHz, CDCl3) δ = 8.39 (s, 1H), 7.41 (d, J = 9.3 Hz, 1H), 6.36 (d, J = 9.3 Hz, 1H), 5.84 (quin, J = 9.0 Hz, 1H), 5.53-5.12 (m, 1H), 4.23-4.15 (m, 1H), 4.04 (br s, 1H), 3.74 (d, J = 12.8 Hz, 2H), 3.09-2.97 (m, 2H), 2.76 (d, J = 5.3 Hz, 3H), 2.37 (br s, 2H), 2.16 (dd, J = 3.5, 13.1 Hz, 2H), 2.07-1.97 (m, 2H), 1.91-1.80 (m, 2H), 1.75-1.63 (m, 4H) |
| 12 (A) | 4-[(8-cyclopentyl-7-oxo-7,8-dihydropyrido[2,3-d]pyrimidin-2-yl)amino]-N,N-dimethylpiperidine-1-sulfonamide | 421 | 1H NMR (400 MHz, CDCl3) δ = 8.40 (s, 1H), 7.42 (d, J = 9.3 Hz, 1H), 6.37 (d, J = 9.3 Hz, 1H), 5.84 (quin, J = 8.9 Hz, 1H), 5.31 (br s, 1H), 4.04 (br s, 1H), 3.72 (d, J = 13.1 Hz, 2H), 3.11-2.98 (m, 2H), 2.85 (s, 6H), 2.37 (br s, 2H), 2.14 (dd, J = 3.5, 13.1 Hz, 2H), 2.03 (d, J = 7.0 Hz, 2H), 1.91-1.79 (m, 2H), 1.75-1.62 (m, 4H) |
| 13 (A) | 4-[(8-cyclopentyl-7-oxo-7,8-dihydropyrido[2,3-d]pyrimidin-2-yl)amino]-1-sulfonamide | 393 | 1H NMR (400 MHz, DMSO-d6) δ = 8.61-8.58 (m, 1H), 7.87-7.66 (m, 2H), 6.78 (s, 2H), 6.24-6.21 (m, 1H), 5.87-5.73 (m, 1H), 3.89-3.79 (m, 1H), 3.48 (m, 2H), 2.65-2.60 (m, 2H), 2.36-2.18 (m, 2H), 1.97 (m, 4H), 1.73-1.56 (m, 6H) |
| 14 (A) | 8-cyclopentyl-2-({1-[(difluoromethyl)sulfonyl]piperidin-4-yl}amino)pyrido[2,3-d]pyrimidin-7(8H)-one | 428 | 1H NMR (400 MHz, CDCl3) δ = 8.40 (s, 1H), 7.42 (d, J = 9.0 Hz, 1H), 6.42-6.30 (m, 1H), 6.23 (s, 1H), 5.83 (quin, J = 8.9 Hz, 1H), 5.40 (br s, 1H), 4.11 (br s, 1H), 3.99 (d, J = 13.1 Hz, 2H), 3.29 (t, J = 11.5 Hz, 2H), 2.35 (br s, 2H), 2.24-2.13 (m, 2H), 2.02 (d, J = 6.5 Hz, 2H), 1.91-1.78 (m, 2H), 1.67 (br s, 4H) <br> 19F NMR (377MHz, DMSO-d6) δ = -123.3 (br s, 2F) |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 15 (A) | 8-cyclopentyl-2-({1-[(2-methoxyethyl)sulfonyl]piperidin-4-yl}amino)pyrido[2,3-d]pyrimidin-7(8H)-one | 436 | $^1$H NMR (400 MHz, CDCl$_3$) δ = 8.39 (s, 1H), 7.41 (d, J = 9.5 Hz, 1H), 6.36 (d, J = 9.3 Hz, 1H), 5.84 (quin, J = 8.9 Hz, 1H), 5.37 (br s, 1H), 4.12-3.96 (m, 1H), 3.84-3.71 (m, 4H), 3.45-3.37 (m, 3H), 3.23 (t, J = 5.8 Hz, 2H), 3.10-2.95 (m, 2H), 2.38 (br s, 2H), 2.15 (dd, J = 3.5, 13.1 Hz, 2H), 2.02 (br s, 2H), 1.91-1.79 (m, 2H), 1.68 (d, J = 7.5 Hz, 4H) |
| 16 (A) | 8-cyclopentyl-2-({1-(ethylsulfonyl)piperidin-4-yl]amino}pyrido[2,3-d]pyrimidin-7(8H)-one | 406 | $^1$H NMR (400 MHz, CDCl$_3$) δ = 8.39 (s, 1H), 7.41 (d, J = 9.3 Hz, 1H), 6.36 (d, J = 9.3 Hz, 1H), 5.84 (quin, J = 9.0 Hz, 1H), 5.33 (br s, 1H), 4.04 (br s, 1H), 3.83 (d, J = 12.8 Hz, 2H), 3.09-2.92 (m, 4H), 2.45-2.24 (m, 2H), 2.22-2.12 (m, 2H), 2.03 (br s, 2H), 1.91-1.79 (m, 2H), 1.63-1.62 (m, 1H), 1.77-1.62 (m, 3H), 1.39 (t, J = 7.4 Hz, 3H) |
| 17 (A) | 8-cyclopentyl-2-({1-[(2-hydroxy-2-methylpropyl)sulfonyl]piperidin-4-yl}amino)pyrido[2,3-d]pyrimidin-7(8H)-one | 450 | $^1$H NMR (400 MHz, DMSO-d$_6$, 80° C.) δ = 8.55 (s, 1H), 7.63 (d, J = 9.3 Hz, 1H), 7.43 (d, J = 5.4 Hz, 1H), 6.20 (d, J = 9.3 Hz, 1H), 5.81 (quin, J = 8.9 Hz, 1H), 4.45 (br s, 1H), 4.05-3.90 (m, 1H), 3.64 (td, J = 3.4, 12.0 Hz, 2H), 3.14 (s, 2H), 3.01-2.91 (m, 2H), 2.39-2.26 (m, 2H), 2.03-1.92 (m, 4H), 1.84-1.72 (m, 2H), 1.71-1.58 (m, 4H), 1.34 (s, 6H) |
| 18 (A) | 8-cyclopentyl-2-[(1-{[(methylsulfonyl)methyl]sulfonyl}piperidin-4-yl)amino]pyrido[2,3-d]pyrimidin-7(8H)-one | 470 | $^1$H NMR (400 MHz, DMSO-d$_6$, 80° C.) δ = 8.55 (s, 1H), 7.63 (d, J = 9.3 Hz, 1H), 7.45 (d, J = 6.1 Hz, 1H), 6.20 (d, J = 9.3 Hz, 1H), 5.81 (quin, J = 8.9 Hz, 1H), 5.11 (s, 2H), 4.04-3.92 (m, 1H), 3.74 (td, J = 3.4, 12.8 Hz, 2H), 3.18 (s, 3H), 3.15-3.05 (m, 2H), 2.39-2.27 (m, 2H), 2.04-1.92 (m, 4H), 1.84-1.73 (m, 2H), 1.73-1.59 (m, 4H) |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 19 (A) | 8-cycloheptyl-2-{[1-(methylsulfonyl)piperidin-4-yl]amino}pyrido[2,3-d]pyrimidin-7(8H)-one | 420 | 1H NMR (700 MHz, DMSO-d6) δ = 8.56 (br s, 1H), 7.86 (br s, 1H), 7.66 (d, J = 9.2 Hz, 1H), 6.35-6.12 (m, 1H), 5.68-5.21 (m, 1H), 4.03-3.75 (m, 1H), 3.60 (br s, 2H), 2.92-2.80 (m, 5H), 2.59 (d, J = 9.9 Hz, 1H), 2.37 (br s, 1H), 2.10-1.94 (m, 2H), 1.76 (br s, 2H), 1.70-1.54 (m, 8H), 1.49 (br s, 2H) |
| 20 (A) | 4-[(8-cycloheptyl-7-oxo-7,8-dihydropyrido[2,3-d]pyrimidin-2-yl)amino]-N-methylpiperidine-1-sulfonamide | 435 | 1H NMR (400 MHz, CDCl3) δ = 8.38 (s, 1H), 7.42-7.39 (d, J = 9.2 Hz, 1H), 6.39-6.34 (m, 1H), 5.56-5.31 (m, 2H), 4.18-4.17 (m, 1H), 4.07 (m, 1H), 3.78-3.75 (m, 2H), 3.06-3.01 (t, J = 11.0 Hz, 2H), 2.77 (d, J = 5.6 Hz, 3H), 2.59-2.56 (m, 2H), 2.20-2.18 (m, 2H), 1.77-1.64 (m, 10H), 1.55-1.46 (m, 2H) |
| 21 (A) | 4-[(8-cycloheptyl-7-oxo-7,8-dihydropyrido[2,3-d]pyrimidin-2-yl)amino]piperidine-1-sulfonamide | 421 | 1H NMR (400 MHz, DMSO-d6) δ = 8.56 (s, 1H), 7.86 (m, 1H), 7.65 (d, J = 8.8 Hz, 1H), 6.84-6.78 (m, 2H), 6.24-6.18 (m, 1H), 5.56-5.28 (m, 1H), 3.86-3.72 (m, 1H), 3.51 (br s, 2H), 2.62-2.59 (m, 2H), 1.99 (m, 2H), 1.75 (m, 2H), 1.62-1.49 (m, 12H) |
| 22 (A) | 8-cyclopentyl-6-methyl-2-{[1-(methylsulfonyl)piperidin-4-yl]amino}pyrido[2,3-d]pyrimidin-7(8H)-one | 406 | 1H NMR (700 MHz, DMSO-d6) δ = 8.52 (br s, 1H), 7.55 (br s, 2H), 6.00-5.73 (m, 1H), 4.06-3.76 (m, 1H), 3.56 (br s, 2H), 2.96-2.80 (m, 5H), 2.37-2.11 (m, 2H), 2.05-1.90 (m, 7H), 1.74 (br s, 2H), 1.67-1.47 (m, 4H) |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 23 (A) | 4-[(8-cyclopentyl-6-methyl-7-oxo-7,8-dihydropyrido[2,3-d]pyrimidin-2-yl)amino]-N-methylpiperidine-1-sulfonamide | 421 | $^1$H NMR (400 MHz, CDCl$_3$) δ = 8.35 (s, 1H), 7.30 (d, J = 1.3 Hz, 1H), 5.89 (quin, J = 8.9 Hz, 1H), 5.28 (br s, 1H), 4.20 (q, J = 5.3 Hz, 1H), 4.02 (br s, 1H), 3.73 (d, J = 12.5 Hz, 2H), 3.10-2.97 (m, 2H), 2.77 (d, J = 5.3 Hz, 3H), 2.35 (br s, 2H), 2.22-2.12 (m, 5H), 2.04 (m, 2H), 1.91-1.78 (m, 2H), 1.68 (m, 4H) |
| 24 (A) | 4-[(8-cyclopentyl-6-methyl-7-oxo-7,8-dihydropyrido[2,3-d]pyrimidin-2-yl)amino]-N,N-dimethylpiperidine-1-sulfonamide | 435 | $^1$H NMR (400 MHz, CDCl$_3$) δ = 8.35 (s, 1H), 7.30 (d, J = 1.3 Hz, 1H), 5.89 (quin, J = 8.9 Hz, 1H), 5.24 (br s, 1H), 4.03 (d, J = 5.8 Hz, 1H), 3.72 (d, J = 13.3 Hz, 2H), 2.98-3.11 (m, 2H), 2.84 (s, 6H), 2.33 (d, J = 12.0 Hz, 2H), 2.10-2.19 (m, 5H), 2.00-2.09 (m, 2H), 1.78-1.91 (m, 2H), 1.68-1.76 (m, 2H), 1.56-1.65 ppm (m, 2H) |
| 25 (A) | 4-[(8-cyclopentyl-6-methyl-7-oxo-7,8-dihydropyrido[2,3-d]pyrimidin-2-yl)amino]piperidine-1-sulfonamide | 407 | $^1$H NMR (400 MHz, DMSO-d$_6$) δ = 8.50 (s, 1H), 7.66-7.53 (m, 2H), 6.77 (s, 2H), 5.87-5.78 (m, 1H), 3.84-3.77 (m, 1H), 3.60-3.52 (m, 2H), 2.65-2.59 (m, 2H), 2.32-2.16 (m, 2H), 2.02-1.96 (m, 7H), 1.72-1.54 (m, 6H) |
| 26 (A) | 8-cyclopentyl-2-({1-[(difluoromethyl)sulfonyl]piperidin-4-yl}amino)-6-methylpyrido[2,3-d]pyrimidin-7(8H)-one | 442 | $^1$H NMR (400 MHz, CDCl$_3$) δ = 8.35 (s, 1H), 7.31 (s, 1H), 5.88 (quin, J = 8.9 Hz, 1H), 5.22 (br s, 1H), 4.11 (br s, 1H), 3.98 (d, J = 13.6 Hz, 2H), 3.30 (t, J = 11.5 Hz, 2H), 2.33 (br s, 2H), 2.23-2.13 (m, 5H), 2.05 (br s, 2H), 1.90-1.79 (m, 2H), 1.74-1.63 (m, 4H) $^{19}$F NMR (377 MHz, DMSO-d$_6$) δ = −123.2 (s, 2F) |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 27 (A) | 4-{[8-cyclopentyl-6-(2-hydroxyethyl)-7-oxo-7,8-dihydropyrido[2,3-d]pyrimidin-2-yl]amino}-N,N-dimethylpiperidine-1-sulfonamide | 488 [M + Na]⁺ | ¹H NMR (400 MHz, CDCl₃) δ = 8.39 (s, 1H), 7.37 (s, 1H), 5.88 (quin, J = 8.9 Hz, 1H), 5.58-5.06 (m, 1H), 4.12-3.95 (m, 1H), 3.86 (d, J = 4.8 Hz, 2H), 3.76-3.60 (m, 2H), 3.10-2.97 (m, 3H), 2.86-2.79 (m, 8H), 2.34 (br s, 2H), 2.14 (dd, J = 3.3, 13.1 Hz, 2H), 2.09-1.95 (m, 2H), 1.92-1.77 (m, 2H), 1.71-1.54 (m, 4H) |
| 28 (H) | 6-amino-8-cyclopentyl-2-{[1-(methylsulfonyl)piperidin-4-yl]amino}pyrido[2,3-d]pyrimidin-7(8H)-one | 407 | ¹H NMR (400 MHz, DMSO-d₆) δ = 8.40 (s, 1H), 7.13 (d, J = 4.6 Hz, 1H), 6.60 (s, 1H), 6.02-5.85 (m, 1H), 5.15 (s, 2H), 3.86 (br s, 1H), 3.55 (d, J = 12.1 Hz, 2H), 2.93-2.80 (m, 2H), 2.88 (s, 3H), 2.28 (d, J = 10.4 Hz, 2H), 1.97 (d, J = 11.0 Hz, 4H), 1.83-1.71 (m, 2H), 1.69-1.51 (m, 4H) |
| 29 (E) | 6-chloro-8-cyclopentyl-2-{[1-(methylsulfonyl)piperidin-4-yl]amino}pyrido[2,3-d]pyrimidin-7(8H)-one | 426 | ¹H NMR (700 MHz, DMSO-d₆) δ = 8.68-8.51 (m, 1H), 8.04 (br s, 1H), 8.01-7.58 (m, 1H), 6.09-5.70 (m, 1H), 4.12-3.76 (m, 1H), 3.63-3.56 (m, 2H), 2.87 (d, J = 11.3 Hz, 5H), 2.25 (br s, 1H), 2.12 (br s, 1H), 1.95 (br s, 4H), 1.77 (br s, 2H), 1.68-1.51 (m, 4H) |
| 30 (E) | 8-cyclopentyl-6-(difluoromethyl)-2-{[1-(methylsulfonyl)piperidin-4-yl]amino}pyrido[2,3-d]pyrimidin-7(8H)-one | 442 | ¹H NMR (400 MHz, DMSO-d₆, 80° C.) δ = 8.72 (s, 1H), 8.02 (s, 1H), 7.77 (br s, 1H), 6.84 (t, J = 55.0 Hz, 1H), 5.83 (quin, J = 8.7 Hz, 1H), 4.01 (br s, 1H), 3.63 (d, J = 12.3 Hz, 2H), 2.97-2.90 (m, 2H), 2.88 (s, 3H), 2.32 (br s, 2H), 2.08-1.92 (m, 4H), 1.87-1.74 (m, 2H), 1.74-1.58 (m, 4H) ¹⁹F NMR (377 MHz, DMSO-d6, 80° C.) δ = −116.8 (br s, 2F) |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 31 (A) | (8-cyclopentyl-2-{[1-(methylsulfonyl)piperidin-4-yl]amino}-7-oxo-7,8-dihydropyrido[2,3-d]pyrimidin-6-yl)(difluoro)acetic acid | 486 | 1H NMR (400 MHz, DMSO-$d_6$, 80° C.) δ = 8.65 (s, 1H), 7.85 (s, 1H), 7.56 (br s, 1H), 5.72-5.87 (m, 1H), 3.90-4.10 (m, 1H), 3.56-3.68 (m, 2H), 2.89-2.96 (m, 2H), 2.88 (s, 3H), 2.22-2.36 (m, 2H), 1.94-2.07 (m, 4H), 1.56-1.84 (m, 6H) 19F NMR (377 MHz, DMSO-$d_6$) δ = −100.9 (br s, 2F) |
| 32 (A) | (+)-8-[(1R*,3R*)-3-hydroxycyclohexyl]-6-methyl-2-{[1-(methylsulfonyl)piperidin-4-yl]amino}pyrido[2,3-d]pyrimidin-7(8H)-one | 436 | 1H NMR (400 MHz, CDCl$_3$) δ = 8.34 (s, 1H), 7.30 (s, 1H), 5.97 (br s, 1H), 5.38 (br s, 1H), 4.35 (br s, 1H), 3.97 (br s, 1H), 3.81 (dd, J = 5.3, 10.3 Hz, 2H), 3.01-2.88 (m, 3H), 2.87-2.79 (m, 3H), 2.69 (d, J = 10.0 Hz, 1H), 2.22 (d, J = 12.0 Hz, 2H), 2.13 (s, 3H), 1.94-1.67 (m, 8H) $[\alpha]_D^{20}$ + 11.8 (c 0.13, CHCl$_3$) 99% ee; absolute stereochemistry unknown Enantiomer of Ex. 33 |
| 33 (A) | (−)-8-[(1R*,3R*)-3-hydroxycyclohexyl]-6-methyl-2-{[1-(methylsulfonyl)piperidin-4-yl]amino}pyrido[2,3-d]pyrimidin-7(8H)-one | 436 | 1H NMR (400 MHz, CDCl$_3$) δ = 8.34 (s, 1H), 7.30 (d, J = 1.0 Hz, 1H), 5.97 (br s, 1H), 5.35 (br s, 1H), 4.35 (br s, 1H), 3.96 (br s, 1H), 3.81 (dd, J = 5.9, 10.2 Hz, 2H), 3.01-2.87 (m, 3H), 2.86-2.79 (m, 3H), 2.75-2.61 (m, 1H), 2.22 (d, J = 12.8 Hz, 2H), 2.13 (s, 3H), 1.91-1.65 (m, 8H) $[\alpha]_D^{20}$ − 17.8 (c 0.13, CHCl$_3$) >99% ee; absolute stereochemistry unknown Enantiomer of Ex. 32 |
| 34 (D) | (+)-6-chloro-8-[(1R*,3R*)-3-hydroxycyclohexyl]-2-{[1-(methylsulfonyl)piperidin-4-yl]amino}pyrido[2,3-d]pyrimidin-7(8H)-one | 478 [M + Na]+ | 1H NMR (400 MHz, DMSO-$d_6$) δ = 8.65-8.52 (m, 1H), 8.11-7.97 (m, 2H), 6.18-5.67 (m, 1H), 4.52 (br s, 1H), 4.12 (br s, 1H), 3.82 (br s, 1H), 3.59 (br s, 2H), 3.00-2.76 (m, 6H), 2.26-1.89 (m, 2H), 1.85-1.32 (m, 9H) $[\alpha]_D^{20}$ + 4.3 (c 0.2, DMSO) >99% ee; absolute stereochemistry unknown. Enantiomer of Ex.35 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 35 (D) | (-)-6-chloro-8-[(1R*,3R*)-3-hydroxycyclohexyl]-2-{[1-(methylsulfonyl)piperidin-4-yl]amino}pyrido[2,3-d]pyrimidin-7(8H)-one | 478 [M + Na]+ | 1H NMR (400 MHz, DMSO-$d_6$) δ = 8.62-8.54 (m, 1H), 8.10-7.92 (m, 2H), 6.16-5.65 (m, 1H), 4.51 (br s, 1H), 4.13 (br s, 1H), 3.83 (br s, 1H), 3.60 (br s, 2H), 2.95-2.74 (m, 6H), 2.20-1.89 (m, 2H), 1.89-1.36 (m, 9H) $[\alpha]_D^{20}$ − 8.7 (c 0.2, DMSO) 93% ee; absolute stereochemistry unknown. Enantiomer of Ex. 34 |
| 36 (A) | 8-[(1R,2S)-2-methylcyclopentyl]-2-{[1-(methylsulfonyl)piperidin-4-yl]amino}pyrido[2,3-d]pyrimidin-7(8H)-one | 406 | 1H NMR (400 MHz, CDCl$_3$) δ = 8.38 (s, 1H), 7.41 (d, J = 9.3 Hz, 1H), 6.34 (d, J = 9.3 Hz, 1H), 6.01-5.86 (m, 1H), 4.10-3.95 (m, 1H), 3.79 (d, J = 10.5 Hz, 2H), 2.93 (br s, 2H), 2.83 (s, 3H), 2.79-2.51 (m, 1H), 2.34 (br s, 1H), 2.19 (d, J = 12.3 Hz, 2H), 2.10-1.99 (m, 1H), 1.89 (dd, J = 7.7, 18.7 Hz, 4H), 1.76-1.61 (m, 2H), 1.60-1.45 (m, 1H), 0.78 (d, J = 7.0 Hz, 3H) 95% ee; Single enantiomer, absolute stereochemistry known. |
| 37 (A) | 6-methyl-8-[(1R,2S)-2-methylcyclopentyl]-2-{[1-(methylsulfonyl)piperidin-4-yl]amino}pyrido[2,3-d]pyrimidin-7(8H)-one | 420 | 1H NMR (400 MHz, CDCl$_3$) δ = 8.34 (s, 1H), 7.30 (s, 1H), 6.04-5.91 (m, 1H), 4.08-3.95 (m, 1H), 3.85-3.72 (m, 2H), 3.01-2.88 (m, 2H), 2.83 (s, 3H), 2.41-2.28 (m, 1H), 2.24-2.16 (m, 2H), 2.14 (s, 3H), 2.10-2.02 (m, 1H), 2.00-1.80 (m, 3H), 1.73 (br s, 4H), 1.63-1.53 (m, 1H), 0.76 (d, J = 7.0 Hz, 3H); 96% ee; Single enantiomer, absolute stereochemistry known. |
| 38 (D) | 6-chloro-8-[(1R,2S)-2-methylcyclopentyl]-2-{[1-(methylsulfonyl)piperidin-4-yl]amino}pyrido[2,3-d]pyrimidin-7(8H)-one | 440 | 1H NMR (400 MHz, CDCl$_3$) δ = 8.38 (s, 1H), 7.65 (s, 1H), 5.99 (d, J = 7.3 Hz, 1H), 4.10-3.93 (m, 1H), 3.79 (d, J = 8.8 Hz, 2H), 2.92 (br s, 2H), 2.83 (s, 3H), 2.41-2.27 (m, 1H), 2.18 (d, J = 12.0 Hz, 2H), 2.11-2.02 (m, 1H), 2.00-1.76 (m, 4H), 1.74-1.63 (m, 2H), 1.61-1.48 (m, 1H), 0.77 (d, J = 7.0 Hz, 3H); 96% ee; Single enantiomer, absolute stereochemistry known. Enantiomer of Ex. 39 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 39 (D) | 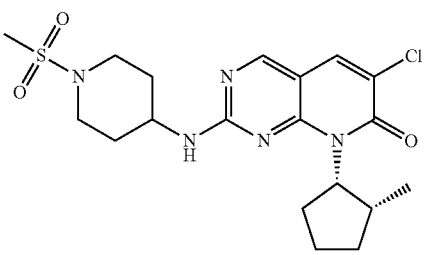<br>6-chloro-8-[(1S,2R)-2-methylcyclopentyl]-2-{[1-(methylsulfonyl)piperidin-4-yl]amino}pyrido[2,3-d]pyrimidin-7(8H)-one | 462 [M + Na]+ | 1H NMR (400 MHz, CDCl3) δ = 8.39 (s, 1H), 7.65 (s, 1H), 6.00 (dt, J = 7.0, 9.8 Hz, 1H), 4.02 (td, J = 2.1, 4.1 Hz, 1H), 3.88-3.72 (m, 2H), 3.01-2.90 (m, 2H), 2.83 (s, 3H), 2.35 (tt, J = 7.0, 10.4 Hz, 1H), 2.24-2.16 (m, 2H), 2.12-2.03 (m, 1H), 2.01-1.82 (m, 3H), 1.77-1.61 (m, 3H), 1.59-1.48 (m, 1H), 0.78 (d, J = 7.0 Hz, 3H); 97% ee; Single enantiomer, absolute stereochemistry known. Enantiomer of Ex. 38 |
| 40 (A) | 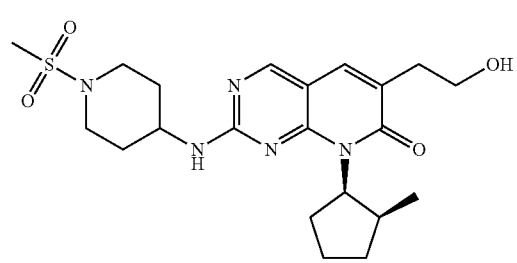<br>6-(2-hydroxyethyl)-8-[(1R,2S)-2-methylcyclopentyl]-2-{[1-(methylsulfonyl)piperidin-4-yl]amino}pyrido[2,3-d]pyrimidin-7(8H)-one | 450 | 1H NMR (400 MHz, CDCl3) δ = 8.39 (s, 1H), 7.38 (s, 1H), 6.06-5.92 (m, 1H), 4.10-3.97 (m, 1H), 3.90-3.72 (m, 4H), 3.03-2.89 (m, 2H), 2.86-2.75 (m, 5H), 2.42-2.29 (m, 1H), 2.25-2.15 (m, 2H), 2.12-2.01 (m, 1H), 2.01-1.81 (m, 3H), 1.79-1.48 (m, 4H), 0.77 (d, J = 7.0 Hz, 3H); 95% ee; Single enantiomer, absolute stereochemistry known. Enantiomer of Ex. 41 |
| 41 (A) | 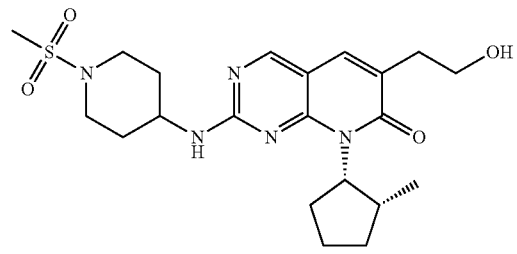<br>6-(2-hydroxyethyl)-8-[(1S,2R)-2-methylcyclopentyl]-2-{[1-(methylsulfonyl)piperidin-4-yl]amino}pyrido[2,3-d]pyrimidin-7(8H)-one | 450 | 1H NMR (400 MHz, CDCl3) δ = 8.39 (s, 1H), 7.38 (s, 1H), 6.04-5.94 (m, 1H), 4.08-3.98 (m, 1H), 3.91-3.74 (m, 4H), 3.02-2.89 (m, 3H), 2.86-2.78 (m, 5H), 2.42-2.29 (m, 1H), 2.25-2.15 (m, 2H), 2.11-2.01 (m, 1H), 2.01-1.80 (m, 3H), 1.70-1.63 (m, 2H), 1.62-1.49 (m, 1H), 0.77 (d, J = 7.0 Hz, 3H); >99% ee; Single enantiomer, absolute stereochemistry known. Enantiomer of Ex. 40 |
| 42 (A) | 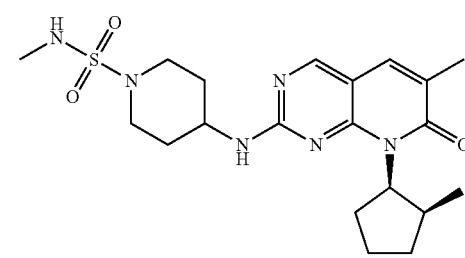<br>N-methyl-4-({6-methyl-8-[(1R,2S)-2-methylcyclopentyl]-7-oxo-7,8-dihydropyrido[2,3-d]pyrimidin-2-yl}amino)piperidine-1-sulfonamide | 435 | 1H NMR (400 MHz, CDCl3) δ = 8.45-8.24 (m, 1H), 7.29 (s, 1H), 6.03-5.93 (m, 1H), 5.38-5.11 (m, 1H), 4.22-4.10 (m, 1H), 4.08-3.94 (m, 1H), 3.78-3.67 (m, 2H), 3.10-2.95 (m, 2H), 2.76 (d, J = 5.5 Hz, 3H), 2.41-2.27 (m, 1H), 2.20-2.13 (m, 4H), 2.10-2.01 (m, 1H), 2.00-1.79 (m, 3H), 1.73-1.59 (m, 5H), 0.76 (d, J = 7.0 Hz, 3H); 96% ee; Single enantiomer, absolute stereochemistry known. Enantiomer of Ex. 43 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 43 (A) | N-methyl-4-({6-methyl-8-[(1S,2R)-2-methylcyclopentyl]-7-oxo-7,8-dihydropyrido[2,3-d]pyrimidin-2-yl}amino)piperidine-1-sulfonamide | 435 | $^1$H NMR (400 MHz, CDCl$_3$) δ = 8.34 (s, 1H), 7.30 (d, J = 0.8 Hz, 1H), 6.01-5.93 (m, 1H), 4.20 (d, J = 5.0 Hz, 1H), 4.07-3.96 (m, 1H), 3.72 (dd, J = 2.8, 12.3 Hz, 2H), 3.08-2.97 (m, 2H), 2.76 (d, J = 5.3 Hz, 3H), 2.39-2.28 (m, 1H), 2.17 (d, J = 3.8 Hz, 1H), 2.14 (s, 3H), 2.10-2.01 (m, 1H), 1.99-1.81 (m, 3H), 1.73-1.56 (m, 5H), 0.76 (d, J = 7.0, 3H); 96% ee; Single enantiomer, absolute stereochemistry known. Enantiomer of Ex. 42 |
| 44 (A) | N-methyl-4-({8-[(1R,2S)-2-methylcyclopentyl]-7-oxo-7,8-dihydropyrido[2,3-d]pyrimidin-2-yl}amino)piperidine-1-sulfonamide | 421 | $^1$H NMR (400 MHz, CDCl$_3$) δ = 8.38 (s, 1H), 7.41 (d, J = 9.3 Hz, 1H), 6.34 (d, J = 9.3 Hz, 1H), 6.00-5.87 (m, 1H), 4.40-4.29 (m, 1H), 4.08-3.96 (m, 1H), 3.78-3.65 (m, 2H), 3.02 (br s, 2H), 2.75 (d, J = 5.3 Hz, 3H), 2.40-2.29 (m, 1H), 2.20-2.11 (m, 2H), 2.10-2.00 (m, 1H), 1.89 (d, J = 9.8 Hz, 3H), 1.75-1.55 (m, 4H), 0.78 (d, J = 7.0 Hz, 3H); >99% ee; Single enantiomer, absolute stereochemistry known. Enantiomer of Ex. 45 |
| 45 (A) | N-methyl-4-({8-[(1S,2R)-2-methylcyclopentyl]-7-oxo-7,8-dihydropyrido[2,3-d]pyrimidin-2-yl}amino)piperidine-1-sulfonamide | 421 | $^1$H NMR (400 MHz, CDCl$_3$) δ = 8.38 (s, 1H), 7.41 (d, J = 9.3 Hz, 1H), 6.34 (d, J = 9.3 Hz, 1H), 5.93 (dt, J = 7.5, 9.8 Hz, 1H), 4.24 (q, J = 4.9 Hz, 1H), 4.10-3.96 (m, 1H), 3.78-3.68 (m, 2H), 3.08-2.98 (m, 2H), 2.76 (d, J = 5.3 Hz, 3H), 2.41-2.28 (m, 1H), 2.20-2.11 (m, 2H), 2.09-1.98 (m, 1H), 1.96-1.82 (m, 3H), 1.73-1.61 (m, 4H), 0.78 (d, J = 7.0 Hz, 3H); 97% ee; Single enantiomer, absolute stereochemistry known. Enantiomer of Ex. 44 |
| 46 (A) | 4-({6-(2-hydroxyethyl))-8-[(1S,2R)-2-methylcyclopentyl]-7-oxo-7,8-dihydropyrido[2,3-d]pyrimidin-2-yl}amino)-N-methylpiperidine-1-sulfonamide | 487 [M + Na]⁺ | $^1$H NMR (400 MHz, CDCl$_3$) δ = 8.39 (s, 1H), 7.38 (s, 1H), 6.07-5.91 (m, 1H), 5.69-5.30 (m, 1H), 4.47-4.26 (m, 1H), 4.12-3.96 (m, 1H), 3.85 (br s, 2H), 3.78-3.63 (m, 2H), 3.12-2.92 (m, 3H), 2.81 (s, 2H), 2.76 (d, J = 5.3 Hz, 3H), 2.71-2.59 (m, 1H), 2.43-2.28 (m, 1H), 2.21-2.13 (m, 2H), 2.11-2.00 (m, 1H), 2.00-1.81 (m, 3H), 1.70-1.48 (m, 3H), 0.77 (d, J = 7.0 Hz, 3H); >99% ee; Single enantiomer, absolute stereochemistry known. Enantiomer of Ex. 4 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 47 (F) | 2-(8-[(1R,2S)-2-methylcyclopentyl]-2-{[1-(methylsulfonyl)piperidin-4-yl]amino}-7-oxo-7,8-dihydropyrido[2,3-d]pyrimidin-6-yl)acetamide | 463 | ¹H NMR (400 MHz, CDCl₃) δ = 8.43 (s, 1H), 7.56 (s, 1H), 6.74 (br s, 1H), 5.95-6.09 (m, 1H), 5.31 (s, 2H), 4.04 (br s, 1H), 3.70-3.89 (m, 2H), 3.36-3.56 (m, 2H), 2.95 (br s, 2H), 2.84 (s, 3H), 2.67 (br s, 1H), 2.30-2.44 (m, 1H), 2.20 (d, J = 10.3 Hz, 2H), 2.01-2.13 (m, 1H), 1.83-1.98 (m, 3H), 1.72 (d, J = 11.5 Hz, 2H), 1.51-1.62 (m, 1H), 0.76 ppm (d, J = 7.0 Hz, 3H); 96% ee; Single enantiomer, absolute stereochemistry known. |
| 48 (A) | 6-(methoxymethyl)-8-[(1R,2S)-2-methylcyclopentyl]-2-{[1-(methylsulfonyl)piperidin-4-yl]amino}pyrido[2,3-d]pyrimidin-7(8H)-one | 472 [M + Na]⁺ | ¹H NMR (400 MHz, CDCl₃) δ = 8.42 (s, 1H), 7.53 (s, 1H), 5.97 (dt, J = 7.5, 9.8 Hz, 1H), 4.39 (d, J = 1.3 Hz, 2H), 4.08-3.97 (m, 1H), 3.84-3.72 (m, 2H), 3.50 (s, 3H), 3.00-2.87 (m, 2H), 2.83 (s, 3H), 2.39-2.28 (m, 1H), 2.25-2.15 (m, 2H), 2.09-1.99 (m, 1H), 1.99-1.82 (m, 3H), 1.74-1.65 (m, 2H), 1.60-1.48 (m, 2H), 0.76 (d, J = 7.3 Hz, 3H); 95% ee; Single enantiomer, absolute stereochemistry known. Enantiomer of Ex. 49 |
| 49 (A) | 6-(methoxymethyl)-8-[(1S,2R)-2-methylcyclopentyl]-2-{[1-(methylsulfonyl)piperidin-4-yl]amino}pyrido[2,3-d]pyrimidin-7(8H)-one | 450 | ¹H NMR (400 MHz, CDCl₃) δ = 8.42 (s, 1H), 7.54 (s, 1H), 5.97 (td, J = 9.8, 7.5 Hz, 1H), 5.31 (br s,, 1H), 4.40 (d, J = 1.3 Hz, 2H), 4.04 (d, J = 6.8 Hz, 1H), 3.80 (d, J = 10.8 Hz, 2H), 3.50 (s, 3H), 2.88-3.03 (m, 2H), 2.84 (s, 3H), 2.68 (d, J = 16.1 Hz, 1H), 2.35 (tquin, J = 10.4, 7.1 Hz, 1H), 2.21 (d, J = 12.5 Hz, 2H), 2.02-2.12 (m, 1H), 1.80-1.99 (m, 3H), 1.67-1.77 (m, 2H), 1.49-1.61 (m, 1H), 0.77 ppm (d, J = 7.0 Hz, 3H); 97% ee; Single enantiomer, absolute stereochemistry known. Enantiomer of Ex. 48 |
| 50 (A) | 6-(hydroxymetyl)-8-[(1R,2S)-2-methylcyclopentyl]-2-{[1-(methylsulfonyl)piperidin-4-yl]amino}pyrido[2,3-d]pyrimidin-7(8H)-one | 458 [M + Na]⁺ | ¹H NMR (400 MHz, CDCl₃) δ = 8.42 (s, 1H), 7.45 (s, 1H), 5.97 (dt, J = 7.3, 9.8 Hz, 1H), 4.56 (br s, 2H), 4.04 (dt, J = 1.6, 3.2 Hz, 1H), 3.86-3.71 (m, 2H), 3.19-3.06 (m, 1H), 3.01-2.88 (m, 2H), 2.83 (s, 3H), 2.36 (ddd, J = 3.0, 7.2, 10.1 Hz, 1H), 2.24-2.15 (m, 2H), 2.10-1.99 (m, 1H), 1.98-1.81 (m, 3H), 1.77-1.67 (m, 2H), 1.61-1.48 (m, 2H), 0.77 (d, J = 7.0 Hz, 3H); 97% ee; Single enantiomer, absolute stereochemistry known. Enantiomer of Ex. 51 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 51 (A) | 6-(hydroxymetyl)-8-[(1S,2R)-2-methylcyclopentyl]-2-{[1-(methylsulfonyl)piperidin-4-yl]amino}pyrido[2,3-d]pyrimidin-7(8H)-one | 458 [M + Na]⁺ | ¹H NMR (400 MHz, CDCl₃) δ = 8.42 (s, 1H), 7.45 (s, 1H), 6.01-5.93 (m, 1H), 4.56 (s, 2H), 4.09-3.98 (m, 1H), 3.86-3.72 (m, 2H), 3.19-3.04 (m, 1H), 3.01-2.87 (m, 1H), 2.83 (s, 3H), 2.40-2.27 (m, 1H), 2.24-2.15 (m, 2H), 2.12-1.99 (m, 1H), 1.98-1.82 (m, 3H), 1.79-1.63 (m, 4H), 1.58-1.51 (m, 1H), 0.77 (d, J = 7.0 Hz, 3H); 97% ee; Single enantiomer, absolute stereochemistry known. Enantiomer of Ex. 50 |
| 52 (A) | 2-({1-[(2-methoxyethyl)sulfonyl]piperidin-4-yl}amino)-8-[(1R,2S)-2-methylcyclopentyl]pyrido[2,3-d]pyrimidin-7(8H)-one | 472 [M + Na]⁺ | ¹H NMR (400 MHz, CDCl₃) δ = 8.39 (s, 1H), 7.41 (d, J = 9.3 Hz, 1H), 6.35 (d, J = 9.3 Hz, 1H), 6.05-5.87 (m, 1H), 5.38 (br s, 1H), 4.04 (br s, 1H), 3.86-3.71 (m, 4H), 3.39 (s, 3H), 3.23 (t, J = 5.8 Hz, 2H), 3.10-2.96 (m, 2H), 2.69 (br s,, 1H), 2.45-2.26 (m, 1H), 2.21-2.10 (d, J = 12.8 Hz, 2H), 2.08-1.97 (m, 1H), 1.95-1.79 (m, 3H), 1.64-1.47 (m, 3H), 0.79 (d, J = 7.0 Hz, 3H); >99% ee; Single enantiomer, absolute stereochemistry known |
| 53 (A) | (+)-8-[(1R*,3R*)-3-hydroxycyclopentyl]-2-{[1-(methylsulfonyl)piperidin-4-yl]amino}pyrido[2,3-d]pyrimidin-7(8H)-one | 408 | ¹H NMR (400 MHz, DMSO-d₆) δ = 8.59 (br s, 1H), 7.90-7.69 (m, 1H), 7.67 (d, J = 9.3 Hz, 1H), 6.21 (d, J = 7.8 Hz, 1H), 6.11 (br s, 1H). 4.63-4.46 (m, 1H), 4.42 (br s, 1H), 4.08-3.79 (m, 1H), 3.60-3.53 (m, 2H), 2.88 (s, 3H), 2.87-2.81 (m, 2H), 2.20 (br s, 2H), 2.06-1.83 (m, 4H), 1.70-1.52 (m, 4H); [α]_D²² + 15.0 (c 0.1, MeOH) >99% ee Absolute stereochemistry unknown. Enantiomer of Ex. 54 |
| 54 (A) | (-)-8-[(1R*,3R*)-3-hydroxycyclopentyl]-2-{[1-(methylsulfonyl)piperidin-4-yl]amino}pyrido[2,3-d]pyrimidin-7(8H)-one | 408 | ¹H NMR (400 MHz, DMSO-d₆) δ = 8.59 (br s, 1H), 7.91-7.69 (m, 1H), 7.67 (d, J = 9.3 Hz, 1H), 6.21 (d, J = 7.3 Hz, 1H), 6.11 (br s, 1H), 4.62-4.47 (m, 1H), 4.42 (br s, 1H), 4.13-3.80 (m, 1H), 3.60-3.53 (m, 2H), 2.88 (s, 3H), 2.87-2.82 (m, 2H), 2.20 (br s, 2H), 2.06-1.83 (m, 4H), 1.69-1.53 (m, 4H); [α]_D²² − 16.1 (c 0.1, MeOH) >99% ee; absolute stereochemistry unknown. Enantiomer of Ex. 53 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 55 (A) | 4-({8-[(1R,2R)-2-hydroxycyclopentyl]-6-methyl-7-oxo-7,8-dihydropyrido[2,3-d]pyrimidin-2-yl}amino)-N-methylpiperidine-1-sulfonamide | 459.0 [M + Na]+ | $^1$H NMR (400 MHz, CDCl$_3$) δ = 8.37 (s, 1H), 7.33 (d, J = 1.3 Hz, 1H), 5.84-5.68 (m, 1H), 5.00 (m, 1H), 4.09 (m, 1H), 4.00 (br s, 1H), 3.73 (d, J = 12.3 Hz, 2H), 3.03 (t, J = 11.7 Hz, 2H), 2.76 (d, J = 5.2, 3H), 2.42-2.26 (m, 2H), 2.15 (d, J = 1.3 Hz, 5H), 2.08-1.96 (m, 2H), 1.90 (dd, J = 6.1, 12.7 Hz, 1H), 1.77-1.63 (m, 3H); 98% ee; Single enantiomer, absolute stereochemistry known. |
| 56 (A) | (-)-4-({8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 459 [M + Na]+ | $^1$H NMR (400 MHz, CDCl$_3$) δ = 8.42 (s 1H), 7.45 (d, J = 9.3 Hz, 1H), 6.34 (d J = 9.0 Hz, 1H), 5.67 (br s, 2H), 4.77-4.35 (m, 1H), 4.03 (d, J = 6.0 Hz, 1H) 3.75 (d, J = 11.5 Hz, 2H), 3.03 (t, J = 10.8 Hz, 2H), 2.93-2.79 (m, 1H), 2.75 (d, J = 5.3 Hz, 3H), 2.28-2.09 (m, 3H) 2.06-1.80 (m, 4H), 1.72-1.58 (m, 3H) 1.17 (s, 3H); [α]$_D^{20}$ − 13.0 (c 0.20, CHCl$_3$) >99% ee; absolute stereochemistry unknown. Enantiomer of Ex. 57 |
| 57 (A) | (+)-4-({8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 459 [M + Na]+ | $^1$H NMR (400 MHz, CDCl$_3$) δ = 8.42 (s, 1H), 7.45 (d, J = 9.3 Hz, 1H), 6.35 (d, J = 9.5 Hz, 1H), 5.71 (br s, 1H), 5.51 (br s, 1H), 4.26 (br s, 1H), 4.01 (br s, 1H), 3.65-3.83 (m, 2H), 2.97-3.13 (m, 2H), 2.78-2.95 (m, 1H), 2.76 (d, J = 5.5 Hz, 3H), 2.11-2.29 (m, 3H), 1.80-2.08 (m, 4H), 1.62-1.74 (m, 3H), 1.17 ppm (s, 3H); [α]$_D^{20}$ + 8.6 (c 0.17, CHCl$_3$) >99% ee; absolute stereochemistry unknown. Enantiomer of Ex. 56 |
| 58 (A) | (-)-2-({1-[(fluoromethyl)sulfonyl]piperidin-4-yl}amino)-8-[(1R*,2R*)-2-hydroxy-2-methylcyclopentyl]pyrido[2,3-d]pyrimidin-7(8H)-one | 462 [M + Na]+ | $^1$H NMR (400 MHz, CDCl$_3$) δ = 8.43 (s, 1H), 7.46 (d, J = 9.3 Hz, 1H), 6.36 (d, J = 9.0 Hz, 1H), 5.82-5.66 (m, 1H), 5.49 (br s, 1H), 5.14 (d, J = 48 Hz, 2H), 4.05 (br s, 1H), 3.97-3.86 (m, 2H), 3.26-3.11 (m, 2H), 2.83 (br s, 1H), 2.30-2.16 (m, 3H), 2.07-1.97 (m, 2H), 1.95-1.80 (m, 2H), 1.67 (br s, 2H), 1.17 (s, 3H) $^{19}$F NMR (377 MHz, DMSO-d$_6$) δ = −215.3 (s, 1F) [α]$_D^{22}$ − 18.7 (c 0.5, CHCl$_3$) [α]$_D^{22}$ − 30.1 (c 0.5, MeOH) 99% ee; absolute stereochemistry unknown. Enantiomer of Ex. 59 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 59 (A) | (+)-2-({1-[(fluoromethyl)sulfonyl]piperidin-4-yl}amino)-8-[(1R*,2R*)-2-hydroxy-2-methylcyclopentyl]pyrido[2,3-d]pyrimidin-7(8H)-one | 462 [M + Na]⁺ | $^1$H NMR (400 MHz, CDCl$_3$) δ = 8.43 (s, 1H), 7.45 (d, J = 9.3 Hz, 1H), 6.36 (d, J = 9.3 Hz, 1H), 5.73 (br s, 1H), 5.40 (br s, 1H), 5.26-5.02 (m, 2H), 4.07 (br s, 1H), 3.93 (t, J = 11.9 Hz, 2H), 3.27-3.11 (m, 2H), 2.93-2.73 (m, 1H), 2.30-2.18 (m, 3H), 2.06-1.98 (m, 2H), 1.96-1.79 (m, 2H), 1.71-1.61 (m, 2H), 1.18 (s, 3H) $^{19}$F NMR (377 MHz, DMSO-d$_6$) δ = −215.3 (s, 1F) [α]$_D^{22}$ + 33.3 (c 0.5, MeOH) 99% ee; absolute stereochemistry unknown. Enantiomer of Ex. 58 |
| 60 (A) | (−)-4-({8-[(1R*,2R*)-2-hydroxy-2-methylcyclopentyl]-7-oxo-7,8-dihydropyrido[2,3-d]pyrimidin-2-yl}amino)-N-(2-methoxy-2-methylpropyl)piperidine-1-sulfonamide | 531 [M + Na]⁺ | $^1$H NMR (400 MHz, CDCl$_3$) δ = 8.43 (s, 1H), 7.45 (d, J = 9.3 Hz, 1H), 6.35 (d, J = 8.8 Hz, 1H), 5.72 (br s, 1H), 5.55-5.23 (m, 1H), 4.64-4.57 (m, 1H), 4.13-3.89 (m, 1H), 3.78-3.68 (m, 2H), 3.20 (s, 3H), 3.03 (d, J = 5.8 Hz, 4H), 2.94-2.77 (m, 1H), 2.68-2.36 (m, 1H), 2.17 (d, J = 13.3 Hz, 3H), 2.04-1.82 (m, 4H), 1.66 (d, J = 10.5 Hz, 2H), 1.22 (s, 6H), 1.17 (s, 3H); [α]$_D^{20}$ − 13.3 (c 0.27, MeOH) 98% ee; absolute stereochemistry unknown. Enantiomer of Ex. 61 |
| 61 (A) | (+)-4-({8-[(1R*,2R*)-2-hydroxy-2-methylcyclopentyl]-7-oxo-7,8-dihydropyrido[2,3-d]pyrimidin-2-yl}amino)-N-(2-methoxy-2-methylpropyl)piperidine-1-sulfonamide | 531 [M + Na]⁺ | $^1$H NMR (400 MHz, CDCl$_3$) δ = 8.43 (s, 1H), 7.45 (d, J = 9.3 Hz, 1H), 6.35 (d, J = 9.5 Hz, 1H), 5.72 (br s, 1H), 5.55-5.26 (m, 1H), 4.61 (t, J = 5.6 Hz, 1H), 4.00 (br s, 1H), 3.74 (d, J = 11.8 Hz, 2H), 3.20 (s, 3H), 3.05-2.96 (m, 4H), 2.86 (br s, 1H), 2.70-2.30 (m, 1H), 2.25-2.13 (m, 3H), 2.04-1.83 (m, 4H), 1.67-1.61 (m, 2H), 1.22 (s, 6H), 1.17 (s, 3H); [α]$_D^{20}$ + 13.8 (c 0.27, MeOH) >99% ee; absolute stereochemistry unknown. Enantiomer of Ex. 60 |
| 62 (A) | (−)-4-({8-[(1R*,2R*)-2-hydroxy-2-methylcyclopentyl]-7-oxo-7,8-dihydropyrido[2,3-d]pyrimidin-2-yl}amino)-N-[(2S)-tetrahdyrofuran-2-ylmethyl]piperidine-1-sulfonamide | 529 [M + Na]⁺ | $^1$H NMR (400 MHz, CD$_3$OD) δ = 8.55 (br s, 1H), 7.71 (d, J = 9.3 Hz, 1H), 6.28 (d, J = 9.3 Hz, 1H), 6.12-5.95 (m, 1H), 4.15-3.97 (m, 2H), 3.89 (m, 1H), 3.81-3.75 (m, 1H), 3.69 (m, 2H), 3.09 (m, 2H), 3.04-2.93 (m, 2H), 2.67-2.54 (m, 1H), 2.42-2.28 (m, 1H), 2.26-2.03 (m, 4H), 2.02-1.88 (m, 4H), 1.84-1.77 (m, 2H), 1.69-1.59 (m, 2H), 1.12 (s, 3H); [α]$_D^{20}$ − 10.8 (c 0.12, MeOH) >99% de; Single diastereomer. Absolute stereochemistry known (S) at THF center; relative (but not absolute) stereochemistry known at the cyclopentyl chiral centers. Made from (S)-tetrahydro-furfurylamine and racemic Intermediate 1. |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 63 (A) | 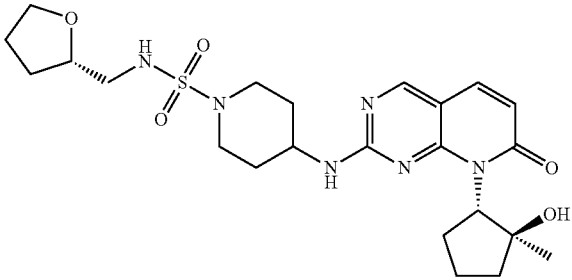<br>(+)-4-({8-[(1R*,2R*)-2-hydroxy-2-methylcyclopentyl]-7-oxo-7,8-dihydropyrido[2,3-d]pyrimidin-2-yl}amino)-N-[(2S)-tetrahdyrofuran-2-ylmethyl]piperidine-1-sulfonamide | 529 [M + Na]+ | 1H NMR (400 MHz, CD3OD) δ = 8.54 (br s, 1H), 7.71 (d, J = 9.3 Hz, 1H), 6.37-6.24 (m, 1H), 6.07 (br s, 1H), 4.14-3.98 (m, 2H), 3.89 (td, J = 6.6, 8.1 Hz, 1H), 3.83-3.74 (m, 1H), 3.69 (br d, J = 11.0 Hz, 2H), 3.15-3.04 (m, 2H), 2.99 (br s, 2H), 2.68-2.52 (m, 1H), 2.35 (br d, J = 11.5 Hz, 1H), 2.27-2.02 (m, 4H), 2.02-1.86 (m, 4H), 1.83-1.71 (m, 2H), 1.69-1.51 (m, 2H), 1.12 (s, 3H); $[\alpha]_D^{20}$ + 10 (c 0.12, MeOH) >99% de; Single diastereomer. Absolute stereochemistry known (S) at THF center; relative (but not absolute) stereochemistry known at the cyclopentyl chiral centers. Made from (S)-tetrahydro-furfurylamine and racemic Intermediate 1. |
| 64 (A) | 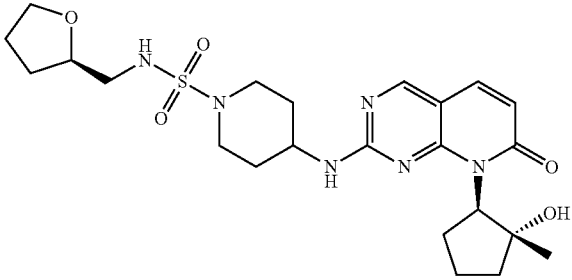<br>(-)-4-({8-[(1R*,2R*)-2-hydroxy-2-methylcyclopentyl]-7-oxo-7,8-dihydropyrido[2,3-d]pyrimidin-2-yl}amino)-N-[(2R)-tetrahdyrofuran-2-ylmethyl]piperidine-1-sulfonamide | 529 [M + Na]+ | 1H NMR (400 MHz, CD3OD) δ = 8.54 (s, 1H), 7.69 (d, J = 9.3 Hz, 1H), 6.27 (d, J = 9.2 Hz, 1H), 6.04 (s, 1H), 4.12-3.97 (m, 2H), 3.91-3.83 (m, 1H), 3.79-3.63 (m, 3H), 3.12-2.92 (m, 4H), 2.59 (s, 1H), 2.33 (s, 1H), 2.25-1.85 (m, 8H), 1.81-1.74 (m, 1H), 1.73-1.54 (m, 3H), 1.10 (s, 3H); $[\alpha]_D^{20}$ − 13.9 (c 0.13, MeOH) >99% de; Single diastereomer. Absolute stereochemistry known (R) at THF center; relative (but not absolute) stereochemistry known at the cyclopentyl chiral centers. Made from (R)-tetrahydro-furfurylamine and racemic Intermediate 1. |
| 65 (A) | 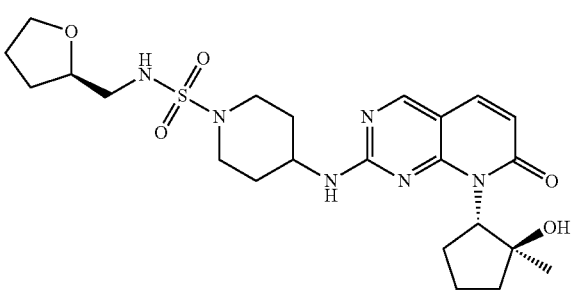<br>(+)-4-({8-[(1R*,2R*)-2-hydroxy-2-methylcyclopentyl]-7-oxo-7,8-dihydropyrido[2,3-d]pyrimidin-2-yl}amino)-N-[(2R)-tetrahdyrofuran-2-ylmethyl]piperidine-1-sulfonamide | 529 [M + Na]+ | 1H NMR (400 MHz, CD3OD) δ = 8.53 (s, 1H), 7.69 (d, J = 9.3 Hz, 1H), 6.26 (d, J = 9.3 Hz, 1H), 6.05 (br s, 1H), 4.14-3.96 (m, 2H), 3.92-3.83 (m, 1H), 3.79-3.62 (m, 3H), 3.13-2.91 (m, 4H), 2.59 (s, 1H), 2.40-2.26 (m, 1H), 2.23-1.88 (m, 8H), 1.81-1.56 (m, 4H), 1.10 (s, 3H); $[\alpha]_D^{20}$ + 8.4 (c 0.10, MeOH) >99% de; Single diastereomer. Absolute stereochemistry known (R) at THF center; relative (but not absolute) stereochemistry known at the cyclopentyl chiral centers. Made from (R)-tetrahydro-furfurylamine and racemic Intermediate 1. |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 66 (A) | (−)-N-(2,2-difluoropropyl)-4-({8-[(1R*,2R*)-2-hydroxy-2-methylcyclopentyl]-7-oxo-7,8-dihydropyrido[2,3-d]pyrimidin-2-yl}amino)piperidine-1-sulfonamide | 523 [M + Na]+ | 1H NMR (400 MHz, CD3OD) δ = 8.57 (br s, 1H), 7.71 (d, J = 9.0 Hz, 1H), 6.28 (d, J = 9.0 Hz, 1H), 6.07 (br s, 1H), 4.08 (br s, 1H), 3.74-3.65 (m, 2H), 3.39 (t, J = 13.1 Hz, 2H), 3.00 (br s, 2H), 2.61 (br s, 1H), 2.35 (q, J = 10.5 Hz, 1H), 2.28-2.06 (m, 3H), 2.00 (br s, 2H), 1.80 (d, J = 12.5 Hz, 1H), 1.67 (t, J = 18.8 Hz, 5H), 1.12 (s, 3H); 19F NMR (377 MHz, DMSO-d6) δ = −94.4 to −94.6 (m, 2F) [α]$_D^{20}$ − 11.3 (c 0.15, MeOH) >99% ee; absolute stereochemistry unknown. Enantiomer of Ex. 67 |
| 67 (A) | (+)-N-(2,2-difluoropropyl)-4-({8-[(1R*,2R*)-2-hydroxy-2-methylcyclopentyl]-7-oxo-7,8-dihydropyrido[2,3-d]pyrimidin-2-yl}amino)piperidine-1-sulfonamide | 523 [M + Na]+ | 1H NMR (400 MHz, CD3OD) δ = 8.53 (br s, 1H), 7.69 (d, J = 9.2 Hz, 1H), 6.27 (d, J = 9.5 Hz, 1H), 6.11-5.89 (m, 1H), 4.15-3.96 (m, 1H), 3.74-3.65 (m, 2H), 3.41-3.34 (m, 2H), 3.02-2.92 (m, 2H), 2.65-2.56 (m, 1H), 2.33 (q, J = 10.3 Hz, 1H), 2.23-2.04 (m, 3H), 1.99-1.91 (m, 2H), 1.78 (d, J = 12.8 Hz, 1H), 1.69-1.58 (m, 5H), 1.10 (s, 3H) 19F NMR (377 MHz, DMSO-d6) δ = −94.4 to −94.6 (m, 2F) [α]$_D^{20}$ + 8.4 (c 0.13, MeOH) 99% ee; absolute stereochemistry unknown. Enantiomer of Ex. 66 |
| 68 (A) | (−)-4-({8-[(1R*,2R*)-2-hydroxy-2-methylcyclopentyl]-7-oxo-7,8-dihydropyrido[2,3-d]pyrimidin-2-yl}amino)-N-(tetrahydro-2H-pyran-4-yl)piperidine-1-sulfonamide | 529 [M + Na]+ | 1H NMR (400 MHz, CDCl3) δ = 8.42 (s, 1H), 7.45 (d, J = 9.3 Hz, 1H), 6.39-6.31 (m, 1H), 5.77-5.48 (m, 2H), 4.48-4.36 (m, 1H), 3.98 (d, J = 11.3 Hz, 3H), 3.74 (d, J = 12.3 Hz, 2H), 3.50-3.37 (m, 3H), 2.99 (br s, 3H), 2.59-2.30 (m, 1H), 2.27-2.11 (m, 3H), 2.06-1.95 (m, 4H), 1.94-1.81 (m, 2H), 1.73-1.65 (m, 2H), 1.60-1.51 (m, 2H), 1.17 (s, 3H); [α]$_D^{20}$ − 12.7 (c 0.44, MeOH) 99% ee; absolute stereochemistry unknown. Enantiomer of Ex. 69 |
| 69 (A) | (+)-4-({8-[(1R*,2R*)-2-hydroxy-2-methylcyclopentyl]-7-oxo-7,8-dihydropyrido[2,3-d]pyrimidin-2-yl}amino)-N-(tetrahydro-2H-pyran-4-yl)piperidine-1-sulfonamide | 529 [M + Na]+ | 1H NMR (400 MHz, CDCl3) δ = 8.42 (s, 1H), 7.45 (d, J = 9.3 Hz, 1H), 6.35 (d, J = 9.8 Hz, 1H), 5.81-5.65 (m, 1H), 5.60-5.40 (m, 1H), 4.39-4.24 (m, 1H), 3.98 (d, J = 11.5 Hz, 3H), 3.73 (br s, 2H), 3.51-3.39 (m, 3H), 2.98 (br s, 3H), 2.57-2.31 (m, 1H), 2.29-2.13 (m, 3H), 1.99 (d, J = 10.3 Hz, 4H), 1.94-1.80 (m, 2H), 1.76-1.64 (m, 2H), 1.56 (dd, J = 4.3, 12.8 Hz, 2H), 1.17 (s, 3H); [α]$_D^{20}$ + 12.8 (c 0.25, MeOH) 99% ee; absolute stereochemistry unknown. Enantiomer of Ex. 68 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 70 (A) | 2-[(1-{[(3ξ)-1,1-dioxidotetrahydrothiophen-3-yl]sulfonyl}piperidin-4-yl)amino]-8-[(1R,2R)-2-hydroxy-2-methylcyclopentyl]pyrido[2,3-d]pyrimidin-7(8H)-one-Isomer (A) | 526 | 1H NMR (400 MHz, CDCl3) δ = 8.43 (s, 1H), 7.54-7.41 (m, 1H), 6.36 (d, J = 9.3 Hz, 1H), 5.73 (br s, 1H), 5.46 (br s, 1H), 4.05 (br s, 1H), 3.94-3.79 (m, 3H), 3.48-3.26 (m, 3H), 3.22-3.03 (m, 3H), 2.82 (br s, 1H), 2.66-2.52 (m, 2H), 2.31-2.17 (m, 3H), 2.06-1.78 (m, 4H), 1.65-1.56 (m, 3H), 1.17 (s, 3H); $[\alpha]_D^{20}$ − 32.0 (c 0.2, CHCl3) >99% de; Single diasteromer, absolute stereochemistry known (R,R) at the cyclopentyl chiral centers, but unknown at sulfolane center. Made from (±)-tetrahydro-3-thiophenesulfonyl chloride 1,1-dioxide and single enantiomer intermediate 2B from Ex. 2 |
| 71 (A) | 2-[(1-{[(3ξ)-1,1-dioxidotetrahydrothiophen-3-yl]sulfonyl}piperidin-4-yl)amino]-8-[(1R,2R)-2-hydroxy-2-methylcyclopentyl]pyrido[2,3-d]pyrimidin-7(8H)-one-Isomer (B) | 526 | 1H NMR (400 MHz, CDCl3) δ = 8.43 (s, 1H), 7.46 (d, J = 9.3 Hz, 1H), 6.36 (d, J = 9.3 Hz, 1H), 5.73 (t, J = 7.8 Hz, 1H), 5.46 (br s, 1H), 4.05 (br s, 1H), 3.94-3.81 (m, 3H), 3.45-3.29 (m, 3H), 3.21-3.08 (m, 3H), 2.82 (br s, 1H), 2.66-2.51 (m, 2H), 2.30-2.17 (m, 3H), 2.05-1.80 (m, 4H), 1.65-1.57 (m, 3H), 1.17 (s, 3H); $[\alpha]_D^{20}$ − 1.3 (c 0.2, CHCl3) >99% de; Single diasteromer, absolute stereochemistry known (R,R) at the cyclopentyl chiral centers, but unknown at sulfolane center. Made from (±)-tetrahydro-3-thiophenesulfonyl chloride 1,1-dioxide and single enantiomer intermediate 2B from Ex. 2 |
| 72 (A) | (−)-8-[(1R*,2R*)-2-hydroxy-2-methylcyclopentyl]-2-({1-[(2-methoxyethyl)sulfonyl]piperidin-4-yl}amino)pyrido[2,3-d]pyrimidin-7(8H)-one | 488 [M + Na]+ | 1H NMR (400 MHz, CDCl3) δ = 8.42 (s, 1H), 7.45 (d, J = 9.3 Hz, 1H), 6.35 (d, J = 9.3 Hz, 1H), 5.71 (t, J = 8.3 Hz, 1H), 5.44 (br s, 1H), 3.99 (br s, 1H), 3.82-3.74 (m, 4H), 3.40 (s, 3H), 3.22 (t, J = 5.8 Hz, 2H), 3.06-2.97 (m, 2H), 2.89 (d, J = 8.8 Hz, 1H), 2.61-2.35 (m, 1H), 2.28-2.12 (m, 3H), 2.05-1.96 (m, 2H), 1.94-1.81 (m, 2H), 1.72-1.61 (m, 2H), 1.17 (s, 3H); $[\alpha]_D^{20}$ − 14.5 (c 0.17, MeOH) 95% ee; absolute stereochemistry unknown. Enantiomer of Ex. 73 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 73 (A) | 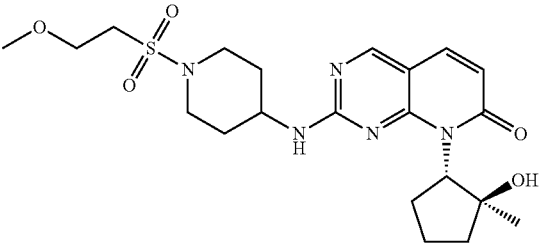<br>(+)-8-[(1R*,2R*)-2-hydroxy-2-methylcyclopentyl]-2-({1-[(2-methoxyethyl)sulfonyl]piperidin-4-yl}amino)pyrido[2,3-d]pyrimidin-7(8H)-one | 488 [M + Na]+ | $^1$H NMR (400 MHz, CDCl$_3$) δ = 8.43 (s, 1H), 7.45 (d, J = 9.3 Hz, 1H), 6.36 (d, J = 9.0 Hz, 1H), 5.72 (t, J = 8.5 Hz, 1H), 5.48 (br s, 1H), 3.98 (br s, 1H), 3.86-3.69 (m, 4H), 3.40 (s, 3H), 3.23 (t, J = 5.9 Hz, 2H), 3.08-2.96 (m, 2H), 2.88 (br s, 1H), 2.62-2.38 (m, 1H), 2.30-2.11 (m, 3H), 2.06-1.95 (m, 2H), 1.95-1.79 (m, 2H), 1.64-1.56 (m, 2H), 1.17 (s, 3H); [α]$_D^{20}$ + 14.2 (c 0.15, MeOH) 99% ee; absolute stereochemistry unknown. Enantiomer of Ex. 72 |
| 74 (A) | 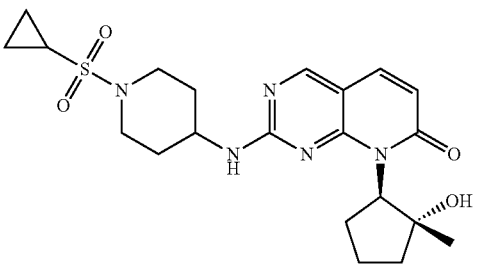<br>(-)-2-{[1-(cyclopropylsulfonyl)piperidin-4-yl]amino}-8-[(1R*,2R*)-2-hydroxy-2-methylcyclopentyl]pyrido[2,3-d]pyrimidin-7(8H)-one | 470 [M + Na]+ | $^1$H NMR (400 MHz, CD$_3$OD) δ = 8.54 (s, 1H), 7.69 (d, J = 9.6 Hz, 1H), 6.27 (d, J = 9.2 Hz, 1H), 6.06 (s, 1H), 4.16-4.04 (m, 1H), 3.83-3.70 (m, 2H), 3.17-3.04 (m, 2H), 2.64-2.46 (m, 2H), 2.40-1.88 (m, 6H), 1.82-1.55 (m, 3H), 1.11 (s, 3H), 1.09-1.02 (m, 4H); [α]$_D^{20}$ − 14.2 (c 0.12, MeOH) >99% ee; absolute stereochemistry unknown. Enantiomer of Ex. 75 |
| 75 (A) | 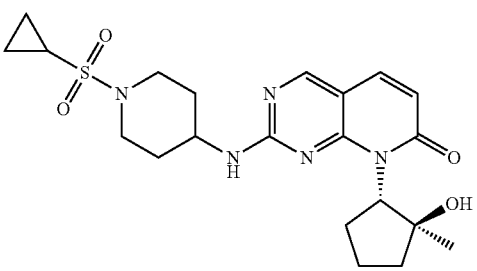<br>(+)-2-{[1-(cyclopropylsulfonyl)piperidin-4-yl]amino}-8-[(1R*,2R*)-2-hydroxy-2-methylcyclopentyl]pyrido[2,3-d]pyrimidin-7(8H)-one | 470 [M + Na]+ | $^1$H NMR (400 MHz, CD$_3$OD) δ = 8.54 (s, 1H), 7.69 (d, J = 9.2 Hz, 1H), 6.27 (d, J = 9.6 Hz, 1H), 6.14-5.90 (m, 1H), 4.16-4.03 (m, 1H), 3.83-3.69 (m, 2H), 3.18-3.04 (m, 2H), 2.66-2.44 (m, 2H), 2.37-1.93 (m, 6H), 1.82-1.55 (m, 3H), 1.11 (s, 3H), 1.09-1.02 (m, 4H); [α]$_D^{20}$ + 11.9 (c 0.16, MeOH) 99% ee; absolute stereochemistry unknown. Enantiomer of Ex. 74 |
| 76 (A) | 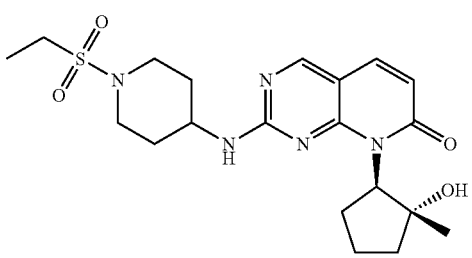<br>(-)-2-{[1-(ethylsulfonyl)piperidin-4-yl]amino}-8-[(1R*,2R*)-2-hydroxy-2-methylcyclopentyl]pyrido[2,3-d]pyrimidin-7(8H)-one | 436 | $^1$H NMR (400 MHz, CD$_3$OD) δ = 8.54 (s, 1H), 7.69 (d, J = 9.2 Hz, 1H), 6.26 (d, J = 9.2 Hz, 1H), 6.05 (s, 1H), 4.17-4.03 (m, 1H), 3.85-3.69 (m, 2H), 3.15-3.00 (m, 4H), 2.64-2.52 (m, 1H), 2.40-1.92 (m, 6H), 1.81-1.52 (m, 3H), 1.34 (t, J = 7.6 Hz, 3H), 1.10 (s, 3H); [α]$_D^{20}$ − 16.9 (c 0.16, MeOH) >99% ee; absolute stereochemistry unknown. Enantiomer of Ex. 77 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 77 (A) | (+)-2-{[1-(ethylsulfonyl)piperidin-4-yl]amino}-8-[(1R*,2R*)-2-hydroxy-2-methylcyclopentyl]pyrido[2,3-d]pyrimidin-7(8H)-one | 436 | 1H NMR (400 MHz, CD3OD) δ = 8.54 (s, 1H), 7.69 (d, J = 9.2 Hz, 1H), 6.26 (d, J = 9.2 Hz, 1H), 6.13-5.88 (m, 1H), 4.16-4.02 (m, 1H), 3.84-3.69 (m, 2H), 3.16-2.99 (m, 4H), 2.65-2.50 (m, 1H), 2.39-1.91 (m, 6H), 1.81-1.51 (m, 3H), 1.34 (t, J = 7.6 Hz, 3H), 1.11 (s, 3H); [α]$_D^{20}$ + 16.9 (c 0.13, MeOH) 99% ee; absolute stereochemistry unknown. Enantiomer of Ex. 76 |
| 78 (A) | (−)-8-[(1R*,2R*)-2-hydroxy-2-methylcyclopentyl]-2-{[1-(1,3-thiazol-2-ylsulfonyl)piperidin-4-yl]amino}pyrido[2,3-d]pyrimidin-7(8H)-one | 513 [M + Na]+ | 1H NMR (400 MHz, CD3OD) δ = 8.53 (br s, 1H), 8.08 (d, J = 3.0 Hz, 1H), 8.00 (d, J = 3.2 Hz, 1H), 7.68 (d, J = 9.0 Hz, 1H), 6.26 (d, J = 9.2 Hz, 1H), 6.05-5.88 (m, 1H), 4.10-3.97 (m, 1H), 3.87 (br d, J = 12.0 Hz, 2H), 3.01 (t, J = 11.6 Hz, 2H), 2.62-2.49 (m, 1H), 2.37-2.17 (m, 2H), 2.15-2.00 (m, 2H), 1.99-1.88 (m, 2H), 1.80-1.53 (m, 3H), 1.09 (s, 3H); [α]$_D^{20}$ − 7.5 (c 0.12, MeOH) >99% ee; absolute stereochemistry unknown. Enantiomer of Ex. 79 |
| 79 (A) | (+)-8-[(1R*,2R*)-2-hydroxy-2-methylcyclopentyl]-2-{[1-(1,3-thiazol-2-ylsulfonyl)piperidin-4-yl]amino}pyrido[2,3-d]pyrimidin-7(8H)-one | 513 [M + Na]+ | 1H NMR (400 MHz, CD3OD) δ = 8.54 (br s, 1H), 8.10 (d, J = 3.0 Hz, 1H), 8.01 (d, J = 3.3 Hz, 1H), 7.70 (d, J = 9.3 Hz, 1H), 6.27 (d, J = 9.3 Hz, 1H), 6.00 (br s, 1H), 4.04 (br s, 1H), 3.89 (br d, J = 12.3 Hz, 2H), 3.02 (br t, J = 12.2 Hz, 2H), 2.63-2.52 (m, 1H), 2.38-2.19 (m, 2H), 2.17-2.05 (m, 2H), 2.00-1.89 (m, 2H), 1.81-1.62 (m, 3H), 1.09 (s, 3H); [α]$_D^{20}$ + 8.8 (c 0.08, MeOH) >99% ee; absolute stereochemistry unknown. Enantiomer of Ex. 78 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 80 (A) | (−)-8-[(1R*,2R*)-2-hydroxy-2-methylcyclopentyl]-2-{[1-(1,3,4-thiadiazol-2-ylsulfonyl)piperidin-4-yl]amino}pyrido[2,3-d]pyrimidin-7(8H)-one | 514 [M + Na]+ | $^1$H NMR (400 MHz, CD$_3$OD) δ = 9.73 (s, 1H), 8.55 (br s, 1H), 7.70 (d, J = 9.2 Hz, 1H), 6.28 (d, J = 9.2 Hz, 1H), 6.07-5.93 (m, 1H), 4.16-4.05 (m, 1H), 3.95 (br d, J = 12.5 Hz, 2H), 3.16 (t, J = 12.0 Hz, 2H), 2.63-2.50 (m, 1H), 2.40-2.26 (m, 2H), 2.16 (m, 1H), 2.11-2.02 (m, 1H), 2.02-1.90 (m, 2H), 1.82-1.59 (m, 3H), 1.10 (s, 3H); [α]$_D^{20}$ − 13.3 (c 0.12, MeOH) >99% ee; absolute stereochemistry unknown. Enantiomer of Ex. 81 |
| 81 (A) | (+)-8-[(1R*,2R*)-2-hydroxy-2-methylcyclopentyl]-2-{[1-(1,3,4-thiadiazol-2-ylsulfonyl)piperidin-4-yl]amino}pyrido[2,3-d]pyrimidin-7(8H)-one | 514 [M + Na]+ | $^1$H NMR (400 MHz, CD$_3$OD) δ = 9.73 (s, 1H), 8.55 (br s, 1H), 7.70 (d, J = 9.3 Hz, 1H), 6.28 (d, J = 9.0 Hz, 1H), 6.02 (br s, 1H), 4.10 (br s, 1H), 3.95 (br d, J = 12.3 Hz, 2H), 3.16 (br t, J = 12.0 Hz, 2H), 2.57 (br s, 1H), 2.40-2.25 (m, 2H), 2.18-1.91 (m, 4H), 1.83-1.57 (m, 3H), 1.10 (s, 3H); [α]$_D^{20}$ + 10 (c 0.11, MeOH) 95% ee; absolute stereochemistry unknown. Enantiomer of Ex. 80 |
| 82 (A) | (−)-8-[(1R*,2R*)-2-hydroxy-2-methylcyclopentyl]-2-{[1-[(1-methyl-1H-pyrazol-4-yl)sulfonyl]piperidin-4-yl}amino)pyrido[2,3-d]pyrimidin-7(8H)-one | 470 [M − H$_2$O + H]+ | $^1$H NMR (400 MHz, CD$_3$OD) δ = 8.54 (s, 1H), 8.16 (s, 1H), 7.79 (s, 1H), 7.69 (d, J = 9.5 Hz, 1H), 6.27 (d, J = 9.0 Hz, 1H), 6.00 (br s, 1H), 3.99 (s, 3H), 3.96-3.90 (m, 1H), 3.66 (d, J = 12.5 Hz, 2H), 2.66-2.49 (m, 3H), 2.38-2.26 (m, 1H), 2.23 (br s, 1H), 2.19-2.02 (m, 2H), 2.00-1.90 (m, 2H), 1.74 (br s, 3H), 1.10 (s, 3H); [α]$_D^{20}$ − 6.6 (c 0.21, MeOH) >99% ee; absolute stereochemistry unknown. Enantiomer of Ex. 83 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 83 (A) | (+)-8-[(1R*,2R*)-2-hydroxy-2-methylcyclopentyl]-2-{[1-[(1-methyl-1H-pyrazol-4-yl)sulfonyl]piperidin-4-yl}amino)pyrido[2,3-d]pyrimidin-7(8H)-one | 470 [M − H2O + H]+ | 1H NMR (400 MHz, CD3OD) δ = 8.54 (s, 1H), 8.16 (s, 1H), 7.79 (s, 1H), 7.69 (d, J = 9.5 Hz, 1H), 6.27 (d, J = 9.0 Hz, 1H), 6.00 (br s, 1H), 3.99 (s, 3H), 3.97-3.90 (m, 1H), 3.66 (br d, J = 12.5 Hz, 2H), 2.66-2.52 (m, 3H), 2.40-2.27 (m, 1H), 2.16-1.80 (m, 5H), 1.74 (br s, 3H), 1.10 (s, 3H); $[\alpha]_D^{20}$ + 4.7 (c 0.19, MeOH) 93% ee; absolute stereochemistry unknown. Enantiomer of Ex. 82 |
| 84 (A) | (−)-8-[(1R*,2R*)-2-hydroxy-2-methylcyclopentyl]-2-({1-[(1-methyl-1H-imidazol-4-yl)sulfonyl]piperidin-4-yl}amino)pyrido[2,3-d]pyrimidin-7(8H)-one | 470 [M − H2O + H]+ | 1H NMR (400 MHz, CD3OD) δ = 8.53 (s, 1H), 7.81 (d, J = 1.0 Hz, 1H), 7.74 (s, 1H), 7.69 (d, J = 9.3 Hz, 1H), 6.27 (d, J = 9.0 Hz, 1H), 6.00 (br s, 1H), 3.97 (br s, 1H), 3.85-3.71 (m, 5H), 2.80 (t, J = 11.8 Hz, 2H), 2.66-2.50 (m, 1H), 2.39-2.29 (m, 1H), 2.26-1.88 (m, 5H), 1.81-1.53 (m, 3H), 1.10 (s, 3H); $[\alpha]_D^{20}$ − 10.8 (c 0.15, MeOH) >99% ee; absolute stereochemistry unknown. Enantiomer of Ex. 85 |
| 85 (A) | (+)-8-[(1R*,2R*)-2-hydroxy-2-methylcyclopentyl]-2-({1-[(1-methyl-1H-imidazol-4-yl)sulfonyl]piperidin-4-yl}amino)pyrido[2,3-d]pyrimidin-7(8H)-one | 470 [M − H2O + H]+ | 1H NMR (400 MHz, CD3OD) δ = 8.53 (br s, 1H), 7.82 (d, J = 1.0 Hz, 1H), 7.74 (s, 1H), 7.69 (d, J = 9.3 Hz, 1H), 6.27 (d, J = 9.3 Hz, 1H), 6.00 (br s, 1H), 3.98 (br s, 1H), 3.85-3.70 (m, 5H), 2.79 (t, J = 11.5 Hz, 2H), 2.65-2.51 (m, 1H), 2.37-2.27 (m, 1H), 2.24-1.91 (m, 5H), 1.80-1.55 (m, 3H), 1.10 (s, 3H); $[\alpha]_D^{20}$ + 6.0 (c 0.17, MeOH) 99% ee; absolute stereochemistry unknown. Enantiomer of Ex. 84 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 86 (A) | (−)-8-[(1R*,2R*)-2-hydroxy-2-methylcyclopentyl]-2-({1-[(2,2,2-trifluoroethyl)sulfonyl]piperidin-4-yl}amino)pyrido[2,3-d]pyrimidin-7(8H)-one | 512 [M + Na]⁺ | ¹H NMR (400 MHz, CD₃OD) δ = 8.56 (br s, 1H), 7.71 (d, J = 9.3 Hz, 1H), 6.29 (d, J = 9.3 Hz, 1H), 6.07 (br s, 1H), 4.21-4.05 (m, 3H), 3.84 (t, J = 11.2 Hz, 2H), 3.13 (t, J = 11.7 Hz, 2H), 2.60 (br s, 1H), 2.41-2.18 (m, 2H), 2.14 (d, J = 13.6 Hz, 2H), 2.00 (br s, 2H), 1.80 (d, J = 13.1 Hz, 1H), 1.68 (br s, 2H), 1.12 (s, 3H) ¹⁹F NMR (377 MHz, DMSO-d₆) δ = −60.1 to −60.3 (m, 3F) $[\alpha]_D^{20}$ − 18.3 (c 0.12, MeOH) 99% ee; absolute stereochemistry unknown. Enantiomer of Ex. 87 |
| 87 (A) | (+)-8-[(1R*,2R*)-2-hydroxy-2-methylcyclopentyl]-2-({1-[(2,2,2-trifluoroethyl)sulfonyl]piperidin-4-yl}amino)pyrido[2,3-d]pyrimidin-7(8H)-one | 512 [M + Na]⁺ | ¹H NMR (400 MHz, CD₃OD) δ = 8.56 (br s, 1H), 7.71 (d, J = 9.3 Hz, 1H), 6.29 (d, J = 9.3 Hz, 1H), 6.06 (br s, 1H), 4.17 (q, J = 9.7 Hz, 3H), 3.84 (br t, J = 11.2 Hz, 2H), 3.13 (br t, J = 11.2 Hz, 2H), 2.60 (br s, 1H), 2.41-2.19 (m, 2H), 2.16-1.92 (m, 4H), 1.80 (br d, J = 14.3 Hz, 1H), 1.68 (br s, 2H), 1.12 (s, 3H) ¹⁹F NMR (377 MHz, DMSO-d₆) δ = −60.1 to −60.3 (m, 3F) $[\alpha]_D^{20}$ + 19.1 (c 0.11, MeOH) 97% ee; absolute stereochemistry unknown. Enantiomer of Ex. 86 |
| 88 (A) | (−)-8-[(1R*,2R*)-2-hydroxy-2-methylcyclopentyl]-2-({1-[(trifluoromethyl)sulfonyl]piperidin-4-yl}amino)pyrido[2,3-d]pyrimidin-7(8H)-one | 476 | ¹H NMR (400 MHz, CD₃OD) δ = 8.57 (br s, 1H), 7.72 (d, J = 9.3 Hz, 1H), 6.29 (d, J = 9.3 Hz, 1H), 6.08 (br s, 1H), 4.21 (br s, 1H), 4.05-3.89 (m, 2H), 3.49-3.35 (m, 2H), 2.64-2.51 (m, 1H), 2.44-2.26 (m, 2H), 2.16 (d, J = 10.3 Hz, 1H), 2.13-1.93 (m, 2H), 2.11-1.92 (m, 1H), 1.84-1.55 (m, 3H), 1.12 (s, 3H) ¹⁹F NMR (377 MHz, DMSO-d₆) δ = −75.6 (br s, 3F) $[\alpha]_D^{20}$ − 20.5 (c 0.18, MeOH) >99% ee; absolute stereochemistry unknown. Enantiomer of Ex. 89 |
| 89 (A) | (+)-8-[(1R*,2R*)-2-hydroxy-2-methylcyclopentyl]-2-({1-[(trifluoromethyl)sulfonyl]piperidin-4-yl}amino)pyrido[2,3-d]pyrimidin-7(8H)-one | 476 | ¹H NMR (400 MHz, CD₃OD) δ = 8.57 (br s, 1H), 7.72 (d, J = 9.3 Hz, 1H), 6.29 (d, J = 9.3 Hz, 1H), 6.07 (br s, 1H), 4.21 (br s, 1H), 4.04-3.88 (m, 2H), 3.39 (br s, 2H), 2.63-2.51 (m, 1H), 2.41-2.23 (m, 2H), 2.22-2.05 (m, 2H), 2.01 (br d, J = 15.6 Hz, 2H), 1.79 (br d, J = 13.1 Hz, 1H), 1.73-1.50 (m, 2H), 1.12 (s, 3H) ¹⁹F NMR (377 MHz, DMSO-d₆) δ = −75.6 (br s, 3F) $[\alpha]_D^{20}$ + 19.2 (c 0.12, MeOH) 99% ee; absolute stereochemistry unknown. Enantiomer of Ex. 88 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 90 (A) | (-)-2-({1-[(cyclopropylmethyl)sulfonyl]piperidin-4-yl}amino)-8-[(1R*,2R*)-2-hydroxy-2-methylcyclopentyl]pyrido[2,3-d]pyrimidin-7(8H)-one | 484 [M + Na]+ | 1H NMR (400 MHz, CDCl3) δ = 8.43 (s, 1H), 7.46 (d, J = 9.3 Hz, 1H), 6.36 (d, J = 9.0 Hz, 1H), 5.77-5.65 (m, 1H), 5.49-5.25 (m, 1H), 3.98 (br s, 1H), 3.92-3.82 (m, 2H), 3.09-2.98 (m, 2H), 2.95-2.78 (m, 3H), 2.65-2.36 (m, 1H), 2.28-2.13 (m, 3H), 2.07-1.79 (m, 4H), 1.76-1.61 (m, 2H), 1.20-1.09 (m, 4H), 0.78-0.69 (m, 2H), 0.43-0.34 (m, 2H); [α]$_D^{20}$ − 13.1 (c 0.15, MeOH) >99% ee; absolute sterochemistry unknown. Enantiomer of Ex. 91 |
| 91 (A) | (+)-2-({1-[(cyclopropylmethyl)sulfonyl]piperidin-4-yl}amino)-8-[(1R*,2R*)-2-hydroxy-2-methylcyclopentyl]pyrido[2,3-d]pyrimidin-7(8H)-one | 484 [M + Na]+ | 1H NMR (400 MHz, CDCl3) δ = 8.43 (s, 1H), 7.46 (d, J = 9.3 Hz, 1H), 6.36 (d, J = 9.5 Hz, 1H), 5.72 (t, J = 8.3 Hz, 1H), 5.52-5.29 (m, 1H), 3.99 (br s, 1H), 3.92-3.81 (m, 2H), 3.09-2.97 (m, 2H), 2.93-2.77 (m, 3H), 2.62-2.33 (m, 1H), 2.30-2.12 (m, 3H), 2.07-1.80 (m, 4H), 1.67 (d, J = 4.8 Hz, 2H), 1.19-1.09 (m, 4H), 0.77-0.70 (m, 2H), 0.41-0.36 (m, 2H); [α]$_D^{20}$ + 8.4 (c 0.21, MeOH) 93% ee; absolute stereochemistry unknown. Enantiomer of Ex. 90 |
| 92 (A) | (-)-8-[(1R*,2R*)-2-hydroxy-2-methylcyclopentyl]-6-methyl-2-{[1-(methylsulfonyl)piperidin-4-yl]amino}pyrido[2,3-d]pyrimidin-7(8H)-one | 436 | 1H NMR (400 MHz, CDCl3) δ = 8.39 (br s, 1H), 7.33 (s, 1H), 5.75 (t, J = 8.3 Hz, 1H), 5.35 (br s, 1H), 3.99 (br s, 1H), 3.81 (t, J = 10.6 Hz, 2H), 3.01-2.88 (m, 2H), 2.83 (s, 4H), 2.33-2.18 (m, 3H), 2.16 (s, 3H), 2.10-1.79 (m, 4H), 1.75-1.53 (m, 3H), 1.16 (s, 3H); [α]$_D^{22}$ − 29.8 (c 0.1, MeOH) >99% ee; absolute stereochemistry unknown. Enantiomer of Ex. 93 |
| 93 (A) | (+)-8-[(1R*,2R*)-2-hydroxy-2-methylcyclopentyl]-6-methyl-2-{[1-(methylsulfonyl)piperidin-4-yl]amino}pyrido[2,3-d]pyrimidin-7(8H)-one | 436 | 1H NMR (400 MHz, CDCl3) δ = 8.38 (br s, 1H), 7.33 (s, 1H), 5.75 (t, J = 8.4 Hz, 1H), 5.41 (br s, 1H), 4.00 (br s, 1H), 3.81 (t, J = 10.6 Hz, 2H), 3.02-2.88 (m, 2H), 2.83 (s, 4H), 2.33-2.18 (m, 3H), 2.16 (s, 3H), 2.09-1.80 (m, 4H), 1.77-1.58 (m, 3H), 1.16 (s, 3H); [α]$_D^{22}$ + 31.5 (c 0.1, MeOH) 99% ee; absolute stereochemistry unknown. Enantiomer of Ex. 92 |

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 94 (A) | (−)-4-({8-[(1R*,2R*)-2-hydroxy-2-methylcyclopentyl]-6-methyl-7-oxo-7,8-dihydropyrido[2,3-d]pyrimidin-2-yl}amino)-N-methylpiperidine-1-sulfonamide | 451 | ¹H NMR (400 MHz, DMSO-$d_6$, 80° C.) δ = 8.49 (s, 1H), 7.52 (s, 1H), 7.32 (br s, 1H), 6.76 (br s, 1H), 5.87 (t, J = 8.2 Hz, 1H), 4.07 (br s, 1H), 3.93 (d, J = 5.9 Hz, 1H), 3.56 (t, J = 11.5 Hz, 2H), 2.86 (t, J = 11.7 Hz, 2H), 2.55 (d, J = 4.6 Hz, 4H), 2.30-2.18 (m, 1H), 2.03 (s, 3H), 2.00-1.83 (m, 4H), 1.75-1.52 (m, 3H), 0.99 (s, 3H); $[\alpha]_D^{22}$ − 40.5 (c 0.1, MeOH) >99% ee; absolute stereochemistry unknown. Enantiomer of Ex. 95 |
| 95 (A) | (+)-4-({8-[(1R*,2R*)-2-hydroxy-2-methylcyclopentyl]-6-methyl-7-oxo-7,8-dihydropyrido[2,3-d]pyrimidin-2-yl}amino)-N-methylpiperidine-1-sulfonamide | 451 | ¹H NMR (400 MHz, DMSO-$d_6$, 80° C.) δ = 8.49 (br s, 1H), 7.52 (br s, 1H), 7.32 (br s, 1H), 6.77 (br s, 1H), 5.94-5.79 (m, 1H), 4.06 (br s, 1H), 3.92 (br s, 1H), 3.56 (br s, 2H), 2.86 (t, J = 11.7 Hz, 2H), 2.55 (br s, 4H), 2.24 (d, J = 10.0 Hz, 1H), 2.03 (br s, 3H), 2.00-1.81 (m, 4H), 1.77-1.48 (m, 3H), 0.99 (br s, 3H); $[\alpha]_D^{22}$ + 24.9 (c 0.1, MeOH) 90% ee; absolute stereochemistry unknown. Enantiomer of Ex. 94 |
| 96 (A) | (−)-4-({8-[(1R*,2R*)-2-hydroxy-2-methylcyclopentyl]-6-methyl-7-oxo-7,8-dihydropyrido[2,3-d]pyrimidin-2-yl}amino)-N-(tetrahydro-2H-pyran-4-yl)piperidine-1-sulfonamide | 543 [M + Na]⁺ | ¹H NMR (400 MHz, CDCl₃) δ = 8.37 (s, 1H), 7.32 (d, J = 1.0 Hz, 1H), 5.78-5.64 (m, 1H), 5.58-5.33 (br s, 1H), 4.45-4.25 (m, 1H), 4.05-3.92 (m, 3H), 3.73 (d, J = 11.3 Hz, 2H), 3.51-3.39 (m, 3H), 3.12-2.92 (m, 2H), 2.85 (br s, 1H), 2.28-2.11 (m, 6H), 2.06-1.95 (m, 4H), 1.93-1.81 (m, 2H), 1.61-1.48 (m, 3H), 1.40-1.24 (m, 2H), 1.15 (s, 3H); $[\alpha]_D^{22}$ − 5.0 (c 0.1, CHCl₃) 99% ee; absolute stereochemistry unknown. Enantiomer of Ex. 97 |
| 97 (A) | (+)-4-({8-[(1R*,2R*)-2-hydroxy-2-methylcyclopentyl]-6-methyl-7-oxo-7,8-dihydropyrido[2,3-d]pyrimidin-2-yl}amino)-N-(tetrahydro-2H-pyran-4-yl)piperidine-1-sulfonamide | 543 [M + Na]⁺ | ¹H NMR (400 MHz, CDCl₃) δ = 8.37 (s, 1H), 7.32 (s, 1H), 5.71 (br s, 1H), 5.51 (br s, 1H), 4.48 (d, J = 8.0 Hz, 1H), 3.97 (d, J = 11.5 Hz, 3H), 3.73 (d, J = 11.5 Hz, 2H), 3.53-3.34 (m, 3H), 3.09-2.91 (m, 2H), 2.85 (br s, 1H), 2.30-2.11 (m, 6H), 2.06-1.95 (m, 4H), 1.93-1.80 (m, 2H), 1.67-1.49 (m, 4H), 1.46-1.23 (m, 1H), 1.14 (s, 3H); $[\alpha]_D^{22}$ + 5.7 (c 0.1, CHCl₃) 96% ee; absolute stereochemistry unknown. Enantiomer of Ex. 96 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 98 (A) | (−)-4-({8-[(1R*,2R*)-2-hydroxy-2-methylcyclopentyl]-6-methyl-7-oxo-7,8-dihydropyrido[2,3-d]pyrimidin-2-yl}amino)-N-(2-methoxy-2-methylpropyl)piperidine-1-sulfonamide | 545 [M + Na]+ | 1H NMR (400 MHz, CDCl$_3$) δ = 8.38 (s, 1H), 7.33 (d, J = 1.3 Hz, 1H), 5.78-5.69 (m, 1H), 5.51-5.18 (m, 1H), 4.62 (t, J = 5.8 Hz, 1H), 4.06-3.92 (m, 1H), 3.74 (d, J = 11.0 Hz, 2H), 3.20 (s, 3H), 3.05-2.96 (m, 4H), 2.93-2.78 (m, 1H), 2.68-2.38 (m, 1H), 2.30-2.21 (m, 1H), 2.19-2.13 (m, 5H), 2.04-1.82 (m, 4H), 1.71-1.63 (m, 2H), 1.22 (s, 6H), 1.15 (s, 3H); [α]$_D^{22}$ − 10.9 (c 0.33, MeOH) >99% ee; absolute stereochemistry unknown. Enantiomer of Ex. 99 |
| 99 (A) | (+)-4-({8-[(1R*,2R*)-2-hydroxy-2-methylcyclopentyl]-6-methyl-7-oxo-7,8-dihydropyrido[2,3-d]pyrimidin-2-yl}amino)-N-(2-methoxy-2-methylpropyl)piperidine-1-sulfonamide | 545 [M + Na]+ | 1H NMR (400 MHz, CDCl$_3$) δ = 8.38 (s, 1H), 7.33 (d, J = 1.3 Hz, 1H), 5.73 (s, 1H), 5.51-5.18 (m, 1H), 4.63 (t, J = 5.4 Hz, 1H), 3.98 (br s, 1H), 3.74 (d, J = 11.3 Hz, 2H), 3.20 (s, 3H), 3.06-2.95 (m, 4H), 2.86 (br s, 1H), 2.70-2.37 (m, 1H), 2.29-2.21 (m, 1H), 2.15 (s, 5H), 2.04-1.83 (m, 4H), 1.64 (br s, 2H), 1.22 (s, 6H), 1.15 (s, 3H); [α]$_D^{22}$ + 7.6 (c 0.25, MeOH) 99% ee; absolute stereochemistry unknown. Enantiomer of Ex. 98 |
| 100 (A) | (−)-4-({8-[(1R*,2R*)-2-hydroxy-2-methylcyclopentyl]-6-methyl-7-oxo-7,8-dihydropyrido[2,3-d]pyrimidin-2-yl}amino)-N-[(2S)-tetrahydrofuran-2-ylmethyl]piperidine-1-sulfonamide | 543 [M + Na]+ | 1H NMR (400 MHz, CDCl$_3$) δ = 8.38 (s, 1H), 7.33 (d, J = 1.0 Hz, 1H), 5.73 (t, J = 7.9 Hz, 1H), 5.37 (br s, 1H), 4.72-4.62 (m, 1H), 4.11-3.94 (m, 2H), 3.91-3.82 (m, 1H), 3.81-3.66 (m, 3H), 3.25 (ddd, J = 3.4, 7.3, 12.9 Hz, 1H), 3.09-2.96 (m, 3H), 2.85 (br s, 1H), 2.31-2.21 (m, 1H), 2.20-2.11 (m, 5H), 2.06-1.83 (m, 7H), 1.71-1.62 (m, 4H), 1.15 (s, 3H); [α]$_D^{20}$ − 7.0 (c 0.1, MeOH) 94% de; Single diastereomer. Absolute stereochemistry known (S) at THF center; relative (but not absolute) stereochemistry known at the cyclopentyl chiral centers. Made from (S)-tetrahydro-furfurylamine and racemic Intermediate 1. |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 101 (A) | (+)-4-({8-[(1R*,2R*)-2-hydroxy-2-methylcyclopentyl]-6-methyl-7-oxo-7,8-dihydropyrido[2,3-d]pyrimidin-2-yl}amino)-N-[(2S)-tetrahydrofuran-2-ylmethyl]piperidine-1-sulfonamide | 543 [M + Na]+ | $^1$H NMR (400 MHz, CDCl$_3$) δ = 8.39 (s, 1H), 7.33 (d, J = 1.3 Hz, 1H), 5.73 (t, J = 8.2 Hz, 1H), 5.36 (br s, 1H), 4.68-4.58 (m, 1H), 4.09-3.93 (m, 2H), 3.91-3.84 (m, 1H), 3.82-3.66 (m, 3H), 3.25 (ddd, J = 3.4, 7.2, 12.7 Hz, 1H), 3.10-2.95 (m, 3H), 2.85 (br s, 1H), 2.31-2.21 (m, 1H), 2.21-2.11 (m, 5H), 2.07-1.81 (m, 7H), 1.70-1.61 (m, 4H), 1.16 (s, 3H); $[α]_D^{20}$ + 11 (c 0.1, MeOH) >99% de; Single diastereomer. Absolute stereochemistry known (S) at THF center; relative (but not absolute) stereochemistry known at the cyclopentyl chiral centers. Made from (S)-tetrahydro-furfurylamine and racemic Intermediate 1. |
| 102 (A) | (-)-4-({8-[(1R*,2R*)-2-hydroxy-2-methylcyclopentyl]-6-methyl-7-oxo-7,8-dihydropyrido[2,3-d]pyrimidin-2-yl}amino)-N-[(2R)-tetrahydrofuran-2-ylmethyl]piperidine-1-sulfonamide | 543 [M + Na]+ | $^1$H NMR (400 MHz, CDCl$_3$) δ = 8.38 (s, 1H), 7.32 (d, J = 1.3 Hz, 1H), 5.72 (t, J = 8.7 Hz, 1H), 5.56 (br s, 1H), 4.95-4.77 (m, 1H), 4.08-3.92 (m, 2H), 3.86 (td, J = 6.6, 8.5 Hz, 1H), 3.80-3.64 (m, 3H), 3.24 (ddd, J = 3.4, 7.0, 12.9 Hz, 1H), 3.08-2.94 (m, 3H), 2.90-2.77 (m, 1H), 2.30-2.19 (m, 1H), 2.14 (d, J = 1.0 Hz, 5H), 2.04-1.80 (m, 7H), 1.75-1.63 (m, 4H), 1.14 (s, 3H); $[α]_D^{20}$ − 23 (c 0.2, MeOH) >99% de; Single diastereomer. Absolute stereochemistry known (S) at THF center; relative (but not absolute) stereochemistry known at the cyclopentyl chiral centers. Made from (R)-tetrahydro-furfurylamine and racemic Intermediate 1. |
| 103 (A) | (+)-4-({8-[(1R*,2R*)-2-hydroxy-2-methylcyclopentyl]-6-methyl-7-oxo-7,8-dihydropyrido[2,3-d]pyrimidin-2-yl}amino)-N-[(2R)-tetrahydrofuran-2-ylmethyl]piperidine-1-sulfonamide | 543 [M + Na]+ | $^1$H NMR (400 MHz, CDCl$_3$) δ = 8.38 (s, 1H), 7.32 (d, J = 1.0 Hz, 1H), 5.72 (t, J = 8.0 Hz, 1H), 5.55 (br s, 1H), 4.89-4.78 (m, 1H), 4.09-3.92 (m, 2H), 3.86 (td, J = 6.6, 8.3 Hz, 1H), 3.80-3.65 (m, 3H), 3.24 (ddd, J = 3.5, 7.2, 12.9 Hz, 1H), 3.08-2.95 (m, 3H), 2.84 (br s, 1H), 2.30-2.19 (m, 1H), 2.14 (d, J = 1.0 Hz, 5H), 2.06-1.83 (m, 7H), 1.76-1.63 (m, 4H), 1.14 (s, 3H); $[α]_D^{20}$ + 15.3 (c 0.2, MeOH) >99% de; Single diastereomer. Absolute stereochemistry known (S) at THF center; relative (but not absolute) stereochemistry known at the cyclopentyl chiral centers. Made from (R)-tetrahydro-furfurylamine and racemic Intermediate 1. |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 104 (A) | (-)-N-(2,2-difluoropropyl)-4-({8-[(1R*,2R*)-2-hydroxy-2-methylcyclopentyl]-6-methyl-7-oxo-7,8-dihydropyrido[2,3-d]pyrimidin-2-yl}amino)piperidine-1-sulfonamide | 537 [M + Na]+ | 1H NMR (400 MHz, CDCl3) δ = 8.37 (s, 1H), 7.33 (d, J = 1.0 Hz, 1H), 5.72 (br s, 1H), 5.42 (br s, 1H), 4.82 (br s, 1H), 3.99 (br s, 1H), 3.74 (d, J = 11.8 Hz, 2H), 3.42 (dt, J = 6.9, 13.4 Hz, 2H), 3.11-2.98 (m, 2H), 2.85 (br s, 1H), 2.27-2.21 (m, 1H), 2.20-2.11 (m, 5H), 2.05-1.82 (m, 4H), 1.69 (t, J = 18.6 Hz, 6H), 1.15 (s, 3H) 19F NMR (377 MHz, DMSO-d6) δ = −94.5 (br s, 2F) [α]$_D^{20}$ − 11 (c 0.1, MeOH) >99% ee; absolute stereochemistry unknown. Enantiomer of Ex. 105 |
| 105 (A) | (+)-N-(2,2-difluoropropyl)-4-({8-[(1R*,2R*)-2-hydroxy-2-methylcyclopentyl]-6-methyl-7-oxo-7,8-dihydropyrido[2,3-d]pyrimidin-2-yl}amino)piperidine-1-sulfonamide | 537 [M + Na]+ | 1H NMR (400 MHz, CDCl3) δ = 8.37 (s, 1H), 7.33 (d, J = 1.3 Hz, 1H), 5.72 (br s, 1H), 5.50 (br s, 1H), 4.92 (br s, 1H), 4.00 (br s, 1H), 3.75 (d, J = 11.5 Hz, 2H), 3.42 (dt, J = 6.8, 13.3 Hz, 2H), 3.10-2.97 (m, 2H), 2.85 (br s, 1H), 2.27-2.13 (m, 6H), 2.05-1.83 (m, 4H), 1.76-1.63 (m, 6H), 1.15 (s, 3H) 19F NMR (377 MHz, DMSO-d6) δ = −94.49 (br s, 2F) [α]$_D^{20}$ + 8.3 (c 0.1, MeOH) 99% ee; absolute stereochemistry unknown. Enantiomer of Ex. 104 |
| 106 (A) | (-)-2-[(1-{[(3ξ)-1,1-dioxidotetrahydrothiophen-3-yl]sulfonyl}piperidin-4-yl)amino]-8-[(1R*,2R*)-2-hydroxy-2-methylcyclopentyl]-6-methylpyrido[2,3-d]pyrimidin-7(8H)-one-Isomer A | 562 [M + Na]+ | 1H NMR (400 MHz, CDCl3) δ = 8.38 (s, 1H), 7.33 (d, J = 1.3 Hz, 1H), 5.74 (t, J = 8.4 Hz, 1H), 5.30 (br s, 1H), 4.03 (br s, 1H), 3.93-3.80 (m, 3H), 3.43-3.29 (m, 3H), 3.20-3.05 (m, 3H), 2.80 (br s, 1H), 2.65-2.52 (m, 2H), 2.32-2.18 (m, 3H), 2.15 (d, J = 1.0 Hz, 3H), 2.06-1.80 (m, 4H), 1.70-1.60 (m, 3H), 1.15 (s, 3H); [α]$_D^{22}$ − 55.8 (c 0.2, MeOH) >99% de; Single diasteromer, absolute stereochemistry unknown; relative stereochemistry known at cyclopentyl chiral centers. Peak 1 of 4, RT = 4.939 min Chiralcel OD-3 100 × 4.6 mm 3 μm column; 40° C.; mobile phase 5-40% EtOH(0.05% v/v DEA) in CO2; 2.8 mL/min |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 107 (A) | 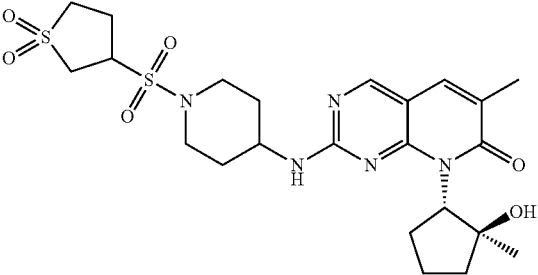<br>(+)-2-[(1-{[(3ξ)-1,1-dioxidotetrahydrothiophen-3-yl]sulfonyl}piperidin-4-yl)amino]-8-[(1R*,2R*)-2-hydroxy-2-methylcyclopentyl]-6-methylpyrido[2,3-d]pyrimidin-7(8H)-one-Isomer B | 540 | 1H NMR (400 MHz, CDCl$_3$) δ = 8.38 (s, 1H), 7.33 (d, J = 1.0 Hz, 1H), 5.73 (t, J = 8.4 Hz, 1H), 5.39 (br s, 1H), 4.03 (br s, 1H), 3.94-3.78 (m, 3H), 3.45-3.29 (m, 3H), 3.19-3.08 (m, 3H), 2.81 (br s, 1H), 2.65-2.51 (m, 2H), 2.32-2.17 (m, 3H), 2.14 (d, J = 0.8 Hz, 3H), 2.07-1.80 (m, 4H), 1.70-1.64 (m, 3H), 1.21-1.09 (m, 3H); [α]$_D^{22}$ + 5.9 (c 0.2, MeOH) >99% de; Single diasteromer, absolute stereochemistry unknown; relative stereochemistry known at cyclopentyl chiral centers. Peak 2 of 4, RT = 5.299 min Chiralcel OD-3 100 × 4.6 mm 3 μm column; 40° C.; mobile phase 5-40% EtOH(0.05% v/v DEA) in CO$_2$; 2.8 ml/min |
| 108 (A) | 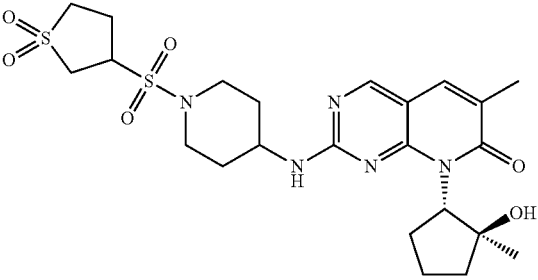<br>(+)-2-[(1-{[(3ξ)-1,1-dioxidotetrahydrothiophen-3-yl]sulfonyl}piperidin-4-yl)amino]-8-[(1R*,2R*)-2-hydroxy-2-methylcyclopentyl]-6-methylpyrido[2,3-d]pyrimidin-7(8H)-one-Isomer C | 540 | 1H NMR (400 MHz, CDCl$_3$) δ = 8.38 (s, 1H), 7.33 (d, J = 1.0 Hz, 1H), 5.74 (t, J = 8.5 Hz, 1H), 5.30 (br s, 1H), 4.03 (br s, 1H), 3.94-3.77 (m, 3H), 3.44-3.28 (m, 3H), 2.87-2.74 (m, 1H), 2.67-2.49 (m, 2H), 2.33-2.18 (m, 3H), 2.15 (d, J = 0.8 Hz, 3H), 2.07-1.80 (m, 4H), 1.71-1.60 (m, 3H), 1.21-1.10 (m, 3H); [α]$_D^{22}$ + 46.8 (c 0.2, MeOH) >99% de; Single diasteromer, absolute stereochemistry unknown; relative stereochemistry known at cyclopentyl chiral centers. Peak 3 of 4, RT = 5.389 min Chiralcel OD-3 100 × 4.6 mm 3 μm column; 40° C.; mobile phase 5-40% EtOH(0.05% v/v DEA) in CO$_2$; 2.8 mL/min |
| 109 (A) | 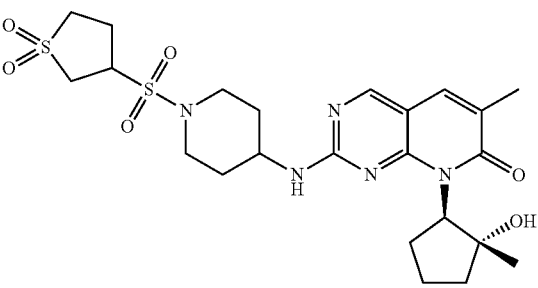<br>(-)-2-[(1-{[(3ξ)-1,1-dioxidotetrahydrothiophen-3-yl]sulfonyl}piperidin-4-yl)amino]-8-[(1R*,2R*)-2-hydroxy-2-methylcyclopentyl]-6-methylpyrido[2,3-d]pyrimidin-7(8H)-one-Isomer D | 532 [M + Na]+ | 1H NMR (400 MHz, CDCl$_3$) δ = 8.38 (s, 1H), 7.33 (s, 1H), 5.74 (t, J = 8.0 Hz, 1H), 5.35 (br s, 1H), 4.04 (br s, 1H), 3.92-3.80 (m, 3H), 3.44-3.29 (m, 3H), 3.20-3.07 (m, 3H), 2.81 (br s, 1H), 2.64-2.51 (m, 2H), 2.33-2.18 (m, 3H), 2.15 (s, 3H), 2.07-1.80 (m, 4H), 1.62 (br s, 3H), 1.15 (s, 3H); [α]$_D^{22}$ − 3.8 (c 0.2, MeOH) 96% de; Single diasteromer, absolute stereochemistry unknown; relative stereochemistry known at cyclopentyl chiral centers. Peak 1 of 4, RT = 4.939 min Chiralcel OD-3 100 × 4.6 mm 3 μm column; 40° C.; mobile phase 5-40% EtOH(0.05% v/v DEA) in CO$_2$; 2.8 mL/min |

| Ex. No. (Method) | Structure/IUPAC name | LCMS [M + H]+ | 1H NMR (ppm); 19F NMR (ppm); optical rotation; stereochem. notes |
| --- | --- | --- | --- |
| 110 (A) | (-)-2-{[1-(ethylsulfonyl)piperidin-4-yl]amino}-8-[(1R*,2R*)-2-hydroxy-2-methylcyclopentyl]-6-methylpyrido[2,3-d]pyrimidin-7(8H)-one | 472 [M + Na]+ | 1H NMR (400 MHz, CDCl$_3$) δ = 8.38 (s, 1H), 7.34 (d, J = 1.0 Hz, 1H), 5.76-5.71 (m, 1H), 5.42-5.19 (m, 1H), 4.00 (br s, 1H), 3.88-3.79 (m, 2H), 3.07-2.96 (m, 4H), 2.84 (br s, 1H), 2.63-2.35 (m, 1H), 2.31-2.16 (m, 3H), 2.15 (d, J = 1.0 Hz, 3H), 2.05-1.83 (m, 4H), 1.73-1.61 (m, 2H), 1.39 (t, J = 7.4 Hz, 3H). 1.16 (s, 3H); [α]$_D^{22}$ − 9.2 (c 0.14, MeOH) >99% ee; absolute stereochemistry unknown. Enantiomer of Ex. 111 |
| 111 (A) | (+)-2-{[1-(ethylsulfonyl)piperidin-4-yl]amino}-8-[(1R*,2R*)-2-hydroxy-2-methylcyclopentyl]-6-methylpyrido[2,3-d]pyrimidin-7(8H)-one | 472 [M + Na]+ | 1H NMR (400 MHz, CDCl$_3$) δ = 8.38 (s, 1H), 7.34 (d, J = 1.0 Hz, 1H), 5.73 (t, J = 8.4 Hz, 1H), 5.40-5.19 (m, 1H), 4.07-3.92 (m, 1H), 3.88-3.79 (m, 2H), 3.07-2.96 (m, 4H), 2.92-2.76 (m, 1H), 2.69-2.34 (m, 1H), 2.32-2.16 (m, 3H), 2.15 (d, J = 0.8 Hz, 3H), 2.06-1.83 (m, 4H), 1.74-1.61 (m, 2H), 1.39 (t, J = 7.5 Hz, 3H), 1.16 (s, 3H); [α]$_D^{22}$ + 11.7 (c 0.18, MeOH) 94% ee; absolute stereochemistry unknown. Enantiomer of Ex. 110 |
| 112 (A) | (-)-2-{[1-(cyclopropylsulfonyl)piperidin-4-yl]amino}-8-[(1R*,2R*)-2-hydroxy-2-methylcyclopentyl]-6-methylpyrido[2,3-d]pyrimidin-7(8H)-one | 484 [M + Na]+ | 1H NMR (400 MHz, CDCl$_3$) δ = 8.39 (s, 1H), 7.34 (d, J = 1.0 Hz, 1H), 5.76-5.71 (m, 1H), 5.44-5.20 (m, 1H), 4.06-3.90 (m, 1H), 3.87-3.78 (m, 2H), 3.11-3.01 (m, 2H), 2.84 (br s, 1H), 2.51 (br s, 1H), 2.33-2.17 (m, 4H), 2.15 (s, 3H), 2.05-1.83 (m, 4H), 1.72-1.63 (m, 2H), 1.22-1.18 (m, 2H), 1.16 (s, 3H), 1.04-0.99 (m, 2H); [α]$_D^{20}$ − 15.3 (c 0.13, MeOH) 95% ee; absolute stereochemistry unknown. Enantiomer of Ex. 113 |
| 113 (A) | (+)-2-{[1-(cyclopropylsulfonyl)piperidin-4-yl]amino}-8-[(1R*,2R*)-2-hydroxy-2-methylcyclopentyl]-6-methylpyrido[2,3-d]pyrimidin-7(8H)-one | 484 [M + Na]+ | 1H NMR (400 MHz, CDCl$_3$) δ = 8.39 (s, 1H), 7.34 (s, 1H), 5.77-5.71 (m, 1H), 5.40-5.17 (m, 1H), 4.08-3.92 (m, 1H), 3.86-3.78 (m, 2H), 3.10-3.01 (m, 2H), 2.84 (br s, 1H), 2.66-2.39 (m, 1H), 2.32-2.18 (m, 4H), 2.15 (s, 3H), 2.03 (br s, 4H), 1.71-1.62 (m, 2H), 1.22-1.18 (m, 2H), 1.16 (s, 3H), 1.02 (dd, J = 2.3, 7.8 Hz, 2H); [α]$_D^{20}$ + 7.3 (c 0.11, MeOH) >99% ee; absolute stereochemistry unknown. Enantiomer of Ex. 112 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 114 (A) | (−)-8-[(1R*,2R*)-2-hydroxy-2-methylcyclopentyl]-2-({1-[(2-methoxyethyl)sulfonyl]piperidin-4-yl}amino)-6-methylpyrido[2,3-d]pyrimidin-7(8H)-one | 502 [M + Na]+ | 1H NMR (400 MHz, CDCl3) δ = 8.38 (s, 1H), 7.34 (d, J = 1.0 Hz, 1H), 5.73 (t, J = 8.3 Hz, 1H), 5.30 (br s, 1H), 3.98 (br s, 1H), 3.83-3.71 (m, 4H), 3.45-3.36 (m, 3H), 3.23 (t, J = 5.9 Hz, 2H), 3.10-2.98 (m, 2H), 2.85 (br s, 1H), 2.50 (d, J = 7.5 Hz, 1H), 2.30-2.17 (m, 2H), 2.15 (d, J = 1.0 Hz, 3H), 2.07-1.81 (m, 4H), 1.65 (d, J = 11.0 Hz, 2H), 1.16 (s, 3H); [α]$_D^{20}$ − 7.7 (c 0.20, CHCl3) 97% ee; absolute stereochemistry unknown. Enantiomer of Ex. 115 |
| 115 (A) | (+)-8-[(1R*,2R*)-2-hydroxy-2-methylcyclopentyl]-2-({1-[(2-methoxyethyl)sulfonyl]piperidin-4-yl}amino)-6-methylpyrido[2,3-d]pyrimidin-7(8H)-one | 502 [M + Na]+ | 1H NMR (400 MHz, CDCl3) δ = 8.39 (s, 1H), 7.34 (d, J = 1.0 Hz, 1H), 5.73 (t, J = 8.4 Hz, 1H), 5.27 (s, 1H), 3.99 (br s, 1H), 3.77 (t, J = 5.9 Hz, 4H), 3.41 (s, 3H), 3.23 (t, J = 5.9 Hz, 2H), 3.10-2.95 (m, 2H), 2.87 (s, 1H), 2.46 (s, 1H), 2.28-2.17 (m, 2H), 2.15 (s, 3H), 2.07-1.79 (m, 4H), 1.71-1.57 (m, 2H), 1.16 (s, 3H); [α]$_D^{20}$ + 1.6 (c 0.12, CHCl3) 98% ee; absolute stereochemistry unknown. Enantiomer of Ex. 114 |
| 116 (A) | (−)-2-({1-[(cyclopropylmethyl)sulfonyl]piperidin-4-yl}amino)-8-[(1R*,2R*)-2-hydroxy-2-methylcyclopentyl]-6-methylpyrido[2,3-d]pyrimidin-7(8H)-one | 498 [M + Na]+ | 1H NMR (400 MHz, CDCl3) δ = 8.39 (s, 1H), 7.34 (d, J = 1.0 Hz, 1H), 5.73 (t, J = 8.4 Hz, 1H), 5.26 (br s, 1H), 3.99 (br s, 1H), 3.91-3.79 (m, 2H), 3.09-2.97 (m, 2H), 2.90 (d, J = 7.0 Hz, 3H), 2.62-2.38 (m, 1H), 2.30-2.18 (m, 2H), 2.15 (d, J = 1.0 Hz, 3H), 2.07-1.81 (m, 4H), 1.72-1.58 (m, 2H), 1.19-1.08 (m, 4H), 0.77-0.65 (m, 2H), 0.43-0.31 (m, 2H); [α]$_D^{20}$ − 3.9 (c 0.19, CHCl3) >99% ee; absolute stereochemistry unknown. Enantiomer of Ex. 117 |
| 117 (A) | (+)-2-({1-[(cyclopropylmethyl)sulfonyl]piperidin-4-yl}amino)-8-[(1R*,2R*)-2-hydroxy-2-methylcyclopentyl]-6-methylpyrido[2,3-d]pyrimidin-7(8H)-one | 498 [M + Na]+ | 1H NMR (400 MHz, CDCl3) δ = 8.38 (s, 1H), 7.33 (d, J = 1.0 Hz, 1H), 5.73 (t, J = 8.4 Hz, 1H), 5.30 (br s, 1H), 3.98 (br s, 1H), 3.86 (t, J = 10.8 Hz, 2H), 3.09-2.97 (m, 2H), 2.92-2.76 (m, 3H), 2.50 (br s, 1H), 2.30-2.18 (m, 2H), 2.14 (d, J = 1.0 Hz, 3H), 2.07-1.81 (m, 4H), 1.65 (dd, J = 3.9, 11.2 Hz, 2H), 1.18-1.08 (m, 4H), 0.77-0.69 (m, 2H), 0.38 (q, J = 5.0 Hz, 2H); [α]$_D^{20}$ + 2.8 (c 0.14, CHCl3) 94% ee; absolute stereochemistry unknown. Enantiomer of Ex. 116 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 118 (A) | (−)-8-[(1R*,2R*)-2-hydroxy-2-methylcyclopentyl]-6-methyl-2-({1-[(2,2,2-trifluoroethyl)sulfonyl]piperidin-4-yl}amino)pyrido[2,3-d]pyrimidin-7(8H)-one | 526 [M + Na]+ | $^1$H NMR (400 MHz, CDCl$_3$) δ = 8.39 (s, 1H), 7.36-7.32 (m, 1H), 5.78-5.71 (m, 1H), 4.11-3.98 (m, 1H), 3.94-3.86 (m, 2H), 3.74 (q, J = 9.3 Hz, 2H), 3.10 (d, J = 10.8 Hz, 2H), 2.90-2.77 (m, 1H), 2.29-2.18 (m, 3H), 2.15 (s, 3H), 2.06-1.83 (m, 4H), 1.73-1.65 (m, 2H), 1.16 (s, 3H); $[α]_D^{20}$ − 17.6 (c 0.07, MeOH) >99% ee; absolute stereochemistry unknown. Enantiomer of Ex. 119 |
| 119 (A) | (+)-8-[(1R*,2R*)-2-hydroxy-2-methylcyclopentyl]-6-methyl-2-({1-[(2,2,2-trifluoroethyl)sulfonyl]piperidin-4-yl}amino)pyrido[2,3-d]pyrimidin-7(8H)-one | 526 [M + Na]+ | $^1$H NMR (400 MHz, CDCl$_3$) δ = 8.39 (s, 1H), 7.34 (d, J = 1.3 Hz, 1H), 5.77-5.72 (m, 1H), 4.11-3.98 (m, 1H), 3.95-3.85 (m, 2H), 3.74 (q, J = 9.4 Hz, 2H), 3.16-3.04 (m, 2H), 2.90-2.77 (m, 1H), 2.29-2.19 (m, 3H), 2.15 (d, J = 1.0 Hz, 3H), 2.07-1.82 (m, 4H), 1.73-1.65 (m, 2H), 1.16 (s, 3H); $[α]_D^{20}$ + 14.0 (c 0.09, MeOH) 99% ee; absolute stereochemistry unknown. Enantiomer of Ex. 118 |
| 120 (F) | (−)-8-[(1R*,2R*)-2-hydroxy-2-methylcyclopentyl]-2-{[1-(methylsulfonyl)piperidin-4-yl]amino}-7-oxo-7,8-dihydropyrido[2,3-d]pyrimidin-6-yl)acetonitrile | 483 [M + Na]+ | $^1$H NMR (400 MHz, CDCl$_3$) δ = 8.51 (s, 1H), 7.72 (s, 1H), 5.78 (br s, 1H), 5.50 (br s, 1H), 3.97 (s, 1H), 3.84 (d, J = 12.3 Hz, 2H), 3.69-3.60 (m, 2H), 3.01-2.87 (m, 2H), 2.83 (s, 3H), 2.76 (br s, 1H), 2.41-2.14 (m, 4H), 2.09-1.80 (m, 4H), 1.74-1.61 (m, 2H), 1.15 (s, 3H); $[α]_D^{20}$ − 10 (c 0.12, MeOH) >99% ee; absolute stereochemistry unknown. Enantiomer of Ex. 121 |
| 121 (F) | (+)-8-[(1R*,2R*)-2-hydroxy-2-methylcyclopentyl]-2-{[1-(methylsulfonyl)piperidin-4-yl]amino}-7-oxo-7,8-dihydropyrido[2,3-d]pyrimidin-6-yl)acetonitrile | 483 [M + Na]+ | $^1$H NMR (400 MHz, CDCl$_3$) δ = 8.51 (s, 1H), 7.72 (s, 1H), 5.78 (br s, 1H), 5.58-5.37 (m, 1H), 3.96 (br s, 1H), 3.84 (d, J = 11.8 Hz, 2H), 3.66 (br s, 2H), 2.98-2.86 (m, 2H), 2.83 (s, 3H), 2.75 (br s, 1H), 2.40-2.12 (m, 4H), 2.07-1.79 (m, 4H), 1.75-1.63 (m, 2H), 1.14 (s, 3H); $[α]_D^{20}$ + 8.5 (c 0.13, MeOH) >99% ee; absolute stereochemistry unknown. Enantiomer of Ex. 120 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 122 (A) | (−)-6-(2-hydroxyethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one | 488 [M + Na]⁺ | ¹H NMR (400 MHz, CDCl₃) δ = 8.42 (s, 1H), 7.41 (s, 1H), 5.75 (t, J = 8.0 Hz, 1H), 5.51-5.26 (m, 1H), 4.10-3.92 (m, 1H), 3.83 (d, J = 14.8 Hz, 4H), 2.99-2.86 (m, 2H), 2.82 (s, 7H), 2.31-2.16 (m, 3H), 2.08-1.78 (m, 4H), 1.76-1.63 (m, 3H), 1.15 (s, 3H); [α]$_D^{20}$ − 6.3 (c 0.14, CHCl₃) >99% ee; absolute stereochemistry unknown. Enantiomer of Ex. 123 |
| 123 (A) | (+)-6-(2-hydroxyethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one | 488 [M + Na]⁺ | ¹H NMR (400 MHz, CDCl₃) δ = 8.43 (s, 1H), 7.42 (s, 1H), 5.79 (t, J = 12.0 Hz, 1H), 5.52-5.24 (m, 1H), 4.10-3.93 (m, 1H), 3.91-3.73 (m, 4H), 3.00-2.87 (m, 2H), 2.85-2.66 (m, 7H), 2.33-2.17 (m, 3H), 2.09-1.78 (m, 4H), 1.75-1.63 (m, 3H), 1.16 (s, 3H); [α]$_D^{20}$ + 7.1 (c 0.13, CHCl₃) >99% ee; absolute stereochemistry unknown. Enantiomer of Ex. 122 |
| 124 (B) | (−)-4-({6-fluoro-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 455 | ¹H NMR (700 MHz, DMSO-d₆) δ = 8.58 (br s, 1H), 7.84 (br s, 1H), 7.73-7.64 (m, 1H), 7.03 (d, J = 4.6 Hz, 1H), 5.89 (br s, 1H), 4.52-4.30 (m, 1H), 4.03-3.82 (m, 1H), 3.57-3.44 (m, 2H), 2.89-2.75 (m, 2H), 2.52 (d, J = 4.6 Hz, 3H), 2.47-2.31 (m, 1H), 2.25-2.08 (m, 2H), 1.96 (br s, 2H), 1.87 (br s, 2H), 1.69 (d, J = 11.0 Hz, 1H), 1.60 (d, J = 11.0 Hz, 1H), 1.45 (d, J = 9.9 Hz, 1H), 0.97 (br s, 3H) ¹⁹F NMR (377 MHz, DMSO-d₆) δ = −136.1 (d, J = 148.8 Hz, 1F) [α]$_D^{20}$ − 17.6 (c 0.1, CHCl₃) 98% ee; absolute stereochemistry unknown. Enantiomer of Ex. 125 |
| 125 (B) | (+)-4-({6-fluoro-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 437 [M − H₂O + H]⁺ | ¹H NMR (700 MHz, DMSO-d₆) δ = 8.58 (br s, 1H), 7.84 (br s, 1H), 7.69 (d, J = 8.6 Hz, 1H), 7.03 (br s, 1H), 5.89 (br s, 1H), 4.49-4.31 (m, 1H), 4.05-3.79 (m, 1H), 3.61-3.42 (m, 2H), 2.81 (br s, 2H), 2.52 (br s, 3H), 2.27-2.04 (m, 2H), 1.96 (br s, 2H), 1.90-1.82 (m, 2H), 1.69 (d, J = 9.0 Hz, 1H), 1.60 (d, J = 10.3 Hz, 1H), 1.45 (br s, 1H), 0.98 (br s, 3H) ¹⁹F NMR (377 MHz, DMSO-d₆) δ = −135.6 to −136.6 (m, 1F) [α]$_D^{20}$ + 18.2 (c 0.1, CHCl₃) >95% ee; absolute stereochemistry unknown. Enantiomer of Ex. 124 |

| Ex. No. (Method) | Structure/IUPAC name | LCMS [M + H]⁺ | $^1$H NMR (ppm); $^{19}$F NMR (ppm); optical rotation; stereochem. notes |
|---|---|---|---|
| 126 (D) | (−)-4-({6-chloro-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 471 | $^1$H NMR (400 MHz, DMSO-d$_6$, 80° C.) δ = 8.59 (s, 1H), 8.01 (s, 1H), 7.60 (br s, 1H), 6.70 (br s, 1H), 5.91 (t, J = 8.2 Hz, 1H), 4.09 (br s, 1H), 4.02-3.90 (m, 1H), 3.57 (t, J = 11.3 Hz, 2H), 2.88 (t, J = 11.9 Hz, 2H), 2.56 (d, J = 5.0 Hz, 3H), 2.26-2.13 (m, 1H), 2.12-1.95 (m, 3H), 1.93-1.82 (m, 2H), 1.76-1.51 (m, 3H), 1.01 (s, 3H) [α]$_D^{22}$ − 13.5 (c 0.1, CHCl$_3$) >99% ee; absolute stereochemistry unknown. Enantiomer of Ex. 127 |
| 127 (D) | (+)-4-({6-chloro-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 471 | $^1$H NMR (400 MHz, DMSO-d$_6$, 80° C.) δ = 8.59 (s, 1H), 8.01 (s, 1H), 7.60 (br s, 1H), 6.70 (br s, 1H), 5.91 (t, J = 8.1 Hz, 1H), 4.09 (br s, 1H), 3.96 (br s, 1H), 3.57 (t, J = 11.2 Hz, 2H), 2.88 (t, J = 11.8 Hz, 2H), 2.56 (d, J = 4.9 Hz, 3H), 2.26-2.13 (m, 1H), 2.11-1.84 (m, 5H), 1.78-1.52 (m, 3H), 1.01 (s, 3H) [α]$_D^{22}$ + 14.4 (c 0.1, CHCl$_3$) >99% ee; absolute stereochemistry unknown. Enantiomer of Ex. 126 |
| 128 (D) | (−)-4-({6-chloro-8-[(1R*,2R*)-2-hydroxy-2-methylcyclopentyl]-7-oxo-7,8-dihydropyrido[2,3-d]pyrimidin-2-yl}amino)piperidine-1-sulfonamide | 457 | $^1$H NMR (400 MHz, DMSO-d$_6$, 80° C.) δ = 8.50 (s, 1H), 7.93 (s, 1H), 7.47 (br s, 1H), 6.38 (br s, 2H), 5.82 (t, J = 8.3 Hz, 1H), 3.99 (br s, 1H), 3.82 (br s, 1H), 3.45 (t, J = 10.8 Hz, 2H), 2.66 (t, J = 11.7 Hz, 2H), 2.05-2.16 (m, 1H), 1.98 (d, J = 10.6 Hz, 1H), 1.91 (d, J = 10.5 Hz, 2H), 1.81 (br s, 2H), 1.60-1.69 (m, 2H), 1.47-1.60 (m, 2H), 0.92 (s, 3H) [α]$_D^{22}$ − 20.2 (c 0.1, CHCl$_3$ w/~10% MeOH) 97% ee; absolute stereochemistry unknown. Enantiomer of Ex. 129 |
| 129 (D) | (+)-4-({6-chloro-8-[(1R*,2R*)-2-hydroxy-2-methylcyclopentyl]-7-oxo-7,8-dihydropyrido[2,3-d]pyrimidin-2-yl}amino)piperidine-1-sulfonamide | 457 | $^1$H NMR (400 MHz, DMSO-d$_6$, 80° C.) δ = 8.50 (s, 1H), 7.92 (s, 1H), 7.46 (br s, 1H), 6.38 (br s, 2H), 5.82 (t, J = 8.2 Hz, 1H), 3.98 (br s, 1H), 3.82 (br s, 1H), 3.45 (t, J = 10.7 Hz, 2H), 2.66 (t, J = 11.8 Hz, 2H), 2.05-2.19 (m, 1H), 1.85-2.04 (m, 3H), 1.72-1.85 (m, 2H), 1.60-1.69 (m, 2H), 1.40-1.60 (m, 2H), 0.93 (s, 3H) [α]$_D^{22}$ + 18.6 (c 0.1, CHCl$_3$ w/~10% MeOH) 99% ee; absolute stereochemistry unknown. Enantiomer of Ex. 128 |

| Ex. No. (Method) | Structure/IUPAC name | LCMS [M + H]+ | 1H NMR (ppm); 19F NMR (ppm); optical rotation; stereochem. notes |
|---|---|---|---|
| 130 (E) | (−)-4-({6-difluoromethyl)-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 487 | 1H NMR (400 MHz, DMSO-d6, 80° C.) δ = 8.72 (s, 1H), 8.03 (s, 1H), 7.76 (br s, 1H), 6.83 (t, J = 55.0 Hz, 2H), 6.71 (br s, 1H), 5.87 (t, J = 8.3 Hz, 1H), 4.09 (br s, 1H), 3.99 (d, J = 9.2 Hz, 1H), 3.58 (t, J = 12.2 Hz, 2H), 2.88 (t, J = 11.8 Hz, 2H), 2.56 (br s, 3H), 2.26-2.13 (m, 1H), 2.12-1.80 (m, 5H), 1.77-1.51 (m, 3H), 1.03 (s, 3H) 19F NMR (377 MHz, DMSO-d6, 30° C.) δ = −117.1 to −117.2 (m, 2F) [α]$_D^{22}$ − 21.5 (c 0.2, CHCl3 w/~10% MeOH) 90% ee; absolute stereochemistry unknown. Enantiomer of Ex. 131 |
| 131 (E) | (+)-4-({6-difluoromethyl)-8-[(1R*,2R*)-2-hydroxy-2-methylcyclopentyl]-7-oxo-7,8-dihydropyrido[2,3-d]pyrimidin-2-yl}amino)-N-methylpiperidine-1-sulfonamide | 487 | 1H NMR (400 MHz, DMSO-d6, 80° C.) δ = 8.72 (s, 1H), 8.03 (s, 1H), 7.76 (br s, 1H), 6.83 (t, J = 54.0 Hz, 1H), 6.71 (s, 1H), 5.86 (t, J = 8.1 Hz, 1H), 4.08 (br s, 1H), 3.97 (br s, 1H), 3.75 (br s, 1H), 3.58 (br s, 2H), 2.88 (t, J = 11.8 Hz, 2H), 2.56 (br s, 3H), 2.26-2.13 (m, 1H), 2.11-1.94 (m, 3H), 1.89 (br s, 2H), 1.77-1.52 (m, 3H), 1.03 (s, 3H) 19F NMR (377 MHz, DMSO-d6, 30° C.) δ = −117.1 to −117.2 (m, 2F) [α]$_D^{22}$ + 20.1 (c 0.1, CHCl3 w/~10% MeOH) 98% ee; absolute stereochemistry unknown. Enantiomer of Ex. 130 |
| 132 (E) | 8-[(1R,2R)-2-hydroxy-2-methylcyclopentyl]-2-{[1-(methylsulfonyl)piperidin-4-yl]amino}-6-(trifluoromethyl)pyrido[2,3-d]pyrimidin-7(8H)-one | 490 | 1H NMR (400 MHz, DMSO-d6, 80° C.) δ = 8.66 (s, 1H), 8.16 (s, 1H), 7.84 (d, J = 7.6 Hz, 1H), 5.62-5.92 (m, 1H), 4.00 (s, 1H), 3.95 (br s, 1H), 3.54 (t, J = 11.5 Hz, 2H), 2.80-2.89 (m, 2H), 2.78 (s, 3H), 2.05-2.16 (m, 1H), 2.00 (br s, 1H), 1.85-1.96 (m, 2H), 1.73-1.85 (m, 2H), 1.58-1.70 (m, 2H), 1.42-1.58 (m, 1H), 0.94 (s, 3H) 19F NMR (377 MHz, DMSO-d6) δ = −63.28 to −63.42 (m, 3F) [α]$_D^{22}$ − 19.6 (c 0.1, CHCl3) >99% ee; Single enantiomer, absolute stereochemistry known. |
| 133-140 | in methods text | | |
| 141 (A) | 8-cyclopentyl-6-ethyl-2-{[1-(methylsulfonyl)piperidin-4-yl]amino}pyrido[2,3-d]pyrimidin-7(8H)-one | 420 | 1H NMR (400 MHz, DMSO-d6) δ = 8.52 (s, 1H), 7.47 (s, 1H), 7.37-7.11 (m, 1H), 5.85 (s, 1H), 4.08-3.86 (m, 1H), 3.62 (d, J = 12.5 Hz, 2H), 2.97-2.89 (m, 2H), 2.88 (s, 3H), 2.47 (q, J = 7.6 Hz, 2H), 2.33 (m, 2H), 2.09-1.93 (m, 4H), 1.84-1.73 (m, 2H), 1.72-1.57 (m, 4H), 1.15 (t, J = 7.4 Hz, 3H) |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 142 (A) | 8-cyclopentyl-6-(methoxymethyl)-2-{[1-(methylsulfonyl)piperidin-4-yl]amino}pyrido[2,3-d]pyrimidin-7(8H)-one | 458 [M + Na]⁺ | ¹H NMR (400 MHz, DMSO-d₆) δ = 8.43 (s, 1H), 7.53 (s, 1H), 5.90-5.85 (m, 1H), 5.30 (m, 1H), 4.40 (s, 2H), 4.95-4.10 (m, 1H), 3.85-3.70 (m, 2H), 3.50 (s, 3H), 2.94-2.75 (m, 5H), 2.40-2.25 (m, 2H), 2.19-2.22 (m, 2H), 1.95-2.10 (m, 2H), 1.80-1.75 (m, 2H), 1.70-1.60 (m, 4H) |
| 143 (A) | 8-cyclopentyl-6-(hydroxymethyl)-2-{[1-(methylsulfonyl)piperidin-4-yl]amino}pyrido[2,3-d]pyrimidin-7(8H)-one | 422 | ¹H NMR (400 MHz, DMSO-d₆, 80° C.) δ = 8.59 (s, 1H), 7.64 (s, 1H), 7.33 (br s, 1H), 5.85 (quin, J = 8.8 Hz, 1H), 4.79 (br s, 1H), 4.36 (br s, 2H), 3.98 (br s, 1H), 3.66-3.58 (m, 2H), 2.96-2.90 (m, 2H), 2.88 (s, 3H), 2.40-2.25 (m, 2H), 2.07-1.95 (m, 4H), 1.85-1.73 (m, 2H), 1.72-1.60 (m, 4H) |
| 144 (A) | 8-cyclopentyl-6-(2-methoxyethyl)-2-{[1-(methylsulfonyl)piperidin-4-yl]amino}pyrido[2,3-d]pyrimidin-7(8H)-one | 450 | ¹H NMR (400 MHz, CDCl₃) δ = 8.38 (s, 1H), 7.38 (s, 1H), 5.88 (quin, J = 8.8 Hz, 1H), 5.23 (br s, 1H), 4.03 (br d, J = 7.0 Hz, 1H), 3.80 (br d, J = 12.0 Hz, 2H), 3.65 (t, J = 6.1 Hz, 2H), 3.36 (s, 3H), 3.01-2.89 (m, 2H), 2.87-2.79 (m, 5H), 2.35 (br s, 2H), 2.20 (br dd, J = 3.1, 13.4 Hz, 2H), 2.10-1.99 (m, 2H), 1.92-1.79 (m, 2H), 1.76-1.63 (m, 4H) |
| 145 (A) | 8-cyclopentyl-6-(2-hydroxyethyl)-2-{[1-(methylsulfonyl)piperidin-4-yl]amino}pyrido[2,3-d]pyrimidin-7(8H)-one | 436 | ¹H NMR (400 MHz, DMSO-d₆) δ = 8.52 (s, 1H), 7.52 (s, 1H), 7.29 (d, J = 7.8 Hz, 1H), 5.86 (quin, J = 8.9 Hz, 1H), 4.24 (br s, 1H), 3.72-3.50 (m, 5H), 2.98-2.85 (m, 5H), 2.63 (t, J = 6.5 Hz, 2H), 2.41-2.24 (m, 2H), 2.10-1.94 (m, 4H), 1.85-1.73 (m, 2H), 1.73-1.61 (m, 4H) |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 146 (A) | 4-{[8-cyclopentyl-6-(2-hydroxyethyl)-7-oxo-7,8-dihydropyrido[2,3-d]pyrimidin-2-yl]amino}-N-methylpiperidine-1-sulfonamide | 451 | $^1$H NMR (400 MHz, CDCl$_3$) δ = 8.40 (s, 1H), 7.38 (s, 1H), 5.89 (quin, J = 8.8 Hz, 1H), 5.31 (s, 1H), 4.19-4.10 (m, 1H), 4.03 (br s, 1H), 3.87 (t, J = 5.6 Hz, 2H), 3.74 (br d, J = 12.8 Hz, 2H), 3.10-2.98 (m, 2H), 2.83 (t, J = 5.5 Hz, 2H), 2.77 (d, J = 5.5 Hz, 3H), 2.35 (br s, 2H), 2.16 (br dd, J = 3.4, 13.2 Hz, 2H), 2.04 (br s, 2H), 1.92-1.80 (m, 2H), 1.74-1.65 (m, J = 10.5 Hz, 4H) |
| 147 (F) | (8-cyclopentyl-2-{[1-(methylsulfonyl)piperidin-4-yl]amino}-7-oxo-7,8-dihydropyrido[2,3-d]pyrimidin-6-yl)acetic acid | 450 | $^1$H NMR (400 MHz, DMSO-d6 + D$_2$O) δ = 8.54 (br s, 1H), 7.60 (s, 1H), 5.77 (br s, 1H), 4.01-3.89 (m, 1H), 3.62-3.50 (m, 2H), 3.42-3.31 (m, 2H), 2.92-2.77 (m, 5H), 2.24 (br s, 1H), 2.17-2.05 (m, 1H), 2.05-1.86 (m, 4H), 1.80-1.50 (m, 6H) |
| 148 (E) | (8-cyclopentyl-2-{[1-(methylsulfonyl)piperidin-4-yl]amino}-6-(trifluoromethyl)pyrido[2,3-d]pyrimidin-7(8H)-one | 460 | $^1$H NMR (400 MHz, DMSO-d$_6$) δ = 8.75 (s, 1H), 8.24 (s, 1H), 7.93 (br s, 1H), 5.83 (quin, J = 8.8 Hz, 1H), 4.05 (dd, J = 6.48, 13.45 Hz, 1H), 3.64 (td, J = 3.42, 12.47 Hz, 2H), 2.99-2.90 (m, 2H), 2.89 (s, 3H), 2.31 (br s, 2H), 2.06-1.95 (m, 4H), 1.88-1.76 (m, 2H), 1.74-1.59 (m, 4H) <br> $^{19}$F NMR (377 MHz, DMSO-d$_6$) δ = −69.27 to −61.50 (m, 3F) |
| 149 (C) | 8-cyclopentyl-6-(2,2-difluoroethyl)-2-{[1-(methylsulfonyl)piperidin-4-yl]amino}pyrido[2,3-d]pyrimidin-7(8H)-one | 456 | $^1$H NMR (400 MHz, CDCl$_3$) δ = 8.38 (br s, 1H), 7.45 (s, 1H), 6.12 (tt, J = 4.6, 57.0 Hz, 1H), 5.84 (quin, J = 8.9 Hz, 1H), 4.18-4.03 (m, 1H), 3.72 (br s, 1H), 3.10 (dt, J = 4.5, 16.4 Hz, 4H), 2.86 (s, 3H), 2.31 (br s, 2H), 2.24-2.13 (m, 3H), 2.11-1.98 (m, 3H), 1.95-1.82 (m, 5H) <br> $^{19}$F NMR (376 MHz, CDCl$_3$) δ = −115.4 (td, J = 16.0, 57.2 Hz, 1F) |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 150 (H) | 6-amino-8-cyclopentyl-2-{[(3R*,4S*)-3-fluoro-1-(methylsulfonyl)piperidin-4-yl]amino}pyrido[2,3-d]pyrimidin-7(8H)-one-Isomer B | 425 | $^1$H NMR (700 MHz, DMSO-d$_6$) δ = 8.40 (br s, 1H), 7.15 (br s, 1H), 6.62 (s, 1H), 5.91 (br s, 1H), 5.16 (br s, 2H), 4.92 (d, J = 49.1 Hz, 1H), 4.14-3.98 (m, 1H), 3.85 (t, J = 11.4 Hz, 1H), 3.13 (dd, J = 13.6, 37.6 Hz, 2H), 3.02-2.94 (m, 1H), 2.91 (s, 3H), 2.19 (br s, 2H), 2.03-1.86 (m, 3H), 1.82-1.73 (m, 3H), 1.61 (br s, 2H) Peak 2 of 2, RT = 2.306 min Chiralcel OJ-3 4.6 × 100 mm 3 μm column; 30% MeOH/DEA @ 120 bar, 4 mL/min 99% ee; absolute stereochemistry unknown Enantiomer of Ex. 151 |
| 151 (H) | 6-amino-8-cyclopentyl-2-{[(3R*,4S*)-3-fluoro-1-(methylsulfonyl)piperidin-4-yl]amino}pyrido[2,3-d]pyrimidin-7(8H)-one-Isomer A | 425 | $^1$H NMR (700 MHz, DMSO-d$_6$) δ = 8.40 (s, 1H), 7.15 (br s, 1H), 6.62 (s, 1H), 5.91 (br s, 1H), 5.16 (br s, 2H), 4.92 (d, J = 48.9 Hz, 1H), 4.17-3.99 (m, 1H), 3.85 (t, J = 10.6 Hz, 1H), 3.13 (dd, J = 13.6, 37.4 Hz, 2H), 2.97 (t, J = 11.4 Hz, 1H), 2.91 (s, 3H), 2.19 (br s, 2H), 2.01-1.87 (m, 3H), 1.83-1.72 (m, 3H), 1.61 (br s, 2H) Peak 1 of 2, RT = 1.212 min Chiralcel OJ-3 4.6 × 100 mm 3 μm column; 30% MeOH/DEA @ 120 bar, 4 mL/min 99% ee; absolute stereochemistry unknown Enantiomer of Ex. 150 |
| 152 (D) | (-)-6-chloro-8-cyclopentyl-2-{[(3R*,4S*)-3-fluoro-1-(methylsulfonyl)piperidin-4-yl]amino}pyrido[2,3-d]pyrimidin-7(8H)-one | 444 | $^1$H NMR (700 MHz, DMSO-d$_6$) δ = 8.58 (d, J = 7.2 Hz, 1H), 8.05-7.77 (m, 2H), 5.96-5.64 (m, 1H), 5.08-4.72 (m, 1H), 4.26-3.97 (m, 1H), 3.91-3.73 (m, 1H), 3.61 (br s, 1H), 3.17-3.04 (m, 1H), 2.95 (br s, 1H), 2.87 (d, J = 15.2 Hz, 3H), 2.10 (br s, 2H), 1.91 (d, J = 15.0 Hz, 3H), 1.74 (br s, 3H), 1.65-1.47 (m, 2H) [α]$_D^{22}$ − 70.3 (c 0.1, MeOH) >99% ee; absolute stereochemistry unknown. Enantiomer of Ex. 153 |
| 153 (D) | (+)-6-chloro-8-cyclopentyl-2-{[(3R*,4S*)-3-fluoro-1-(methylsulfonyl)piperidin-4-yl]amino}pyrido[2,3-d]pyrimidin-7(8H)-one | 444 | $^1$H NMR (700 MHz, DMSO-d$_6$) δ = 8.63 (d, J = 11.3 Hz, 1H), 8.26-7.81 (m, 2H), 6.09-5.72 (m, 1H), 5.08-4.73 (m, 1H), 4.38-4.00 (m, 1H), 3.93-3.77 (m, 1H), 3.24-3.08 (m, 1H), 2.99 (d, J = 9.7 Hz, 1H), 2.91 (d, J = 17.6 Hz, 3H), 2.15 (br s, 2H), 2.04-1.89 (m, 4H), 1.79 (br s, 3H), 1.67-1.53 (m, 2H) $^{19}$F NMR (376 MHz, DMSO-d$_6$) δ = −200.6 (d, J = 251.8 Hz, 1F) [α]$_D^{22}$ + 70.5 (c 0.1, MeOH) >99% ee; absolute stereochemistry unknown. Enantiomer of Ex. 152 |

| Ex. No. (Method) | Structure/IUPAC name | LCMS [M + H]+ | 1H NMR (ppm); 19F NMR (ppm); optical rotation; stereochem. notes |
|---|---|---|---|
| 154 (D) | (−)-6-chloro-8-cyclopentyl-2-{[(3S*,4S*)-3-fluoro-1-(methylsulfonyl)piperidin-4-yl]amino}pyrido[2,3-d]pyrimidin-7(8H)-one | 444 | 1H NMR (700 MHz, DMSO-d6) δ = 8.58 (d, J = 16.2 Hz, 1H), 8.21-7.81 (m, 2H), 5.96-5.69 (m, 1H), 4.88-4.48 (m, 1H), 4.37-4.00 (m, 1H), 3.79-3.61 (m, 1H), 3.49 (s, 1H), 3.18-2.93 (m, 2H), 2.90 (br s, 3H), 2.21 (d, J = 7.3 Hz, 1H), 2.12-1.88 (m, 4H), 1.72 (br s, 2H), 1.66-1.42 (m, 3H)<br>$[\alpha]_D^{22}$ − 5.3 (c 0.1, MeOH)<br>>99% ee; absolute stereochemistry unknown.<br>Enantiomer of Ex. 155 |
| 155 (D) | (+)-6-chloro-8-cyclopentyl-2-{[(3S*,4S*)-3-fluoro-1-(methylsulfonyl)piperidin-4-yl]amino}pyrido[2,3-d]pyrimidin-7(8H)-one | 444 | 1H NMR (700 MHz, DMSO-d6) δ = 8.58 (d, J = 15.5 Hz, 1H), 8.27-7.69 (m, 2H), 6.10-5.25 (m, 1H), 4.80-4.47 (m, 1H), 4.31-4.01 (m, 1H), 3.73-3.58 (m, 1H), 3.51-3.38 (m, 1H), 3.16-2.92 (m, 2H), 2.90 (br s, 3H), 2.21 (br s, 1H), 2.12-1.84 (m, 4H), 1.73 (br s, 2H), 1.66-1.42 (m, 3H)<br>19F NMR (376 MHz, DMSO-d6) δ = −186.8 (d, J = 144.2 Hz, 1F)<br>$[\alpha]_D^{22}$ + 4.1 (c 0.1, MeOH)<br>~98.8% ee; absolute stereochemistry unnknown.<br>Enantiomer of Ex. 154 |
| 156 (G) | (−)-8-cyclopentyl-2-{[(3S*,4S*)-3-fluoro-1-(methylsulfonyl)piperidin-4-yl]amino}-6-(2-hydroxyethyl)pyrido[2,3-d]pyrimidin-7(8H)-one | 455 | 1H NMR (400 MHz, DMSO-d6, 80° C.) δ = 8.54 (s, 1H), 7.53 (s, 2H), 5.94-5.75 (m, 1H), 4.73 (d, J = 49.0 Hz, 1H), 4.25 (br s, 2H), 3.84-3.72 (m, 1H), 3.63 (q, J = 5.7 Hz, 2H), 3.55 (d, J = 11.2 Hz, 1H), 3.15-3.07 (m, 1H), 2.95 (s, 3H), 2.68-2.60 (m, 2H), 2.32 (br s, 2H), 2.14-1.93 (m, 3H), 1.85-1.59 (m, 5H)<br>$[\alpha]_D^{22}$ − 4.9 (c 0.1, MeOH)<br>96% ee; absolute stereochemistry unknown.<br>Enantiomer of Ex. 157 |
| 157 (G) | (+)-8-cyclopentyl-2-{[(3S*,4S*)-3-fluoro-1-(methylsulfonyl)piperidin-4-yl]amino}-6-(2-hydroxyethyl)pyrido[2,3-d]pyrimidin-7(8H)-one | 455 | 1H NMR (400 MHz, DMSO-d6, 80° C.) δ = 8.54 (s, 1H), 7.53 (br s, 2H), 5.85 (t, J = 8.8 Hz, 1H), 4.73 (d, J = 49.0 Hz, 1H), 4.26 (br s, 2H), 3.86-3.48 (m, 4H), 3.16-3.06 (m, 1H), 2.95 (s, 3H), 2.63 (br s, 2H), 2.32 (br s, 2H), 2.16-1.94 (m, 3H), 1.86-1.57 (m, 5H)<br>$[\alpha]_D^{22}$ + 17.6 (c 0.1, MeOH)<br>99% ee; absolute stereochemistry unknown.<br>Enantiomer of Ex. 156 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 158 (G) | (−)-8-cyclopentyl-2-{[(3S*,4S*)-3-fluoro-1-(methylsulfonyl)piperidin-4-yl]amino}-6-(2-methoxyethyl)pyrido[2,3-d]pyrimidin-7(8H)-one | 468 | 1H NMR (400 MHz, CDCl3) δ = 8.40 (s, 1H), 7.38 (s, 1H), 5.92-5.83 (m, 1H), 5.29 (br s, 1H), 4.74-4.60 (m, 1H), 4.30 (br s, 1H), 3.95-3.92 (m, 1H), 3.67-3.63 (m, 3H), 3.36 (s, 3H), 3.21-3.18 (m, 2H), 2.90 (s, 3H), 2.84-2.80 (m, 2H), 2.36-2.35 (m, 3H), 2.05 (br s, 2H), 1.85-1.69 (m, 5H). 19F NMR (376 MHz, DMSO-d6) δ = −186.8 (d, J = 130.5 Hz, 1F) [α]$_D^{22}$ − 12.9 (c 0.10, CHCl3) 99% ee; absolute stereochemistry unknown. Enantiomer of Ex. 159 |
| 159 (G) | (+)-8-cyclopentyl-2-{[(3S*,4S*)-3-fluoro-1-(methylsulfonyl)piperidin-4-yl]amino}-6-(2-methoxyethyl)pyrido[2,3-d]pyrimidin-7(8H)-one | 468 | 1H NMR (400 MHz, CDCl3) δ = 8.41 (s, 1H), 7.39 (s, 1H), 5.88 (quin, J = 9.0 Hz, 1H), 5.29 (br s, 1H), 4.85-4.55 (m, 1H), 4.31 (br d, J = 4.5 Hz, 1H), 4.00-3.86 (m, 1H), 3.66 (t, J = 6.1 Hz, 3H), 3.40-3.34 (m, 3H), 3.20 (br d, J = 12.0 Hz, 2H), 2.91 (s, 3H), 2.83 (t, J = 5.9 Hz, 2H), 2.43-2.26 (m, 3H), 2.06 (br s, 2H), 1.92-1.65 (m, 5H) 19F NMR (376 MHz, DMSO-d6, 80° C.) δ = −186.4 (s, 1F) [α]$_D^{22}$ + 2.86 (c 0.105, CHCl3) 99% ee; absolute stereochemistry unknown. Enantiomer of Ex. 158 |
| 160 (F) | (−)-2-(8-cyclopentyl-2-{[(3S*,4S*)-3-fluoro-1-(methylsulfonyl)piperidin-4-yl]amino}-7-oxo-7,8-dihydropyrido[2,3-d]pyrimidin-6-yl)acetamide | 467 | 1H NMR (400 MHz, DMSO-d6) δ = 8.61 (s, 1H), 8.03-7.72 (m, 1H), 7.60 (s, 1H), 7.34 (br s, 1H), 6.85 (br s, 1H), 6.01-5.71 (m, 1H), 4.83-4.57 (m, 1H), 4.40-4.10 (m, 1H), 3.74 (br s, 1H), 3.49 (br s, 1H), 3.25 (s, 2H), 3.13 (br s, 1H), 3.04 (br t, J = 11.0 Hz, 1H), 2.96 (s, 3H), 2.27-1.90 (m, 5H), 1.80-1.56 (m, 5H) 19F NMR (376 MHz, DMSO-d6, 80° C.) δ = −186.4 (s, 1F) [α]$_D^{22}$ − 12.5 (c 0.1, DMSO) Single enantiomer, absolute stereochemistry unknown. Enantiomer of Ex. 161 |
| 161 (F) | (+)-2-(8-cyclopentyl-2-{[(3S*,4S*)-3-fluoro-1-(methylsulfonyl)piperidin-4-yl]amino}-7-oxo-7,8-dihydropyrido[2,3-d]pyrimidin-6-yl)acetamide | 467 | 1H NMR (400 MHz, DMSO-d6) δ = 8.62 (s, 1H), 7.96-7.78 (d, 1H), 7.61 (s, 1H), 7.35 (s, 1H), 6.86 (s, 1H), 5.81 (m, 1H), 4.76-4.64 (m, 1H), 4.33-4.22 (m, 1H), 3.74 (br s, 1H), 3.49 (br s, 1H), 3.27-3.26 (m, 2H), 3.13-3.07 (m, 1H), 3.04-3.02 (m, 1H), 2.97 (s, 3H), 2.17-1.98 (m, 5H), 1.75-1.66 (m, 5H). Single enantiomer, absolute stereochemistry unknown. Enantiomer of Ex. 160 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 162 (G) | (+)-8-cyclopentyl-2-{[2,2-dimethyl-1-(methylsulfonyl)piperidin-4-yl]amino}-6-(2-hydroxyethyl)pyrido[2,3-d]pyrimidin-7(8H)-one | 465 | 1H NMR (700 MHz, DMSO-d6) δ = 8.56 (d, J = 7.3 Hz, 1H) 8.53 (br s, 1H) 7.66 (d, J = 6.8 Hz, 1H) 7.53 (br s, 2H) 5.86 (t, J = 8.7 Hz, 1H) 4.61 (br s, 1H) 4.08 (br s, 1H) 3.11 (t, J = 12.0 Hz, 2H) 2.97 (s, 4H) 2.57 (t, J = 6.3 Hz, 3H) 1.96 (d, J = 12.3 Hz, 4H) 1.74 (br s, 4H) 1.60 (br s, 2H) 1.50 (s, 6H) [α]$_D^{22}$ + 71.2 (c 0.1, MeOH) 99% ee; absolute stereochemistry unknown. Enantiomer of Ex. 163 |
| 163 (G) | (−)-8-cyclopentyl-2-{[2,2-dimethyl-1-(methylsulfonyl)piperidin-4-yl]amino}-6-(2-hydroxyethyl)pyrido[2,3-d]pyrimidin-7(8H)-one | 465 | 1H NMR (700 MHz, DMSO-d6) δ 8.56 (d, J = 7.3 Hz, 1H) 8.53 (br s, 1H) 7.66 (d, J = 6.8 Hz, 1H) 7.53 (br s, 2H) 5.86 (t, J = 8.7 Hz, 1H) 4.61 (br s, 1H) 4.08 (br s, 1H) 3.11 (t, J = 12.0 Hz, 2H) 2.97 (s, 4H) 2.57 (t, J = 6.3 Hz, 3H) 1.96 (d, J = 12.3 Hz, 4H) 1.74 (br s, 4H) 1.60 (br s, 2H) 1.50 (s, 6H) [α]$_D^{22}$ − 70.7 (c 0.1, MeOH) 99% ee; absolute stereochemistry unknown. Enantiomer of Ex. 162 |
| 164 (A) | 8-cyclohexyl-2-{[1-(methylsulfonyl)-piperidin-4-yl]amino}pyrido[2,3-d]pyrimidin-7(8H)-one | 406 | 1H NMR (400 MHz, CDCl3) δ = 8.38 (s, 1H), 7.41-7.39 (d, 1H), 6.37 (br s, 1H), 5.54 (br s, 1H), 5.40-5.25 (m, 1H), 4.05-3.95 (m, 1H), 3.83-3.81 (m, 2H), 3.00-2.90 (m, 2H), 2.85 (s, 3H), 2.75-2.60 (m, 2H), 2.24-2.21 (m, 2H), 1.90-1.85 (m, 2H), 1.73-1.68 (m, 5H), 1.42-1.25 (m, 3H). |
| 165 (A) | 8-cycloheptyl-6-(2-hydroxyethyl)-2-{[1-(methylsulfonyl)piperidin-4-yl]amino}-pyrido[2,3-d]pyrimidin-7(8H)-one | 486 [M + Na]+ | 1H NMR (400 MHz, DMSO-d6, 80° C.) δ = 8.50 (s, 1H), 7.50 (s, 1H), 7.35 (br s, 1H), 5.49 (br s, 1H), 4.28 (br t, J = 5.0 Hz, 1H), 3.95 (br d, J = 6.5 Hz, 1H), 3.72-3.56 (m, 4H), 2.96-2.86 (m, 5H), 2.61 (t, J = 6.5 Hz, 2H), 2.04 (br dd, J = 3.1, 13.2 Hz, 2H), 1.85-1.76 (m, 2H), 1.75-1.59 (m, 9H), 1.58-1.45 (m, 3H) |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 166 (F) | 2-(8-[(1S,2R)-2-methylcyclopentyl]-2-{[1-(methylsulfonyl)piperidin-4-yl]amino}-7-oxo-7,8-dihydropyrido[2,3-d]pyrimidin-6-yl)acetamide | 463 | 1H NMR (400 MHz, CDCl3) δ = 8.43 (s, 1H), 7.56 (s, 1H), 6.75 (br s, 1H), 6.10-5.92 (m, 1H), 5.67-5.07 (m, 2H), 4.03 (br s, 1H), 3.79 (br s, 2H), 3.56-3.40 (m, 2H), 2.95 (br s, 2H), 2.84 (s, 3H), 2.77-2.56 (m, 1H), 2.43-2.30 (m, 1H), 2.20 (d, J = 10.0 Hz, 2H), 2.11-2.02 (m, 1H), 1.98-1.84 (m, 3H), 1.71 (m, 2H), 1.59 (m, 1H), 0.76 (d, J = 7.0 Hz, 3H) [α]$_D^{22}$ + 24.7 (c 0.2, DMSO) Single enantiomer, absolute stereochemistry known. |
| 167 (A) | (−)-8-[(1R*,3R*)-3-hydroxycyclopentyl]-6-methyl-2-{[1-(methylsulfonyl)piperidin-4-yl]amino}pyrido[2,3-d]pyrimidin-7(8H)-one | 422 | 1H NMR (400 MHz, DMSO-d6, 80° C.) δ = 8.49 (s, 1H), 7.51 (s, 1H), 7.27 (d, J = 7.1 Hz, 1H), 6.14 (quin, J = 8.4 Hz, 1H), 4.47 (br s, 1H), 4.26 (d, J = 3.3 Hz, 1H), 3.89-4.03 (m, 1H), 3.62 (d, J = 12.1 Hz, 2H), 2.88-2.96 (m, 3H), 2.87 (s, 3H), 2.14-2.30 (m, 2H), 2.04 (s, 3H), 1.88-2.03 (m, 3H), 1.58-1.74 (m, 4H) [α]$_D^{22}$ − 14.8 (c 0.1, CHCl3) 99% ee; absolute stereochemistry unknown. Enantiomer of Ex. 168 |
| 168 (A) | (+)-8-[(1R*,3R*)-3-hydroxycyclopentyl]-6-methyl-2-{[1-(methylsulfonyl)piperidin-4-yl]amino}pyrido[2,3-d]pyrimidin-7(8H)-one | 422 | 1H NMR (400 MHz, DMSO-d6, 80° C.) δ = 8.49 (br s, 1H), 7.51 (br s, 1H), 7.27 (br s, 1H), 6.14 (br s, 1H), 4.48 (br s, 1H), 4.26 (br s, 1H), 3.96 (br s, 1H), 3.62 (d, J = 10.0 Hz, 2H), 2.92 (br s, 3H), 2.87 (br s, 3H), 2.22 (br s, 2H), 2.04 (br s, 6H), 1.65 (d, J = 9.0 Hz, 4H) [α]$_D^{22}$ + 12.1 (c 0.1, CHCl3) 99% ee; absolute stereochemistry unknown. Enantiomer of Ex. 167 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 169 (D) | (+)-6-chloro-8-[(1R*,3R*)-3-hydroxycyclopentyl]-2-{[1-(methylsulfonyl)piperidin-4-yl]amino}pyrido[2,3-d]pyrimidin-7(8H)-one | 442 | $^1$H NMR (400 MHz, CDCl$_3$) δ = 8.42 (s, 1H), 7.68 (s, 1H), 6.40-6.22 (m, 1H), 5.73-5.27 (m, 1H), 4.72 (br s, 1H), 4.03 (br s, 1H), 3.80 (br d, J = 12.0 Hz, 2H), 3.85-3.71 (m, 1H), 3.02-2.91 (m, 2H), 2.84 (s, 3H), 2.56 (br s, 1H), 2.46 (dtd, J = 4.6, 8.5, 12.7 Hz, 1H), 2.32-2.07 (m, 4H), 1.88 (br t, J = 11.2 Hz, 1H), 1.74 (br d, J = 12.5 Hz, 3H) [α]$_D^{22}$ + 9.5 (c 1.9, CHCl$_3$) 99% ee; absolute stereochemistry unknown. Enantiomer of Ex. 170 |
| 170 (D) | (−)-6-chloro-8-[(1R*,3R*)-3-hydroxycyclopentyl]-2-{[1-(methylsulfonyl)piperidin-4-yl]amino}pyrido[2,3-d]pyrimidin-7(8H)-one | | $^1$H NMR (400 MHz, CDCl$_3$) δ = 8.42 (s, 1H), 7.68 (s, 1H), 6.40-6.21 (m, 1H), 5.66-5.27 (m, 1H), 4.72 (br s, 1H), 4.03 (br s, 1H), 3.80 (br d, J = 12.3 Hz, 2H), 3.02-2.88 (m, 2H), 2.84 (s, 3H), 2.56 (br s, 1H), 2.47 (dtd, J = 4.5, 8.6, 12.9 Hz, 1H), 2.32-2.07 (m, 4H), 1.88 (br t, J=11.3 Hz, 1H), 1.94-1.84 (m, 1H), 1.81-1.67 (m, 3H) [α]$_D^{22}$ − 9.66 (c 2.9, CHCl$_3$) 99% ee; absolute stereochemistry unknown. Enantiomer of Ex. 169 |
| 171 (J) | (+)-6-(2,2-difluoroethyl)-8-[(1R*,3R*)-3-hydroxycyclopentyl]-2-{[1-(methylsulfonyl)piperidin-4-yl]amino}pyrido[2,3-d]pyrimidin-7(8H)-one | 472 | $^1$H NMR (400 MHz, DMSO-d$_6$, 80° C.) δ = 8.58 (s, 1H), 7.69 (s, 1H), 7.52 (d, J = 5.9 Hz, 1H), 6.18-6.09 (m, 1H), 6.21 (tt, J = 4.3, 57.1 Hz, 1H), 4.47 (br s, 1H), 4.32 (br s, 1H), 3.97 (br s, 1H), 3.62 (d, J = 11.7 Hz, 2H), 3.13-2.98 (m, 2H), 2.96-2.90 (m, 2H), 2.88 (s, 3H), 2.21 (br s, 2H), 1.99 (br s, 3H), 1.77-1.55 (m, 4H) $^{19}$F NMR (376 MHz, DMSO-d$_6$) δ = −114.4 (td, J = 17.2, 57.2 Hz, 1F) [α]$_D^{22}$ + 13.9 (c 0.1, MeOH) ~99% ee; absolute stereochemistry unknown. Enantiomer of Ex. 172 |

| Ex. No. (Method) | Structure/IUPAC name | LCMS [M + H]+ | 1H NMR (ppm); 19F NMR (ppm); optical rotation; stereochem. notes |
|---|---|---|---|
| 172 (J) | (-)-6-(2,2-difluoroethyl)-8-[(1R*,3R*)-3-hydroxycyclopentyl]-2-{[1-(methylsulfonyl)piperidin-4-yl]amino}pyrido[2,3-d]pyrimidin-7(8H)-one | 472 | 1H NMR (400 MHz, DMSO-d6, 80° C.) δ = 8.58 (s, 1H), 7.69 (s, 1H), 7.52 (br s, 1H), 6.19-6.09 (m, 1H), 6.21 (tt, J = 4.6, 57.2 Hz, 1H), 4.47 (br s, 1H), 3.97 (br s, 1H), 3.69-3.54 (m, 2H), 3.05 (dt, J =4.5, 17.2 Hz, 2H), 2.96-2.88 (m, 2H), 2.88 (s, 3H), 2.31-2.14 (m, 2H), 2.07-1.88 (m, 4H), 1.77-1.58 (m, 4H) 19F NMR (376 MHz, DMSO-d6) δ = -114.4 (td, J = 17.7, 56.1 Hz, 1F) [α]$_D^{22}$ − 5.1 (c 0.1, MeOH) >99% ee; absolute stereochemistry unknown. Enantiomer of Ex. 171 |
| 173 (A) | 8-[(1R,2R)-2-hydroxycyclopentyl]-6-methyl-2-{[1-(methylsulfonyl)piperidin-4-yl]amino}pyrido[2,3-d]pyrimidin-7(8H)-one | 444 [M + Na]+ | 1H NMR (400 MHz, CDCl3) δ = 8.38 (s, 1H), 7.34 (d, J = 1.0 Hz, 1H), 5.83-5.70 (m, 1H), 5.26 (br s, 1H), 5.00 (d, J = 5.5 Hz, 1H), 4.01 (br s, 1H), 3.79 (d, J = 10.3 Hz, 2H), 2.95 (t, J = 11.4 Hz, 2H), 2.83 (s, 3H), 2.47-2.28 (m, 2H), 2.20 (dd, J = 4.1, 12.9 Hz, 2H), 2.16 (s, 3H), 2.06-1.86 (m, 3H), 1.71 (dd, J = 6.5, 12.3 Hz, 3H) [α]$_D^{22}$ + 16.7 (c 0.1, MeOH) 98% ee; Single enantiomer, absolute stereochemistry known |
| 174 (A) | 8-[(1S,2S)-2-hydroxy-2-methylcyclopentyl]-2-{[1-(methylsulfonyl)piperidin-4-yl]amino}pyrido[2,3-d]pyrimidin-7(8H)-one | 444 | 1H NMR (400 MHz, CDCl3) δ = 8.43 (s, 1H), 7.45 (d, J = 9.3 Hz, 1H), 6.36 (d, J = 9.3 Hz, 1H), 5.73 (t, J = 8.5 Hz, 1H), 5.52-5.30 (m, 1H), 4.10-3.89 (m, 1H), 3.82 (t, J = 10.3 Hz, 2H), 3.01-2.86 (m, 2H), 2.83 (s, 3H), 2.33-2.13 (m, 3H), 2.09-1.96 (m, 2H), 1.96-1.80 (m, 2H), 1.75-1.62 (m, 3H), 1.18 (s, 3H) [α]$_D^{22}$ + 7.28 (c 2.06, CHCl3) 99% ee; Single enantiomer, absolute stereochemistry known. Enantiomer of Ex. 2 |
| 175 (D) | 6-chloro-8-[(1S,2S)-2-hydroxy-2-methylcyclopentyl]-2-{[1-(methylsulfonyl)piperidin-4-yl]amino}pyrido[2,3-d]pyrimidin-7(8H)-one | 456 | 1H NMR (400 MHz, DMSO-d6) δ = 8.67-8.57 (m, 1H), 8.09 (s, 1H), 8.06-7.73 (m, 1H), 5.90 (t, J = 7.9 Hz, 1H), 4.48-4.33 (m, 1H), 4.05-3.82 (m, 1H), 3.57 (br s, 2H), 2.88 (s, 4H), 2.86-2.76 (m, 1H), 2.45-2.29 (m, 1H), 2.17 (d, J = 9.2 Hz, 2H), 2.03-1.77 (m, 4H), 1.73-1.40 (m, 3H), 0.87-1.07 [α]$_D^{22}$ + 15.4 (c 0.1 MeOH) 99% ee; Single enantiomer, absolute stereochemistry known. Enantiomer of Ex. 9 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 176 (E) | 6-(difluoromethyl)-8-[(1S,2S)-2-hydroxy-2-methylcyclopentyl]-2-{[1-(methylsulfonyl)piperidin-4-yl]amino}pyrido[2,3-d]pyrimidin-7(8H)-one | 472 | ¹H NMR (400 MHz, DMSO-d₆, 80° C.) δ = 8.73 (s, 1H), 8.03 (s, 1H), 7.76 (br s, 1H), 6.83 (t, J = 56.0 Hz, 1H), 5.87 (t, J = 8.3 Hz, 1H), 4.11-3.96 (m, 2H), 3.62 (t, J = 11.6 Hz, 2H), 2.97-2.89 (m, 2H), 2.87 (s, 3H), 2.26-2.14 (m, 1H), 2.14-1.82 (m, 5H), 1.79-1.51 (m, 3H), 1.03 (s, 3H) ¹⁹F NMR (376 MHz, DMSO-d₆) δ = −125.2 to −113.7 (m, 2F) [α]_D²² + 24.7 (c 0.2, CHCl₃) >99% ee; Single enantiomer, absolute stereochemistry known. Enantiomer of Ex. 10 |
| 177 (I) | (−)-6-acetyl-8-[(1R*,2R*)-2-hydroxy-2-methylcyclopentyl]-5-methyl-2-{[1-(methylsulfonyl)piperidin-4-yl]amino}pyrido[2,3-d]pyrimidin-7(8H)-one | 479 | ¹H NMR (400 MHz, DMSO-d₆) δ = 8.91-8.71 (m, 1H), 8.12-7.64 (m, 1H), 5.87 (t, J = 8.4 Hz, 1H), 4.44-4.22 (m, 1H), 3.91 (br s, 1H), 3.66-3.49 (m, 2H), 2.95-2.79 (m, 6H), 2.38 (s, 3H), 2.27 (s, 3H), 2.18 (d, J = 9.4 Hz, 2H), 2.02-1.89 (m, 3H), 1.85 (br s, 2H), 1.72-1.59 (m, 2H), 1.07-0.94 (m, 3H) [α]_D²² − 36.5 (c 0.1, MeOH) 99% ee; absolute stereochemistry unknown. Enantiomer of Ex. 178 |
| 178 (I) | (+)-6-acetyl-8-[(1R*,2R*)-2-hydroxy-2-methylcyclopentyl]-5-methyl-2-{[1-(methylsulfonyl)piperidin-4-yl]amino}pyrido[2,3-d]pyrimidin-7(8H)-one | 479 | ¹H NMR (400 MHz, DMSO-d₆) δ = 8.86-8.77 (m, 1H), 8.08-7.74 (m, 1H), 5.94-5.80 (m, 1H), 4.40-4.27 (m, 1H), 4.13-3.82 (m, 1H), 3.64-3.51 (m, 2H), 2.94-2.82 (m, 5H), 2.38 (s, 3H), 2.27 (s, 3H), 2.18 (d, J = 10.0 Hz, 2H), 2.07-1.90 (m, 3H), 1.85 (br s, 2H), 1.65 (br s, 3H), 0.99 (br s, 3H) [α]_D²² + 27.0 (c 0.1, MeOH) 99% ee; absolute stereochemistry unknown. Enantiomer of Ex. 177 |
| 179 (F) | (−)-2-(8-[(1R*,2R*)-2-hydroxy-2-methylcyclopentyl]-2-{[1-(methylsulfonyl)piperidin-4-yl]amino}-7-oxo-7,8-dihydropyrido[2,3-d]pyrimidin-6-yl)acetamide | 501 [M + Na]⁺ | ¹H NMR (400 MHz, CDCl₃) δ = 8.45 (s, 1H), 7.58 (s, 1H), 6.61 (br s, 1H), 5.79 (br s, 1H), 5.58 (br s, 1H), 5.38 (br s, 1H), 3.99 (br s, 1H), 3.89-3.76 (m, 2H), 3.54-3.38 (m, 2H), 3.02-2.87 (m, 2H), 2.83 (s, 4H), 2.35-2.13 (m, 4H), 2.06-1.82 (m, 4H), 1.75-1.69 (m, 2H), 1.15 (s, 3H) [α]_D²² − 11.81 (c 0.11, MeOH)) 99% ee; absolute stereochemistry unknown. Enantiomer of Ex. 180 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 180 (F) | (+)-2-(8-[(1R*,2R*)-2-hydroxy-2-methylcyclopentyl]-2-{[1-(methylsulfonyl)piperidin-4-yl]amino}-7-oxo-7,8-dihydropyrido[2,3-d]pyrimidin-6-yl)acetamide | 501 [M + Na]+ | 1H NMR (400 MHz, CDCl3) δ = 8.45 (s, 1H), 7.58 (s, 1H), 6.60 (br s, 1H), 5.82 (br s, 1H), 5.53 (br s, 1H), 5.33 (br s, 1H), 3.98 (br s, 1H), 3.83 (d, J = 10.5 Hz, 2H), 3.55-3.41 (m, 2H), 3.00-2.72 (m, 6H), 2.37-2.14 (m, 4H), 2.07-1.83 (m, 4H), 1.77-1.65 (m, 2H), 1.15 (s, 3H) [α]$_D^{22}$ + 10.90 (c 0.11, MeOH) 99% ee; absolute stereochemistry unknown. Enantiomer of Ex. 179 |
| 181 (A) | (-)-8-[(1R*,2R*)-2-hydroxy-2-methylcyclopentyl]-6-methyl-2-({1-[(trifluoromethyl)sulfonyl]piperidin-4-yl}amino)pyrido[2,3-d]pyrimidin-7(8H)-one | 490 | 1H NMR (400 MHz, DMSO-d6, 80° C.) δ = 8.51 (s, 1H), 7.53 (s, 1H), 7.40 (d, J = 7.7 Hz, 1H), 5.94-5.80 (m, 1H), 4.09 (d, J = 7.2 Hz, 1H), 4.04 (s, 1H), 3.92-3.76 (m, 2H), 3.43-3.27 (m, 2H), 2.29-2.11 (m, 2H), 2.11-2.00 (m, 1H), 2.03 (s, 3H), 2.00-1.81 (m, 3H), 1.77-1.51 (m, 3H), 0.99 (s, 3H) 19F NMR (376 MHz, DMSO-d6, 80° C.) δ = -75.41 (s, 3F) [α]$_D^{22}$ - 11.6 (c 0.3, CHCl3) 99% ee; absolute stereochemistry unknown. Enantiomer of Ex. 182 |
| 182 (A) | (+)-8-[(1R*,2R*)-2-hydroxy-2-methylcyclopentyl]-6-methyl-2-({1-[(trifluoromethyl)sulfonyl]piperidin-4-yl}amino)pyrido[2,3-d]pyrimidin-7(8H)-one | 490 | 1H NMR (400 MHz, DMSO-d6, 80° C.) δ = 8.51 (s, 1H), 7.53 (s, 1H), 7.41 (d, J = 7.0 Hz, 1H), 6.97 (br s, 1H), 5.87 (t, J = 8.3 Hz, 1H), 4.15-4.06 (m, 1H), 4.05 (s, 1H), 3.93-3.76 (m, 2H), 3.35 (q, J = 10.8 Hz, 2H), 2.28-2.11 (m, 2H), 2.11-2.00 (m, 1H), 2.03 (s, 3H), 2.00-1.81 (m, 3H), 1.76-1.46 (m, 3H), 0.99 (s, 3H) 19F NMR (376 MHz, DMSO-d6, 80° C.) δ = -75.41 (s, 3F) [α]$_D^{22}$ + 5.82 (c 0.33, CHCl3) 99% ee; absolute stereochemistry unknown. Enantiomer of Ex. 181 |
| 183 (A) | (-)-4-({8-[(1R*,2R*)-2-hydroxy-2-methylcyclopentyl]-7-oxo-7,8-dihydropyrido[2,3-d]pyrimidin-2-yl}amino)piperidine-1-sulfonamide | 423 | 1H NMR (400 MHz, DMSO-d6, 80° C.) δ = 8.55 (s, 1H), 7.64 (d, J = 9.3 Hz, 1H), 7.42 (br s, 1H), 6.48 (br s, 2H), 6.19 (d, J = 9.2 Hz, 1H), 5.85 (t, J = 8.4 Hz, 1H), 4.03 (s, 1H), 3.97-3.82 (m, 1H), 3.53 (t, J = 10.6 Hz, 2H), 2.73 (t, J = 11.6 Hz, 2H), 2.62-2.52 (m, 1H), 2.28-2.13 (m, 1H), 2.13-1.80 (m, 5H), 1.75-1.56 (m, 3H), 1.02 (s, 3H) [α]$_D^{22}$ = -24.1 (c 0.1, MeOH) 99% ee; absolute stereochemistry unknown Enantiomer of Ex. 184 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 184 (A) | (+)-4-({8-[(1R*,2R*)-2-hydroxy-2-methylcyclopentyl]-7-oxo-7,8-dihydropyrido[2,3-d]pyrimidin-2-yl}amino)piperidine-1-sulfonamide | 423 | 1H NMR (400 MHz, DMSO-d6, 80° C.) δ = 8.55 (s, 1H), 7.64 (d, J = 9.3 Hz, 1H), 7.42 (br s, 1H), 6.49 (br s, 2H), 6.19 (d, J = 9.2 Hz, 1H), 5.85 (t, J = 8.3 Hz, 1H), 4.03 (s, 1H), 3.98-3.82 (m, 1H), 3.53 (t, J = 10.6 Hz, 2H), 2.73 (t, J = 11.6 Hz, 2H), 2.62-2.52 (m, 1H), 2.28-2.14 (m, 1H), 2.12-1.79 (m, 5H), 1.77-1.51 (m, 3H), 1.02 (s, 3H) $[α]_D^{22}$ = +18.0 (c 0.1, MeOH) 95% ee; absolute stereochemistry unknown Enantiomer of Ex. 183 |
| 185 (A) | (−)-6-(hydroxymethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one | 452 | 1H NMR (400 MHz, CDCl3) δ = 8.47 (s, 1H), 7.49 (s, 1H), 5.82-5.73 (m, 1H), 5.44 (br s, 1H), 4.57 (s, 2H), 4.02 (br d, J = 7.8 Hz, 1H), 3.82 (br t, J = 10.8 Hz, 2H), 2.97-2.89 (m, 2H), 2.83 (s, 3H), 2.31-2.18 (m, 3H), 2.12-1.78 (m, 5H), 1.74-1.64 (m, 2H), 1.17 (s, 3H) $[α]_D^{22}$ − 20.7 (c 2, CHCl3) 99% ee; absolute stereochemistry unknown Enantiomer of Ex. 186 |
| 186 (A) | (+)-6-(hydroxymethyl)-8-[(1R*,2R*)-2-hydroxy-2-methylcyclopentyl]-2-{[1-(methylsulfonyl)piperidin-4-yl]amino}pyrido[2,3-d]pyrimidin-7(8H)-one | 452 | 1H NMR (400 MHz, CDCl3) δ = 8.47 (s, 1H), 7.49 (s, 1H), 5.77 (br t, J = 7.9 Hz, 1H), 5.41 (br s, 1H), 4.57 (br s, 2H), 3.99 (br s, 1H), 3.87-3.68 (m, 2H), 2.99-2.89 (m, 2H), 2.83 (s, 3H), 2.29-2.17 (m, 3H), 2.13-1.77 (m, 5H), 1.69 (br s, 2H), 1.17 (s, 3H) $[α]_D^{22}$ + 4.3 (c 2, CHCl3) 99% ee; absolute stereochemistry unknown Enantiomer of Ex. 185 |
| 187 (E) | (−)-4-({6-(difluoromethyl)-8-[(1R*,2R*)-2-hydroxy-2-methylcyclopentyl]-7-oxo-7,8-dihydropyrido[2,3-d]pyrimidin-2-yl}amino)piperidine-1-sulfonamide | 473 | 1H NMR (400 MHz, DMSO-d6) δ = 8.73 (s, 1H), 8.03 (s, 1H), 7.72 (d, J = 3.7 Hz, 1H), 7.01-6.65 (m, 1H), 6.48 (br s, 2H), 5.96-5.71 (m, 1H), 4.07 (s, 1H), 3.95 (d, J = 7.1 Hz, 2H), 3.55 (t, J = 10.4 Hz, 2H), 2.76 (t, J = 11.7 Hz, 2H), 2.60-2.54 (m, 1H), 2.27-2.16 (m, 1H), 2.14-1.95 (m, 3H), 1.95-1.84 (m, 2H), 1.77-1.72 (m, 1H), 1.71-1.54 (m, 2H), 1.04 (s, 3H) $[α]_D^{22}$ − 18.3 (c 0.4, CHCl3) 91% ee; absolute stereochemistry unknown Enantiomer of Ex. 188 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 188 (E) | (+)-4-({6-(difluoromethyl)-8-[(1R*,2R*)-2-hydroxy-2-methylcyclopentyl]-7-oxo-7,8-dihydropyrido[2,3-d]pyrimidin-2-yl}amino)piperidine-1-sulfonamide | 473 | 1H NMR (400 MHz, DMSO-d6) δ = 8.73 (s, 1H), 8.03 (s, 1H), 7.72 (d, J = 3.7 Hz, 1H), 7.01-6.65 (m, 1H), 6.48 (br s, 2H), 5.96-5.71 (m, 1H), 4.07 (s, 1H), 3.95 (d, J = 7.1 Hz, 1H), 3.55 (t, J = 10.4 Hz, 2H), 2.76 (t, J = 11.7 Hz, 2H), 2.60-2.54 (m, 1H), 2.27-2.16 (m, 1H), 2.14-1.95 (m, 3H), 1.95-1.84 (m, 2H), 1.77-1.72 (m, 1H), 1.71-1.54 (m, 2H), 1.04 (s, 3H) [α]$_D^{22}$ + 15.8 (c 0.1, CHCl$_3$) 99% ee; absolute stereochemistry unknown Enantiomer of Ex. 187 |
| 189 (A) | 8-[(1R,2R)-2-hydroxy-2-methylcyclopentyl]-2-({1-[(2-hydroxy-2-methylpropyl)sulfonyl]piperidin-4-yl}amino)pyrido[2,3-d]pyrimidin-7(8H)-one | 462 [M − H$_2$O + 1]+ | 1H NMR (400 MHz, CDCl$_3$) δ = 8.42 (s, 1H), 7.45 (d, J = 9.5 Hz, 1H), 6.34 (br d, J = 9.3 Hz, 1H), 5.81-5.54 (m, 2H), 3.99 (br s, 1H), 3.88-3.77(m, 2H), 3.65 (br s, 1H), 3.07 (s, 2H), 3.02-2.91 (m, 2H), 2.83 (br s, 1H), 2.31-2.12 (m, 3H), 2.06-1.83 (m, 5H), 1.76-1.56 (m, 2H), 1.45 (s, 6H), 1.16 (s, 3H) 99% ee; Single enantiomer, absolute stereochemistry known |
| 190 (A) | 8-[(1R,2R)-2-hydroxy-2-methylcyclopentyl]-2-[(1-{[(methylsulfonyl)methyl]sulfonyl}piperidin-4-yl)amino]pyrido[2,3-d]pyrimidin-7(8H)-one | 500 | 1H NMR (400 MHz, CDCl$_3$) δ = 8.43 (s, 1H), 7.45 (d, J = 9.3 Hz, 1H), 6.35 (d, J = 9.3 Hz, 1H), 5.74 (br s, 1H), 5.46 (br s, 1H), 4.44 (s, 2H), 4.12-3.97 (m, 1H), 3.94-3.82 (m, 2H), 3.36-3.24 (m, 1H), 3.24 (s, 3H), 3.20 (d, J = 2.8 Hz, 1H), 2.94-2.73 (m, 1H), 2.31-2.16 (m, 3H), 2.05-1.97 (m, 2H), 1.97-1.87 (m, 1H), 1.87-1.78 (m, 1H), 1.77-1.63 (m, 2H), 1.17 (s, 3H) Single enantiomer, absolute stereochemistry known |
| 191 (D) | (−)-6-chloro-2-{[(3R*,4S*)-3-fluoro-1-(methylsulfonyl)piperidin-4-yl]amino}-8-[(1R,2R)-2-hydroxy-2-methylcyclopentyl]pyrido[2,3-d]pyrimidin-7(8H)-one | 474 | 1H NMR (700 MHz, DMSO-d$_6$) δ = 8.65 (s, 1H), 8.20 (d, J = 5.5 Hz, 1H), 8.12-7.83 (m, 1H), 5.87 (t, J = 8.0 Hz, 1H), 5.41-4.82 (m, 1H), 4.48 (s, 1H), 4.28-3.95 (m, 1H), 3.81 (t, J = 11.6 Hz, 1H) 3.70 (d, J = 11.9 Hz, 1H), 3.20-2.99 (m, 2H), 2.92 (s, 3H), 2.48-2.33 (m, 1H), 2.23-2.07 (m, 1H), 2.06-1.89 (m, 2H), 1.88-1.73 (m, 3H), 1.68 (d, J = 7.0 Hz, 1H), 1.01-0.89 (m, 3H) 19F NMR (565 MHz, DMSO-d$_6$) δ = −201.1 (br s, 1F) [α]$_D^{22}$ − 99.6 (c 0.1, CHCl$_3$) 98% de; Single diastereomer, absolute stereochemistry known R,R at cyclopentyl chiral centers, relative stereochemistry known to be cis at piperidine chiral centers. Diastereomer of Ex. 192 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 192 (D) | (+)-6-chloro-2-{[(3R*,4S*)-3-fluoro-1-(methylsulfonyl)piperidin-4-yl]amino}-8-[(1R,2R)-2-hydroxy-2-methylcyclopentyl]pyrido[2,3-d]pyrimidin-7(8H)-one | 474 | $^1$H NMR (700 MHz, DMSO-d$_6$) δ = 8.65 (d, J = 7.9 Hz, 1H), 8.11 (br s, 1H), 7.88 (br s, 1H), 5.97-5.74 (m, 1H), 5.13-4.84 (m, 1H), 4.55-4.32 (m, 1H), 4.29-4.02 (m, 1H), 3.96-3.78 (m, 1H), 3.67 (d, J = 11.9 Hz, 1H), 3.24-2.97 (m, 2H), 2.93 (d, J = 7.5 Hz, 3H), 2.38 (br s, 1H), 2.24-2.09 (m, 1H), 2.04-1.75 (m, 5H), 1.68 (d, J = 8.8 Hz, 1H), 0.98 (d, J = 7.5 Hz, 3H)<br>$^{19}$F NMR (565 MHz, DMSO-d$_6$) δ = −200.8 (brs, 1F)<br>$[α]_D^{22}$ + 8.9 (c 0.2, CHCl$_3$)<br>99% de; Single diastereomer, absolute stereochemistry known R,R at cyclopentyl chiral centers, relative stereochemistry known to be cis at piperidine chiral centers.<br>Diastereomer of Ex. 191 |
| 193 (A) | (-)-(8-[(1R*,2R*)-2-ethyl-2-hydroxycyclopentyl]-2-{[1-(methylsulfonyl)piperidin-4-yl]amino}pyrido[2,3-d]pyrimidin-7(8H)-one | 436 | $^1$H NMR (400 MHz, CDCl$_3$) δ = 8.42 (s, 1H), 7.45 (d, J = 9.3 Hz, 1H), 6.35 (d, J = 9.3 Hz, 1H), 5.75 (br s, 1H), 5.48 (br s, 1H), 3.99 (br s, 1H), 3.87-3.76 (m, 2H), 2.99-2.90 (m, 2H), 2.87-2.77 (m, 4H), 2.22 (d, J = 12.3 Hz, 3H), 2.09-1.98 (m, 2H), 1.95-1.87 (m, 1H), 1.78 (dd, J = 6.7, 12.4 Hz, 1H), 1.73-1.65 (m, 3H), 1.57-1.45 (m, 1H), 1.27 (qd, J = 7.3, 14.1 Hz, 1H), 0.87 (t, J = 7.4 Hz, 3H)<br>$[α]_D^{22}$ − 5.26 (c 0.5, CHCl$_3$)<br>99% ee; absolute stereochemistry unknown<br>Enantiomer of Ex. 194 |
| 194 (A) | (+)-(8-[(1R*,2R*)-2-ethyl-2-hydroxycyclopentyl]-2-{[1-(methylsulfonyl)piperidin-4-yl]amino}pyrido[2,3-d]pyrimidin-7(8H)-one | 436 | $^1$H NMR (400 MHz, CDCl$_3$) δ = 8.42 (s, 1H), 7.45 (d, J = 9.3 Hz, 1H), 6.35 (d, J = 9.3 Hz, 1H), 5.75 (br s, 1H), 5.46 (br s, 1H), 3.98 (br s, 1H), 3.82 (t, J = 10.8 Hz, 2H), 2.98-2.89 (m, 2H), 2.87-2.72 (m, 4H), 2.22 (d, J = 11.8 Hz, 3H), 2.08-1.99 (m, 2H), 1.96-1.85 (m, 1H), 1.78 (dd, J = 6.7, 12.4 Hz, 1H), 1.72-1.63 (m, 3H), 1.56-1.47 (m, 1H), 1.32-1.23 (m, 1H), 0.87 (t, J = 7.3 Hz, 3H)<br>$[α]_D^{22}$ + 2.73 (c 0.5, CHCl$_3$)<br>99% ee; absolute stereochemistry unknown<br>Enantiomer of Ex. 193 |
| 195 (D) | (-)-6-chloro-8-[(1R*,2R*)-2-ethyl-2-hydroxycyclopentyl]-2-{[1-(methylsulfonyl)piperidin-4-yl]amino}pyrido[2,3-d]pyrimidin-7(8H)-one | 470 | $^1$H NMR (400 MHz, CDCl$_3$) δ = 8.43 (s, 1H), 7.69 (s, 1H), 5.86 (br s, 1H), 5.49 (br s, 1H), 3.97 (br s, 1H), 3.89-3.77 (m, 2H), 2.99-2.88 (m, 2H), 2.83 (s, 3H), 2.66 (br s, 1H), 2.35-2.17 (m, 3H), 2.10-2.03 (m, 2H), 1.98-1.88 (m, 1H), 1.77 (dd, J = 6.3, 12.5 Hz, 2H), 1.60 (s, 2H), 1.48 (dd, J = 7.4, 13.9 Hz, 1H), 1.27 (qd, J = 7.2, 14.2 Hz, 1H), 0.87 (t, J = 7.4 Hz, 3H)<br>$[α]_D^{22}$ − 2.08 (c 0.4, CHCl$_3$)<br>99% ee; absolute stereochemistry unknown<br>Enantiomer of Ex. 196 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 196 (D) | (+)-6-chloro-8-[(1R*,2R*)-2-ethyl-2-hydroxycyclopentyl]-2-{[1-(methylsulfonyl)piperidin-4-yl]amino}pyrido[2,3-d]pyrimidin-7(8H)-one | 470 | 1H NMR (400 MHz, CDCl3) δ = 8.43 (s, 1H), 7.69 (s, 1H), 5.87 (br s, 1H), 5.50 (br s, 1H), 3.97 (br s, 1H), 3.89-3.73 (m, 2H), 3.00-2.88 (m, 2H), 2.86-2.80 (m, 3H), 2.66 (br s, 1H), 2.36-2.16 (m, 3H), 2.12-2.02 (m, 2H), 1.99-1.87 (m, 1H), 1.77 (dd, J = 7.0, 12.3 Hz, 2H), 1.61 (s, 2H), 1.54-1.44 (m, 1H), 1.27 (qd, J = 7.3, 14.1 Hz, 1H), 0.87 (t, J = 7.2 Hz, 3H) [α]$_D^{22}$ + 1.66 (c 0.4, CHCl3) 99% ee; absolute stereochemistry unknown Enantiomer of Ex. 195 |
| 197 (A) | (−)-8-[(3R*,4S*)-4-hydroxy-4-methyltetrahydrofuran-3-yl]-6-methyl-2-{[1-(methylsulfonyl)piperidin-4-yl]amino}pyrido[2,3-d]pyrimidin-7(8H)-one | 438 | 1H NMR (400 MHz, CDCl3) δ = 8.41 (s, 1H), 7.37 (s, 1H), 6.06 (br s, 1H), 5.51 (d, J = 7.8 Hz, 1H), 4.65 (br s, 1H), 4.38-4.26 (m, 2H), 4.04 (br s, 1H), 3.91 (d, J = 9.0 Hz, 1H), 3.83 (t, J = 11.2 Hz, 2H), 2.96-2.87 (m, 2H), 2.83 (s, 3H), 2.29-2.14 (m, 5H), 1.77-1.68 (m, 2H), 1.16 (s, 3H) [α]$_D^{22}$ − 20.5 (c 0.12, MeOH) 99% ee; absolute stereochemistry unknown Enantiomer of Ex. 198 |
| 198 (A) | (+)-8-[(3R*,4S*)-4-hydroxy-4-methyltetrahydrofuran-3-yl]-6-methyl-2-{[1-(methylsulfonyl)piperidin-4-yl]amino}pyrido[2,3-d]pyrimidin-7(8H)-one | 438 | 1H NMR (400 MHz, CDCl3) δ = 8.41 (s, 1H), 7.37 (d, J = 1.0 Hz, 1H), 6.06 (br s, 1H), 5.41 (br s, 1H), 4.65 (br s, 1H), 4.29 (t, J = 9.0 Hz, 2H), 4.10-3.99 (m, 1H), 3.91 (d, J = 8.8 Hz, 1H), 3.87-3.79 (m, 2H), 2.96-2.88 (m, 2H), 2.83 (s, 3H), 2.29-2.14 (m, 5H), 1.70 (m, J = 12.8 Hz, 2H), 1.16 (s, 3H) [α]$_D^{22}$ + 11.21 (c 0.116, MeOH) 99% ee; absolute stereochemistry unknown Enantiomer of Ex. 197 |
| 199 (A) | (−)-8-[(1R*,2S*,4R*)-4-hydroxy-2-methylcyclopentyl]-6-methyl-2-{[1-(methylsulfonyl)piperidin-4-yl]amino}pyrido[2,3-d]pyrimidin-7(8H)-one | 458 [M + Na]+ | 1H NMR (400 MHz, CDCl3) δ = 8.39 (s, 1H), 7.36 (d, J = 1.3 Hz, 1H), 6.12-5.92 (m, 1H), 5.32 (br s, 1H), 4.43 (br d, J = 6.3 Hz, 1H), 4.04 (br d, J = 7.3 Hz, 1H), 3.88-3.50 (m, 1H), 2.98 (br d, J = 14.8 Hz, 2H), 2.88-2.78 (m, 3H), 2.57-2.41 (m, 3H), 2.28 (td, J = 7.6, 12.7 Hz, 1H), 2.23-2.13 (m, 5H), 2.08-1.95 (m, 1H), 1.78-1.68 (m, 2H), 0.80 (d, J = 7.0 Hz, 3H) [α]$_D^{22}$ − 14.5 (c 0.2, MeOH) 99% ee; absolute stereochemistry unknown Enantiomer of Ex. 200 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 200 (A) | (+)-8-[(1R*,2S*,4R*)-4-hydroxy-2-methylcyclopentyl]-6-methyl-2-{[1-(methylsulfonyl)piperidin-4-yl]amino}pyrido[2,3-d]pyrimidin-7(8H)-one | 458 [M + Na]+ | 1H NMR (400 MHz, CDCl3) δ = 8.39 (s, 1H), 7.36 (d, J = 1.3 Hz, 1H), 6.13-5.90 (m, 1H), 5.29 (br s, 1H), 4.42 (br t, J = 6.4 Hz, 1H), 4.04 (br s, 1H), 3.88-3.45 (m, 3H), 2.96 (br s, 2H), 2.83 (s, 3H), 2.55-2.39 (m, 3H), 2.36-2.24 (m, 1H), 2.17 (d, J = 1.3 Hz, 5H), 2.09-1.95 (m, 1H), 1.74-1.65 (m, 2H), 0.81 (d, J = 7.0 Hz, 3H) [α]$_D^{22}$ + 18.1 (c 0.1, MeOH) 99% ee; absolute stereochemistry unknown Enantiomer of Ex. 199 |
| 201 (A) | (-)-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 422 | 1H NMR (400 MHz, DMSO-d6) δ = 8.56 (s, 1H), 7.65 (d, J = 9.3 Hz, 1H), 7.47 (d, J = 4.8 Hz, 1H), 6.21 (d, J = 9.2 Hz, 1H), 5.84-5.63 (m, 1H), 4.23 (d, J = 3.7 Hz, 1H), 4.13 (br s, 1H), 4.00-3.88 (m, 1H), 3.70-3.50 (m, 2H), 2.95-2.89 (m, 3H), 2.89-2.79 (m, 3H), 2.31-2.17-(m, 2H), 2.03-1.86-(m, 2H), 1.77-1.56 (m, 3H), 0.84 (d, J = 6.8 Hz, 3H) [α]$_D^{22}$ − 17.2 (c 0.1, MeOH) 99% ee; absolute stereochemistry unknown Enantiomer of Ex. 202 |
| 202 (A) | (+)-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 422 | 1H NMR (400 MHz, DMSO-d6) δ = 8.56 (s, 1H), 7.65 (d, J = 9.3 Hz, 1H), 7.48 (br s, 1H), 6.21 (d, J = 9.3 Hz, 1H), 5.87-5.63 (m, 1H), 4.23 (d, J = 3.7 Hz, 1H), 4.13 (br s, 1H), 3.99-3.83 (m, 1H), 3.70-3.45 (m, 2H), 2.98-2.788 (m, 6H), 2.29-2.14 (m, 2H), 2.03-1.97 (m, 2H), 1.97-1.86 (m, 1H), 1.76-1.56 (m, 3H), 0.84 (d, J = 6.8 Hz, 3H) [α]$_D^{22}$ + 19.9 (c 0.1, MeOH) 99% ee; absolute stereochemistry unknown Enantiomer of Ex. 201 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 203 (D) | (−)-6-chloro-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 456 | $^1$H NMR (400 MHz, DMSO-d$_6$) δ = 8.61 (br s, 1H), 8.08 (s, 1H), 8.05-7.69 (m, 1H), 5.79 (br s, 1H), 4.53 (br s, 1H), 4.09 (br s, 1H), 4.04-3.74 (m, 1H), 3.57 (d, J = 10.5 Hz, 2H), 2.97-2.73 (m, 6H), 2.18 (br s, 2H), 1.96 (br s, 3H), 1.78-1.46 (m, 3H), 0.81 (d, J = 6.8 Hz, 3H) $[α]_D^{22}$ − 9.5 (c 0.1, MeOH) Single enantiomer, absolute stereochemistry unknown Made from Ex. 201 |
| 204 (E) | (−)-6-(difluoromethyl)-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 472 | $^1$H NMR (400 MHz, DMSO-d$_6$, 80° C.) δ = 8.64 (s, 1H), 7.94 (s, 1H), 7.72 (br s, 1H), 6.94-6.47 (m, 1H), 5.65 (d, J = 6.7 Hz, 1H), 4.18 (d, J = 3.3 Hz, 1H), 4.05 (br s, 1H), 3.87 (br s, 1H), 3.54 (dd, J = 4.40, 11.49 Hz, 2H), 2.87-2.75 (m, 6H), 2.14 (br s, 2H), 1.99-1.80 (m, 3H), 1.70-1.46 (m, 3H), 0.76 (d, J = 6.8 Hz, 3H) $^{19}$F NMR (376 MHz, DMSO-d$_6$) δ = −118.6 to −114.9 (m, 2F) $[α]_D^{22}$ − 29.9 (c 0.4, MeOH) Single enantiomer, absolute stereochemistry unknown Made from Ex. 201 Enantiomer of Ex. 205 |
| 205 (E) | (+)-6-(difluoromethyl)-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 472 | $^1$H NMR (400 MHz, DMSO-d$_6$) δ = 8.73 (s, 1H), 8.04 (s, 1H), 7.83 (br s, 1H), 7.04-6.55 (m, 1H), 5.84-5.63 (m, 1H), 4.27 (d, J = 3.8 Hz, 1H), 4.14 (br s, 1H), 3.96 (br s, 1H), 3.64 (dd, J = 4.03, 12.35 Hz, 2H), 2.96-2.82 (m, 6H), 2.23 (br s, 2H), 2.07-1.91 (m, 3H), 1.77-1.55 (m, 3H), 0.86 (d, J = 6.8 Hz, 3H). $^{19}$F NMR (376 MHz, CDCl$_3$) δ = −119.9 to −118.0 (m, 2F). $[α]_D^{22}$ + 19.6 (c 0.5, MeOH) Single enantiomer, absolute stereochemistry unknown Made from Ex. 202 Enantiomer of Ex. 204 |

TABLE 1-continued

| Ex. No. (Method) | Structure/IUPAC name | LCMS [M + H]⁺ | ¹H NMR (ppm); ¹⁹F NMR (ppm); optical rotation; stereochem. notes |
|---|---|---|---|
| 206 (E) | (−)-6-(difluoromethyl)-8-[(1R*,2S*,3R*)-3-hydroxy-2-methylcyclopentyl]-2-{[1-(methylsulfonyl)piperidin-4-yl]amino}pyrido[2,3-d]pyrimidin-7(8H)-one | 486 | ¹H NMR (400 MHz, DMSO-d₆, 80° C.) δ = 8.60 (br s, 1H), 7.88 (br s, 1H), 7.73 (s, 1H), 6.22 (tt, J = 4.6, 57.1 Hz, 1H), 5.75 (br s, 1H), 4.51 (br s, 1H), 4.09 (br s, 1H), 4.05-3.74 (m, 1H), 3.65-3.51 (m, 2H), 3.04 (dt, J = 4.2, 17.1 Hz, 2H), 2.89 (s, 3H), 2.88-2.77 (m, 3H), 2.20 (br s, 2H), 1.95 (br s, 3H), 1.78-1.45 (m, 3H), 0.80 (d, J=6.8 Hz, 3H) [α]$_D^{22}$ − 10.3 (c 0.1, MeOH) Single enantiomer, absolute stereochemistry unknown Made from Ex. 201 |
| 207 (A) | (+)-8-[(1R*,2R*,3S*)-3-hydroxy-2-methylcyclopentyl]-2-{[1-(methylsulfonyl)piperidin-4-yl]amino}pyrido[2,3-d]pyrimidin-7(8H)-one | 422 | ¹H NMR (400 MHz, DMSO-d₆) δ = 8.57 (s, 1H), 7.69 (d, J = 9.2 Hz, 1H), 7.56 (d, J = 6.6 Hz, 1H), 6.19 (d, J = 9.2 Hz, 1H), 6.16-5.95 (m, 1H), 4.96 (d, J = 10.8 Hz, 1H), 4.00-3.73 (m, 2H), 3.63-3.42 (m, 2H), 2.91-2.811 (m, 2H), 2.79 (s, 3H), 2.70-2.56 (m, 1H), 2.39-2.29 (m, 1H), 1.98-1.85 (m, 2H), 1.82-1.70 (m, 2H), 1.71-1.49 (m, 3H), 0.57 (d, J = 7.5 Hz, 3H) [α]$_D^{22}$ + 27.3 (c 0.1, MeOH) 99% ee; absolute stereochemistry unknown Enantiomer of Ex. 208 |
| 208 (A) | (−)-8-[(1R*,2R*,3S*)-3-hydroxy-2-methylcyclopentyl]-2-{[1-(methylsulfonyl)piperidin-4-yl]amino}pyrido[2,3-d]pyrimidin-7(8H)-one | 422 | ¹H NMR (400 MHz, DMSO-d₆) δ = 8.67 (s, 1H), 7.79 (d, J = 9.3 Hz, 1H), 7.66 (d, J = 6.5 Hz, 1H), 6.29 (d, J = 9.2 Hz, 1H), 6.06-6.24 (m, 1H), 5.06 (d, J = 10.5 Hz, 1H), 3.90-4.10 (m, 2H), 3.61 (dd, J = 6.72, 10.88 Hz, 2H), 2.91-3.01 (m, 2H), 2.88 (s, 3H), 2.64-2.79 (m, 1H), 2.39-2.46 (m, 1H), 1.95-2.06 (m, 2H), 1.78-1.91 (m, 2H), 1.60-1.79 (m, 3H), 0.67 (d, J = 7.3 Hz, 3H) [α]$_D^{22}$ − 33.1 (c 0.1, MeOH) 99% ee; absolute stereochemistry unknown Enantiomer of Ex. 207 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 209 (A) | 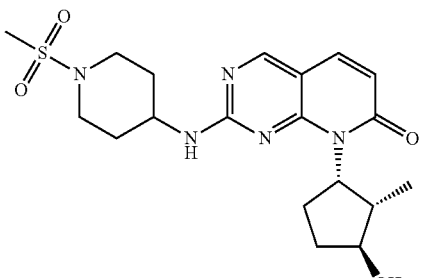 (+)-8-[(1R*,2R*,3R*)-3-hydroxy-2-methylcyclopentyl]-2-{[1-(methylsulfonyl)piperidin-4-yl]amino}pyrido[2,3-d]pyrimidin-7(8H)-one | 422 | $^1$H NMR (400 MHz, DMSO-d$_6$) δ = 8.47 (s, 1H), 7.56 (d, J = 9.3 Hz, 1H), 7.39 (d, J = 6.2 Hz, 1H), 6.10 (d, J = 9.3 Hz, 1H), 5.98 (dt, J = 7.15, 10.06 Hz, 1H), 4.24 (d, J = 5.3 Hz, 1H), 4.18-4.07 (m, 1H), 3.97-3.82 (m, 1H), 3.57-3.46 (m, 2H), 2.91-2.81 (m, 2H), 2.79 (s, 3H), 2.14-2.02 (m, 1H), 1.99-1.88 (m, 3H), 1.88-1.76 (m, 1H), 1.66-1.45 (m, 2H), 1.45-1.28 (m, 1H), 0.62 (d, J = 7.2 Hz, 3H) $[α]_D^{22}$ + 3.1 (c 0.1, MeOH) 99% ee; absolute stereochemistry unknown Enantiomer of Ex. 210 |
| 210 (A) | 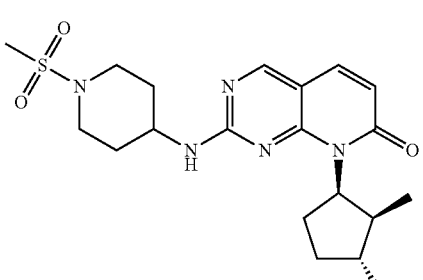 (-)-8-[(1R*,2R*,3R*)-3-hydroxy-2-methylcyclopentyl]-2-{[1-(methylsulfonyl)piperidin-4-yl]amino}pyrido[2,3-d]pyrimidin-7(8H)-one | 422 | $^1$H NMR (400 MHz, DMSO-d$_6$) δ = 8.56 (s, 1H), 7.66 (d, J = 9.3 Hz, 1H), 7.48 (d, J = 7.0 Hz, 1H), 6.20 (d, J = 9.3 Hz, 1H), 6.08 (dt, J = 6.91, 10.18 Hz, 1H), 4.33 (d, J = 5.1 Hz, 1H), 4.14-4.28 (m, 1H), 4.05-3.89 (m, 1H), 3.68-3.54 (m, 2H), 2.99-2.90 (m, 2H), 2.88 (s, 3H), 2.26-2.11 (m, 1H), 2.09-1.99 (m, 3H), 1.92 (dtd, J = 2.51, 9.60, 12.41 Hz, 1H), 1.74-1.57 (m, 2H), 1.54-1.40 (m, 1H), 0.71 (d, J = 7.2 Hz, 3H) $[α]_D^{22}$ − 5.1 (c 0.1, MeOH) 99% ee; absolute stereochemistry unknown Enantiomer of Ex. 209 |
| 211 (A) | 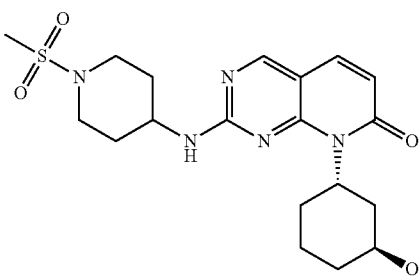 8-[(1S,3S)-3-hydroxycyclohexyl]-2-{[1-(methylsulfonyl)piperidin-4-yl]amino}pyrido[2,3-d]pyrimidin-7(8H)-one | 444 [M + Na]+ | $^1$H NMR (400 MHz, CDCl$_3$) δ = 8.38 (s, 1H), 7.41 (d, J = 9.3 Hz, 1H), 6.32 (d, J = 8.8 Hz, 1H), 5.95 (br s, 1H), 5.52 (br s, 1H), 4.35 (br s, 1H), 4.05-3.87 (m, 1H), 3.86-3.77 (m, 2H), 3.02-2.85 (m, 3H), 2.83 (s, 3H), 2.67 (d, J = 11.3 Hz, 1H), 2.22 (d, J = 12.0 Hz, 2H), 1.92-1.69 (m, 8H) $[α]_D^{22}$ − 11.52 (c 0.11, CHCl$_3$) 98% ee; Single enantiomer, absolute stereochemistry known Enantiomer of Ex. 3 |

TABLE 1-continued

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 212 (E) | 6-(difluoromethyl)-8-[(1R,3R)-3-hydroxycyclohexyl]-2-{[1-(methylsulfonyl)piperidin-4-yl]amino}pyrido[2,3-d]pyrimidin-7(8H)-one | 472 | $^1$H NMR (700 MHz, DMSO-d$_6$) δ = 8.78-8.65 (m, 1H), 8.15 (d, J = 6.4 Hz, 1H), 8.06-7.82 (m, 1H), 6.98-6.71 (m, 1H), 6.18-5.49 (m, 1H), 4.49 (br s, 1H), 4.13 (br s, 1H), 4.05-3.75 (m, 1H), 3.68-3.48 (m, 2H), 3.02-2.73 (m, 6H), 2.24-1.90 (m, 2H), 1.86-1.69 (m, 2H), 1.68-1.44 (m, 6H), 1.43-1.31 (m, 1H) $[α]_D^{22}$ + 18.1 (c 0.1, CHCl$_3$) Single enantiomer, absolute stereochemistry known. |
| 213 (F) | (+)-2-(8-[(1R*,3R*)-3-hydroxycyclohexyl]-2-{[1-(methylsulfonyl)piperidin-4-yl]amino}-7-oxo-7,8-dihydropyrido[2,3-d]pyrimidin-6-yl)acetamide | 479 | $^1$H NMR (400 MHz, DMSO-d$_6$) δ = 8.56 (br s, 1H), 7.95-7.68 (m, 1H), 7.56 (br s, 1H), 7.34 (br s, 1H), 6.86 (br s, 1H), 6.08-5.60 (m, 1H), 4.49 (br s,1H), 4.12 (br s, 1H), 3.83 (br s, 1H), 3.68-3.46 (m, 2H), 3.22 (br s, 2H), 2.89 (br s, 3H), 2.84 (br s, 2H), 2.48-2.35 (m, 2H), 1.99 (br s, 2H), 1.77-1.32 (m, 8H) $[α]_D^{22}$ + 9.67 (c 0.2, DMSO) 98% ee; absolute stereochemistry unknown Enantiomer of Ex. 214 |
| 214 (F) | (-)-2-(8-[(1R*,3R*)-3-hydroxycyclohexyl]-2-{[1-(methylsulfonyl)piperidin-4-yl]amino}-7-oxo-7,8-dihydropyrido[2,3-d]pyrimidin-6-yl)acetamide | 479 | $^1$H NMR (400 MHz, DMSO-d$_6$) δ = 8.56 (br s, 1H), 7.94-7.70 (m, 1H), 7.56 (br s, 1H), 7.34 (br s, 1H), 6.86 (br s, 1H), 6.13-5.62 (m, 1H), 4.49 (br s, 1H), 4.12 (br s, 1H), 3.83 (br s, 1H), 3.68-3.50 (m, 2H), 3.22 (br s, 2H), 2.89 (br s, 3H), 2.83 (d, J = 8.8 Hz, 2H), 2.48-2.35 (m, 2H), 2.13-1.90 (m, 2H), 1.86-1.33 (m, 8H) $[α]_D^{22}$ - 26.33 (c 0.2, DMSO) 98% ee; absolute stereochemistry unknown Enantiomer of Ex. 213 |

TABLE 1-continued

| Ex. No. (Method) | Structure/IUPAC name | LCMS [M + H]+ | ¹H NMR (ppm); ¹⁹F NMR (ppm); optical rotation; stereochem. notes |
|---|---|---|---|
| 215 (A) | 8-(cis-4-hydroxycyclohexyl)-2-{[1-(methylsulfonyl)piperidin-4-yl]amino}pyrido[2,3-d]pyrimidin-7(8H)-one | 422 | ¹H NMR (400 MHz, DMSO-d₆) δ = 8.58-8.51 (m, 1H), 7.83-7.74 (m, 1H), 7.65 (d, J = 9.3 Hz, 1H), 6.28-6.19 (m, 1H), 5.23-5.08 (m, 1H), 4.56-4.43 (m, 1H), 4.41-4.19 (m, 1H), 3.96-3.87 (m, 1H), 3.58-3.48 (m, 2H), 3.29-2.89 (m, 4H), 2.88-2.81 (m, 3H), 1.99-1.87 (m, 2H), 1.85-1.77 (m, 2H), 1.63-1.47 (m, 4H), 1.30-1.21 (m, 2H) |
| 216 (A) | 8-[(1S,2S,5R)-5-hydroxy-2-methylcyclohexyl]-2-{[1-(methylsulfonyl)piperidin-4-yl]amino}pyrido[2,3-d]pyrimidin-7(8H)-one | 436 | ¹H NMR (400 MHz, DMSO-d₆) δ = 8.54 (s, 1H), 7.64 (d, J = 9.3 Hz, 1H), 7.51 (br s, 1H), 6.17 (br s, 1H), 5.92-5.23 (m, 1H), 4.23 (br s, 1H), 4.12 (br s 1H), 3.93 (br d, J = 7.3 Hz, 1H), 3.65 (br d, J = 12.0 Hz, 2H), 3.04-2.80 (m, 6H), 2.79-2.62 (m, 1H), 2.26-1.89 (m, 2H), 1.85-1.47 (m, 7H), 0.65 (d, J = 6.5 Hz, 3H)<br>[α]$_D^{22}$ + 12.0 (c 0.3, MeOH)<br>Single enantiomer, absolute stereochemistry known |
| 217 (A) | (+)-8-[(1S*,2S*,5R*)-2-fluoro-5-hydroxycyclohexyl]-2-{[1-(methylsulfonyl)piperidin-4-yl]amino}pyrido[2,3-d]pyrimidin-7(8H)-one | 440 | ¹H NMR (400 MHz, CDCl₃) δ = 8.41 (s, 1H), 7.46 (d, J = 9.4 Hz, 1H), 6.34 (br d, J = 9.1 Hz, 1H), 6.25 (br s, 1H), 5.82-5.55 (m, 2H), 4.28 (br d, J = 2.9 Hz, 1H), 4.04-3.68 (m, 3H), 3.03-2.88 (m, 2H), 2.84 (s, 3H), 2.23 (br d, J = 12.1 Hz, 2H), 2.18-2.03 (m, 2H), 1.98-1.75 (m, 5H), 1.74-1.69 (m, 2H)<br>[α]$_D^{22}$ + 3.67 (c 0.2, CHCl₃)<br>99% ee; absolute stereochemistry unknown<br>Enantiomer of Ex. 218 |

| Ex. No. (Method) | Structure/IUPAC name | LCMS [M + H]+ | $^1$H NMR (ppm); $^{19}$F NMR (ppm); optical rotation; stereochem. notes |
|---|---|---|---|
| 218 (A) | (−)-8-[(1S*,2S*,5R*)-2-fluoro-5-hydroxycyclohexyl]-2-{[1-(methylsulfonyl)piperidin-4-yl]amino}pyrido[2,3-d]pyrimidin-7(8H)-one | 440 | $^1$H NMR (400 MHz, CDCl$_3$) δ = 8.41 (s, 1H), 7.46 (d, J = 9.3 Hz, 1H), 6.33 (br d, J = 8.8 Hz, 2H), 5.87-5.57 (m, 1H), 5.48 (br s, 1H), 4.29 (br s,1H), 4.13-3.75 (m, 3H), 3.03-2.88 (m, 2H), 2.84 (s, 3H), 2.24 (br s, 1H), 2.13 (br s, 2H), 1.91 (br s, 1H), 1.80 (br d, J = 15.3 Hz, 4H), 1.69-1.59 (m, 3H) [α]$_D^{22}$ − 2.98 (c 0.28, CHCl$_3$) 99% ee; absolute stereochemistry unknown Enantiomer of Ex. 217 |
| 219 (A) | (+)-4-({8-[(1S*,2S*,5R*)-2-fluoro-5-hydroxycyclohexyl]-7-oxo-7,8-dihydropyrido[2,3-d]pyrimidin-2-yl}amino)-N-methylpiperidine-1-sulfonamide | 455 | $^1$H NMR (400 MHz, CDCl$_3$) δ = 8.41 (s, 1H), 7.46 (d, J = 9.4 Hz, 1H), 6.33 (br d, J = 9.4 Hz, 2H), 5.87-5.56 (m, 1H), 5.44 (br s, 1H), 4.28 (br s, 1H), 4.15 (br d, J = 4.7 Hz, 1H), 3.93 (br d, J = 19.8 Hz, 1H), 3.81-3.68 (m, 2H), 3.10-2.97 (m, 2H), 2.83 (br s, 1H), 2.76 (d, J = 5.4 Hz, 3H), 2.32-2.00 (m, 4H), 1.96-1.76 (m, 3H), 1.75-1.61 (m, 3H) [α]$_D^{22}$ + 2.9 (c 0.25, CHCl$_3$) 96% ee; absolute stereochemistry unknown Enantiomer of Ex. 220 |
| 220 (A) | (−)-4-({8-[(1S*,2S*,5R*)-2-fluoro-5-hydroxycyclohexyl]-7-oxo-7,8-dihydropyrido[2,3-d]pyrimidin-2-yl}amino)-N-methylpiperidine-1-sulfonamide | 455 | $^1$H NMR (400 MHz, CDCl$_3$) δ = 8.40 (s, 1H), 7.46 (d, J = 9.3 Hz, 1H), 6.32 (br d, J = 9.3 Hz, 2H), 5.85-5.59 (m, 1H), 5.53 (br d, J = 6.8 Hz, 1H), 4.28 (br s, 2H), 3.96 (br s, 1H), 3.74 (br s, 2H), 3.01 (br t, J = 10.7 Hz, 2H), 2.93-2.80 (m, 1H), 2.76 (d, J = 5.0 Hz, 3H), 2.38-2.00(m, 4H), 1.98-1.69 (m, 6H) $^{19}$F NMR (376 MHz, DMSO-d$_6$) δ = −177.8 (d, J = 48.6 Hz, 1F) [α]$_D^{22}$ − 3.6 (c 0.3, CHCl$_3$) 99% ee; absolute stereochemistry unknown Enantiomer of Ex. 219 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 221 (A) | (−)-8-[(1S*,2R*,3S*)-3-hydroxy-2-methylcyclohexyl]-2-{[1-(methylsulfonyl)piperidin-4-yl]amino}pyrido[2,3-d]pyrimidin-7(8H)-one | 436 | 1H NMR (400 MHz, DMSO-d6, 80° C.) δ = 8.53 (s, 1H), 7.63 (d, J = 9.3 Hz, 1H), 7.47 (br s, 1H), 6.19 (br s, 1H), 5.95-5.22 (m, 1H), 4.16 (d, J = 3.5 Hz, 1H), 3.88 (br s, 2H), 3.71-3.57 (m, 2H), 2.94-2.78 (m, 6H), 2.23-1.95 (m, 2H), 1.95-1.71 (m, 3H), 1.73-1.60 (m, 2H), 1.54 (t, J = 11.1 Hz, 3H), 0.65 (d, J = 6.4 Hz, 3H) [α]$_D^{22}$ − 12.3 (c 0.1, MeOH) 99% ee; absolute stereochemistry unknown Enantiomer of Ex. 222 |
| 222 (A) | (+)-8-[(1S*,2R*,3S*)-3-hydroxy-2-methylcyclohexyl]-2-{[1-(methylsulfonyl)piperidin-4-yl]amino}pyrido[2,3-d]pyrimidin-7(8H)-one | 436 | 1H NMR (400 MHz, DMSO-d6, 80° C.) δ = 8.53 (s, 1H), 7.63 (d, J = 9.3 Hz, 1H), 7.46 (br s, 1H), 6.18 (br s, 1H), 5.88-5.27 (m, 1H), 4.16 (d, J = 3.4 Hz, 1H), 3.87 (br s, 2H), 3.65 (s, 2H), 2.95-2.81 (m, 6H), 2.24-1.93 (m, 2H), 1.94-1.73 (m, 3H), 1.73-1.59 (m, 2H), 1.54 (t, J = 10.9 Hz, 3H), 0.65 (d, J = 6.5 Hz, 3H) [α]$_D^{22}$ + 9.4 (c 0.2, MeOH) 99% ee; absolute stereochemistry unknown Enantiomer of Ex. 221 |
| 223 (A) | 8-(3-hydroxycycloheptyl)-6-methyl-2-{[1-(methylsulfonyl)piperidin-4-yl]amino}pyrido[2,3-d]pyrimidin-7(8H)-one-Isomer A | 450 | 1H NMR (400 MHz, DMSO-d6, 80° C.) δ = 8.48 (s, 1H), 7.51 (s, 1H), 7.30 (d, J = 5.8 Hz, 1H), 5.51 (br s, 1H), 4.18 (d, J = 2.0 Hz, 1H), 3.96 (br s, 1H), 3.77-3.69 (m, 1H), 3.65 (d, J = 12.5 Hz, 2H), 2.98-2.90 (m, 3H), 2.88 (s, 3H), 2.04 (s, 3H), 2.11-2.00 (m, 2H), 1.93 (br s, 1H), 1.83-1.45 (m, 10H)\ Peak 1 of 4, rt 3.91 min; Chiralcel OJ-3 4.6 × 100 mm 3 μ column; 10% MeOH @ 120 bar, 4 mL/min [α]$_D^{22}$ − 1.2 (c 0.1, MeOH) >98% de, single diastereomer, absolute and relative stereochemistry unknown Enantiomer of Ex. 224 |
| 224 (A) | 8-(3-hydroxycycloheptyl)-6-methyl-2-{[1-(methylsulfonyl)piperidin-4-yl]amino}pyrido[2,3-d]pyrimidin-7(8H)-one-Isomer B | 450 | 1H NMR (400 MHz, DMSO-d6, 80° C.) δ = 8.48 (s, 1H), 7.51 (s, 1H), 7.31 (d, J = 5.0 Hz, 1H), 5.50 (br s, 1H), 4.19 (br s, 1H), 3.95 (br s, 1H), 3.79-3.69 (m, J = 8.7 Hz, 1H), 3.65 (d, J = 12.4 Hz, 2H), 2.98-2.90 (m, 3H), 2.88 (s, 3H), 2.04 (s, 3H), 2.07 (br s, 2H), 1.99-1.90 (m, 1H), 1.83-1.49 (m, 10H) Peak 2 of 4, rt 4.52 min [α]$_D^{22}$ + 1.6 (c 0.1, MeOH) ~95% de, single diastereomer, absolute and relative stereochemistry unknown Enantiomer of Ex. 223 |

TABLE 1-continued

| Ex. No. (Method) | Structure/IUPAC name | LCMS [M + H]+ | 1H NMR (ppm); 19F NMR (ppm); optical rotation; stereochem. notes |
|---|---|---|---|
| 225 (A) | 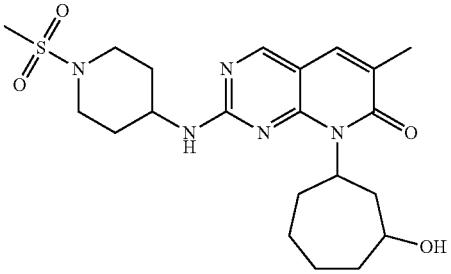<br>8-(3-hydroxycycloheptyl)-6-methyl-2-{[1-(methylsulfonyl)piperidin-4-yl]amino}pyrido[2,3-d]pyrimidin-7(8H)-one-Isomer C | 450 | 1H NMR (400 MHz, DMSO-d6, 80° C.) δ = 8.47 (s, 1H), 7.49 (s, 1H), 7.26 (br s, 1H), 5.88 (br s, 1H), 4.09 (br s, 1H), 4.06-3.88 (m, 2H), 3.65 (d, J = 12.1 Hz, 2H), 2.97-2.90 (m, 2H), 2.88 (s, 3H), 2.81-2.69 (m, J = 11.9 Hz, 1H), 2.48-2.36 (m, 1H), 2.15-2.05 (m, 2H), 2.04 (s, 3H), 1.87-1.50 (m, 9H), 1.50-1.36 (m, 1H)<br>Peak 3 of 4, rt 5.15 min<br>$[\alpha]_D^{22}$ + 21.4 (c 0.1, MeOH)<br>~95% de, single diastereomer, absolute and relative stereochemistry unknown<br>Enantiomer of Ex. 226 |
| 226 (A) | 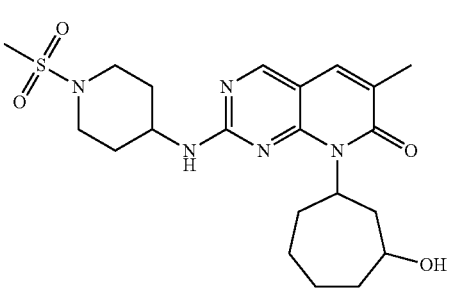<br>8-(3-hydroxycycloheptyl)-6-methyl-2-{[1-(methylsulfonyl)piperidin-4-yl]amino}pyrido[2,3-d]pyrimidin-7(8H)-one-Isomer D | 450 | 1H NMR (400 MHz, DMSO-d6, 80° C.) δ = 8.47 (s, 1H), 7.49 (s, 1H), 7.26 (br s, 1H), 5.88 (br s, 1H), 4.09 (br s, 1H), 4.06-3.89 (m, 2H), 3.71-3.60 (m, 2H), 2.98-2.90 (m, 2H), 2.88 (s, 3H), 2.75 (t, J = 10.3 Hz, 1H), 2.48-2.37 (m, 1H), 2.17-2.06 (m, 2H), 2.04 (s, 3H), 1.85-1.52 (m, 9H), 1.50-1.35 (m, 1H)<br>Peak 4 of 4, rt 5.89 min<br>$[\alpha]_D^{22}$ − 22.9 (c 0.1, MeOH)<br>~95% de, single diastereomer, absolute and relative stereochemistry unknown<br>Enantiomer of Ex. 225 |

Biological Assays and Data

CDK2/Cyclin E1 Mobility Shift Assay

The purpose of the CDK2/Cyclin E1 assay is to evaluate the inhibition (% inhibition, $K_{iapp}$ and $K_i$ values) of small molecule inhibitors by using a fluorescence-based microfluidic mobility shift assay. CDK2/Cyclin E1 catalyzes the production of ADP from ATP that accompanies the phosphoryl transfer to the substrate peptide FL-Peptide-18 (5-FAM-QSPKKG-CONH$_2$) (SEQ ID NO:1). (CPC Scientific, Sunnyvale, Calif.). The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Wild-type full length CDK2/wild-type full length Cyclin E1 enzyme complex was produced in-house (baculoviral expression, LJIC-2080/LJIC-2103) and phosphorylated by CDK7/Cyclin H1/Mat1 enzyme complex with CDK2:CDK7 ratio of 50:1 (concentration mg/mL) in the presence of 10 mM MgCl$_2$ and 5 mM ATP at room temperature for one hour. Typical reaction solutions (50 µL final reaction volume) contained 2% DMSO (±inhibitor), 4 mM MgCl$_2$, 1 mM DTT, 150 µM ATP (ATP K$_m$=67.4 µM), 0.005% Tween-20, 3 µM FL-Peptide-18, and 0.36 nM (catalytically competent active site) phosphorylated wild-type full length CDK2/Cyclin E1 enzyme complex in 25 mM HEPES buffer at pH 7.15. The assay was initiated with the addition of ATP, following a fifteen minutes pre-incubation of enzyme and inhibitor at room temperature in the reaction mixture. The reaction was stopped after 45 minutes at room temperature by the addition of 50 µL of 80 mM EDTA, pH 7.5. The $K_i$ value was determined from the fit of the data to the Morrison tight-binding competitive inhibition equation with the enzyme concentration as a variable.

CDK6/Cyclin D1 Mobility Shift Assay

The purpose of the CDK6/Cyclin D1 assay is to evaluate the inhibition (% inhibition, $K_{iapp}$ and $K_i$ values) in the presence of small molecule inhibitors by using a fluorescence based microfluidic mobility shift assay. CDK6/Cyclin D1 catalyzes the production of ADP from ATP that accompanies the phosphoryl transfer to the substrate peptide 5-FAM-Dyrktide (5-FAM-RRRFRPASPLRGPPK) (SEQ ID NO:2). The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 10 mM MgCl$_2$, 1 mM DTT, 2 mM ATP, 0.005% Tween 20 (TW-20), 3 µM 5-FAM-Dyrktide, 3 nM (active sites) CDK6/Cyclin D1 in 40 mM HEPES buffer at pH 7.5.

Inhibitor K$_i$ determinations for non-phosphorylated CDK6/CyclinD1 (LJIC-2003A2/1865) were initiated with the addition of ATP (50 µL final reaction volume), following a twelve minute pre-incubation of enzyme and inhibitor at 22° C. in the reaction mix. The reaction was stopped after 35 minutes by the addition of 50 µL of 25 mM EDTA. K$_i$ determinations were made from a plot of the fractional velocity as a function of inhibitor concentration fit to the Morrison equation with the enzyme concentration as a variable.

For CDK2, CDK4 and CDK6 mobility shift assays, see also Morrison, J. F. (1969) Kinetics of the reversible inhibition of enzyme-catalysed reactions by tight-binding inhibitors, *Biochimica et biophysica acta* 185, 269-286; and Murphy, D. J. (2004) Determination of accurate KI values for tight-binding enzyme inhibitors: an in silico study of experimental error and assay design, *Analytical biochemistry* 327, 61-67.

CDK4/Cyclin D3 Mobility Shift Assay

The purpose CDK4/Cyclin D3 assay is to evaluate the inhibition (% inhibition, $K_{iapp}$ and $K_i$ values) in the presence of small molecule inhibitors by using a fluorescence based microfluidic mobility shift assay. CDK4/Cyclin D3 catalyzes the production of ADP from ATP that accompanies the phosphoryl transfer to the substrate peptide 5-FAM-Dyrktide (5-FAM-RRRFRPASPLRGPPK) (SEQ ID NO:2). The mobility shift assay electrophoretically separates the fluorescently labeled peptides (substrate and phosphorylated product) following the kinase reaction. Both substrate and product are measured and the ratio of these values is used to generate % Conversion of substrate to product by the LabChip EZ Reader. Typical reaction solutions contained 2% DMSO (±inhibitor), 10 mM $MgCl_2$, 1 mM DTT, 2 mM ATP, 0.005% TW-20, 3 μM 5-FAM-Dyrktide, 2 nM (active sites) CDK4/Cyclin D3 in 40 mM HEPES buffer at pH 7.5.

Inhibitor $K_i$ determinations for non-phosphorylated CDK4/Cyclin D3 (LJIC-2007/2010) were initiated with the addition of ATP (50 μL final reaction volume), following a twelve minute pre-incubation of enzyme and inhibitor at 22° C. in the reaction mix. The reaction was stopped after 35 minutes by the addition of 50 μL of 25 mM EDTA. $K_i$ determinations were made from a plot of the fractional velocity as a function of inhibitor concentration fit to the Morrison equation with the enzyme concentration as a variable.

Biological Activity

Biological activity data for selected compounds in the CDK2, CDK6 and CDK4 mobility shift assays are provided in Table 2 as Ki (nM).

TABLE 2

| Example # | CDK2_Ki (nM) | CDK6_Ki (nM) | CDK4_Ki (nM) |
|---|---|---|---|
| 1 | 0.71 | 1.20 | |
| 2 | 0.20 | 2.91 | 1.55 |
| 3 | 0.26 | 1.17 | 3.43 |
| 4 | 0.06 | 0.12 | |
| 5 | 4.75 | 13.07 | |
| 6 | 0.48 | 2.38 | 3.94 |
| 7 | 1.87 | 2.04 | |
| 8 | 0.09 | 0.13 | 0.16 |
| 9 | 0.16 | 0.25 | 1.12 |
| 10 | 0.12 | 0.08 | 1.37 |
| 11 | 0.67 | 2.99 | |
| 12 | 1.12 | | |
| 13 | 0.19 | 0.88 | |
| 14 | 2.50 | | |
| 15 | 0.46 | 0.76 | |
| 16 | 0.48 | 1.14 | |
| 17 | 1.79 | 2.33 | |
| 18 | 1.19 | 2.44 | |
| 19 | 0.35 | 0.96 | |
| 20 | 0.42 | 1.95 | |
| 21 | 0.29 | 7.00 | |
| 22 | 0.63 | 0.33 | |
| 23 | 0.78 | 0.62 | |
| 24 | 1.59 | | |
| 25 | 0.22 | 0.23 | |
| 26 | 3.84 | | |
| 27 | 3.85 | | |
| 28 | 1.88 | 1.20 | |
| 29 | 1.40 | 0.31 | 0.66 |
| 30 | 1.35 | 0.34 | |
| 31 | 2.43 | 0.87 | |
| 32 | 0.84 | 1.10 | |
| 33 | 42.61 | | |
| 34 | 1.34 | 0.42 | |
| 35 | 19.19 | 7.82 | |
| 36 | 0.09 | 0.13 | |
| 37 | 0.06 | 0.06 | |
| 38 | 0.27 | 0.42 | |
| 39 | 1.28 | | |
| 40 | 0.08 | 0.14 | |
| 41 | 0.48 | 0.36 | |
| 42 | 155.10 | 46.13 | |
| 43 | 1.56 | | |
| 44 | 0.09 | 0.82 | |
| 45 | 0.93 | | |
| 46 | 0.77 | | |
| 47 | 0.27 | 1.09 | |
| 48 | 1.39 | 0.54 | |
| 49 | 4.43 | 1.63 | |
| 50 | 0.27 | 0.08 | |
| 51 | 1.74 | 0.13 | |
| 52 | 0.12 | 0.24 | |
| 53 | 1.09 | 3.79 | |
| 54 | 1.44 | | |
| 55 | 4.66 | | |
| 56 | 0.28 | 1.77 | |
| 57 | 5.21 | | |
| 58 | 0.27 | 0.49 | |
| 59 | 4.13 | 3.37 | |
| 60 | 0.48 | 3.18 | |
| 61 | 4.55 | 19.66 | |
| 62 | 0.35 | 5.69 | |
| 63 | 4.51 | 16.54 | |
| 64 | 0.35 | 4.69 | |
| 65 | 4.85 | 25.55 | |
| 66 | 0.21 | 2.47 | |
| 67 | 4.05 | 21.58 | |
| 68 | 0.41 | 3.23 | |
| 69 | 4.48 | 22.25 | |
| 70 | 0.35 | 0.83 | |
| 71 | 0.25 | 1.55 | |
| 72 | 0.42 | 1.09 | |
| 73 | 5.03 | 8.95 | |
| 74 | 0.20 | 1.01 | |
| 75 | 3.85 | 4.96 | |
| 76 | 0.21 | 1.24 | |
| 77 | 4.07 | 6.60 | |
| 78 | 0.25 | 1.63 | |
| 79 | 7.32 | 9.59 | |
| 80 | 0.25 | 1.53 | |
| 81 | 7.03 | 6.24 | |
| 82 | 0.10 | 1.21 | |
| 83 | 1.98 | 9.77 | |
| 84 | 0.08 | 0.92 | |
| 85 | 1.98 | 8.29 | |
| 86 | 0.45 | 1.60 | |
| 87 | 4.38 | 8.23 | |
| 88 | 1.34 | 1.99 | |
| 89 | 17.61 | 11.33 | |
| 90 | 0.25 | 0.88 | |
| 91 | 3.01 | 2.72 | |
| 92 | 0.08 | 0.26 | |
| 93 | 1.67 | 5.74 | |
| 94 | 0.09 | 0.33 | |
| 95 | 1.39 | | |
| 96 | 0.24 | 1.06 | |
| 97 | 2.47 | 11.83 | |
| 98 | 0.33 | 0.74 | |
| 99 | 2.88 | 14.33 | |
| 100 | 0.27 | 1.07 | |

TABLE 2-continued

| Example # | CDK2_Ki (nM) | CDK6_Ki (nM) | CDK4_Ki (nM) |
|---|---|---|---|
| 101 | 3.59 | 23.51 | |
| 102 | 0.24 | 0.80 | |
| 103 | 3.46 | 19.55 | |
| 104 | 0.14 | 0.77 | |
| 105 | 3.35 | 22.74 | |
| 106 | 0.16 | 0.11 | |
| 107 | 9.91 | 184.11 | |
| 108 | 3.27 | 3.99 | |
| 109 | 0.14 | 0.19 | |
| 110 | 0.10 | 0.28 | |
| 111 | 2.14 | 4.90 | |
| 112 | 0.12 | 1.24 | |
| 113 | 1.99 | 4.15 | |
| 114 | 0.17 | 0.15 | |
| 115 | 2.39 | 3.17 | |
| 116 | 0.15 | 0.21 | |
| 117 | 1.74 | 2.46 | |
| 118 | 0.34 | 4.36 | |
| 119 | 2.87 | 4.15 | |
| 120 | 0.16 | 0.18 | 0.34 |
| 121 | 2.15 | 0.82 | |
| 122 | 0.11 | 0.23 | 0.92 |
| 123 | 0.76 | 6.14 | |
| 124 | 0.69 | 3.84 | |
| 125 | 6.21 | 36.60 | |
| 126 | 0.20 | 0.96 | |
| 127 | 3.46 | 12.56 | |
| 128 | 0.12 | 0.53 | |
| 129 | 1.47 | 5.73 | |
| 130 | 0.17 | 0.43 | |
| 131 | 3.24 | 23.10 | |
| 132 | 0.57 | 0.37 | |
| 133 | 2.37 | 0.94 | |
| 134 | 1.25 | 0.53 | |
| 135 | 0.84 | 0.44 | |
| 136 | 3.14 | 1.35 | |
| 137 | 4.08 | 6.30 | |
| 138 | 0.87 | | |
| 139 | 4.05 | | |
| 140 | 1.97 | 0.63 | |
| 141 | 1.25 | 0.37 | |
| 142 | 1.88 | 0.55 | |
| 143 | 2.42 | 0.19 | |
| 144 | 2.16 | 10.50 | |
| 145 | 1.41 | 1.40 | |
| 146 | 1.51 | 1.10 | |
| 147 | 1.57 | 0.45 | |
| 148 | 4.18 | 0.26 | |
| 149 | 2.29 | | |
| 150 | 2.63 | 1.32 | |
| 151 | | 7.29 | |
| 152 | 1.36 | 0.43 | |
| 153 | 63.24 | 2.23 | |
| 154 | 1.91 | 0.27 | |
| 155 | 35.94 | 2.26 | |
| 156 | 1.40 | 1.94 | |
| 157 | 36.03 | | |
| 158 | 3.89 | 0.66 | |
| 159 | 95.18 | | |
| 160 | 4.07 | 3.55 | |
| 161 | 134.51 | | |
| 162 | 3.92 | 12.34 | |
| 163 | 63.16 | | |
| 164 | 2.13 | 2.82 | |
| 165 | 1.51 | 2.65 | |
| 166 | 2.23 | 6.71 | |
| 167 | 1.47 | 1.63 | |
| 168 | 1.31 | 1.34 | |
| 169 | 2.76 | 1.11 | |
| 170 | 6.03 | 1.82 | |
| 171 | 1.73 | 1.55 | |
| 172 | 4.38 | 2.08 | |
| 173 | 2.95 | 3.52 | |
| 174 | 3.07 | 6.94 | |
| 175 | 3.14 | 3.49 | |
| 176 | 1.27 | 1.87 | |
| 177 | 1.22 | 0.14 | |
| 178 | 9.04 | | |
| 179 | 0.38 | 2.18 | |
| 180 | 3.76 | 28.93 | |
| 181 | 1.32 | 0.85 | |
| 182 | 12.58 | 9.50 | |
| 183 | 0.10 | 1.99 | |
| 184 | 1.46 | 11.79 | |
| 185 | 0.43 | 0.38 | |
| 186 | 5.65 | 3.62 | |
| 187 | 0.08 | 0.29 | |
| 188 | 0.70 | 2.40 | |
| 189 | 1.20 | 1.98 | |
| 190 | 0.51 | 184.11 | |
| 191 | 0.40 | 0.58 | |
| 192 | 20.89 | 10.06 | |
| 193 | 2.55 | 2.27 | |
| 194 | 4.01 | 5.37 | |
| 195 | 5.49 | 4.68 | |
| 196 | 5.72 | 3.84 | |
| 197 | 4.26 | 4.78 | |
| 198 | 26.90 | 30.96 | |
| 199 | 2.92 | 1.09 | |
| 200 | 9.51 | 4.72 | |
| 201 | 0.12 | 0.85 | |
| 202 | 0.80 | 2.44 | |
| 203 | 0.51 | 1.53 | |
| 204 | 0.51 | 0.18 | |
| 205 | 5.22 | 1.27 | |
| 206 | 0.57 | | |
| 207 | 5.05 | | |
| 208 | 12.37 | | |
| 209 | 0.50 | 0.75 | |
| 210 | 5.36 | 3.15 | |
| 211 | 2.19 | 2.22 | |
| 212 | 1.20 | 0.17 | |
| 213 | 1.73 | 9.15 | |
| 214 | 27.78 | 83.34 | |
| 215 | 1.57 | 2.84 | |
| 216 | 1.48 | | |
| 217 | 0.55 | 2.00 | |
| 218 | 6.28 | 14.35 | |
| 219 | 0.78 | 3.90 | |
| 220 | 7.46 | 18.29 | |
| 221 | 0.13 | 0.36 | |
| 222 | 2.06 | | |
| 223 | 57.15 | 20.99 | |
| 224 | 24.91 | 12.00 | |
| 225 | 4.63 | 3.13 | |
| 226 | 310.07 | 6.58 | |

Cell Based Assays

Cell Proliferation Assay

OVCAR3 or HCC1806 cells were seeded 3000 cells/well in 96-well plates in growth media containing 10% FBS and cultured overnight at 37° C. 5% $CO_2$. The following day, compounds were serially diluted from a 10 mM top dose for an 11-point 3 fold dilution curve in DMSO. Compounds were intermediately diluted 1:200 into growth media prior to diluting 1:5 on cells for final concentration 10 µM to 0.1 nM in 0.1% DMSO on cells. Cells were incubated at 37° C. 5% $CO_2$ for 7 days. CYQUANT Direct Cell Proliferation Assay (Molecular Probes, Eugene, Oreg.) was then performed following manufacturer recommendations to determine the relative viable cell numbers on the Perkin Elmer Envision 2104 Multi Label Reader at 508 nM excitation and 527 nM emission wavelengths. $IC_{50}$ values were calculated by concentration-response curve fitting utilizing a four-parameter analytical method using GraphPad Prism software.

Figure 2A:
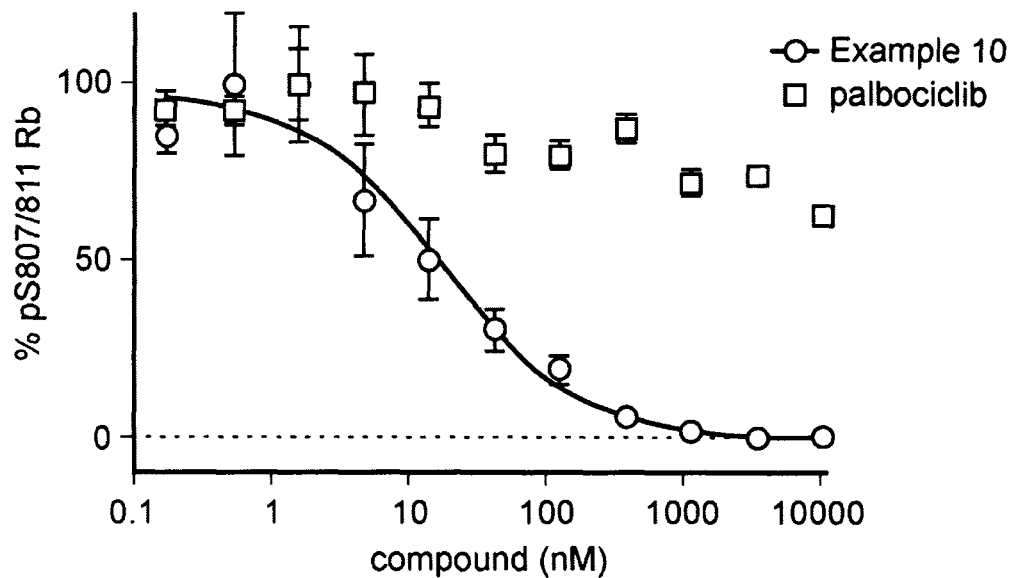
FIGS. 2A-2D show in vitro $IC_{50}$ data for the compound of Example 10 and palbociclib in Ovcar3 (CCNE amplified ovarian carcinoma) Rb ELISA assay in FIG. 2A; HCC1806 (CCNE amplified breast carcinoma) Rb ELISA assay in FIG. 2B; Ovcar3 cell proliferation assay in FIG. 2C; and HCC1806 cell proliferation assay in FIG. 2D.
Figure 2B:
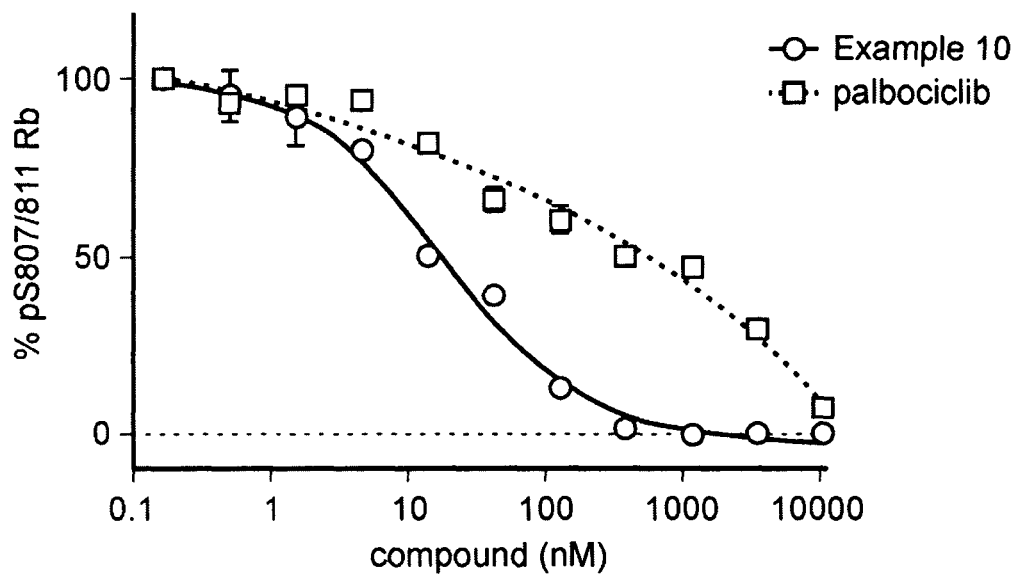
Figure 2C:
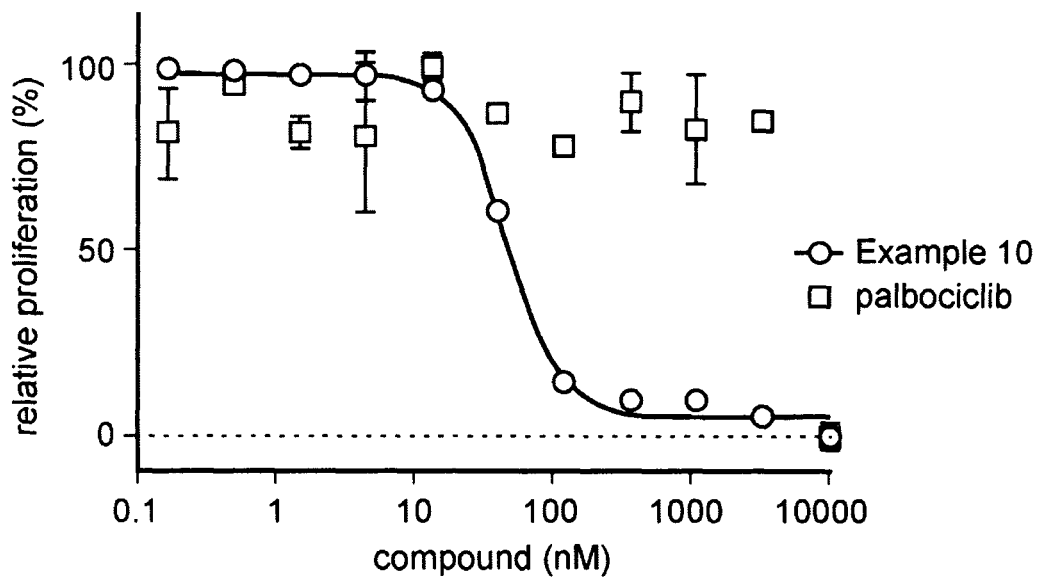
Figure 2D:
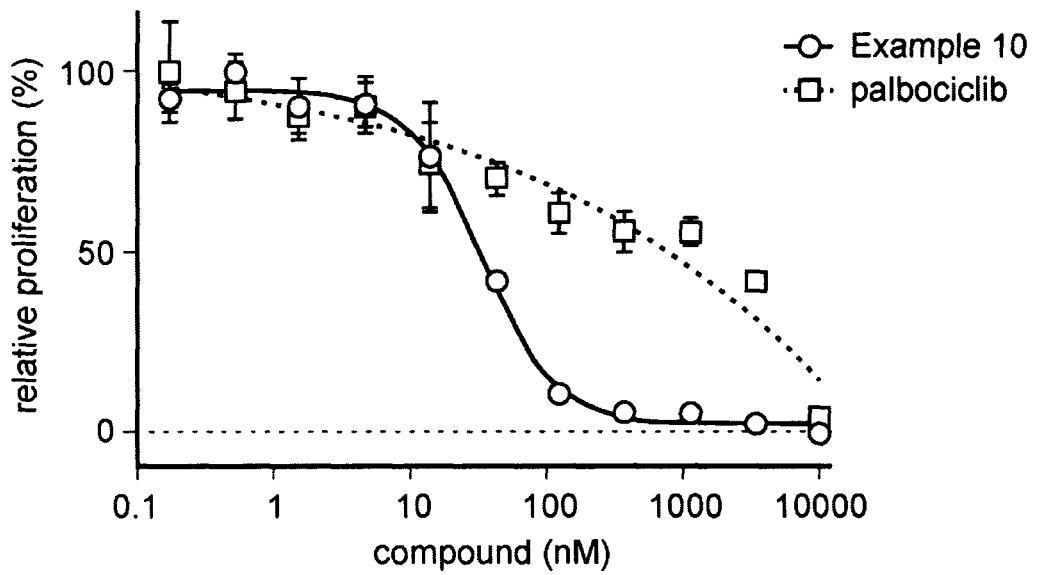

FIG. 2C shows $IC_{50}$ results for Example 10 and palbociclib in the OVCAR3 cell proliferation assay. FIG. 2D shows $IC_{50}$ results for Example 10 and palbociclib in the HCC1806 cell proliferation assay.

Phospho-Serine 807/811 Rb ELISA

OVCAR3 or HCC1806 cells were seeded at 25,000 cells/well in 100 μL growth media and allowed to adhere at 37° C. with 5% $CO_2$ overnight. The following day, compounds were serially diluted from a 10 mM top dose for an 11-point 3 fold dilution curve in DMSO. Compounds were intermediately diluted 1:200 into growth media prior to diluting 1:5 on cells for final concentration 10 μM to 0.1 nM in 0.1% DMSO on cells. OVCAR3 cells were treated for 1 hour, while HCC1806 cells were treated overnight, at 37° C. with 5% $CO_2$. Cells were lysed in 100 μL/well CST lysis buffer on ice and transferred to pre-coated and blocked anti-phospho-Ser807/811 Rb ELISA plates for overnight incubation at 4° C. Plates were washed to remove residual, unbound cellular proteins and total Rb detection antibody added for 90 minutes at 37° C. Following wash to remove unbound total Rb antibody, HRP tagged antibody was allowed to bind for 30 minutes at 37° C. Following wash to remove unbound HRP antibody, Glo Substrate Reagent was added and incubated protected from light for 5 to 10 minutes. Plates were read in luminescence mode and $IC_{50}$ values calculated.

FIG. 2A shows $IC_{50}$ results for Example 10 and palbociclib in the OVCAR3 Rb ELISA assay. FIG. 2B shows $IC_{50}$ results for Example 10 and palbociclib in the HCC1806 Rb ELISA assay.

Tumor Models

Ovcar3 Tumor Model

Ovcar3 tumor cell line, purchased from ATCC (ATCC HTB-161™) was cultured in RPMI1640 (1×) media (Gibco™ cat #11875-093) with 10% FBS (Gibco™ cat #26140-079). To establish a Ovcar3 xenograft model, 5×106 cells per mouse was implanted subcutaneously into right hind flank NSG mice (#5557-NOD.cg-Prkdc<scid>Jackson Lab). Cells were suspended in 50% matrigel (Cultrex Basement Membrane Extract (BME), Trevigen's Basement Membrane Matrix) and 50% RPMI1640 (1×) media (Gibco™ cat #11875-093) serum free media prior to implantation.

Animals were randomized 39 days after cells implantation with each group consisted of 4 mice. Treatment began when tumors reached 100 $mm^3$-190 $mm^3$ in size. Test compounds were prepared in 40% Captisol and dosed PO at 10 and 50 mg/kg QD or at 50 mg/kg BID as a suspension for 14 days. Animals were taken down at designated time. Mice receiving no drugs were given vehicle QD or BID for 14 days. Tumor volumes were measured once prior to randomization with an electric caliper, with tumor volumes were calculated using Length×Width×Width/2 formulation. Tumor volumes were measured twice a week with an electric caliper, with tumor volumes calculated using Length×Width×Width/2 formula. Animal weights were recorded twice weekly.

Figure 3:
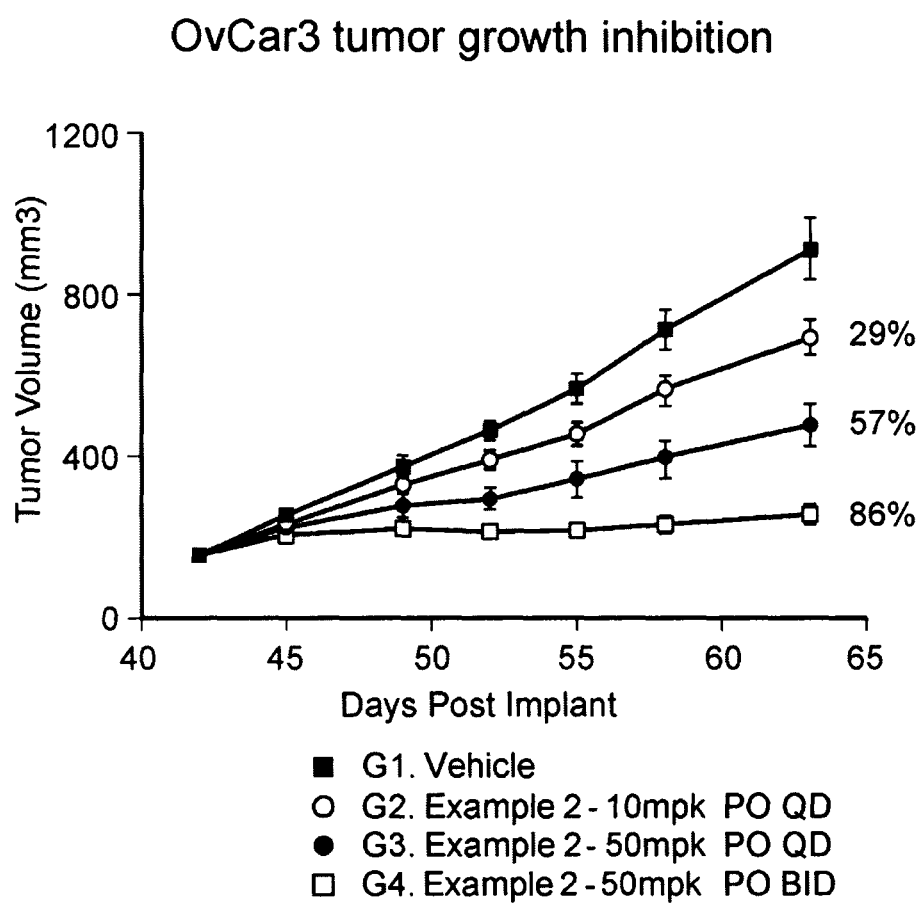
FIG. 3 shows tumor growth inhibition for the compound of Example 2 in Ovcar3 mouse tumor xenograft model at 10 mpk PO QD, 50 mpk PO QD and 50 mpk PO BID.

FIG. 3 shows dose dependent inhibition of tumor growth ($mm^3$) for Example 2 in the OVCAR3 mouse tumor xenograft model dosed at 10 mpk PO QD, 50 mpk PO QD and 50 mpk PO BID.

HCC1806 Tumor Model

Source: HCC1806 (# CRL 2335, ATCC, Manassas, Va.)

The HCC1806 tumor cell line was cultured in RPMI1640 media supplemented with 10% Fetal Bovine Serum (FBS). To establish a HCC1806 xenograft model, 5×106 cells per mouse were implanted subcutaneously into right hind flank NU/NU female mice. Cells were suspended in 50% Cultrex Basement Membrane Extract and 50% RPMI 1640 media serum free media prior to implantation.

Animals were randomized 7 days after cells implantation with each group consisting of 13 mice. Treatment began when tumors reached 100 $mm^3$ to 170 $mm^3$ in size on Day 7. Test compounds were prepared in 0.1% Tween, 0.5% Methyl cellulose in water and dosed PO at 30, 50, and 75 mg/kg as a suspension BID for 14 days. Mice receiving no drugs were given vehicle BID for 14 days. Tumor volumes were measured twice a week with an electric caliper, with tumor volumes calculated using Length×Width×Width/2 formula. Animal weights were recorded twice weekly.

Figure 4:
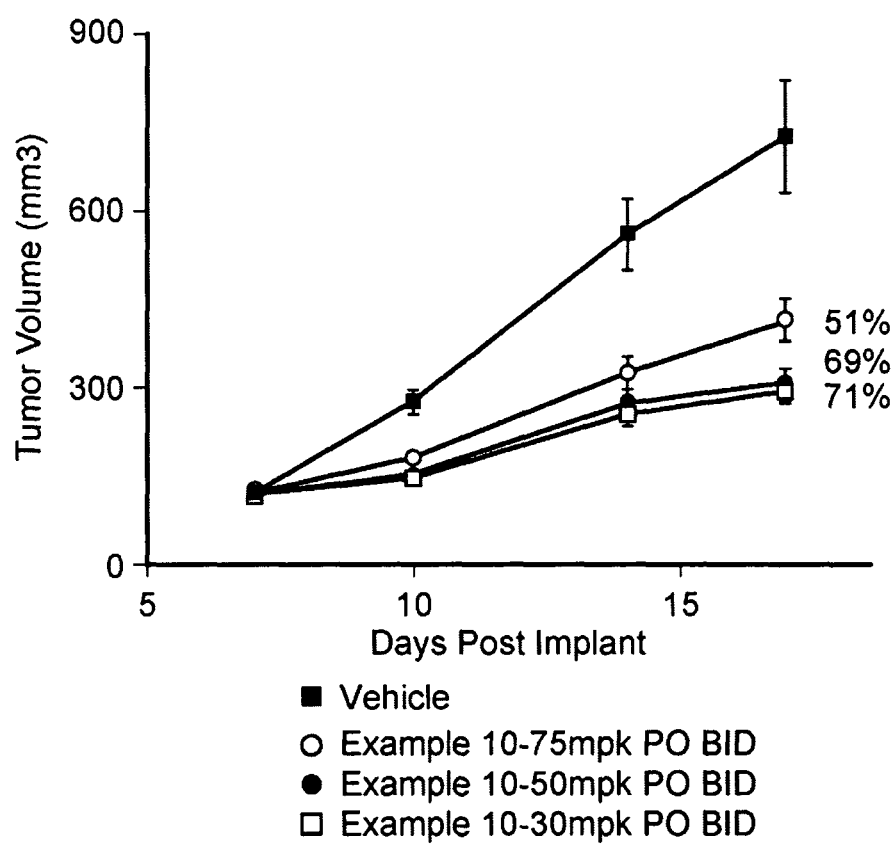
FIG. 4 shows tumor growth inhibition for the compound of Example 10 in HCC1806 mouse tumor xenograft model at 30 mpk PO BID, 50 mpk PO BID and 75 mpk PO BID.

FIG. 4 shows dose dependent inhibition of tumor growth ($mm^3$) for Example 2 in the HCC1806 mouse tumor xenograft model dosed at 30 mpk PO BID, 50 mpk PO BID and 75 mpk PO BID.

All publications and patent applications cited in the specification are herein incorporated by reference in their entirety. It will be apparent to those of ordinary skill in the art that certain changes and modifications may be made thereto without departing from the spirit or scope of the appended claims.

The invention claimed is:

1. A compound of Formula (VI):

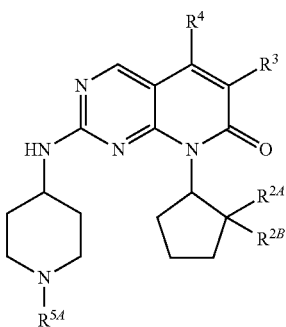

(VI)

or a pharmaceutically acceptable salt thereof, wherein:

$R^{2A}$ and $R^{2B}$ are independently H, OH or $C_1$-$C_4$ alkyl, provided at least one of $R^{2A}$ and $R^{2B}$ is not H;

$R^3$ is $C_1$-$C_4$ fluoroalkyl, where said $C_1$-$C_4$ fluoroalkyl is optionally substituted by OH;

$R^4$ is H;

$R^{5A}$ is $SO_2R^7$; and $R^7$ is $C_1$-$C_4$ alkyl.

2. The compound of claim 1, or a pharmaceutically acceptable salt thereof, wherein $R^{2A}$ is OH and $R^{2B}$ is $CH_3$.

3. The compound of claim 1, or a pharmaceutically acceptable salt thereof, wherein $R^3$ is $C_1$-$C_2$ fluoroalkyl.

4. The compound of claim 3, or a pharmaceutically acceptable salt thereof, wherein $R^3$ is $CF_2H$ or $CH_2CF_2H$.

5. The compound of claim 1, or a pharmaceutically acceptable salt thereof, wherein $R^7$ is $CH_3$.

6. A pharmaceutical composition comprising the compound of claim 1, or a pharmaceutically acceptable salt thereof, and a pharmaceutically acceptable carrier or excipient.

7. A compound of Formula (VI-B):

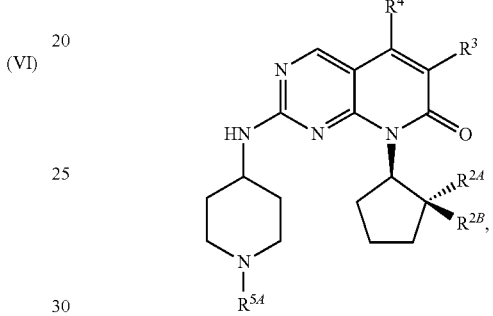

(VI-B)

or a pharmaceutically acceptable salt thereof, wherein:

$R^{2A}$ and $R^{2B}$ are independently H, OH or $C_1$-$C_4$ alkyl, provided at least one of $R^{2A}$ and $R^{2B}$ is not H;

$R^3$ is $C_1$-$C_4$ fluoroalkyl, where said $C_1$-$C_4$ fluoroalkyl is optionally substituted by OH;

$R^4$ is H;

$R^{5A}$ is $SO_2R^7$; and $R^7$ is $C_1$-$C_4$ alkyl.

8. The compound of claim 7, or a pharmaceutically acceptable salt thereof, wherein $R^{2A}$ is OH and $R^{2B}$ is $CH_3$.

9. The compound of claim 7, or a pharmaceutically acceptable salt thereof, wherein $R^3$ is $C_1$-$C_2$ fluoroalkyl.

10. The compound of claim 9, or a pharmaceutically acceptable salt thereof, wherein $R^3$ is $CF_2H$ or $CH_2CF_2H$.

11. The compound of claim 7, or a pharmaceutically acceptable salt thereof, wherein $R^7$ is $CH_3$.

12. A pharmaceutical composition comprising the compound of claim 7, or a pharmaceutically acceptable salt thereof, and a pharmaceutically acceptable carrier or excipient.

13. 6-(difluoromethyl)-8-[(1R,2R)-2-hydroxy-2-methylcyclopentyl]-2-{[1-(methylsulfonyl)piperidin-4-yl]amino}pyrido[2,3-d]pyrimidin-7(8H)-one.

14. A pharmaceutical composition comprising the compound of claim 13 and a pharmaceutically acceptable carrier or excipient.

15. A pharmaceutically acceptable salt of 6-(difluoromethyl)-8-[(1R,2R)-2-hydroxy-2-methylcyclopentyl]-2-{[1-(methylsulfonyl)piperidin-4-yl]amino}pyrido[2,3-d]pyrimidin-7(8H)-one.

16. A pharmaceutical composition comprising the pharmaceutically acceptable salt of claim 15 and a pharmaceutically acceptable carrier or excipient.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5'FAM labeled Glutamine
<220> FEATURE:
<221> NAME/KEY: MISC_FEATURE
<222> LOCATION: (6)..(6)
<223> OTHER INFORMATION: Glycine carboxamide

<400> SEQUENCE: 1

Gln Ser Pro Lys Lys Gly
1               5

<210> SEQ ID NO 2
```

```
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5'FAM labeled Arginine

<400> SEQUENCE: 2

Arg Arg Arg Phe Arg Pro Ala Ser Pro Leu Arg Gly Pro Pro Lys
1               5                   10                  15
```